United States Patent [19]
Gyorkos et al.

[11] Patent Number: 5,998,379
[45] Date of Patent: *Dec. 7, 1999

[54] SERINE PROTEASE INHIBITORS-PROLINE ANALOGS

[75] Inventors: Albert Gyorkos, Westminster, Colo.; Lyle W. Spruce, Chula Vista, Calif.

[73] Assignee: Cortech Inc., Bedminster, N.J.

[*] Notice: This patent is subject to a terminal disclaimer.

[21] Appl. No.: 08/985,056

[22] Filed: Dec. 4, 1997

Related U.S. Application Data

[63] Continuation-in-part of application No. 08/771,317, Dec. 6, 1996, Pat. No. 5,801,148, which is a continuation-in-part of application No. 08/345,820, Nov. 21, 1994, Pat. No. 5,618,792.

[51] Int. Cl.[6] .......................... A61K 38/05; A61K 38/06; C07K 5/078; C07K 5/097

[52] U.S. Cl. .............................. 514/18; 514/19; 514/307; 514/309; 514/361; 514/362; 514/363; 514/364; 514/383; 530/331; 546/146; 548/128; 548/131; 548/136; 548/143; 548/266.8

[58] Field of Search .............................. 530/331; 514/18, 514/19, 307, 309, 361, 362, 363, 364, 383; 546/141, 142, 146; 548/128, 131, 136, 143, 266.8

[56] References Cited

U.S. PATENT DOCUMENTS

| | | | |
|---|---|---|---|
| 4,338,453 | 7/1982 | Gall | 548/263 |
| 5,055,450 | 10/1991 | Edwards et al. | 514/19 |
| 5,164,371 | 11/1992 | Edwards et al. | 514/18 |
| 5,550,139 | 8/1996 | Groutas | 514/362 |
| 5,618,792 | 4/1997 | Gyorkos et al. | 514/18 |

FOREIGN PATENT DOCUMENTS

| | | | |
|---|---|---|---|
| 0 291 234 | 11/1988 | European Pat. Off. | C07K 5/06 |
| 0 480 044 | 4/1992 | European Pat. Off. | C07D 413/12 |
| 0 528 633 A1 | 2/1993 | European Pat. Off. | C07D 239/46 |
| 0 529 568 A1 | 3/1993 | European Pat. Off. | C07D 5/08 |
| 2 694 295 | 2/1994 | France | C07K 5/12 |
| 2224338 | 11/1972 | Germany | C07D 85/52 |
| 1397073 | 6/1975 | United Kingdom | C07D 271/06 |
| WO 93/21212 | 10/1993 | WIPO | C07K 5/06 |
| WO 95 33762 | 12/1995 | WIPO | C07K 5/06 |
| WO 96/16080 | 5/1996 | WIPO | C07K 5/062 |

OTHER PUBLICATIONS

Edwards, P. D., et al. "Peptidyl Alpha–Ketoheterocyclic Inhibitors of Human Neutrophil Elastase. 3. In Vitro and in Vivo Potency of a Series of Peptidyl Alpha–Ketobenzoxazoles," J. Med. Chem. 38, 3972–3982 (1995).

Edwards, P. D., et al. "Nonpeptic Inhibitors of Human Neutrophil Elastase. 7. Design, Synthesis, and in Vitro Activity of a Series of Pyridopyrimidine Trifluoromethyl Ketones," J. Med. Chem. 39, 1112–1124 (1996).

Edwards, P. D., et al. "Peptidyl Alpha–Ketoheterocyclic Inhibitors of Human Neutrophil Elastase. 2. Effect of Varying the Heterocyclic Ring on in Vitro Potency," J. Med. Chem. 38, 76–85 (1995).

Veale, C. A., et al. "Non–peptidic Inhibitors of Human Leukocyte Elastase. 4. Design, Synthesis, and in Vitro and in Vivo Activity of a Series of Beta–Carbolinone–Containing Trifluoromethyl Ketones," J. Med. Chem. 38, 86–97 (1995).

Veale, C. A., et al. "Nonpeptidic Inhibitors of Human Leukocyte Elastase. 5. Design, Synthesis, and X–ray Crystallography of a Series of Orally Active 5–Aminopyrimidin–6–one–Containing Trifluoromethyl Ketones," J. Med. Chem. 38, 98–108 (1995).

(List continued on next page.)

Primary Examiner—Jeffrey E. Russel
Attorney, Agent, or Firm—Dechert Price & Rhoads

[57] ABSTRACT

The present invention relates to certain substituted oxadiazole, thiadiazole, and triazole peptoids that are useful as inhibitors of serine proteases, in particular human neutrophil elastase. Serine protease inhibitors of the invention are useful in the treatment of, for example, adult respiratory distress syndrome, septic shock, and myocardial ischemia-reperfusion injury.

13 Claims, 39 Drawing Sheets

General Synthetic Scheme for P$_2$-P$_3$ Modified Inhibitors

OTHER PUBLICATIONS

Goddard, C. J., "Antiinflammatory 1–Phenylpyrazole–4–Heteroarylalkanoic Acids," J. Heterocyclic Chem., 28, 1607–1612 (1991).

LaMattina, J. L., et al. "Utility of 24 p–Nitrophenyl 3–Bromo–2,2–diethoxypropionate (NPBDP) in Heterocyclic Synthesis," J. Org. Chem. 49, 4800–4805 (1984).

Unangst, P. C., et al. "Novel 1,2,4–Oxadiazoles and 1,2,4–Thiadiazoles as Dual 5–Lipoxygenase and Cyclooxygenase Inhibitors," J. Med. Chem. 35, 3691–3698 (1992).

Kitatani, K., et al. "A Novel Oxazole Synthesis Utilizing Tungsten(VI) Catalyzed Decomposition of Alpha–Diazo Carbonyl Compounds in Nitriles," Tet. Lett. 16, 1531–1532 (1974).

Wiley, R. H., "Chemistry of the Oxazoles," Chem. Rev. 37, 401–442 (1945).

Davidson, D., et al. "The Action of Ammonia on Benzoin," J. Org. Chem. 2, 328–334 (1937).

Wiegand, Edwin E., et al. "Polyphosphoric Acid Cyclization of Acetamidoketones to 2,5–Dimethyl–1,3–oxazoles," Synthesis 12, 648–649 (1970).

Wasserman, H.H., et al. "The Oxazole–Triamide Rearrangement. Application To Peptide Synthesis," Tet. Lett. vol. 23, No. 37, 3831–3834 (1982).

Cornforth, J. W., et al. "A New Synthesis of Oxazoles and Iminazoles including its Application to the Preparation of Oxazole." J. Chem. Soc. 96–102 (1947).

Cornforth, J. W., et al. "Synthesis of Oxazoles from Ethyl Acetoacetate. Ring–fission of Some Oxazole–5–carboxylic Acids." J. Chem. Soc. 93–98 (1953).

Bernstein, P. R., et al. "Nonpeptidic Inhibitors of Human Leukocyte Elastase. 3. Design, Synthesis, X–Ray Crystallographic Analysis, and Structure–Activity Relationships for a Series of Orally Active 3–Amino–6–phenylpyridin–2–one Trifluoromethyl Ketones," J. Med. Chem. 37, 3313–3326 (1994).

Brown, F. J., et al. "Design of Orally Active, Non–Peptidic Inhibitors of Human Leukocyte Elastase," J. Med. Chem. 37, 1259–1261 (1994).

Warner, P., et al. "Non–peptidic Inhibitors of Human Leukocyte Elastase. 1. The Design and Synthesis of Pyridone–Containing Inhibitors," J. Med. Chem. 37, 3090–3099 (1994).

Budavari, Susan (Editor), "The Merck Index" An Encyclopedia of Chemicals, Drugs, and Biologicals; Merck & Co., Inc., p. 294 (1989).

Damewood, J. R., Jr. et al. "Nonpeptidic Inhibitors of Human Leukocyte Elastase. 2. Design, Synthesis, and in vitro Activity of a Series of 3–Amino–6–arylopyridin–2–one Trifluoromethyl Ketones," J. Med. Chem. 37, 3303–3312 (1994).

Skiles, J.W., et al. "Elastase Inhibitors Containing Conformationally Restricted Lactams as $P_3$–$P_2$ Dipeptide Replacements," Bio. & Med. Chem. Ltrs. 3, 773–778 (1993).

General Synthetic Scheme for 1,3,4-Oxadiazole Inhibitors

General Scheme for 1,3,4-Oxadiazole Inhibitors - Continued

General Synthetic Scheme for 1,2,4-Oxadiazole Inhibitors

General Synthetic Scheme for 1,2,4-Oxadiazole inhibitors (Continued)

General Synthetic Scheme for $P_2$-$P_3$ Modified Based Inhibitors

Synthetic Scheme for P₂-P₃ Modified Inhibitors

Synthetic Scheme for P₂-P₃ Modified Inhibitors

General Synthetic Scheme for $P_2$-$P_3$ Modified Inhibitors

Synthetic Scheme for $P_2$-$P_3$ Modified Inhibitors

General Synthetic Scheme for P₂-P₃ Modified Inhibitors

General Synthetic Scheme for P2-P3 Lactam Based Inhibitors

General Synthetic Scheme for P$_2$-P$_3$ Lactam Based Inhibitors

General Synthetic Scheme for Metathiazanone Based Inhibitors

General Synthetic Scheme for Thiazolidinone Based Inhibitors

General Synthetic Scheme for Pyridazinedione Based Inhibitors

General Synthetic Scheme for Benzopyridazinedione Based Inhibitors

General Synthetic Scheme for Quinolone and N-Substituted Quinolone Based Inhibitors General Synthetic Scheme for 3,4-Dihydroquinolone Based Inhibitors General Synthetic Scheme for Benzylidene Diketopiperazine Based Inhibitors General Synthetic Scheme for Diketopiperazine Based Inhibitors Synthetic Scheme for Hydantoin Based Inhibitors General Synthetic Scheme for Hydantoin Based Inhibitors

| CE# | R | $K_i$ (nM) | CE# | R | $K_i$ (nM) |
|---|---|---|---|---|---|
| 2039 | phenyl | 2.0 | 2054 | 3,5-bis(CF₃)phenyl | 0.29 |
| 2042 | 2-OMe phenyl | 2.5 | 2055 | 3-Me phenyl | 0.49 |
| 2045 | 4-OMe phenyl | 1.0 | 2058 | 4-biphenyl | 0.56 |
| 2048 | 3-CF₃ phenyl | 0.36 | 2062 | 3-biphenyl | 0.30 |
| 2049 | 3-OMe phenyl | 0.5 | 2066 | 3-phenoxyphenyl | 0.98 |
| 2052 | 3,5-diMe phenyl | 0.37 | 2096 | 3,5-diPh phenyl | 0.8 |
| 2053 | 3,5-diOMe phenyl | 0.41 | 2115 | 4-NMe₂ phenyl | 1.0 |

| CE# | R | $K_l$ (nM) | CE# | R | $K_l$ (nM) |
|---|---|---|---|---|---|
| 2046 | phenyl | 9.9 | 2077 | 1-naphthyl | 0.15 |
| 2047 | propylphenyl | 3.8 | 2078 | pyridyl | 1.05 |
| 2050 | butylphenyl | 1.84 | 2092 | propylmorpholine | 6.3 |
| 2057 | diphenylethyl | 0.38 | 2103 | dimethylaminoethyl | 12.4 |
| 2069 | cyclohexyl | 4.4 | 2119 | methyl butanoate | 7.7 |
| 2073 | t-butyl-CF₃-phenyl | 0.24 | 2152 | 2-naphthyl | 0.24 |
| 2076 | adamantyl | 1.46 | | | |

| CE# | R | $K_i$ (nM) |
|---|---|---|
| 2072 | 3-methylphenyl-CH2- (ethyl linker to 3-CH3 phenyl) | 0.025 |
| 2074 | —CH3 | 0.99 |
| 2075 | 3-CF3-phenyl-CH2CH2- | 0.11 |
| 2100 | 4-(N-methylamino)phenyl-CH2CH2- | 0.069 |
| 2123 | —N(CH3)2 | 15.1 |
| 2124 | 1-naphthyl-CH2CH2- | 0.033 |

| CE# | R₁ | R₂ | R₃ | HET | $K_i$ (nM) |
|---|---|---|---|---|---|
| 2083 | Cbz- | CH₃ | CH₃ | methyl-oxadiazole-CH₂-(3-methylphenyl) | 73.0 |
| 2098 | morpholine-C(O)- | i-Propyl | H | methyl-oxadiazole-CH₂CH₂-morpholine | 85.0 |
| 2104 | morpholine-C(O)- | i-Propyl | H | methyl-oxadiazole-CH₂-(3-methylphenyl) | 0.33 |
| 2109 | morpholine-C(O)- | i-Propyl | H | methyl-oxadiazole-CH₂CH₂-N(CH₃)₂ | 126 |
| 2110 | 4-MeO-C₆H₄-C(O)- | i-Propyl | H | methyl-oxadiazole-CH₂-(3-CF₃-phenyl) | 0.13 |

| CE# | R | $K_i$ (nM) |
|---|---|---|
| 2072 | 3-methylphenyl-CH₂- | 0.025 |
| 2074 | —CH₃ | 0.99 |
| 2075 | 3-CF₃-phenyl-CH₂- | 0.11 |
| 2100 | 4-(N,N-dimethylamino)phenyl-CH₂- | 0.069 |
| 2123 | —N(CH₃)₂ | 15.1 |
| 2124 | 1-naphthyl-CH₂- | 0.033 |

| CE# | R | HET | $K_i$ (nM) |
|---|---|---|---|
| 2130 | | B | 10.0 |
| 2132 | | A | 24.0 |
| 2134 | | B | 2.0 |
| 2135 | | A | 17 |
| 2126 | | B | 5.05 |
| 2127 | | A | 33.9 |

Heterocycles:

| CE# | R | HET | $K_i$ (nM) |
|---|---|---|---|
| 2125 | Cbz-HN-CH(iPr)-C(O)-N(indoline-2-yl-C(O)CH3) | A | 0.40 |
| 2145 | Cbz-HN-CH(iPr)-C(O)-N(indoline-2-yl-C(O)CH3) | B | 0.038 |
| 2143 | H3C-C(O)-N(indoline-2-yl-C(O)CH3) | A | 25.0 |
| 2056 | Cbz-HN-CH(iPr)-C(O)-N(Bn)(CH2C(O)CH3) | A | 0.98 |
| 2097 | pyrrole-2-C(O)-N(Bn)(CH2C(O)CH3) | A | 60.0 |
| 2156 | H2N-benzazepinone-N-CH2C(O)CH3 | A | 512.0 |

Heterocycles:

| CE# | R | HET | $K_i$ (nM) |
|---|---|---|---|
| 2089 | Cbz-NH- | A | 1.5 |
| 2090 | NH$_2$- | A | 2.7 |
| 2095 | Cbz-NH- | B | 0.21 |
| 2101 | NH$_2$- | B | 0.64 |

Heterocycles:

| CE# | R₁ | R₂ | $K_i$ (nM) |
|---|---|---|---|
| 2107 | Cbz-NH- | N-methylpiperidinyl | 17.0 |
| 2108 | Cbz-NH- | H | 10.5 |
| 2113 | H₂N- | H | 38.8 |
| 2116 | morpholinyl-CH₂-C(O)-NH(Me)- | H | 76.3 |
| 2117 | MeO-CH(Me)-C(O)-O- | F | 587.0 |

CE-2088     $K_i$ = 66.0 nM

| CE# | R | Structure | HET | $K_l$(nM) |
|---|---|---|---|---|
| 2138 | acetylphenyl | I | B | 294.0 |
| 2147 | phenyl | I | B | 1590 |
| 2148 | phenyl | I | A | >6000 |
| 2140 | acetylphenyl | II | B | 204.4 |

Heterocycles:

A                B

| CE# | R₁ | R₂ | $K_i$ (nM) |
|---|---|---|---|
| 2079 | Cbz-NH- | H | 35.5 |
| 2080 | H₂N- | H | 62.0 |
| 2087 | H |  | 19.8 |
| 2091 |  | H | 270.0 |

| CE# | n | X | HET | R | $K_i$ (nM) |
|---|---|---|---|---|---|
| 2118 | 2 | S | N-N, CH₃ (oxadiazole-CH₂-Ph-CH₃) | Ph | 13.2 |
| 2121 | 1 | S | N-N, CH₃ (oxadiazole-CH₂-Ph-CH₃) | Ph | 28.0 |
| 2122 | 1 | S | N-N, CH₃ (oxadiazole-CH₂-Ph-CH₃) | CH₂-Ph | 62.7 |
| 2136 | 1 | SO | N-N, CH₃ (oxadiazole-CH₂-Ph-CH₃) | CH₂-Ph | 104.0 |
| 2137 | 1 | SO | N-O, CF₃ (oxadiazole-CH₂-Ph-CF₃) | CH₂-Ph | 557.0 |

| CE# | R | $K_i$ (nM) |
|---|---|---|
| 2099 | phenyl | 1.9 |
| 2105 | 4-fluorophenyl | 0.72 |
| 2111 | 4-(N-methylamino)phenyl | 20.1 |
| 2112 | 4-(CO₂Me)phenyl | 1.17 |
| 2114 | 4-pyridyl | 25.1 |

| CE# | R₁ | R₂ | R₃ | HET | $K_i$ (nM) |
|---|---|---|---|---|---|
| 2084 | CH₃ | phenyl | H | A | 133.0 |
| 2106 | CH₃ | phenyl | H | B | 40.7 |
| 2120 | CH₃CO- | benzyl | H | B | 50.9 |
| 2128 | benzyl | —H | benzyl | B | 64.0 |
| 2129 | benzyl | —H | benzyl | A | 300.3 |
| 2133 | benzyl | —H | benzyl | C | 33200 |
| 2139 | H— | benzyl | H | B | 41.0 |
| 2144 | benzyl | benzyl | —H | B | 9.3 |
| 2146 | benzyl | benzyl | —H | A | 67.3 |

Heterocycles:

A

B

C

| CE# | R₁ | R₂ | HET | $K_I$ (nM) |
|---|---|---|---|---|
| 2141 | phenyl-CH₂ | H | A | 64.0 |
| 2142 | phenyl-CH₂ | H | B | 8.7 |
| 2149** | phenyl-CH₂ | H | B | 0.28 |
| 2154 | H | phenyl-CH₂ | B | 10.0 |
| 2155 | H | phenyl-CH₂ | A | 57.0 |

** Stereochemistry not definitive

Heterocycles:

| CE# | HET | $K_I$ (nM) |
|---|---|---|
| 2150 | ![N-O oxadiazole with CH3 and CH2-phenyl-CF3] | >1000 |
| 2151 | ![N-N oxadiazole with CH3 and CH2-phenyl-CH3] | 60 |

SERINE PROTEASE INHIBITORS-PROLINE ANALOGS

This application is a continuation-in-part of U.S. Ser. No. 08/771,317, filed Dec. 6, 1996, now U.S. Pat. No. 5,801,148, which is a continuation-in-part of U.S. Ser. No. 08/345,820 filed Nov. 21, 1994, now U.S. Pat. No. 5,618,792.

The present invention relates to certain substituted oxadiazole, thiadiazole and triazole peptoids which are useful as inhibitors of serine proteases.

BACKGROUND PF THE INVENTION

The serine proteases are a class of enzymes which includes elastase, chymotrypsin, cathepsin G, trypsin and thrombin. These proteases have in common a catalytic triad consisting of Serine-195, Histidine-57 and Aspartic acid-102 (chymotrypsin numbering system). Human neutrophil elastase (HNE) is a proteolytic enzyme secreted by polymorphonuclear leukocytes (PMNs) in response to a variety of inflammatory stimuli. This release of HNE and its extracellular proteolytic activity are highly regulated and are normal, beneficial functions of PMNs. The degradative capacity of HNE, under normal circumstances, is modulated by relatively high plasma concentrations of $\alpha_1$-proteinase inhibitor ($\alpha_1$-PI). However, stimulated PMNs produce a burst of active oxygen metabolites, some of which (hypochlorous acid for example) are capable of oxidizing a critical methionine residue in $\alpha_1$-PI. Oxidized $\alpha_1$-PI has been shown to have limited potency as an HNE inhibitor and it has been proposed that alteration of this protease/antiprotease balance permits HNE to perform its degradative functions in localized and controlled environments.

Despite this balance of protease/antiprotease activity, there are several human disease states in which a breakdown of this control mechanism is implicated in the pathogenesis of the condition. Improper modulation of HNE activity has been suggested as a contributing factor in adult respiratory distress syndrome, septic shock and multiple organ failure. A series of studies also have indicated the involvement of PMNs and neutrophil elastase in myocardial ischemia-reperfusion injury. Humans with below-normal levels of $\alpha_1$-PI have an increased probability of developing emphysema. HNE-mediated processes are implicated in other conditions such as arthritis, periodontal disease, glomerulonephritis, dermatitis, psoriasis, cystic fibrosis, chronic bronchitis, atherosclerosis, Alzheimer's disease, organ transplantation, corneal ulcers, and invasion behavior of malignant tumors.

There is a need for effective inhibitors of HNE as therapeutic and as prophylactic agents for the treatment and/or prevention of elastase-mediated problems.

SUMMARY OF THE INVENTION

The present invention provides compounds which are useful as serine protease inhibitors, including human neutrophil elastase. These compounds are characterized by their relatively low molecular weight, high potency and selectivity with respect to HNE. Additionally, certain compounds of the invention have demonstrated oral bioavailability as exhibited by their higher blood levels after oral dosing. Oral bioavailability allows oral dosing for use in chronic disease, with the advantages of self-administration and decreased cost over other means of adminstration. The compounds described herein can be used effectively to prevent, alleviate or otherwise treat disease states characterized by the degradation of connective tissue by proteases in humans.

The present invention provides compounds comprising oxadiazole, thiadiazole or triazole ring structures, and can be generically described by the formula:

wherein Z is a serine protease binding moiety, preferably an elastase binding moiety, and most preferably a human neutrophil elastase binding moiety. Specifically, Z is a carbonyl containing group, preferably an $\alpha$-amino carbonyl containing group where the carbonyl carbon is covalently attached to the carbon of the heterocycle.

$R_1$ is alkyl, alkenyl or alkynyl optionally substituted with 1 or more, preferably 1-3, halo, hydroxyl, cyano, nitro, haloalkyl, alkylamino, dialkylamino, alkoxy, haloalkoxy, carboxyl, carboalkoxy, alkylcarboxamide, arylcarboxamide or —O—($C_5$–$C_6$)aryl; hydroxyl, amino, alkylamino or dialkylamino; or cycloalkyl, alkylcycloalkyl, alkenylcycloalkyl, cycloalkenyl, alkylcycloalkenyl, alkenylcycloalkenyl, ($C_5$–$C_{12}$)aryl, ($C_5$–$C_{12}$)arylalkyl, ($C_5$–$C_{12}$)arylalkenyl, fused ($C_5$–$C_{12}$)aryl-cycloalkyl or alkyl fused ($C_5$–$C_{,12}$)aryl-cycolalkyl optionally comprising 1–4 heteroatoms selected from N, O and S, and optionally substituted with halo, cyano, nitro, hydroxyl, haloalkyl, amino, aminoalkyl, dialkylamino, alkyl, alkenyl, alkylenedioxy, alkynyl, alkoxy, haloalkoxy, carboxyl, carboalkoxy, alkylcarboxamide, ($C_5$–$C_6$)aryl, —O—($C_5$–$C_6$)aryl, arylcarboxamide, alkylthio or haloalkylthio.

X and Y are independently O, S or N, wherein N is optionally substituted with alkyl or alkenyl optionally substituted with 1–3 halo atoms; ($C_5$–$C_6$)aryl, arylalkyl or arylalkenyl optionally comprising 1–3 heteroatoms selected from N, O and S, and optionally substituted with halo, cyano, nitro, hydroxyl, haloalkyl, amino, aminoalkyl, dialkylamino, alkyl, alkenyl, alkynyl, alkoxy, haloalkoxy, carboxyl, carboalkoxy, alkylcarboxamide, arylcarboxamide, alkylthio or haloalkylthio. Preferably, at least one of X or Y is N. It will be understood that where X or Y is a substituted N, both X and Y are N. Preferably, the compounds of the present invention comprise 1,2,4-oxadiazole (i.e., X is O; Y is N) or 1,3,4 oxadiazole rings (i.e., X is N; Y is O).

The compounds of the present invention may be conveniently categorized as Groups I through VI.

In one preferred embodiment, the invention provides compounds of the formula (Group I):

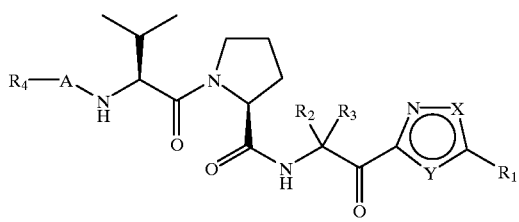

wherein X, Y and $R_1$ are described above;

$R_2$ and $R_3$ are independently or together H; alkyl or alkenyl optionally substituted with 1–3 halo, hydroxyl, thio, alkylthio, amino, alkylamino, dialkylamino, alkylguanidinyl, dialkylguanidinyl, guanidinyl, or amidylguanidine; —RCOR', —RCOOR', —RNR'R"R° or —RC(O)NR'R" where R is alkyl or alkenyl, and R', R" and R° are independently H, alkyl, alkenyl, cycloalkyl or (C$_5$–C$_6$)aryl; or cycloalkyl, alkylcycloalkyl, alkenylcycloalkyl, alkyl-oxyaryl, alkyl-thioaryl, alkyl-aminoaryl, (C$_5$–C$_{12}$)aryl, (C$_5$–C$_{12}$)arylalkyl or (C$_5$–C$_{12}$)arylalkenyl optionally comprising 1–4 heteroatoms selected from N, O and S, and optionally substituted with halo, cyano, keto, nitro, hydroxyl, haloalkyl, amino, aminoalkyl, dialkylamino, amidine, alkylamidine, dialkylamidine, alkyl, alkenyl, alkylenedioxy, alkynyl, alkoxy, haloalkoxy, carboxyl, carboalkoxy, alkylcarboxamide, (C$_5$–C$_6$)aryl, —O—(C$_5$–C$_6$)aryl, arylcarboxamide, alkylthio or haloalkylthio;

A is a direct bond, —C(O)—, —NH—C(O)—, —S(O)$_2$—, —NH—S(O)$_2$—, —OC(O)—, —C— or an amino acid selected from, but not limited to, proline, isoleucine, cyclohexylalanine, cysteine optionally substituted at the sulfur with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; phenylalanine, homo-phenylalanine, dehydrophenylalanine, indoline-2-carboxylic acid; tetrahydrosioquinoline-2-carboxylic acid optionally substituted with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; tryptophan, tyrosine, serine or threonine optionally substituted with alkyl or aryl; histidine, methionine, valine, norvaline, norleucine, octahydroindole-2-carboxylic acid; asparagine, glutamine, ornithine and lysine optionally substituted at the side chain nitrogen with alkyl, alkenyl, alkynyl, alkoxyalkyl, alkylthioalkyl, alkylaminoalkyl, dialkylaminoalkyl, carboxyalkyl, alkoxycarbonyl alkyl or aryl, arylalkyl, cycloalkyl, alkylcycloalkyl, fused aryl-cycloalkyl or alkyl fused aryl-cycloalkyl optionally comprising 1 or more heteroatoms selected from N, O and S; and R$_4$ is H, alkyl, alkenyl or alkynyl; or cycloalkyl, alkylcycloalkyl, (C$_5$–C$_{12}$)aryl, (C$_5$–C$_{12}$)arylalkyl, fused (C$_5$–C$_{12}$)aryl-cycloalkyl or fused alkyl (C$_5$–C$_{12}$) aryl-cycloalkyl optionally comprising one or more heteroatoms selected from N, O and S, and optionally substituted with alkyl, alkenyl, alkynyl, halo, cyano, nitro, hydroxyl, haloalkyl, alkoxy, amino, alkylamino, dialkylamino, carboxyl, haloalkoxy, carboalkoxy, alkylcarboxamide, aryl, arylalkyl, arylcarboxamido, alkylthio or haloalkylthio or is absent.

In a preferred embodiment, X is N and Y is O. In another preferred embodiment, X is O and Y is N. Preferably, R$_4$—A is an arylalkyloxycarbonyl such as benzyloxycarbonyl; alkoxycarbonyl, arylsulfonyl, alkylsulfonyl or alkyl.

Preferably, R$_2$ and R$_3$ are alkyl such as methyl or isopropyl, or H. In one preferred embodiment, R$_2$ is isopropyl and R$_3$ is H.

In a preferred embodiment of the invention, R$_1$ is an optionally substituted aryl or arylalkyl group, such as an α,α-dimethylbenzyl, benzyl or phenyl group. According to several preferred embodiments, the benzene ring is substituted with an alkyl, such as methyl; with a haloalkyl, such as trifluoromethyl; or with a dialkylamino, preferably dimethylamino. In yet another embodiment, R$_1$ is a fused arylalkyl group such as methylenenaphthyl; or a fused aryl-cycloalkyl or alkyl fused aryl-cycloalkyl such as 3,4-methylenedioxybenzyl. In another embodiment, R$_1$ is an alkyl group, preferably (C$_1$–C$_8$)alkyl, either straight chain or branched, such as methyl, ethyl, propyl, isopropyl, n-butyl, isobutyl, t-butyl, etc.

The present invention further provides compounds of the formula (Group II):

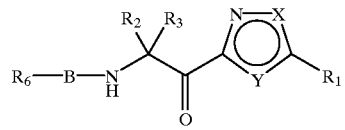

wherein

X, Y, R$_1$, R$_2$ and R$_3$ are as described above;

B is —S(O)$_2$—, —C(O)—, —OC(O)— or —CH$_2$C(O)—;

R$_6$ is

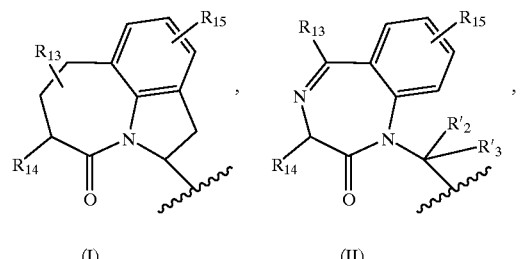

(I)         (II)

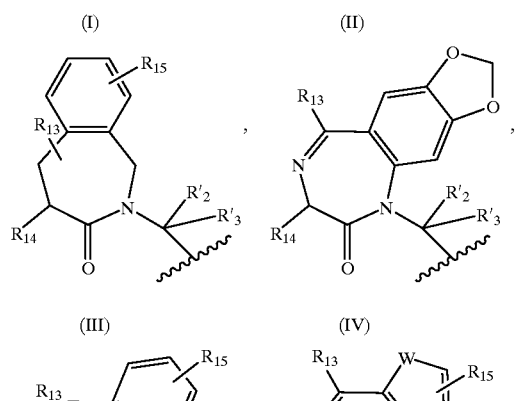

(III)        (IV)

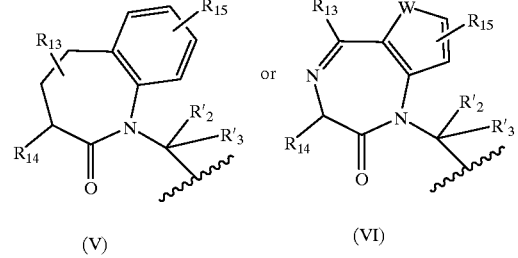

(V)         (VI)

wherein

R'$_2$ and R'$_3$ are independently or together H; alkyl or alkenyl optionally substituted with 1–3 halo, hydroxyl, thio, alkylthio, amino, alkylamino, dialkylamino, alkylguanidinyl, dialkylguanidinyl, guanidinyl, or amidylguanidine; —RCOR', —RCOOR', —RNR'R"R° or —RC(O)NR'R" where R is alkyl or alkenyl, and R', R" and R° are independently H, alkyl, alkenyl, cycloalkyl or (C$_5$–C$_6$)aryl; or cycloalkyl, alkylcycloalkyl, alkenylcycloalkyl, alkyl-oxyaryl, alkyl-thioaryl, alkyl-aminoaryl, (C$_5$–C$_{12}$)aryl, (C$_5$–C$_{12}$)arylalkyl or (C$_5$–C$_{12}$)arylalkenyl optionally comprising 1–4 heteroatoms selected from N, O and S, and optionally substituted with halo, cyano, keto, nitro, hydroxyl, haloalkyl, amino, aminoalkyl, dialkylamino, amidine, alkylamidine, dialkylamidine, alkyl, alkenyl, alkylenedioxy, alkynyl, alkoxy, haloalkoxy, carboxyl, carboalkoxy, alkylcarboxamide, ($C_5$–$C_6$)aryl, —O—($C_5$–$C_6$)aryl, arylcarboxamide, alkylthio or haloalkylthio;

$R_{13}$ is H, alkyl, halo, alkoxy, carboalkoxy, carboxyl, alkylthio, amino, alkylamino, dialkylamino, or aryl, arylalkyl, cycloalkyl, alkylcycloalkyl, fused aryl-cycloalkyl or alkyl fused aryl-cycloalkyl optionally comprising 1 or more heteroatoms selected from O, N and S, and optionally substituted with halo or alkyl;

$R_{14}$ is H, alkyl, alkenyl, amino, alkylamino, dialkylamino; or aryl, arylalkyl, cycloalkyl, alkylcycloalkyl, fused aryl-cycloalkyl, alkyl fused aryl-cycloalkyl or aryloxycarboxamide optionally comprising 1 or more heteroatoms selected from N, O and S, and optionally substituted with alkyl, halo, alkoxy, amino, alkylamino, dialkylamino, carboxyl, alkenyl, alkynyl, haloalkoxy, carboalkoxy, alkylcarboxamide, aryl, arylalkyl, arylcarboxamide, arylalkylcarboxamide, alkylthio or haloalkylthio;

$R_{15}$ is H, alkyl, halo, alkoxy, carboalkoxy, carboxyl, alkylthio, amino, alkylamino, dialkylamino, or aryl, arylalkyl, cycloalkyl, alkylcycloalkyl, fused aryl-cycloalkyl or alkyl fused aryl-cycloalkyl optionally comprising 1 or more heteroatoms selected from O, N and S; and W is O or S; or C or N optionally substituted with H, alkyl or aryl.

In a preferred embodiment, X is N and Y is O. In another preferred embodiment, X is O and Y is N. According to several preferred embodiments, $R_{13}$ is an optionally substituted phenyl or benzyl; pyridyl, piperidinyl, alkyl or H or a fused ring system such as 3,4-methylenedioxybenzyl; $R_{14}$ is optionally substituted amino or an arylalkyloxycarboxamide such as benzyloxycarboxamide; and $R_{15}$ is H or halo.

Preferably, $R_2$ is isopropyl and $R_3$ is H.

In a preferred embodiment of the invention, $R_1$ is an optionally substituted aryl or arylalkyl group, such as a α,α-dimethylbenzyl, benzyl or phenyl group. According to several preferred embodiments, the benzene ring is substituted with an alkyl, such as methyl; with a haloalkyl, such as trifluoromethyl; or with a dialkylamino, preferably dimethylamino. In yet another embodiment, $R_1$ is a fused arylalkyl group such as methylenenaphthyl; or a fused aryl-cycloalkyl or alkyl fused aryl-cycloalkyl such as 3,4-methylenedioxybenzyl. In another embodiment, $R_1$ is an alkyl group, preferably ($C_1$–$C_8$)alkyl, either straight chain or branched, such as methyl, ethyl, propyl, isopropyl, n-butyl, isobutyl, t-butyl, etc.

The present invention also provides compounds of the formula (Group III):

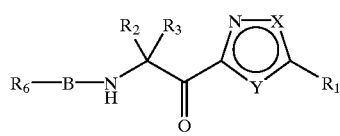

wherein X, Y, $R_1$, $R_2$, $R_3$ and B are as described above; and $R_6$ is of formula (I):

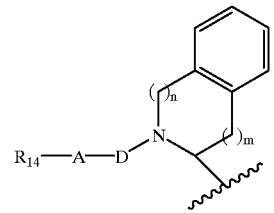

(I)

where m is 0 or 1; n is 0 or 1;

D is a direct bond or an amino acid selected from, but not limited to, proline, isoleucine, cyclohexylalanine, cysteine optionally substituted at the sulfur with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; phenylalanine, homophenylalanine, dehydrophenylalanine, indoline-2-carboxylic acid; tetrahydrosioquinoline-2-carboxylic acid optionally substituted with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; tryptophan, tyrosine, serine or threonine optionally substituted with alkyl or aryl; histidine methionine, valine, norvaline, norleucine, octahydroindole-2-carboxylic acid; asparagine, glutamine, ornithine and lysine optionally substituted at the side chain nitrogen with alkyl, alkenyl, alkynyl, alkoxyalkyl, alkylthioalkyl, alkylaminoalkyl, dialkylaminoalkyl, carboxyalkyl, alkoxycarbonyl alkyl or aryl, arylalkyl, cycloalkyl, alkylcycloalkyl, fused aryl-cycloalkyl or alkyl fused aryl-cycloalkyl optionally comprising 1 or more heteroatoms selected from N, O and S;

A is a direct bond, —C(O)—, —NH—C(O)—, —S(O)$_2$—, —OC(O)— or —C—; and $R_{14}$ is H, alkyl, alkenyl, amino, alkylamino or dialkylamino; or aryl, arylalkyl, cycloalkyl, alkylcycloalkyl, fused aryl-cycloalkyl or alkyl fused aryl-cycloalkyl optionally comprising 1 or more heteroatoms selected from N, O and S, and optionally substituted with alkyl, halo, alkoxy, amino, alkylamino, dialkylamino, carboxy, alkenyl, alkynyl, haloalkoxy, carboalkoxy, alkylcarboxamide, aryl, arylalkyl, arylcarboxamide, alkylthio or haloalkylthio.

Alternatively, $R_6$ is of formula (II):

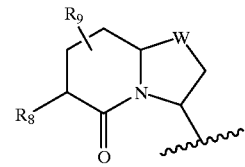

(II)

where
W is S or O;

$R_8$ is alkylamino, dialkylamino or amino;

$R_9$ is H, alkyl or halo.

In a preferred embodiment, X is N and Y is O. In another preferred embodiment, X is O and Y is N. According to one embodiment, where $R_6$ is of formula (I), m is 1, n is 0. In another embodiment, m and n are 1. Preferably, $R_{14}$ is benzyl, A is —OC(O)— and D is Val.

Preferably, $R_2$ is isopropyl and $R_3$ is H.

In a preferred embodiment of the invention, $R_1$ is an optionally substituted aryl or arylalkyl group, such as a α,α-dimethylbenzyl, benzyl or phenyl group. According to several preferred embodiments, the benzene ring is substituted with an alkyl, such as methyl; with a haloalkyl, such as trifluoromethyl; or with a dialkylamino, preferably dimethylamino. In yet another embodiment, $R_1$ is a fused arylalkyl group such as methylenenaphthyl; or a fused aryl-cycloalkyl or alkyl fused aryl-cycloalkyl such as 3,4-methylenedioxybenzyl. In another embodiment, $R_1$ is an alkyl group, preferably $(C_1-C_8)$alkyl, either straight chain or branched, such as methyl, ethyl, propyl, isopropyl, n-butyl, isobutyl, t-butyl, etc.

According to one embodiment, W is S; $R_8$ is amino and $R_9$ is H.

In yet a further embodiment of the invention of Group (III) compounds, $R_6$ is aryl, arylalkyl, cycloalkyl or alkylcycloalkyl. According to one embodiment, $R_6$-B is Cbz.

The present invention further provides compounds of the formula (Group IV):

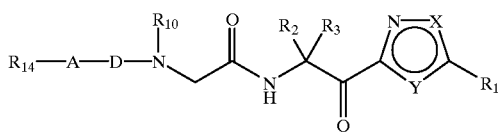

wherein

X, Y, $R_1$, $R_2$ and $R_3$ are as described above;

$R_{10}$ is $(C_5-C_6)$aryl, $(C_5-C_6)$arylalkyl, $(C_5-C_6)$arylalkenyl, cycloalkyl, fused aryl-cycloalkyl optionally comprising one or more heteroatoms selected from N, S and non-peroxide O, and optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamide, alkylthio or haloalkylthio;

D is a direct bond, —C(O)—, or an amino acid selected from, but not limited to, proline, isoleucine, cyclohexylalanine, cysteine optionally substituted at the sulfur with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; phenylalanine, homophenylalanine, dehydrophenylalanine, indoline-2-carboxylic acid; tetrahydrosioquinoline-2-carboxylic acid optionally substituted with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; tryptophan, tyrosine, serine or threonine optionally substituted with alkyl or aryl; histidine methionine, valine, norvaline, norleucine, octahydroindole-2-carboxylic acid; asparagine, glutamine, ornithine and lysine optionally substituted at the side chain nitrogen with alkyl, alkenyl, alkynyl, alkoxyalkyl, alkylthioalkyl, alkylaminoalkyl, dialkylaminoalkyl, carboxyalkyl, alkoxycarbonyl alkyl or aryl, arylalkyl, cycloalkyl, alkylcycloalkyl, fused aryl-cycloalkyl or alkyl fused aryl-cycloalkyl optionally comprising 1 or more heteroatoms selected from N, O and S;

A is a direct bond, —C(O)—, —NH—C(O)—, —S(O)$_2$—, —NH—S(O)$_2$—, —S(O)$_2$—NH—, —OC(O)NH—, —OC(O)— or —C—; and $R_{14}$ is as described above.

In a preferred embodiment, X is N and Y is O. In another preferred embodiment, X is O and Y is N. Preferably, D is Val, A is —OC(O)— and $R_{14}$ is aryl or arylalkyl such as benzyl. In a preferred embodiment, $R_{10}$ is $(C_5-C_6)$aryl or $(C_5-C_6)$arylalkyl, preferably benzyl, or a fused aryl-cycloalkyl such as an indanyl group. According to another preferred embodiment, D is —C(O)—, and $R_{14}$-A is pyrrole.

Preferably, $R_2$ is isopropyl and $R_3$ is H.

In a preferred embodiment of the invention, $R_1$ is an optionally substituted aryl or arylalkyl group, such as a α,α-dimethylbenzyl, benzyl or phenyl group. According to several preferred embodiments, the benzene ring is substituted with an alkyl, such as methyl; with a haloalkyl, such as trifluoromethyl; or with a dialkylamino, preferably dimethylamino. In yet another embodiment, $R_1$ is a fused arylalkyl group such as methylenenaphthyl; or a fused aryl-cycloalkyl or alkyl fused aryl-cycloalkyl such as 3,4-methylenedioxybenzyl. In another embodiment, $R_1$ is an alkyl group, preferably $(C_1-C_8)$alkyl, either straight chain or branched, such as methyl, ethyl, propyl, isopropyl, n-butyl, isobutyl, t-butyl, etc.

The present invention additionally provides compounds of the formula (Group V):

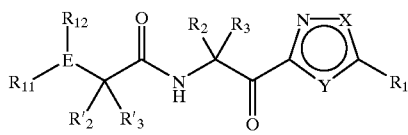

wherein

X, Y, $R_1$, $R_2$, $R_3$, $R'_2$ and $R'_3$ are as described above; and $R_{11}$, $R_{12}$ and E together form a monocyclic or bicyclic ring comprising 5–10 atoms selected from C, N, S and O; said ring containing 1 or more keto groups; and optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamido, alkylthio, haloalkylthio; cycloalkyl, alkylcycloalkyl, alkenylcycloalkyl, $(C_5-C_{12})$aryl, $(C_5-C_{12})$arylalkyl, $((C_5-C_{12})$arylalkyl$)$OC(O)NH— or $(C_5-C_{12})$arylalkenyl optionally comprising one or more heteroatoms selected from N, S and non-peroxide O, and optionally substituted with halo, cyano, nitro, haloalkyl, amino, aminoalkyl, dialkylamino, alkyl, alkenyl, alkynyl, alkoxy, haloalkoxy, carboxyl, carboalkoxy, —C(O)O(alkyl), —C(O)(alkyl), alkylcarboxamido, alkylthio or haloalkylthio.

In a preferred embodiment, X is N and Y is O. In another preferred embodiment, X is O and Y is N.

Preferably, $R_2$ is isopropyl and $R_3$ is H.

In a preferred embodiment of the invention, $R_1$ is an optionally substituted aryl or arylalkyl group, such as a α,α-dimethylbenzyl, benzyl or phenyl group. According to several preferred embodiments, the benzene ring is substituted with an alkyl, such as methyl; with a haloalkyl, such as trifluoromethyl; or with a dialkylamino, preferably dimethylamino. In yet another embodiment, $R_1$ is a fused arylalkyl group such as methylenenaphthyl; or a fused aryl-cycloalkyl or alkyl fused aryl-cycloalkyl such as 3,4-methylenedioxybenzyl. In another embodiment, $R_1$ is an alkyl group, preferably $(C_1-C_8)$alkyl, either straight chain or branched, such as methyl, ethyl, propyl, isopropyl, n-butyl, isobutyl, t-butyl, etc.

According to one embodiment of the invention, $R_{11}$, $R_{12}$, and E together form a ring structure of formulas (I) or (Ia):

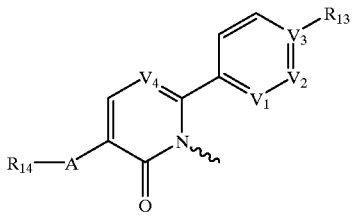

(I)

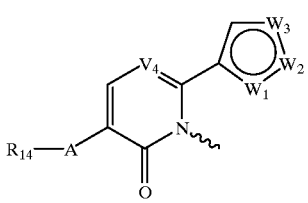

(Ia)

wherein A is as described above for Group (IV);

$V_1$, $V_2$, $V_3$ and $V_4$ are independently or together C or N;

where $V_3$ is C; $R_{13}$ is H, alkyl, halo, alkoxy, carboalkoxy, carboxyl, alkylthio, amino, alkylamino, dialkylamino; or aryl, arylalkyl, cycloalkyl, alkylcycloalkyl, fused aryl-cycloalkyl or alkyl fused aryl-cycloalkyl optionally comprising 1 or more heteroatoms selected from O, N and S, and optionally substituted with halo or alkyl;

$R_{14}$ is H, alkyl, alkenyl, amino, alkylamino or dialkylamino; or aryl, arylalkyl, cycloalkyl, alkylcycloalkyl, fused aryl-cycloalkyl or alkyl fused aryl-cycloalkyl, arylalkylxoxycarbonyl or arylalkylcarboxamide optionally comprising 1 or more heteratoms selected from N, O and S, and optionally substituted with alkyl, halo, alkoxy, amino, alkylamino, dialkylamino, carboxy, alkenyl, alkynyl, haloalkoxy, carboalkoxy, alkylcarboxamide, aryl, arylalkyl, arylcarboxamide, alkylthio or haloalkylthio; and $W_1$, $W_2$ and $W_3$ are independently selected from N optionally substituted with alkyl; C, S and O.

According to one preferred embodiment, $V_4$ is N; and $V_1$, $V_2$ and $V_3$ are C. Preferably, $R_{13}$ is H or halo; $R_{14}$-A is CbzNH, amino or H; and $R'_2$ and $R'_3$ are H. Preferably, $R_{11}$, $R_{12}$ and E together form a ring of formula (I). In a particular embodiment, $R_{13}$ is H or F; and $R_{14}$-A— is H or $H_2N$—. Where $R_{11}$, $R_{12}$ and E together form a ring of formula (Ia), $W_1$ is preferably S, and $W_2$ and $W_3$ are C.

In another embodiment, $R_{11}$, $R_{12}$ and E together form a ring of formula (II)

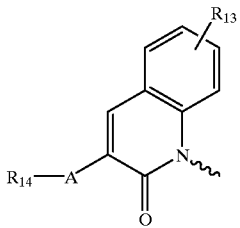

(II)

wherein A, $R_{13}$ and $R_{14}$ are as described above;

Preferably, $R'_2$ and $R'_3$ are H. According to one embodiment, $R_{13}$ is 1-piperidinyl; and $R_{14}$-A is CbzNH. Alternatively, $R_{13}$ is H; and $R_{14}$-A is amino, alkylamino or dialkylamino. In another preferred embodiment, $R_{13}$ is halo; and $R_{14}$-A is $CH_3$—O—C(O)—. In yet another embodiment, $R_{13}$ is H; and $R_{14}$-A is CbzNH.

According to another embodiment of the invention, $R_{11}$, $R_{12}$ and E form a ring of formula (III) or (IV):

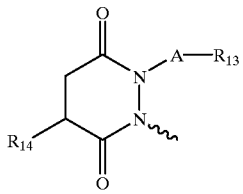

(III)

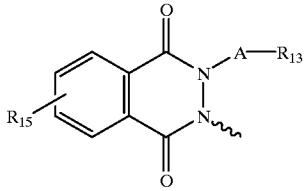

(IV)

wherein
A is a direct bond, —C— or —C(O)—;
$R_{13}$, $R_{14}$ and $R_{15}$ are as defined above.

According to a particular embodiment, $R_{11}$, $R_{12}$ and E form a ring of formula (III); and —A—$R_{13}$ is —C(O)phenyl; $R_{14}$ is H; and $R'_2$ and $R'_3$ are H.

In another embodiment, $R_{11}$, $R_{12}$ and E form a ring of formula (IV); and —A—$R_{13}$ is —C(O)phenyl; $R_{15}$ is H; and $R'_2$ and $R'_3$ and H.

In another embodiment of the invention, $R_{11}$, $R_{12}$ and E form a ring of formula (V):

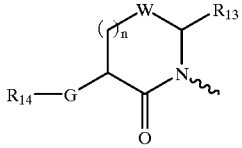

(V)

wherein
W is S, SO, $SO_2$ or C;
n is 0, 1 or 2;
$R_{13}$ and $R_{14}$ are defined above; and
G is —NHC(O)—, —OC(O)NH—, —C(O)—, —NHS$(O)_2$— or a direct bond.

According to one embodiment, n is 0 and W is S, where preferably $R_{14}$—G is H. Preferably, $R_{13}$ is optionally substituted benzyl or phenyl.

In another embodiment, n is 1 and W is C. Preferably, $R_{14}$–G is an arylalkyloxycarboxamide, for example, CbzNH—. In a preferred embodiment, $R_{13}$ is H or phenyl substituted with halo. Preferably, $R'_2$ and $R'_3$ are H.

The invention further provides compounds wherein $R_{11}$, $R_{12}$ and E form a ring of formulas (VI), (VIa), (VII) or (VIII):

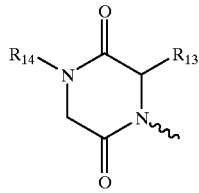

(VI)

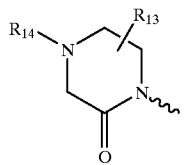

(VIa)

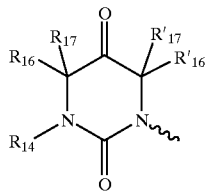

(VII)

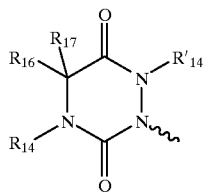

(VIII)

wherein $R_{13}$ is as defined above, or is =CHR$_{15}$ or R$_{15}$ where R$_{15}$ is pyridinyl, phenyl or benzyl optionally substituted with halo, dialkylamino or —C(O)OCH$_3$;

$R_{14}$ and $R'_{14}$ are independently or together H, alkyl, alkenyl, CH$_3$C(O)—; or aryl, arylalkyl, cycloalkyl, alkylcycloalkyl, fused aryl-cycloalkyl or alkyl fused aryl-cycloalkyl, aryloxycarbonyl or arylalkyloxycarbonyl optionally comprising 1 or more heteratoms selected from N, O and S, and optionally substituted with alkyl, halo, alkoxy, amino, alkylamino, dialkylamino, carboxy, alkenyl, alkynyl, haloalkoxy, carboalkoxy, alkylcarboxamide, aryl, arylalkyl, arylcarboxamide, alkylthio or haloalkylthio; and $R_{16}$, $R_{17}$, $R'_{16}$ and $R'_{17}$ are independently or together H, alkyl, alkenyl, alkylthio, alkylthioalkyl; or cycloalkyl, cycloalkenyl, alkylcycloalkyl, aryl, arylalkyl or arylalkenyl optionally substituted with guanidine, carboalkoxy, hydroxyl, haloalkyl, alkylthio, alkylguanidine, dialkylguanidine or amidine.

Preferred compounds are of formula (VI) or (VIa) where $R_{13}$ is =CHR$_{15}$ or R$_{15}$; and $R_{14}$ is H, alkyl, CH$_3$C(O)—, Cbz or benzyl optionally substituted with alkyl, halo or alkylamino; or 3,4-methylenedioxybenzyl or 3,4-ethylenedioxybenzyl; and $R'_2$ and $R'_3$ are H. Preferably, $R_{13}$ is =CHR$_{15}$ where $R_{15}$ is phenyl or benzyl optionally substituted with halo or —C(O)CH$_3$.

In a further embodiment, $R_{11}$, $R_{12}$ and E form a ring of formula (IX) or (IXa):

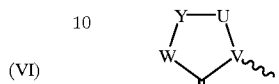

(IX)

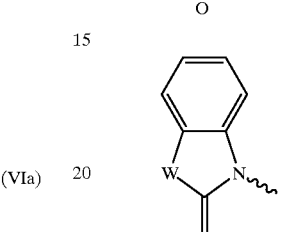

(IXa)

wherein

U, V, W and Y are independently or together N, C, C(O), N(R$_{13}$) where R$_{13}$ is H, alkyl, halo, alkoxy, carboalkoxy, carboxyl, alkylthio, amino, alkylamino, dialkylamino; or aryl, arylalkyl, cycloalkyl, alkylcycloalkyl, fused aryl-cycloalkyl or alkyl fused aryl-cycloalkyl optionally comprising 1 or more heteroatoms selected from O, N and S, and optionally substituted with halo or alkyl; N(R$_{14}$) where R$_{14}$ is H, alkyl, alkenyl, or aryl, arylalkyl, cycloalkyl, alkylcycloalkyl, fused aryl-cycloalkyl or alkyl fused aryl-cycloalkyl optionally comprising 1 or more heteratoms selected from N, O and S, and optionally substituted with alkyl, halo, alkoxy, amino, alkylamino, dialkylamino, carboxy, alkenyl, alkynyl, haloalkoxy, carboalkoxy, alkylcarboxamide, aryl, arylalkyl, arylcarboxamide, alkylthio or haloalkylthio; or C(R$_{16}$)(R$_{17}$) where R$_{16}$ and R$_{17}$ are independently or together H, alkyl, alkylthio, alkylthioalkyl; a carboxylic acid ester of the formula —(CH$_2$)$_m$C(O)OR or an N-substituted alkylamide of the formula —(CH$_2$)$_m$C(O)NRR' where m is 1 to 6 and R and R' are independently or together H or alkyl; or aryl, arylalkyl, cycloalkyl, alkylcycloalkyl, fused aryl-cycloalkyl or alkyl fused aryl-cycloalkyl optionally comprising one or more heteroatoms selected from N, S and non-peroxide O and optionally substituted with amino, alkylamino, dialkylamino, guanidine, carboalkoxy, keto, hydroxyl, alkyl, haloalkyl, alkylthio, alkylguanidine, dialkylguanidine or amidine; or together form a cyclic ring structure comprising 4–8 atoms selected from C, N, O and S.

In one preferred embodiment, U is C(R$_{16}$)(R$_{17}$), V is N, W is N(R$_{14}$) and Y is C(O), where preferably R'$_2$ and R'$_3$ are H; R$_{16}$ is phenyl or benzyl; R$_{17}$ is H; and R$_{14}$ is H or benzyl optionally substituted with alkyl, halo, or alkylamine.

In another preferred embodiment, U is C(O); V is N, W is N, N(R$_{13}$) or N(R$_{14}$); and Y is C(R$_{16}$)(R$_{17}$), where preferably R'$_2$ and R'$_3$ are H; R$_{14}$ is H; R$_{16}$ is H, alkyl, optionally substituted aryl or arylalkyl, preferably benzyl or phenyl optionally substituted with dialkylamino or hydroxyl; pyridinyl, methylene pyridinyl; fused aryl such as an indolyl; or a carboxylic acid ester or N-substituted alkyl amide, as defined above; and $R_{17}$ is H, alkyl, succinimidyl, aryl or arylalkyl.

In yet another preferred embodiment, U is C(O), V is N, W is N, N($R_{13}$) or N($R_{14}$); and Y is N($R_{13}$), where preferably $R'_2$ and $R'_3$ are H; W is NH; $R_{13}$ is arylalkyl; and $R_{14}$ is H.

In a further embodiment, U is C($R_{16}$)($R_{17}$); V is N; W is N or N($R_{13}$); and Y is C(O). Preferably, $R_{13}$ and $R_{16}$ are aryl; and $R_{17}$ is H.

Where $R_{11}$, $R_{12}$ and E form a ring of formula (IXa); W is typically N($R_{13}$) where $R_{13}$ is aryl or cycloalkyl such as piperidinyl.

In another embodiment, $R_{16}$ and $R_{17}$ form a cyclic ring structure, such as a cyclopentyl or cyclohexyl group.

The invention further provides compounds of the formula (Group VI):

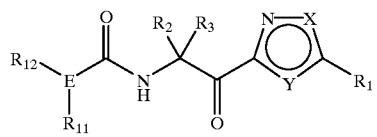

wherein X, Y, $R_1$, $R_2$ and $R_3$ are as described above, and $R_{11}$, $R_{12}$ and E together form a ring of formula (X):

(X)

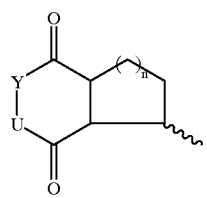

where U and V are independently or together N, C, N($R_{13}$) where $R_{13}$ is H, alkyl, alkoxy, carboalkoxy, carboxyl, alkylthio, amino, alkylamino, dialkylamino; or aryl, arylalkyl, cycloalkyl, alkylcycloalkyl, fused aryl-cycloalkyl or alkyl fused aryl-cycloalkyl optionally comprising 1 or more heteroatoms selected from O, N and S; or C($R_{16}$)($R_{17}$) where $R_{16}$ and $R_{17}$ are as defined above; and and n is 1 or 2.

The present invention further provides methods of synthesizing compounds of formula (A):

(A)

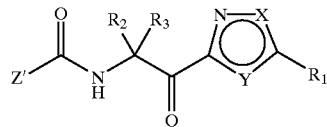

wherein
Z' is defined below;
$R_1$ is alkyl or alkenyl optionally substituted with 1–3 halo or hydroxyl; -alkyl—C(O)OCH$_3$; alkylamino, dialkylamino, alkyldialkylamino; or cycloalkyl, alkylcycloalkyl, alkenylcycloalkyl, ($C_5$–$C_{12}$)aryl, ($C_5$–$C_{12}$)arylalkyl, ($C_5$–$C_{12}$)arylalkenyl, fused ($C_5$–$C_{12}$)aryl-cycloalkyl or fused ($C_5$–$C_{12}$)aryl-cyclalkylalkyl optionally comprising 1–4 heteroatoms selected from N, O and S, and optionally substituted with halo, cyano, nitro, hydroxyl, haloalkyl, amino, aminoalkyl, dialkylamino, alkyl, alkenyl, alkylenedioxy, alkynyl, alkoxy, haloalkoxy, carboxyl, carboalkoxy, alkylcarboxamide, ($C_5$–$C_6$)aryl, —O—($C_5$–$C_6$)aryl, arylcarboxamide, alkylthio or haloalkylthio;

X and Y are independently O, S or N, wherein N is optionally substituted with alkyl or alkenyl optionally substituted with 1–3 halo atoms; ($C_5$–$C_6$)aryl, arylalkyl or arylalkenyl optionally comprising 1–3 heteroatoms selected from N, O and S, and optionally substituted with halo, cyano, nitro, hydroxyl, haloalkyl, amino, aminoalkyl, dialkylamino, alkyl, alkenyl, alkynyl, alkoxy, haloalkoxy, carboxyl, carboalkoxy, alkylcarboxamide, arylcarboxamide, alkylthio or haloalkylthio; and $R_2$ and $R_3$ are independently or together H; alkyl or alkenyl optionally substituted with 1–3 halo, hydroxyl, thio, alkylthio, amino, alkylamino, dialkylamino, alkylguanidinyl, dialkylguanidinyl, guanidinyl, or amidylguanidine; —RCOR', —RCOOR', —RNR'R"R° or —RC(O)NR'R" where R is alkyl or alkenyl, and R', R" and R° are independently H, alkyl, alkenyl, cycloalkyl or ($C_5$–$C_6$)aryl; or cycloalkyl, alkylcycloalkyl, alkenylcycloalkyl, alkyl-oxyaryl, alkyl-thioaryl, alkyl-aminoaryl, ($C_5$–$C_{12}$)aryl, ($C_5$–$C_{12}$)arylalkyl or ($C_5$–$C_{12}$)arylalkenyl optionally comprising 1–4 heteroatoms selected from N, O and S, and optionally substituted with halo, cyano, keto, nitro, hydroxyl, haloalkyl, amino, aminoalkyl, dialkylamino, amidine, alkylamidine, dialkylamidine, alkyl, alkenyl, alkylenedioxy, alkynyl, alkoxy, haloalkoxy, carboxyl, carboalkoxy, alkylcarboxamide, ($C_5$–$C_6$)aryl, —O—($C_5$–$C_6$)aryl, arylcarboxamide, alkylthio or haloalkylthio;

comprising the steps of:
(a) reacting a compound of formula (B):

(B)

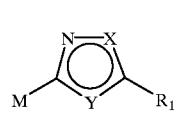

wherein M is Li or MgBr,
with an aldehyde of formula (C):

(C)

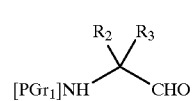

where [PrG$_1$] is a protecting group;
(b) removing the protecting group from the resulting alcohol (D)
(c) coupling the alcohol obtained from step (b) with an acid of formula (E):

Z'—COOH (E)

and
(d) oxidizing the resulting product and further, if desired, removing the protecting group to yield the final compound.

According to one embodiment, the protecting group [PGR$_1$] is removed from alcohol (D) by reacting the aldehyde of formula (C) with hydrochloric acid in dioxane. The protecting group [PGr$_1$] may be any suitable group, preferably Boc.

According to another embodiment, the oxidation step of (d) is performed using Dess Martin reagent.

In a further embodiment, the compound of formula (B) is synthesized by:

(e) treating an acid of the formula (R₁)COOH with thionyl chloride or oxalyl chloride;

(f) treating the resulting acid chloride with hydrazine to yield a hydrazide of the formula (R₁)CONHNH₂;

(g) reacting the hydrazide with triethyl orthoformate or trimethyl orthoformate and TsOH to yield a oxadiazole of the formula (F):

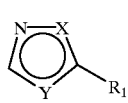

(F)

and (h) treating the oxadiazole with butyllithium and further, is desired, reacting with MgBr.OEt₂ to yield the compound B.

In one embodiment, Z' is

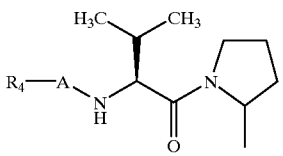

wherein

A is a direct bond, —C(O)—, —NH—C(O)—, —S(O)₂—, —NH—S(O)₂—, —OC(O)—, —C— or an amino acid selected from proline, isoleucine, cyclohexylalanine, cysteine optionally substituted at the sulfur with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; phenylalanine, homo-phenylalanine, dehydrophenylalanine, indoline-2-carboxylic acid; tetrahydrosioquinoline-2-carboxylic acid optionally substituted with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; tryptophan, tyrosine, serine or threonine optionally substituted with alkyl or aryl; histidine, methionine, valine, norvaline, norleucine, octahydroindole-2-carboxylic acid; asparagine, glutamine, omithine and lysine optionally substituted at the side chain nitrogen with alkyl, alkenyl, alkynyl, alkoxyalkyl, alkylthioalkyl, alkylaminoalkyl, dialkylaminoalkyl, carboxyalkyl, alkoxycarbonyl alkyl or aryl, arylalkyl, cycloalkyl, alkylcycloalkyl, fused aryl-cycloalkyl or alkyl fused aryl-cycloalkyl optionally comprising 1 or more heteroatoms selected from N, O and S; and R₄ is H, alkyl, alkenyl, or alkynyl; or cycloalkyl, alkylcycloalkyl, (C₅–C₁₂)aryl, (C₅–C₁₂)arylalkyl, fused (C₅–C₁₂)aryl-cycloalkyl or fused (C₅–C₁₂)aryl-cycloalkylalkyl optionally comprising one or more heteroatoms selected from N, O and S, and optionally substituted with alkyl, alkenyl, alkynyl, halo, cyano, nitro, hydroxyl, haloalkyl, alkoxy, amino, alkylamino, dialkylamino, carboxyl, haloalkoxy, carboalkoxy, alkylcarboxamide, aryl, arylalkyl, arylcarboxamido, alkylthio or haloalkylthio or is absent; or Z' may be

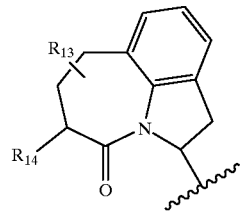

(I)

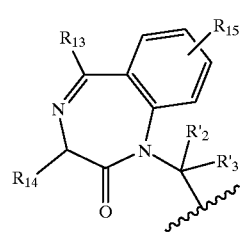

(II)

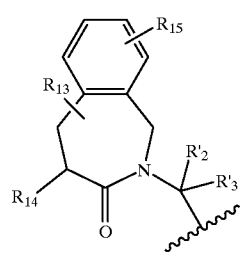

(III)

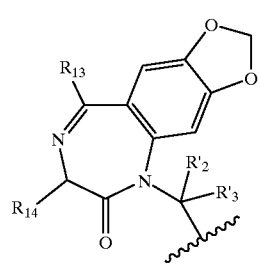

(IV)

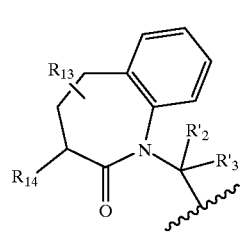

(V)

or

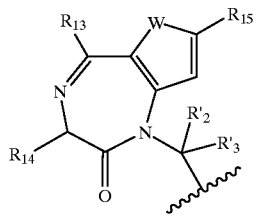
(VI)

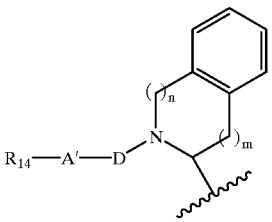
(I)

wherein

R'₂ and R'₃ are independently or together H; alkyl or alkenyl optionally substituted with 1–3 halo, hydroxyl, thio, alkylthio, amino, alkylamino, dialkylamino, alkylguanidinyl, dialkylguanidinyl, guanidinyl or amidylguanidine; —RCOR', —RCOOR', —RNR'R"R° or —RC(O)NR'R" where R is alkyl or alkenyl, and R', R" and R° are independently H, alkyl, alkenyl, cycloalkyl or ($C_5$–$C_6$) aryl; or cycloalkyl, alkylcycloalkyl, alkenylcycloalkyl, alkyl-oxyaryl, alkyl-thioaryl, alkyl-aminoaryl, ($C_5$–$C_{12}$)aryl, ($C_5$–$C_{12}$)arylalkyl or ($C_5$–$C_{12}$)arylalkenyl optionally comprising 1–4 heteroatoms selected from N, O and S, and optionally substituted with halo, cyano, keto, nitro, hydroxyl, haloalkyl, amino, aminoalkyl, dialkylamino, amidine, alkylamidine, dialkylamidine, alkyl, alkenyl, alkylenedioxy, alkynyl, alkoxy, haloalkoxy, carboxyl, carboalkoxy, alkylcarboxamide, ($C_5$–$C_6$) aryl, —O—($C_5$–$C_6$)aryl, arylcarboxamide, alkylthio or haloalkylthio;

$R_{13}$ is H, alkyl, halo, alkoxy, carboalkoxy, carboxyl, alkylthio, amino, alkylamino, dialkylamino, or aryl, arylalkyl, cycloalkyl, alkylcycloalkyl, fused aryl-cycloalkyl or alkyl fused aryl-cycloalkyl optionally comprising 1 or more heteroatoms selected from O, N and S, and optionally substituted with halo or alkyl;

$R_{14}$ is H, alkyl, alkenyl, amino, alkylamino, dialkylamino; or aryl, arylalkyl, cycloalkyl, alkylcycloalkyl, fused aryl-cycloalkyl, alkyl fused aryl-cycloalkyl or aryloxycarboxamide optionally comprising 1 or more heteroatoms selected from N, O and S, and optionally substituted with alkyl, halo, alkoxy, amino, alkylamino, dialkylamino, carboxyl, alkenyl, alkynyl, haloalkoxy, carboalkoxy, alkylcarboxamide, aryl, arylalkyl, arylcarboxamide, arylalkylcarboxamide, alkylthio or haloalkylthio; and $R_{15}$ is H, alkyl, halo, alkoxy, carboalkoxy, carboxyl, alkylthio, amino, alkylamino, dialkylamino; or aryl, arylalkyl, cycloalkyl, alkylcycloalkyl, fused aryl-cycloalkyl or alkyl fused aryl-cycloalkyl optionally comprising 1 or more heteroatoms selected from O, N and S.

In yet a further embodiment, Z' is:

where m is 0 or 1; n is 0 or 1;

D is a direct bond or an amino acid selected from proline, isoleucine, cyclohexylalanine, cysteine optionally substituted at the sulfur with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; phenylalanine, homo-phenylalanine, dehydrophenylalanine, indoline-2-carboxylic acid; tetrahydrosioquinoline-2-carboxylic acid optionally substituted with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; tryptophan, tyrosine, serine or threonine optionally substituted with alkyl or aryl; histidine methionine, valine, norvaline, norleucine, octahydroindole-2-carboxylic acid; asparagine, glutamine, ornithine and lysine optionally substituted at the side chain nitrogen with alkyl, alkenyl, alkynyl, alkoxyalkyl, alkylthioalkyl, alkylaminoalkyl, dialkylaminoalkyl, carboxyalkyl, alkoxycarbonyl alkyl or aryl, arylalkyl, cycloalkyl, alkylcycloalkyl, fused aryl-cycloalkyl or alkyl fused aryl-cycloalkyl optionally comprising 1 or more heteroatoms selected from N, O and S; and A' is a direct bond, —C(O)—, —NH—C(O)—, —S(O)₂—, —NH—S(O)₂—, —OC(O)— or —C—.

In yet another embodiment, Z' is:

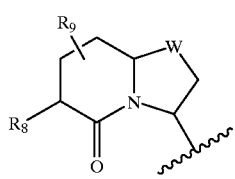
(II)

where
W is S or O;
$R_8$ is alkylamino, dialkylamino or amino; and
$R_9$ is H, alkyl or halo; or
Z' is:

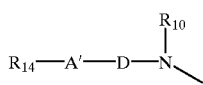

wherein
R$_{10}$ is (C$_5$–C$_6$)aryl, (C$_5$–C$_6$)arylalkyl, (C$_5$-C$_6$) arylalkenyl, cycloalkyl, alkylcycloalkyl, fused aryl-cycloalkyl or alkyl fused aryl-cycloalkyl optionally comprising one or more heteroatoms selected from N, S and non-peroxide O, and optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamide, alkylthio or haloalkylthio.

In a preferred embodiment, Z' is:

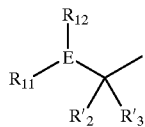

wherein
R$_{11}$, R$_{12}$ and E together form a monocyclic or bicyclic ring comprising 5–10 atoms selected from C, N, S and O; said ring containing 1 or more keto groups; and optionally substituted with halo, cyano, nitro, haloalkyl, amino, aminoalkyl, dialkylamino, alkyl, alkenyl, alkynyl, alkoxy, haloalkoxy, carboxyl, carboalkoxy, alkylcarboxamide, alkylthio, haloalkylthio or cycloalkyl, alkylcycloalkyl, alkenylcycloalkyl, (C$_5$–C$_{12}$)aryl, (C$_5$–C$_{12}$)arylalkyl, ((C$_5$–C$_{12}$)arylalkyl)OC(O)NH— or (C$_5$–C$_{12}$)arylalkenyl optionally comprising one or more heteroatoms selected from N, S and non-peroxide O, and optionally substituted with halo, cyano, nitro, haloalkyl, amino, aminoalkyl, dialkylamino, alkyl, alkenyl, alkynyl, alkoxy, haloalkoxy, carboxyl, carboalkoxy, —C(O)O(alkyl), —C(O)(alkyl), alkylcarboxamide, alkylthio or haloalkylthio.

In a preferred embodiment, the invention provides a method of synthesizing a compound of formula (G):

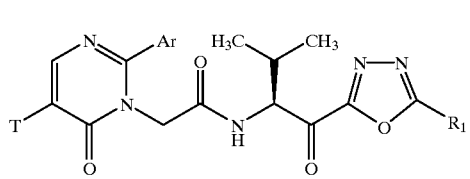

wherein
T is H or NH$_2$;
R$_1$ is alkyl or alkenyl optionally substituted with 1–3 halo or hydroxyl; a carboxylic acid ester such as -alkyl—C(O)OCH$_3$; alkylamino, dialkylamino, alkyldialkylamino; or cycloalkyl, alkylcycloalkyl, alkenylcycloalkyl, (C$_5$–C$_{12}$)aryl, (C$_5$–C$_{12}$)arylalkyl, (C$_5$–C$_{12}$)arylalkenyl, fused (C$_5$–C$_{12}$)aryl-cycloalkyl or fused (C$_5$–C$_{12}$)aryl-cyclalkylalkyl optionally comprising 1–4 heteroatoms selected from N, O and S, and optionally substituted with halo, cyano, nitro, hydroxyl, haloalkyl, amino, aminoalkyl, dialkylamino, alkyl, alkenyl, alkylenedioxy, alkynyl, alkoxy, haloalkoxy, carboxyl, carboalkoxy, alkylcarboxamide, (C$_5$–C$_6$)aryl, —O—(C$_5$–C$_6$)aryl, arylcarboxamide, alkylthio or haloalkylthio; and
Ar is an aryl or arylalkyl optionally substituted with H, alkyl, amino, alkylamino, dialkylamino, halo or hydroxyl;

comprising the steps of:
(a) reacting a compound of formula (B):

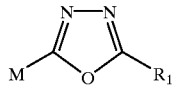

wherein M is Li or MgBr;
with an aldehyde of formula (C):

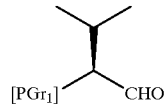

where [PrG$_1$] is a protecting group;
(b) removing the protecting group from the resulting alcohol (D)
(c) coupling the alcohol obtained from step (b) with an acid of formula (H):

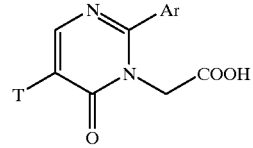

wherein T' is H or [PGr$_2$]NH, where [PGr$_2$] is a protecting group;
(d) oxidizing the resulting product to yield a ketone of formula (J):

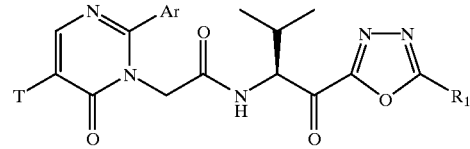

and further, when T' is [PGr$_2$]NH,
(e) removing the protecting group [PGr$_2$] to yield the compound of formula (G). Preferably, [PGr$_2$] is Cbz.

As used herein, the term "optionally substituted" means, when substituted, mono to fully substituted.

As used herein, the term "independently" means that the substituents may be the same or different.

As used herein, the term "alkyl" means C$_1$–C$_{15}$, however, preferably C$_1$–C$_8$.

As used herein, the term "alkenyl" means C$_1$–C$_{15}$, however, preferably C$_1$–C$_8$.

As used herein, the term "alkynyl" means C$_1$–C$_{15}$, however, preferably C$_1$–C$_8$.

It will be understood that alkyl, alkenyl and alkynyl groups, whether substituted or unsubstituted, may be linear or branched.

As used herein, the term "aryl," unless otherwise stated, means aryl groups preferably comprising 5 to 12 carbons, and more preferably 5 to 6 carbons. Unless otherwise indicated, the term includes both mono- and bi-cyclic fused ring systems. As used herein, where the term "arylalkyl" is defined by the general formula ($C_x$—$C_y$)arylalkyl, x and y refer to the number of carbons making up the aryl group. The alkyl group is as defined above. The term include mono-substituted alkyl groups (e.g., benzyl), as well as di-substituted alkyl groups such as -alkyl(aryl)$_2$ (e.g., —CH(phenyl)$_2$). The terms arylalkyl and alkyl fused arylcycloalkyl include ($\alpha,\alpha$)-disubstituted groups such as, for example, ($\alpha,\alpha$)-disubstituted benzyl and ($\alpha,\alpha$)-disubstituted 3,4-methylenedioxybenzyl groups, wherein the a substituents are preferably alkyl groups such as methyl, ethyl or propyl. Specific examples include ($\alpha,\alpha$)-dimethylbenzyl and ($\alpha,\alpha$)-dimethyl-3,4-methylenedioxybenzyl.

As used herein, the term "arylalkenyl" includes aryl groups where the alkenyl group comprises 1–3 or more double bonds. Exemplary arylalkenyl groups include =CH—CH$_2$-aryl and —CH=CH-aryl, where aryl is preferably phenyl.

As used herein, the term "cycloalkyl," unless otherwise stated, means cycloalkyl groups preferably comprising 3 to 12 carbons, and more preferably 3 to 6 carbons. Unless otherwise indicated, the term includes both mono-, bi- and tri-cyclic fused ring systems.

As used herein, the term "Cbz" means benzyloxycarbonyl.

As used herein, the term "carboxamide" is synonymous with amide; i.e., a group of the formula —NHC(O)—.

As used herein, the term "oxycarboxamide" means a group of the formula —O—C(O)NH—.

As used herein, the term "oxycarbonyl" means a group of the formula —OC(O)—.

Pharmaceutically acceptable salts of the compounds described above are within the scope of the invention.

DETAILED DESCRIPTION

Figure 1:
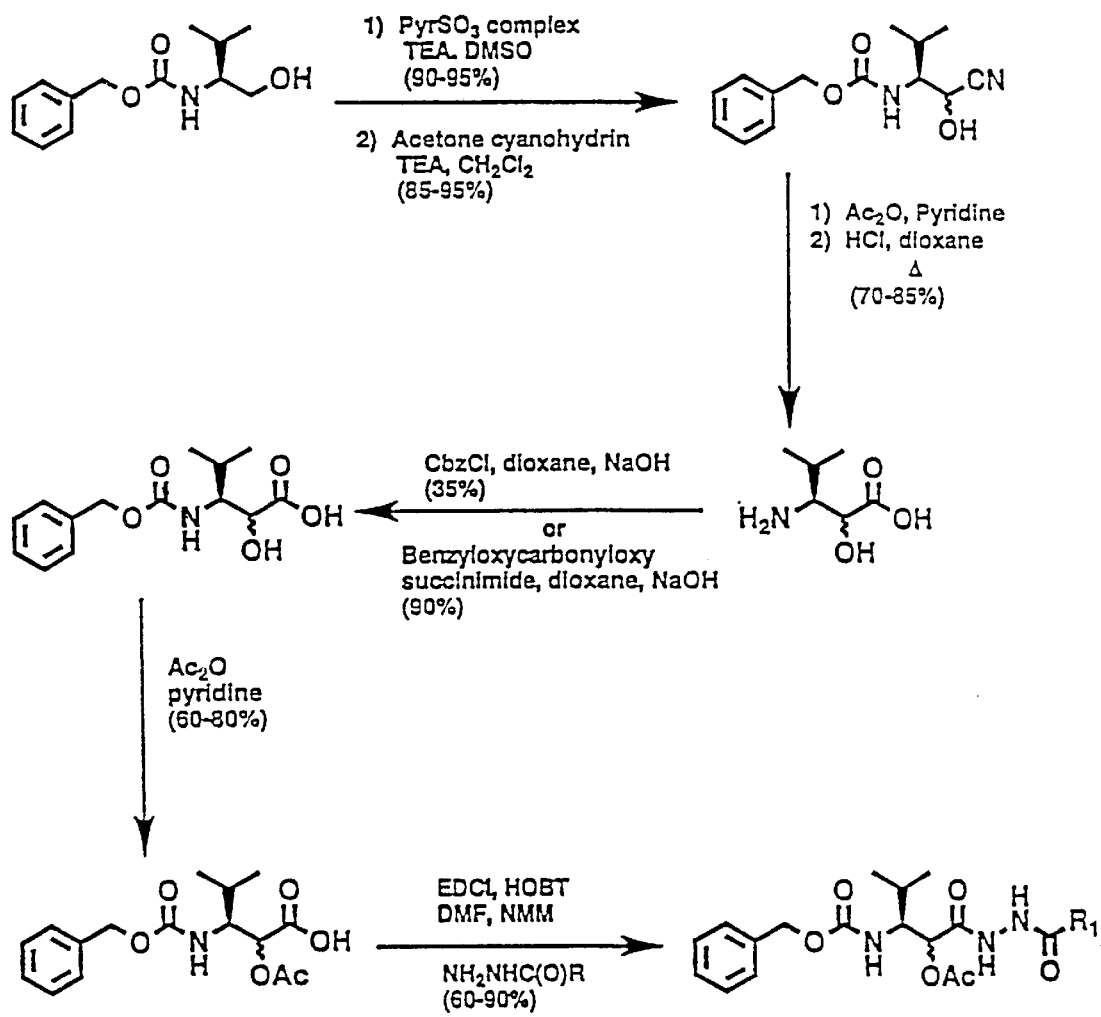
FIG. 1 is a schematic representation of the synthesis of compounds of Group I.
Figure 1:
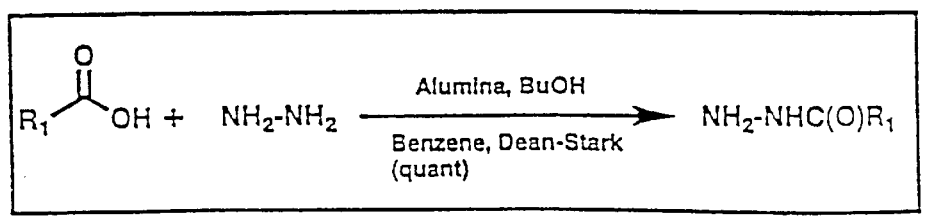

The compounds of the present invention have been found to be potent inhibitors of the serine protease human neutrophil elastase (HNE). They are reversible inhibitors that presumably form a transition state intermediate with the active site serine residue. The compounds are characterized by their low molecular weights, high selectivity with respect to HNE and stability regarding physiological conditions. Therefore, the compounds can be implemented to prevent, alleviate and/or otherwise treat diseases which are mediated by the degradative effects associated with the presence of HNE. Their usage is of particular importance as they relate to various human treatment in vivo but may also be used as a diagnostic tool in vitro.

The present invention provides, but is not limited to, specific embodiments set forth in the Examples as well as those set forth below.

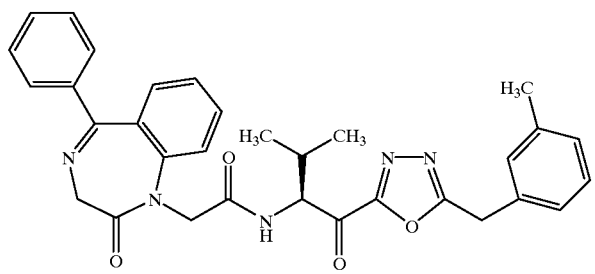
CE-2157
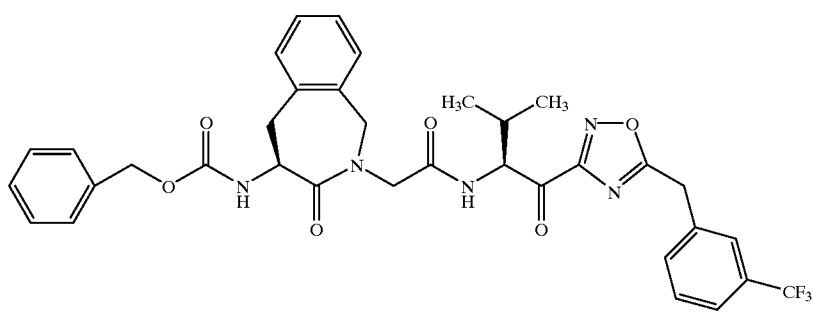
CE-2158
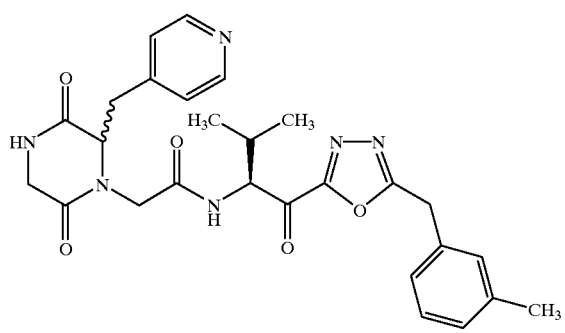
CE-2159
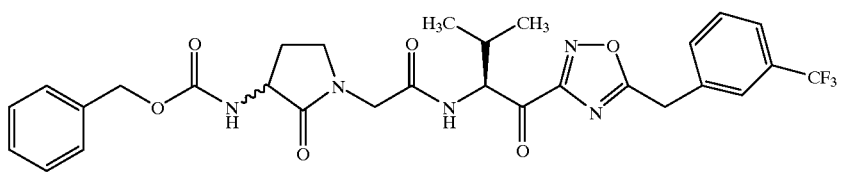
CE-2160
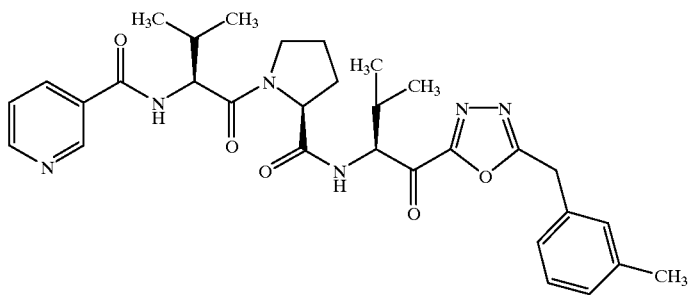
CE-2161

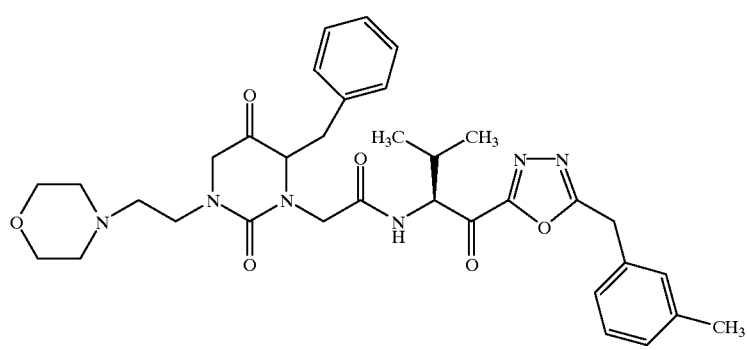
CE-2162
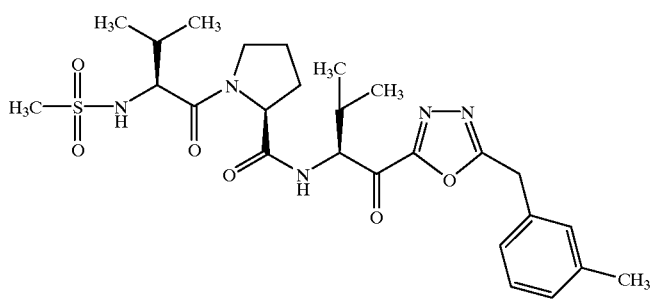
CE-2163
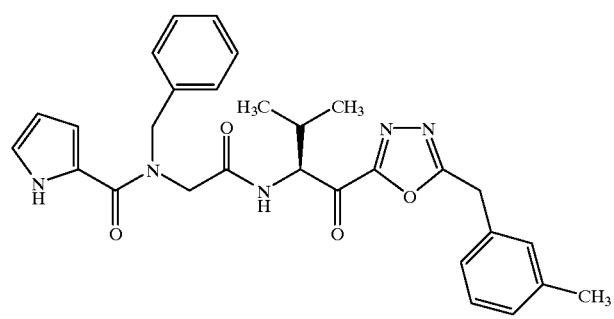
CE-2164
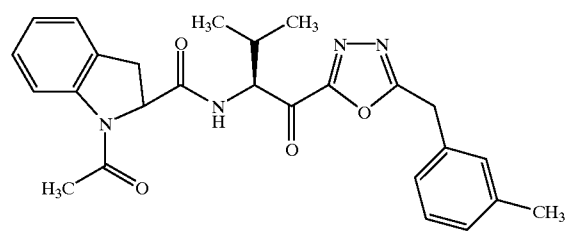
CE-2165
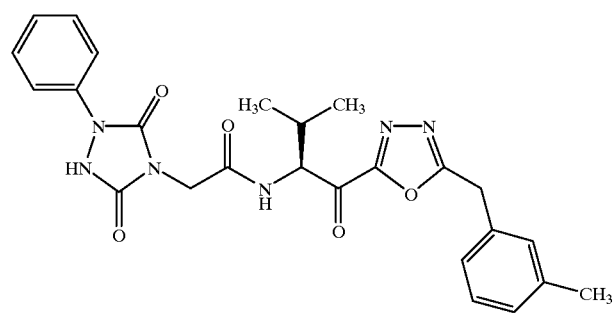
CE-2166

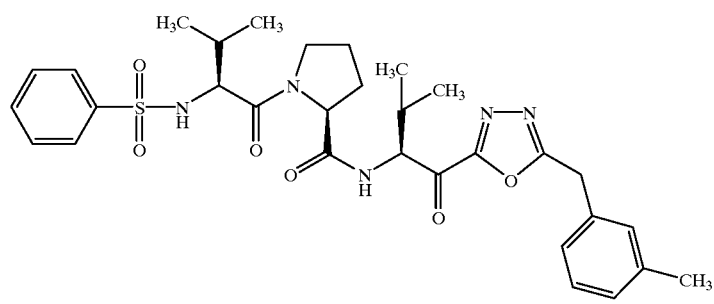
CE-2168
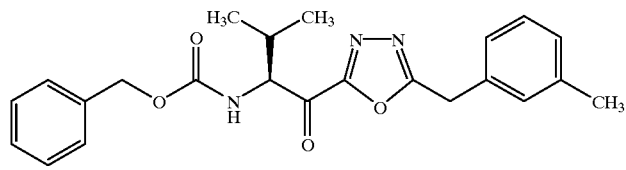
CE-2170
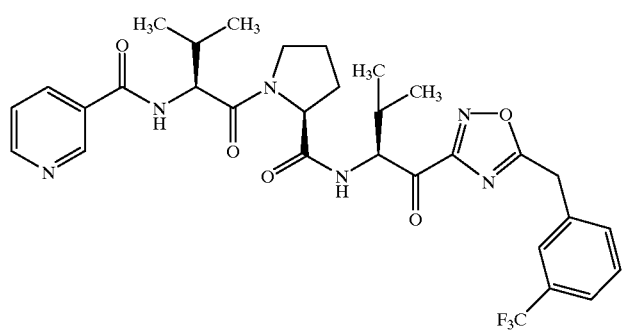
CE-2171
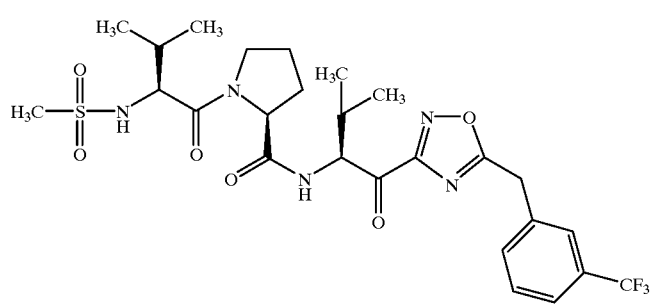
CE-2172
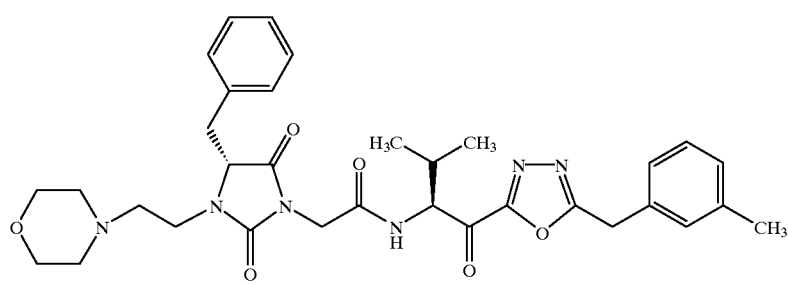
CE-2173

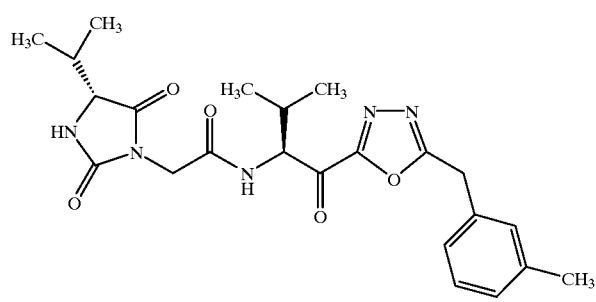
CE-2174
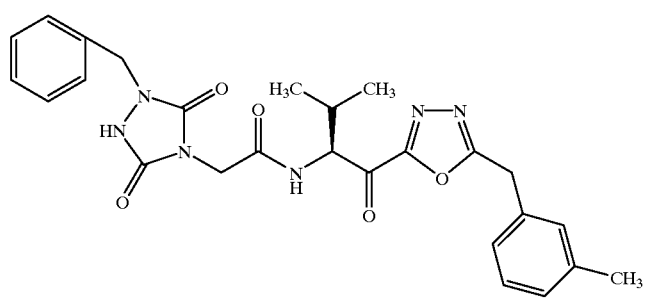
CE-2176
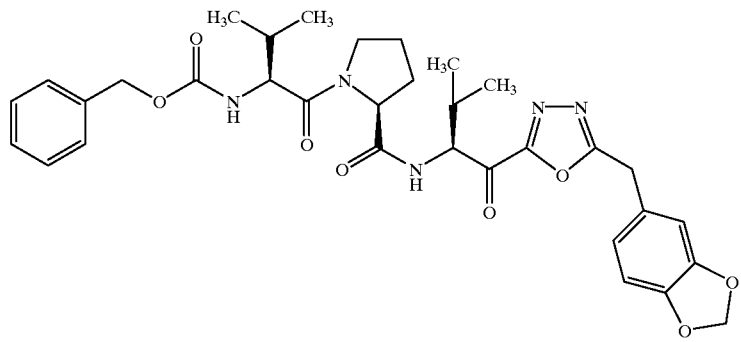
CE-2177
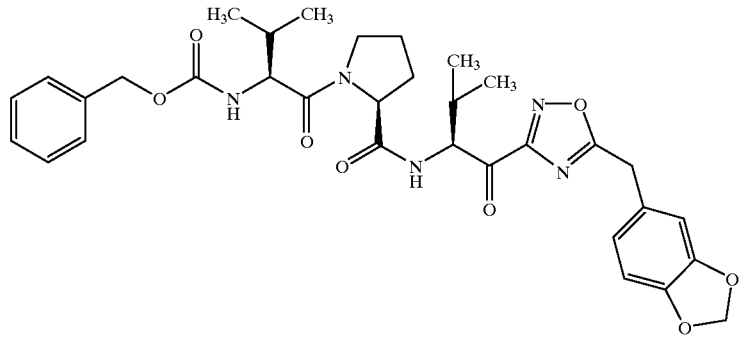
CE-2178

-continued
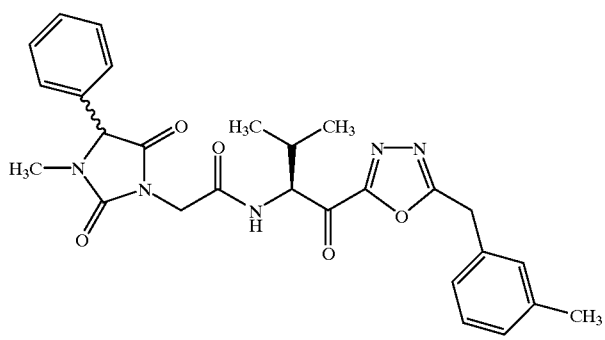
CE-2179
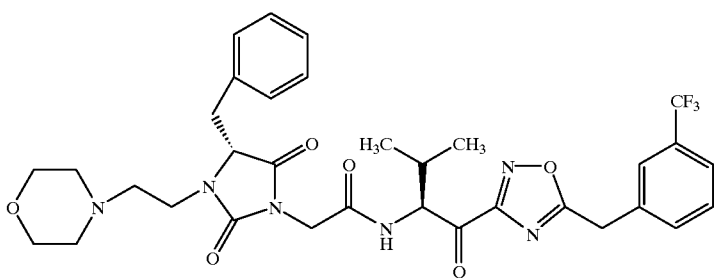
CE-2180
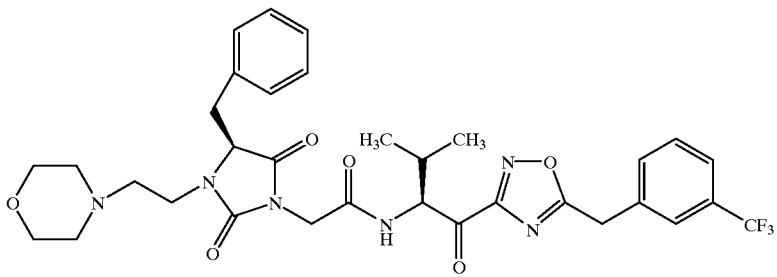
CE-2181
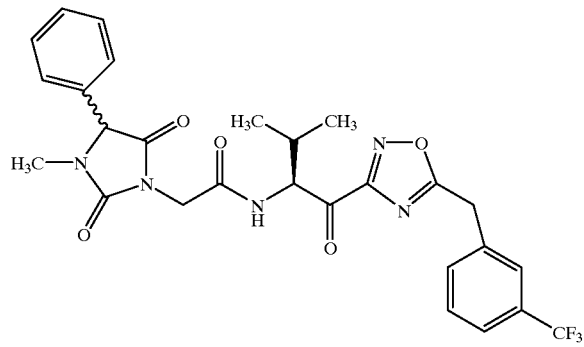
CE-2182

-continued
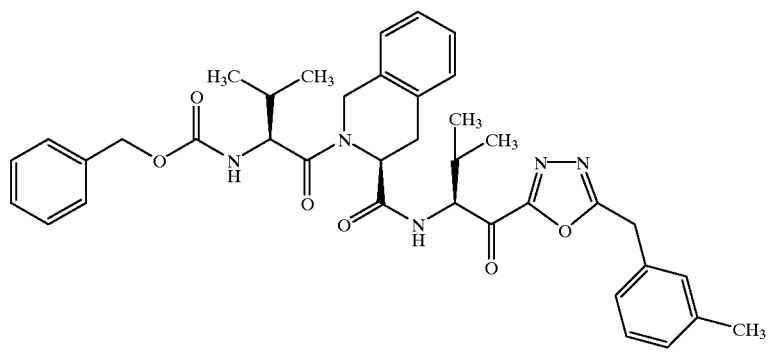
CE-2183
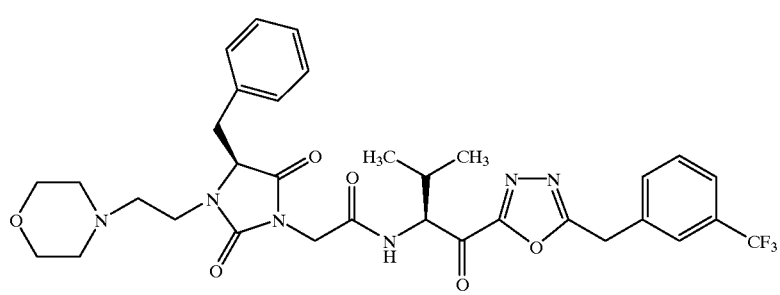
CE-2184
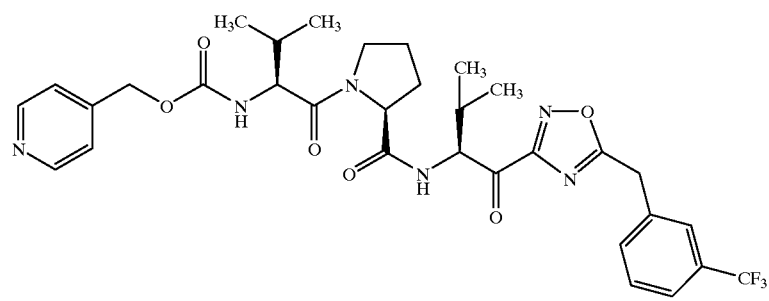
CE-2185
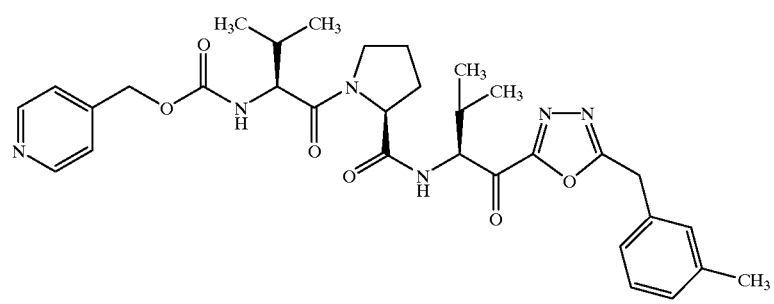
CE-2186
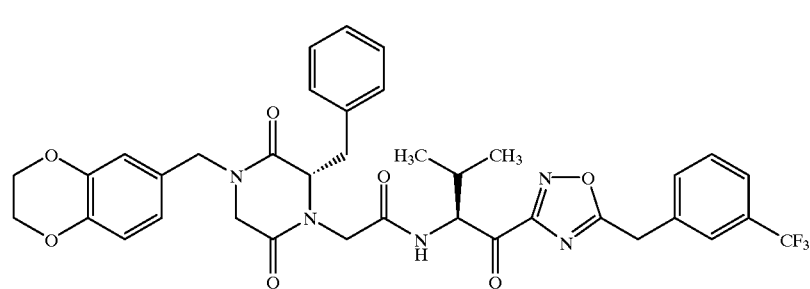
CE-2187

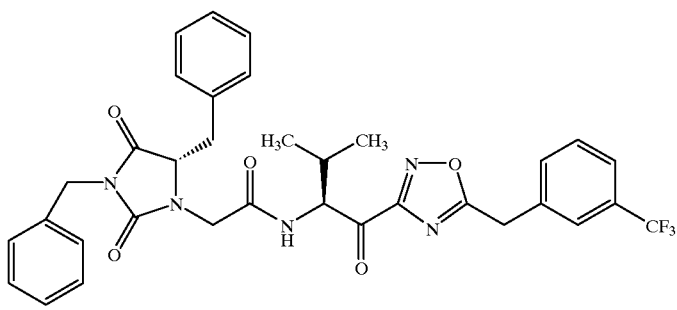
CE-2188
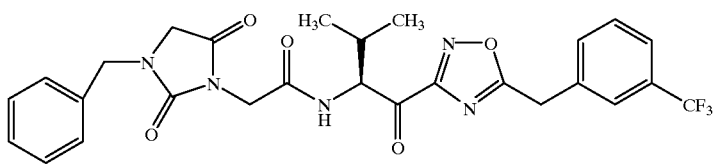
CE-2189
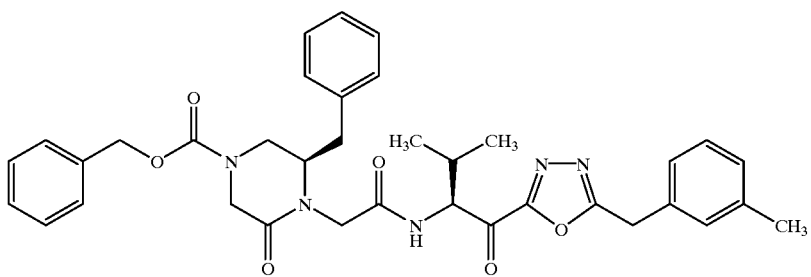
CE-2190
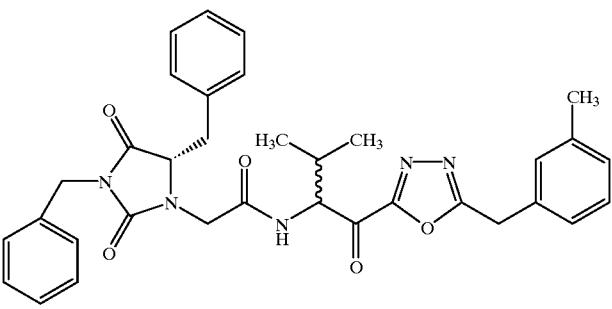
CE-2191
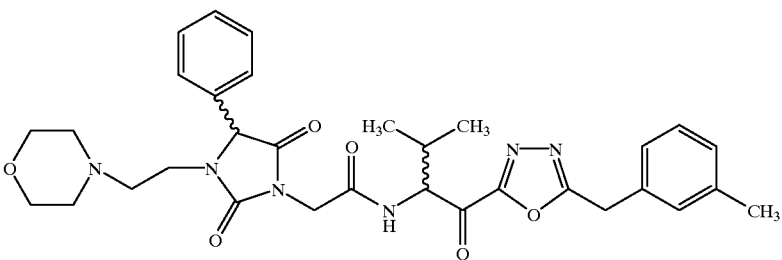
CE-2192

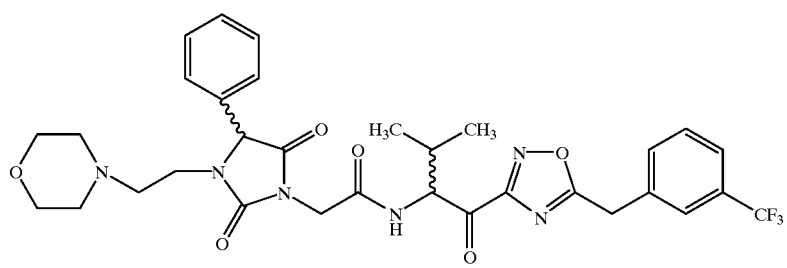
CE-2193
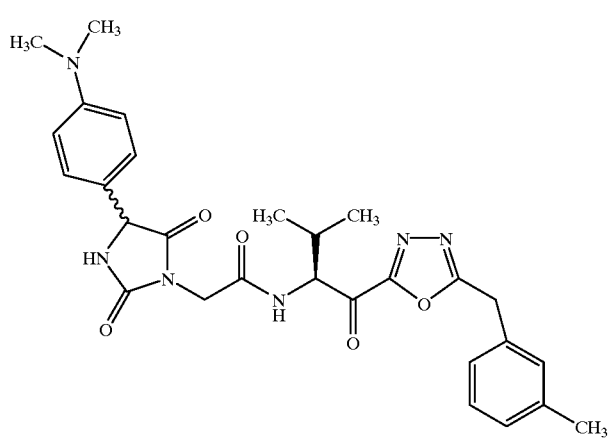
CE-2194
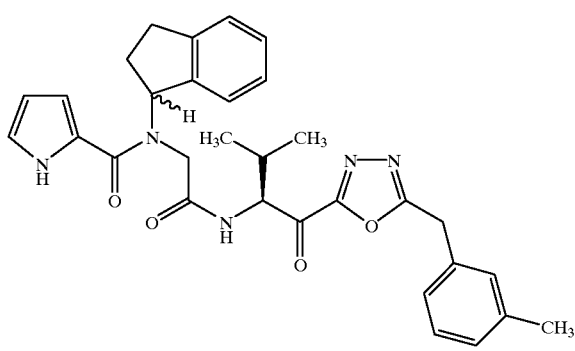
CE-2195
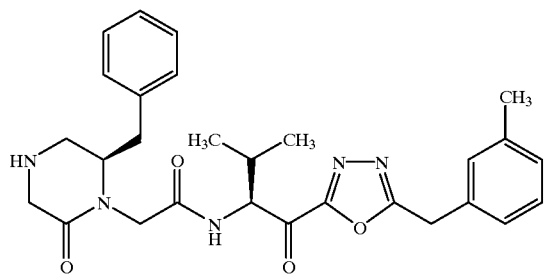
CE-2196

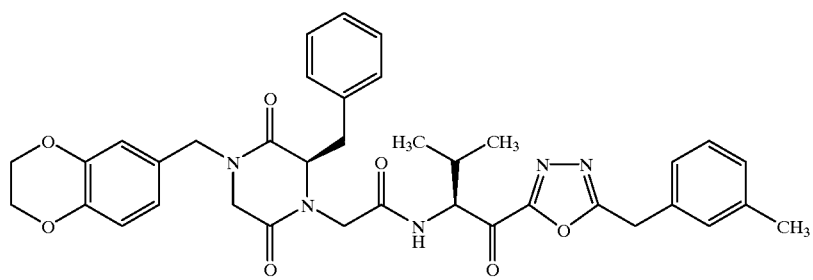
CE-2197
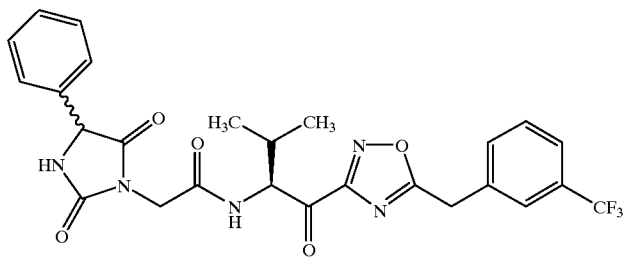
CE-2198
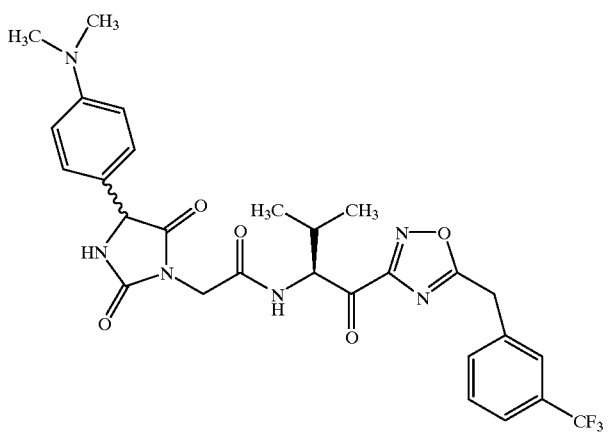
CE-2200
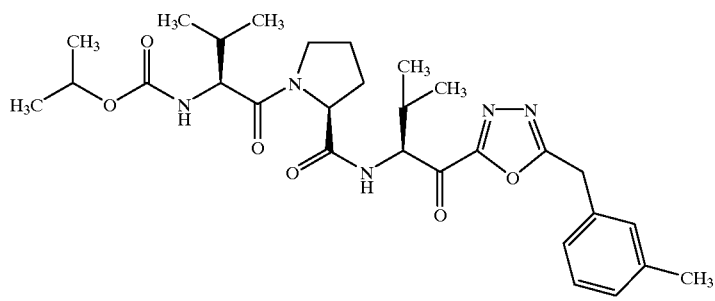
CE-2202

-continued
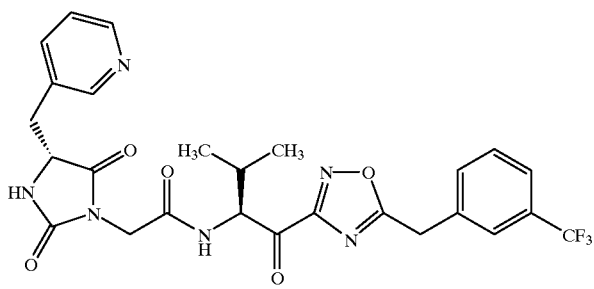
CE-2203
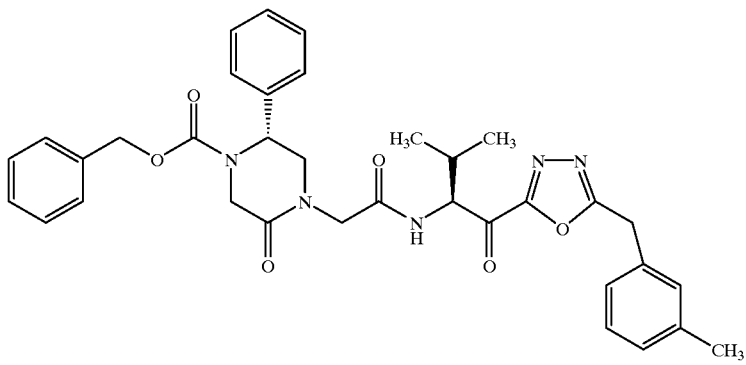
CE-2204
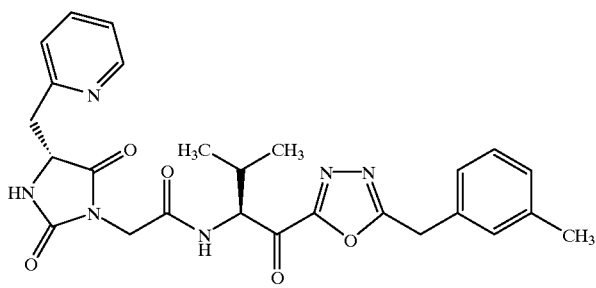
CE-2205
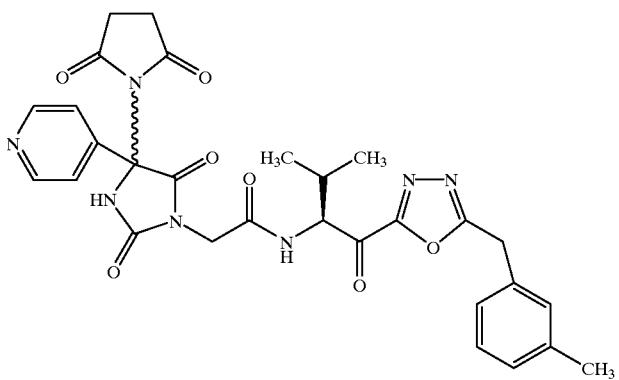
CE-2206

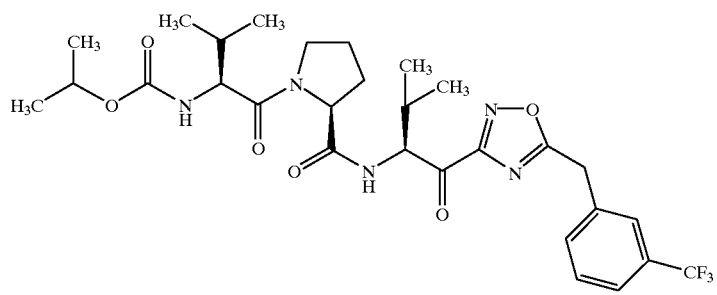
CE-2207
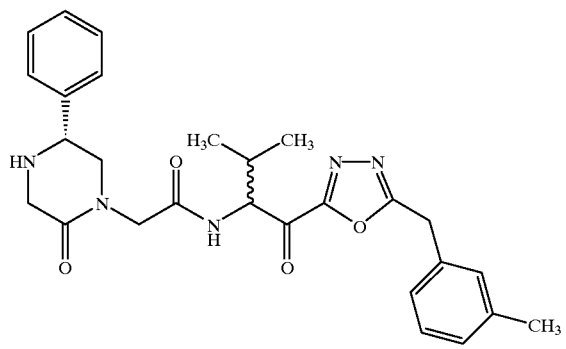
CE-2208
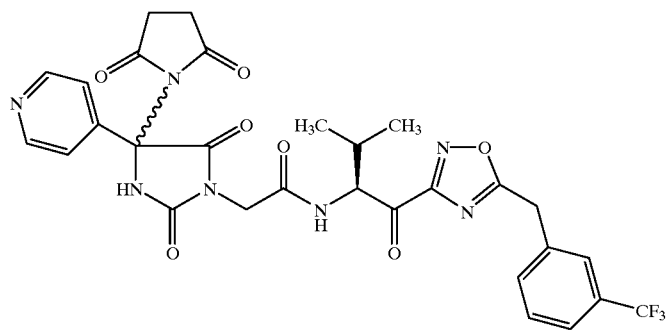
CE-2209
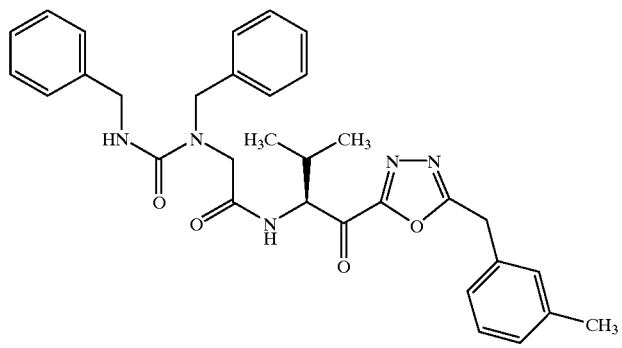
CE-2210

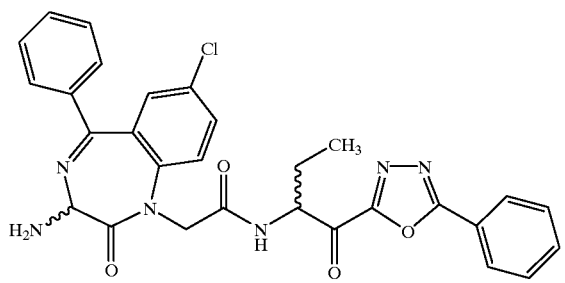
CE-2211
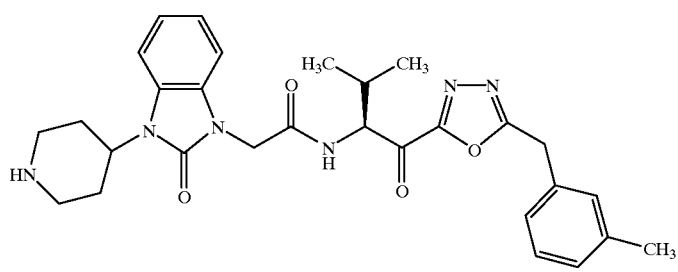
CE-2212
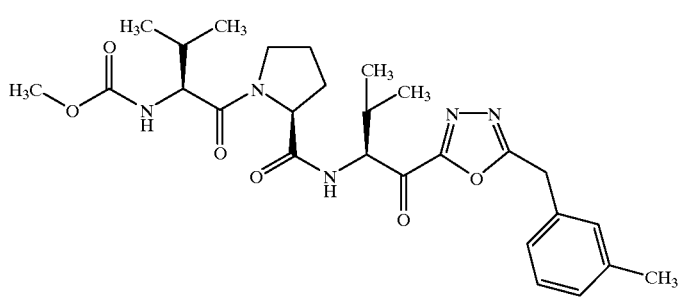
CE-2213
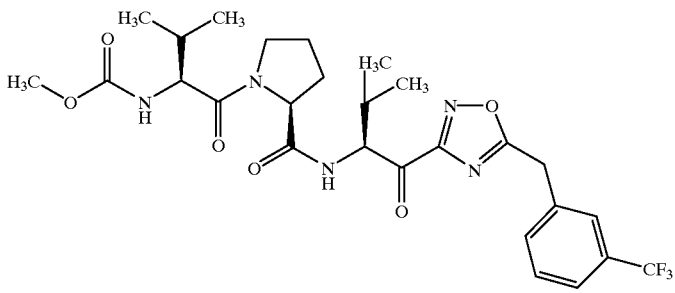
CE-2214
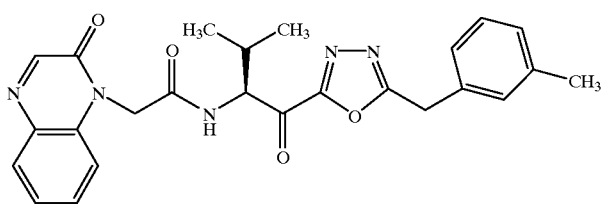
CE-2215

-continued
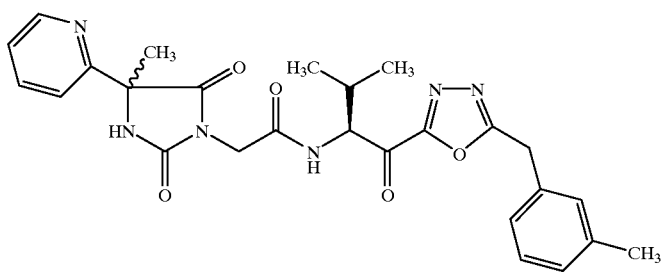
CE-2216
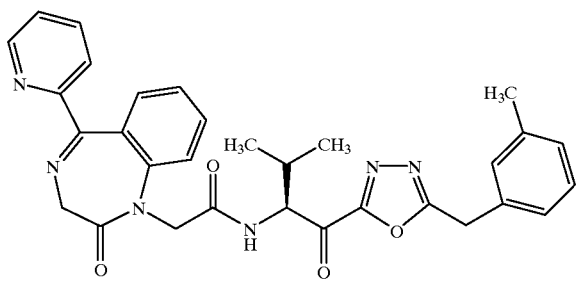
CE-2217
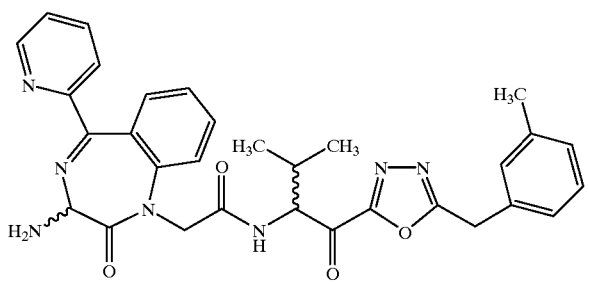
CE-2218
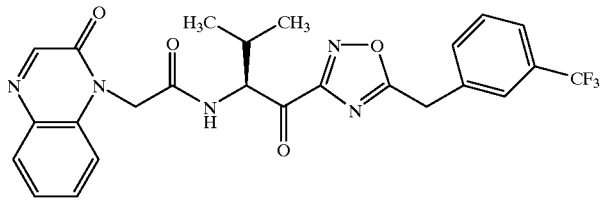
CE-2219
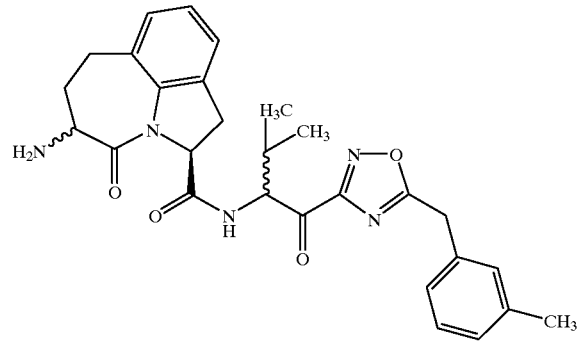
CE-2220

CE-2221
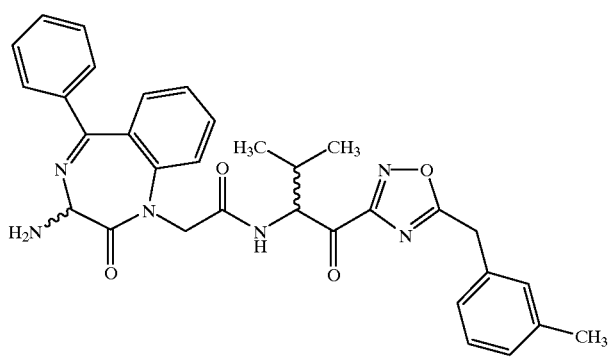
CE-2223
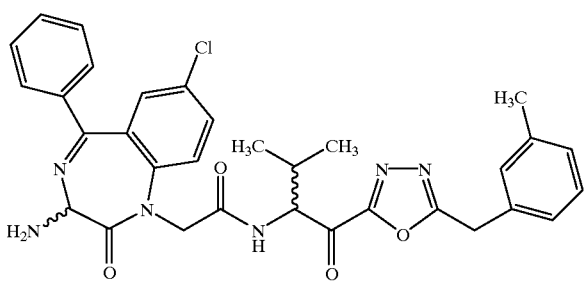
CE-2224
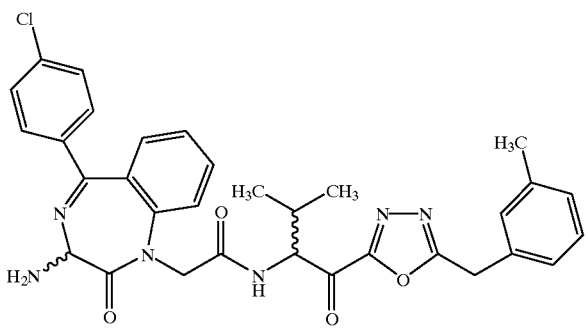
CE-2225
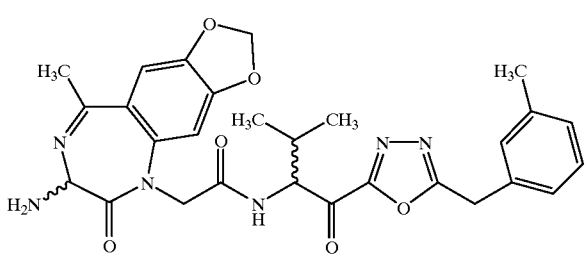
CE-2226
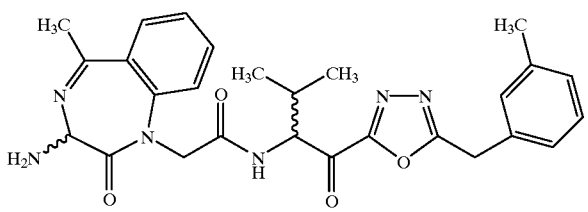

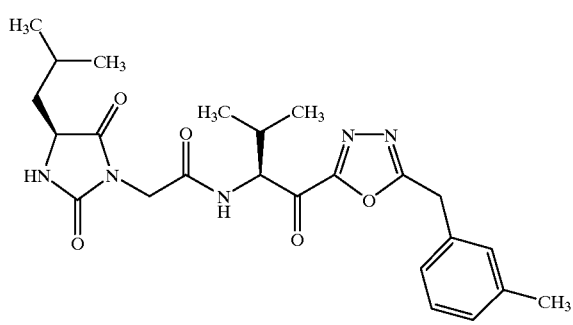
CE-2227
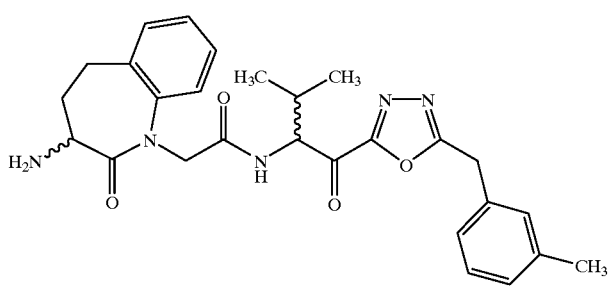
CE-2228
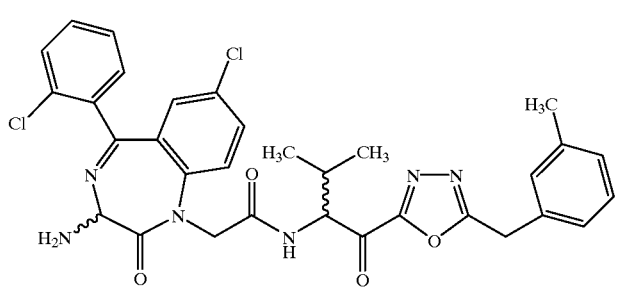
CE-2229
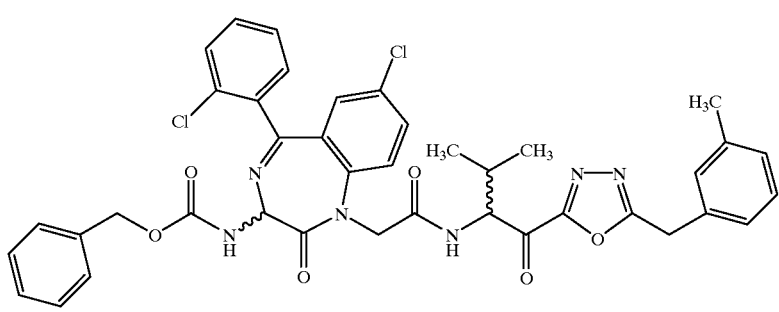
CE-2230
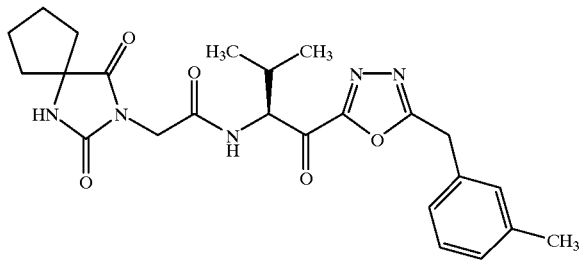
CE-2231

CE-2232
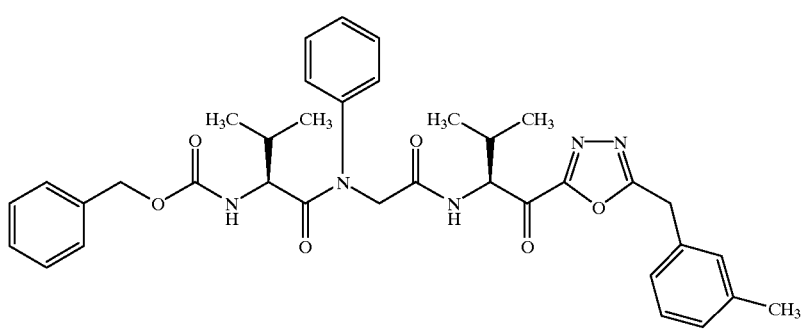
CE-2233
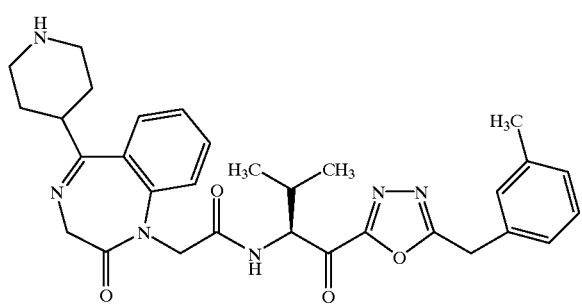
CE-2234
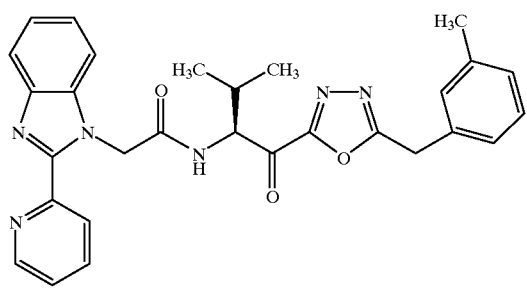
CE-2235
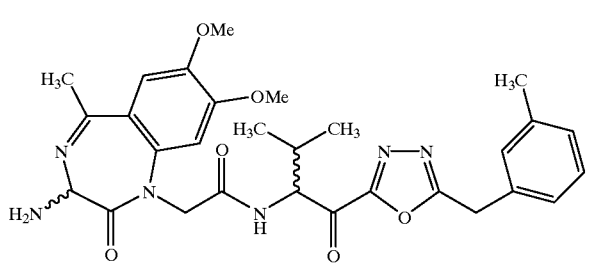
CE-2236
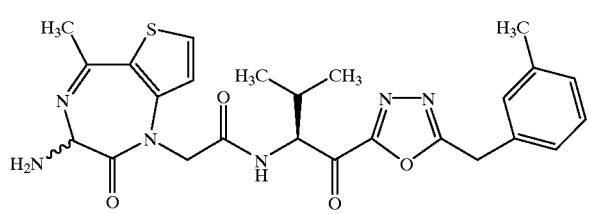

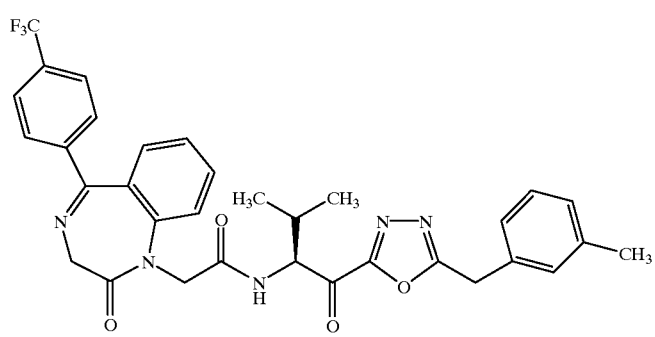
CE-2237
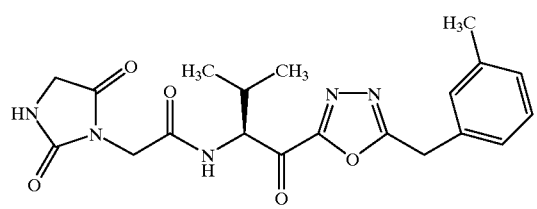
CE-2238
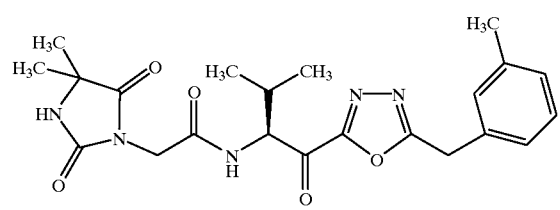
CE-2239
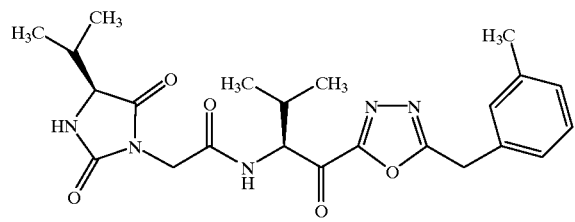
CE-2240
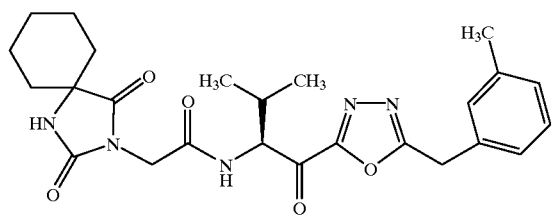
CE-2241

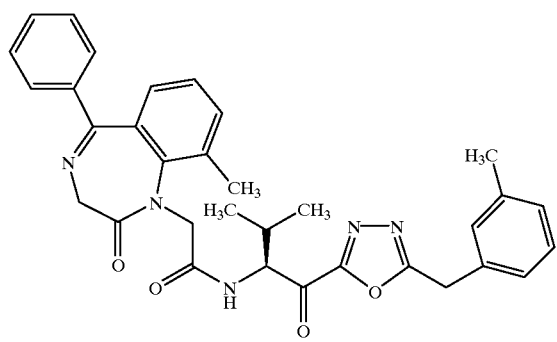
CE-2242
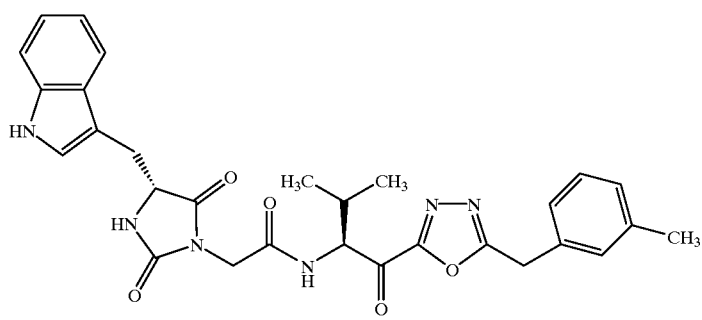
CE-2243
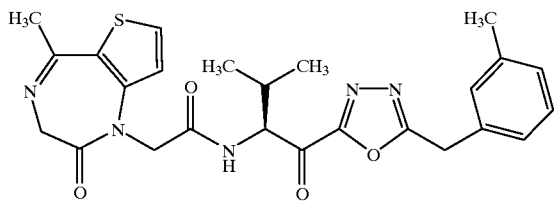
CE-2244
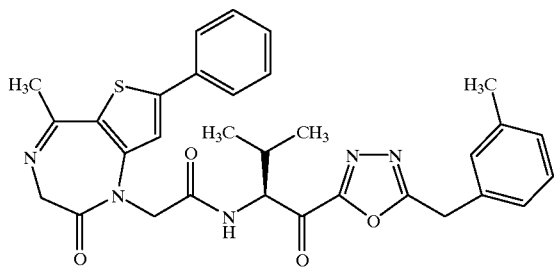
CE-2245
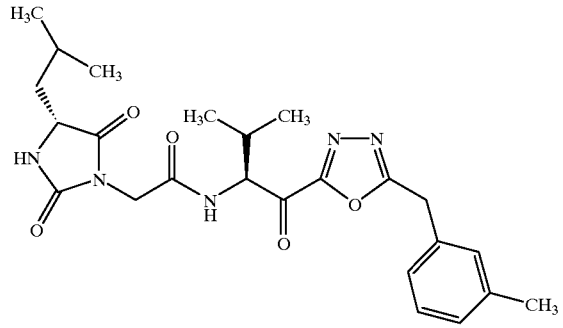
CE-2246

CE-2247
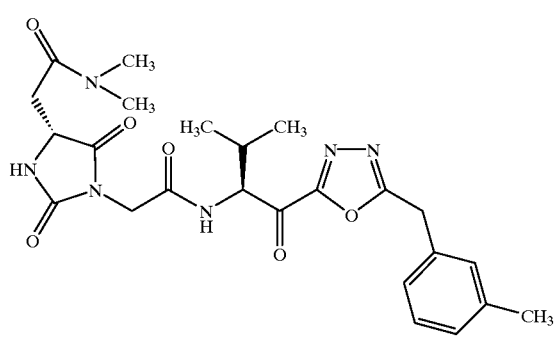
CE-2248
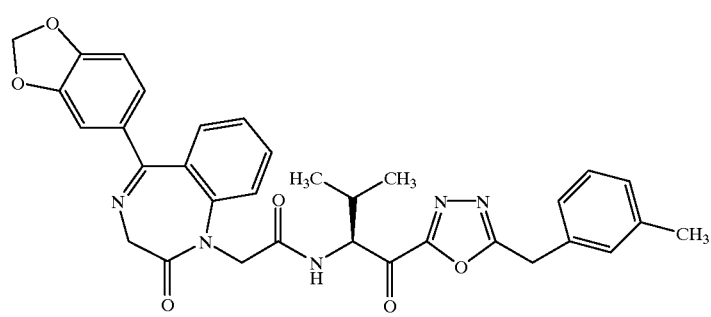
CE-2249
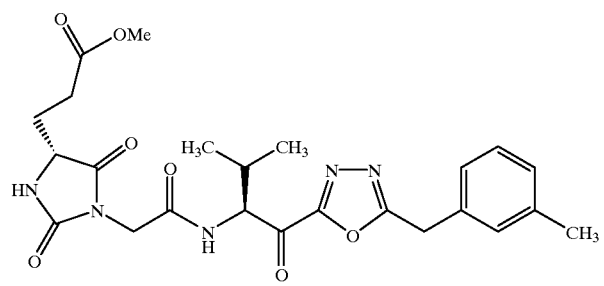
CE-2250
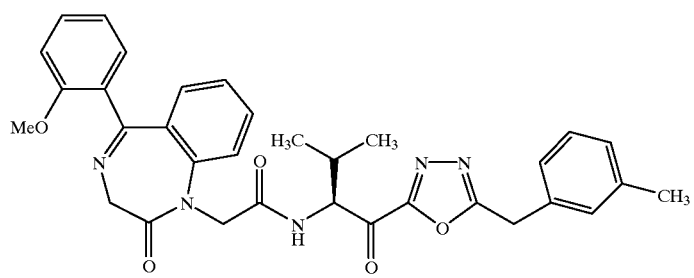
CE-2251
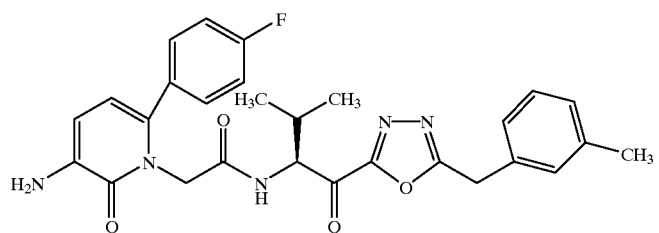

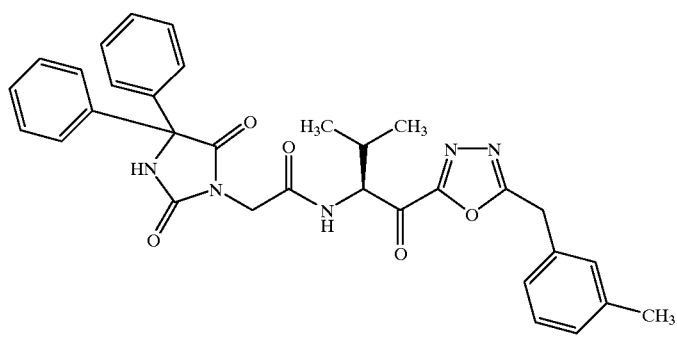
CE-2252
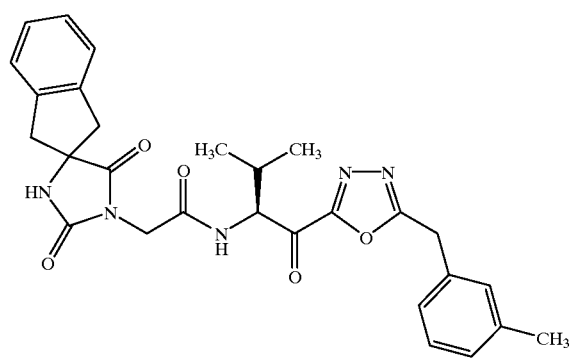
CE-2253
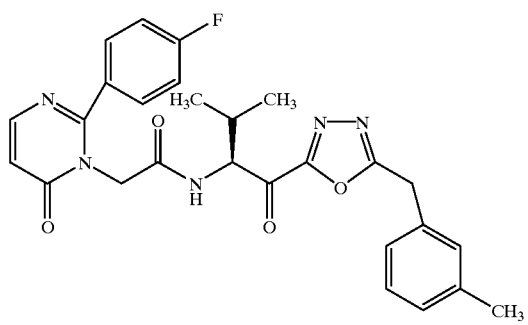
CE-2254
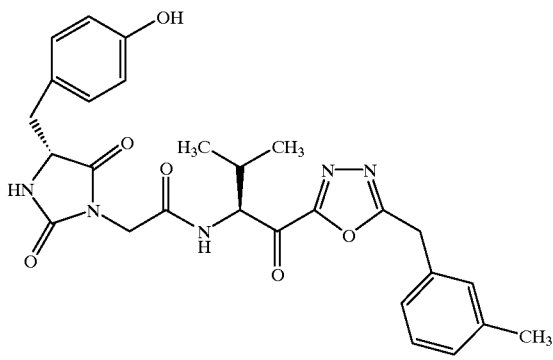
CE-2255

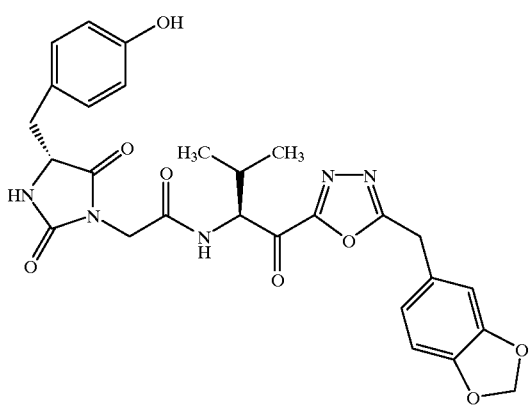
CE-2256
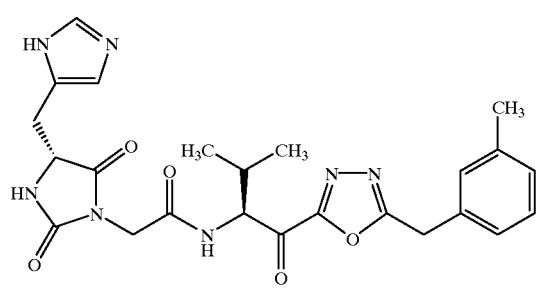
CE-2257
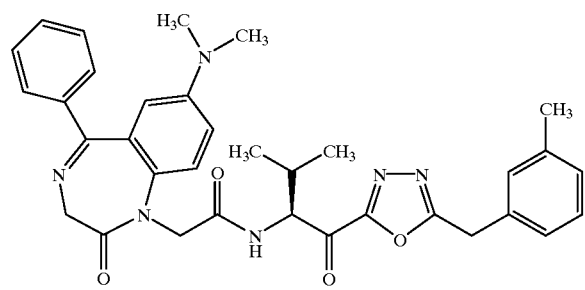
CE-2258
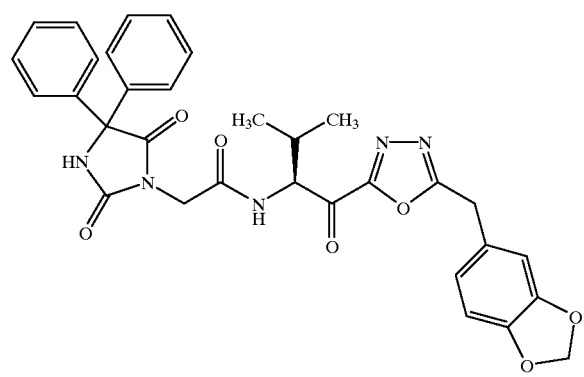
CE-2259

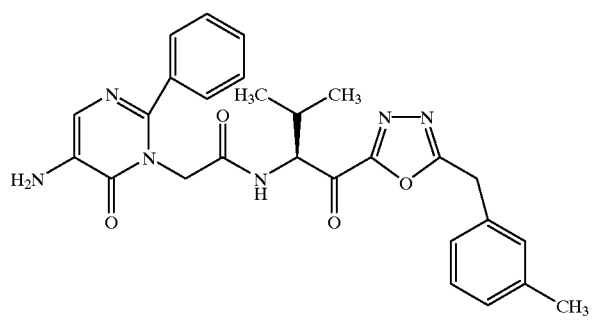
CE-2260
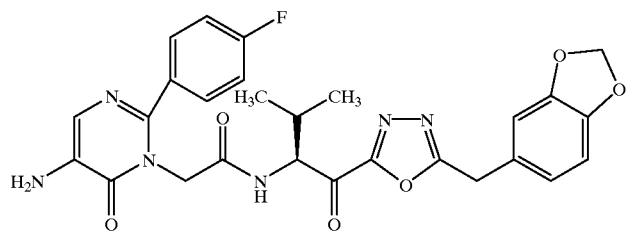
CE-2261
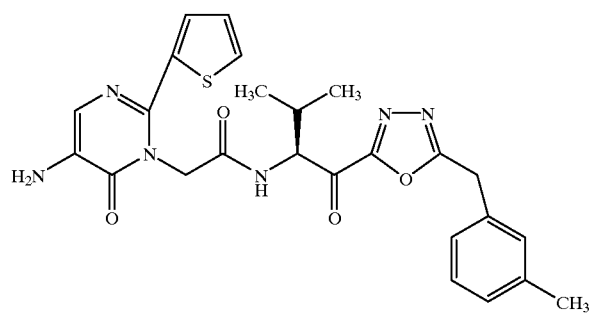
CE-2262
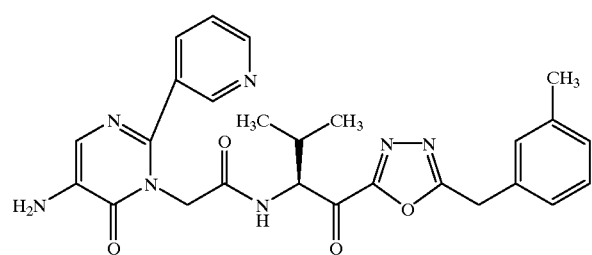
CE-2263
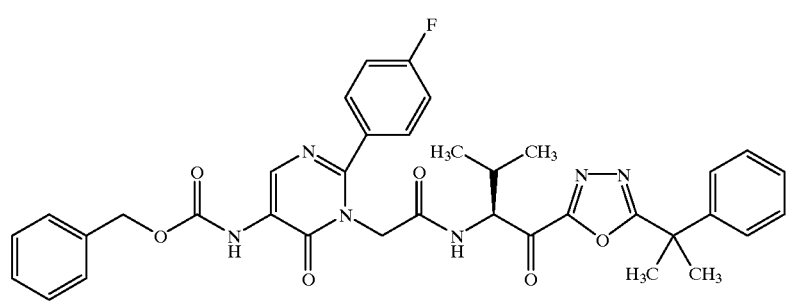
ONO-PO-690

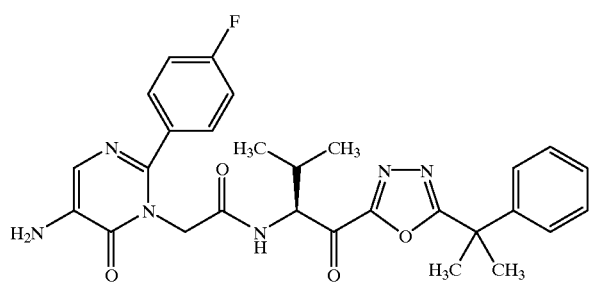
ONO-PO-691
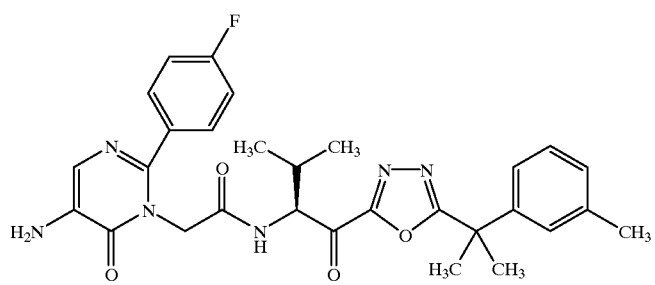
ONO-PO-692
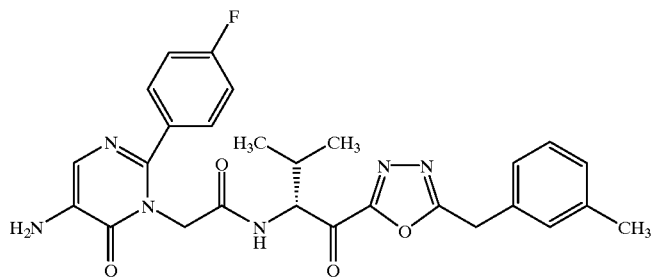
ONO-PO-693
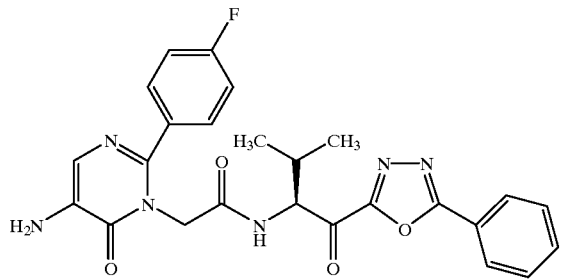
ONO-PO-694
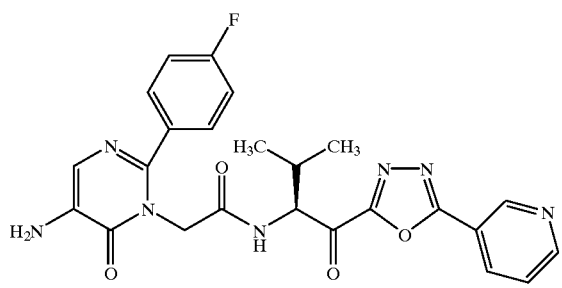
ONO-PO-695

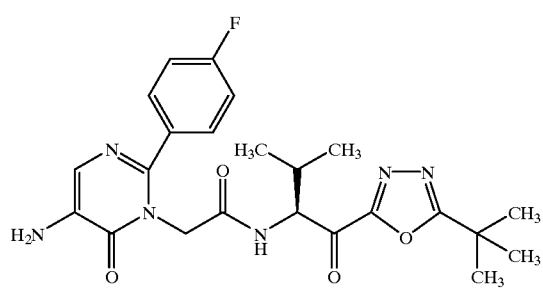
ONO-PO-696
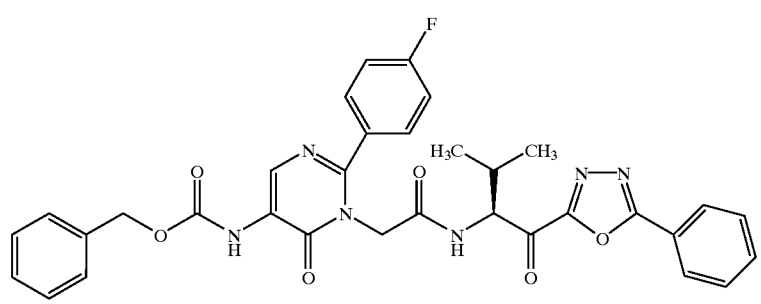
ONO-PO-697
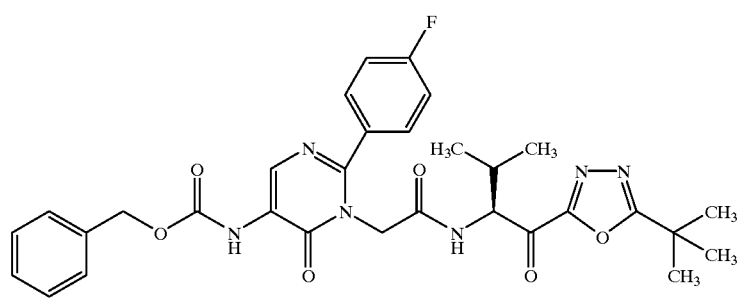
ONO-PO-698
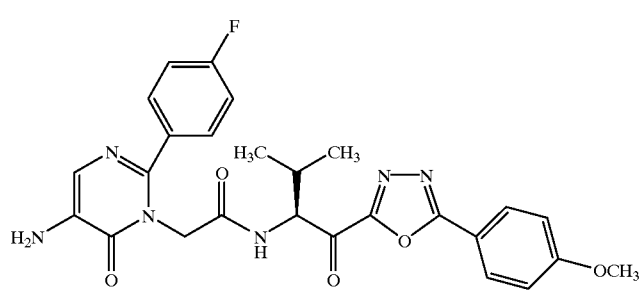
ONO-PO-699
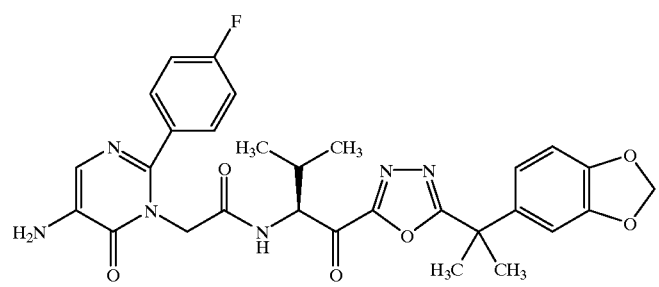
ONO-PO-700

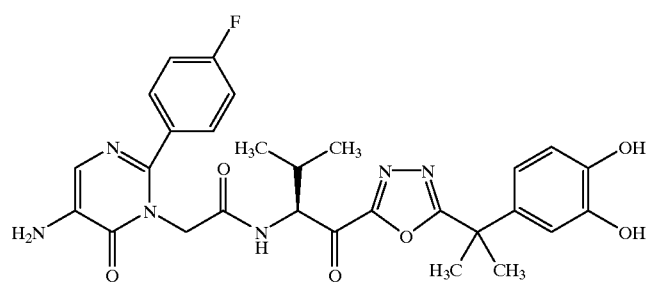
ONO-PO-701
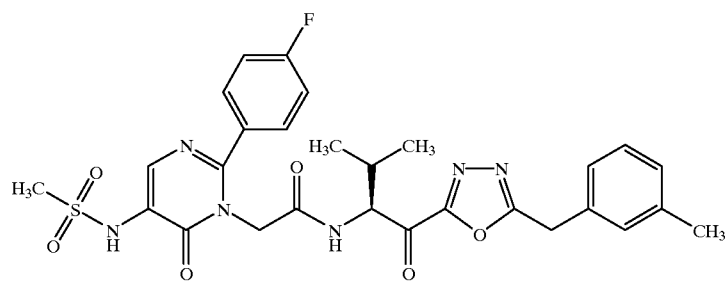
ONO-PO-702
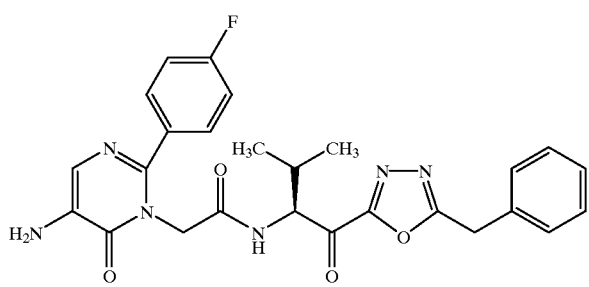
ONO-PO-703
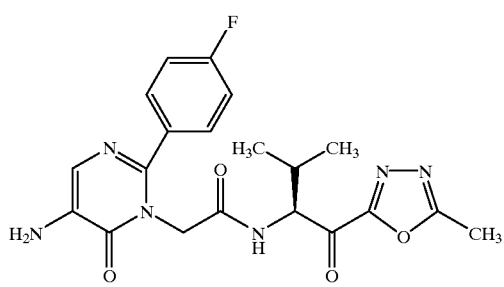
ONO-PO-704
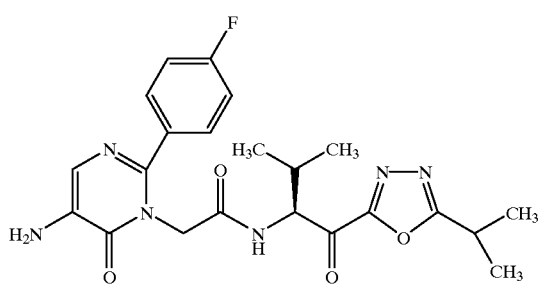
ONO-PO-705

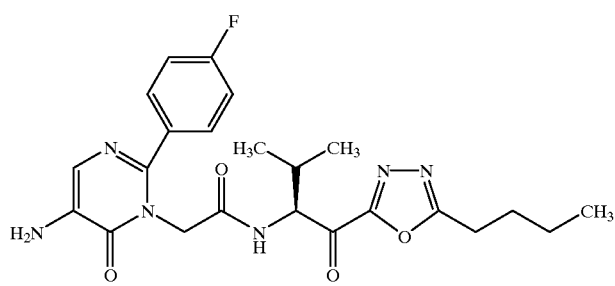
ONO-PO-706
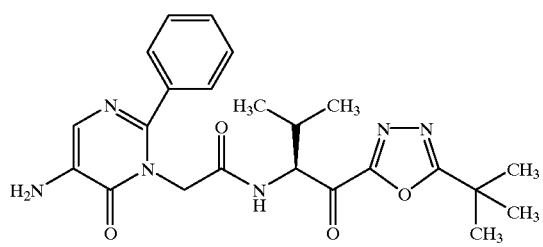
ONO-PO-707
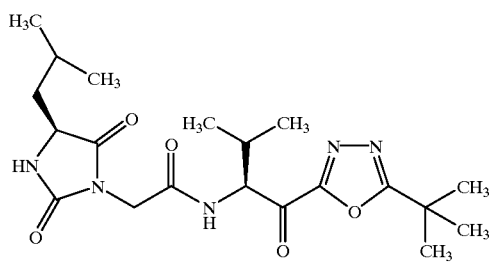
ONO-PO-708
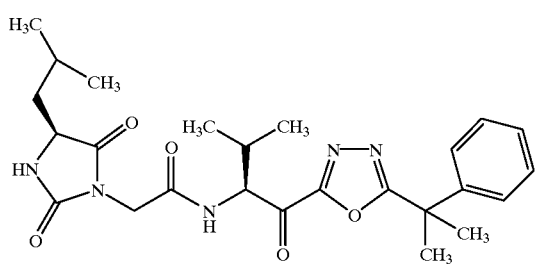
ONO-PO-709
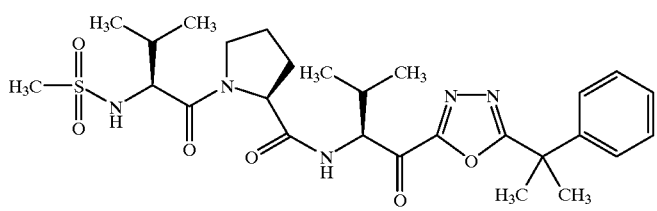
ONO-PO-710
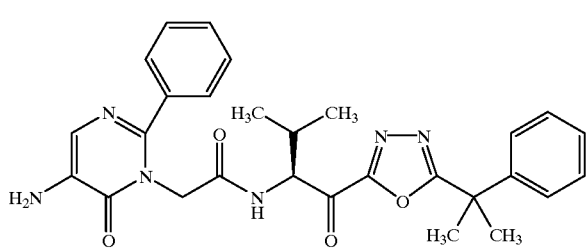
ONO-PO-711

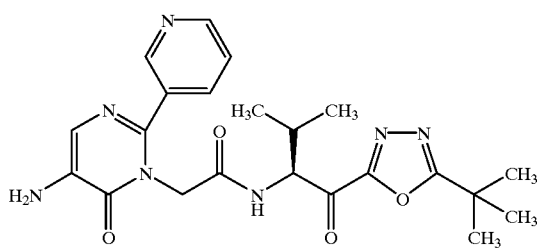
ONO-PO-712
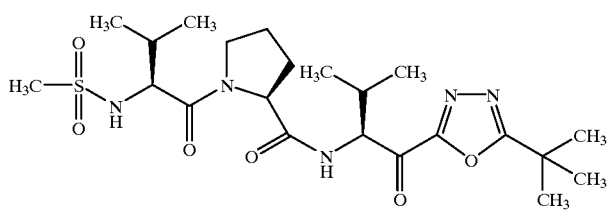
ONO-PO-713
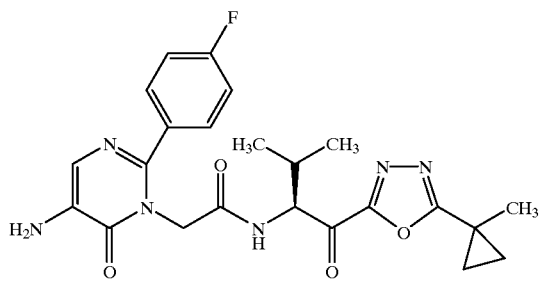
ONO-PO-714
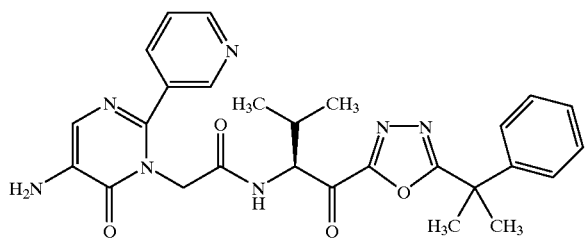
ONO-PO-715
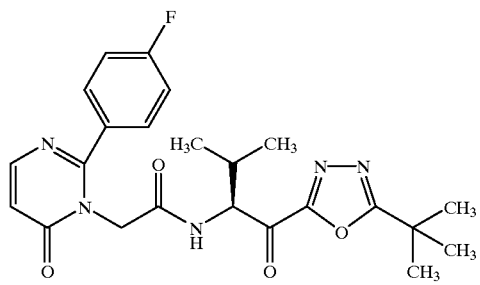
ONO-PO-716

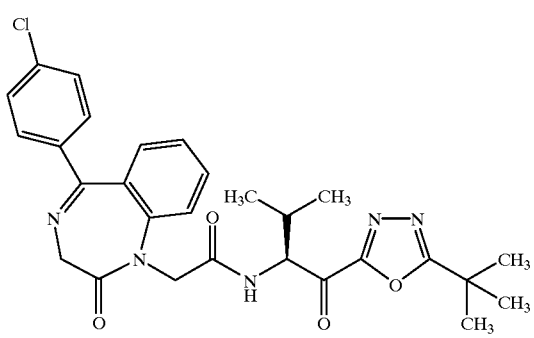
ONO-PO-717
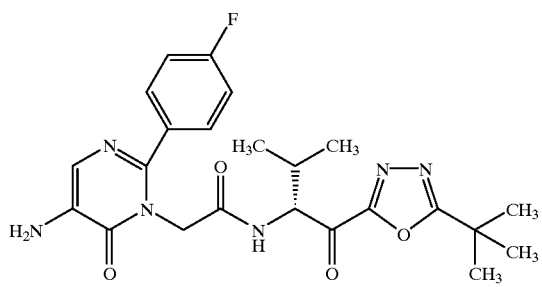
ONO-PO-718
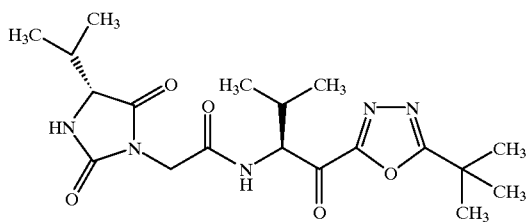
ONO-PO-719
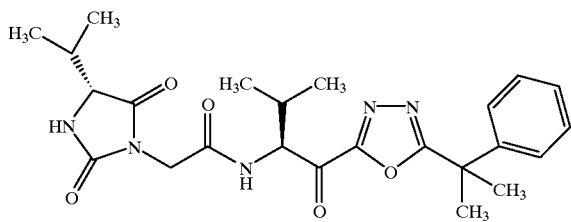
ONO-PO-720
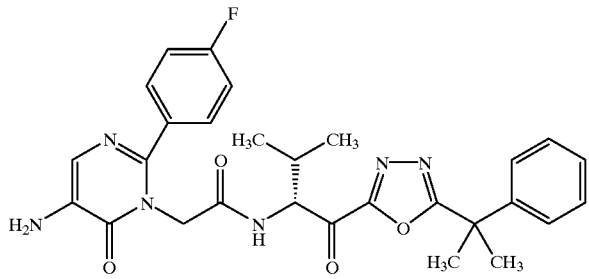
ONO-PO-721

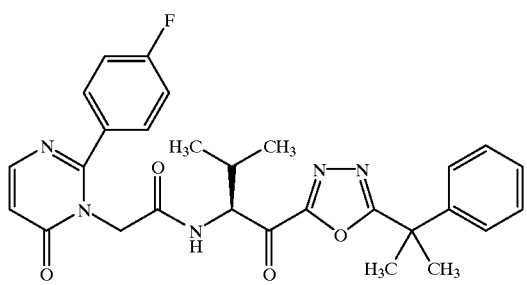
ONO-PO-722
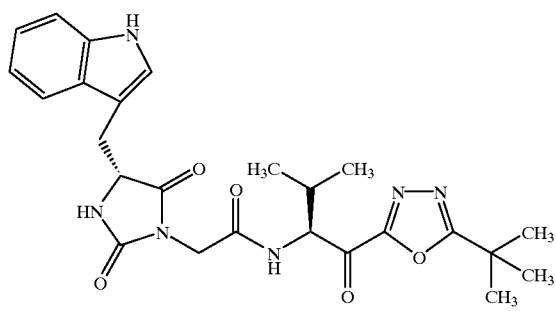
ONO-PO-723
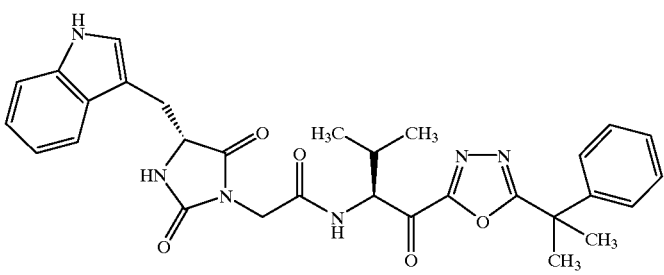
ONO-PO-724
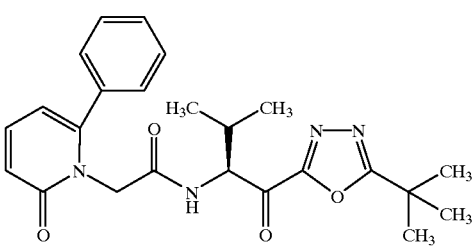
ONO-PO-725
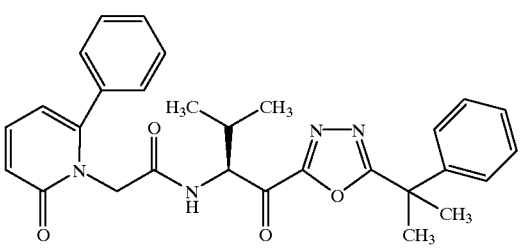
ONO-PO-726

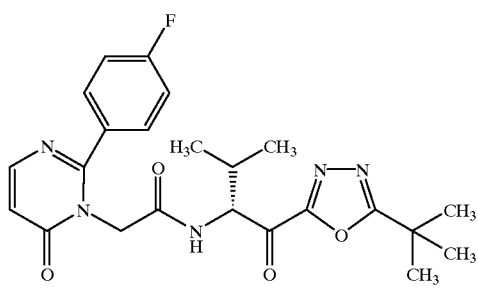
ONO-PO-727
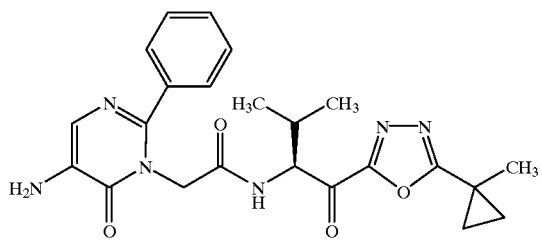
ONO-PO-728
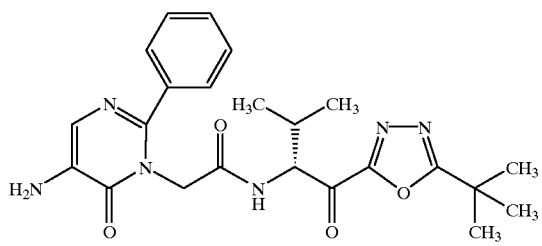
ONO-PO-729
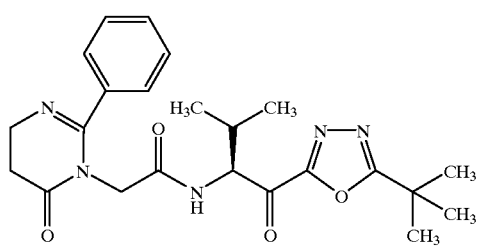
ONO-PO-730
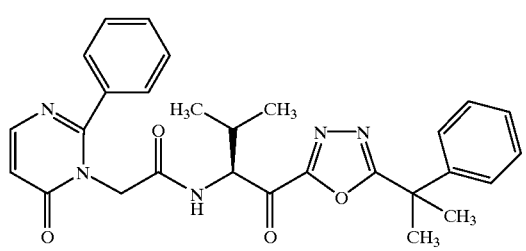
ONO-PO-731
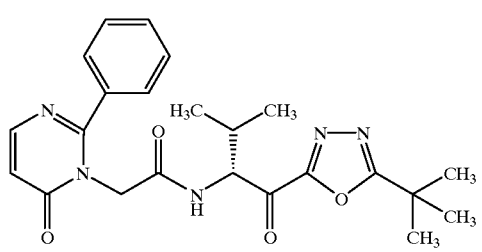
ONO-PO-732

-continued

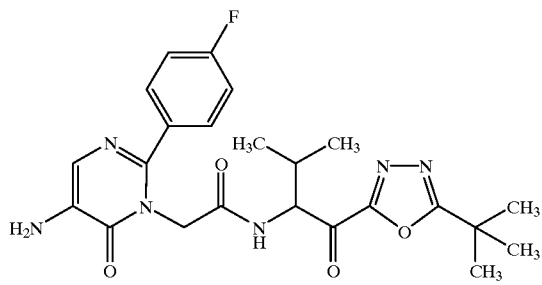

ONO-PO-733

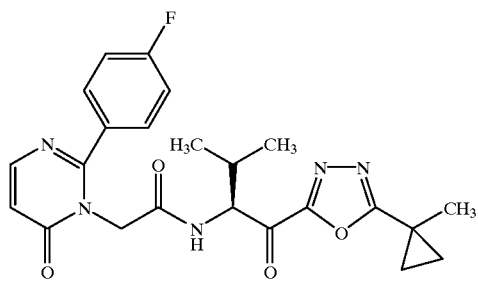

ONO-PO-734

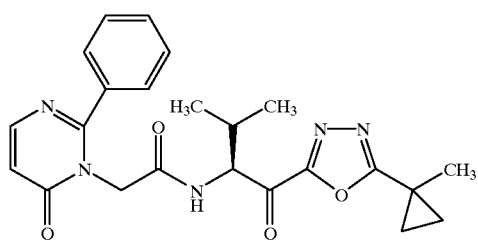

ONO-PO-735

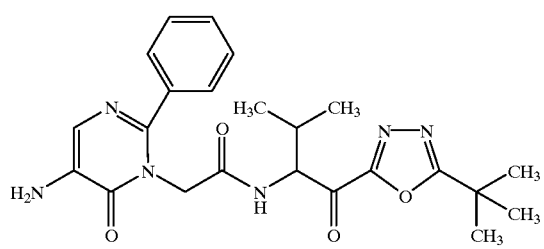

ONO-PO-736

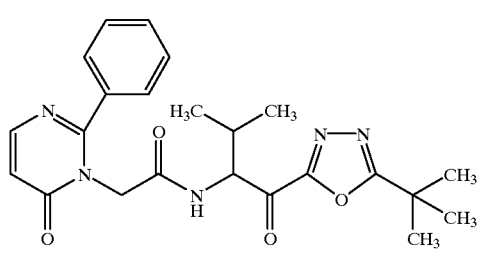

ONO-PO-737

The nomenclature for the above embodiments is as follows (although the majority of the embodiments disclosed indicate the stereochemistry of the 2-methylpropyl group having the (S)-configuration, it will be understood that both the (R)-configuration and the racemic (R,S) are within the scope of the invention):

CE-2157 2-Oxo-5-(phenyl)-1,4-benzodiazepine-N-[1-(2-[5-(3-methylbenzyl-1,3,4-oxadiazolyl]carbonyl)-2-(S)-methylpropyl]acetamide CE-2158 3-(S)-[(Benzyloxycarbonyl)amino-(5,6 phenyl-ϵ-lactam]-N-[1-(3-[5-(3-trifluoromethylbenzyl)-1,2,4-oxadiazolyl]carbonyl)-2-(S)-methylpropyl]acetamide CE-2159 2-(R,S)-[(Methylene-4-pyridyl) piperazine-2,5-dione]-N-[1-(2-[5-(3-methylbenzyl)-1,3,4-oxadiazolyl]carbonyl)-2-(S)-methylpropyl]acetamide CE-2160 3-(R,S)-[(Benzyloxycarbonyl)amino-δ-lactam]-N-[1-(3-[5-(3-trifluoromethylbenzyl)-1,2,4-oxadiazolyl]carbonyl)-2-(S)-methylpropyl]acetamide CE-2161 (Pyridyl-3-carbonyl)-L-valyl-N-[1-(2-[5-(3-methylbenzyl)-1,3,4-oxadiazolyl]carbonyl)-2-(S)-methylpropyl]-L-prolinamide CE-2162 4-[1-(2-N-Morpholino)ethyl-3-(R)-benzyl piperazine-2,5-dione]-N-[1-(2-[5-(3-methylbenzyl)-1,3,4-oxadiazolyl]carbonyl)-2-(S)-methylpropyl]acetamide CE-2163 Methylsulfonyl-L-valyl-N-[1-(2-[5-(3-methylbenzyl)-1,3,4-oxadiazolyl]carbonyl)-2-(S)-methylpropyl]-L-prolinamide CE-2164 (Pyrrole-2-carbonyl)-N-(benzyl)glycyl-N-[1-(2-[5-(3-methylbenzyl)-1,3,4-oxadiazolyl]carbonyl)-2-(S)-methylpropyl]amide CE-2165 N-Acetyl-2-(L)-(2,3-dihydro-1H-indole)-N[1-(2-[5-(3-methylbenzyl)-1,3,4-oxadiazolyl]carbonyl)-2-(S)-methylpropyl]amide CE-2166 1-Phenyl-1,2,4-triazolidine-3,5-dione-N-[1-(2-[5-(3-methylbenzyl)-1,3,4-oxadiazolyl]carbonyl)-2-(S)-methylpropyl]acetamide CE-2168 Phenylsulfonyl-L-valyl-N-[1-(2-[5-(3-methylbenzyl)-1,3,4-oxadiazolyl]carbonyl)-2-(S)-methylpropyl]-L-prolinamide CE-2170 1-[2-(5-[3-Methylbenzyl]-1,3,4-oxadiazolyl]-2-(S)-[(benzyloxycarbonyl)amino]-3-methylbutan-1-one CE-2171 (3-Pyridylcarbonyl)-L-valyl-N-[1-(3-[5-(3-trifluoromethylbenzyl)-1,2,4-oxadiazolyl]carbonyl)-2-(S)-methylpropyl]-L-prolinamide CE-2172 Methylsulfonyl-L-valyl-N-[1-(3-[5-(3-trifluoromethylbenzyl)- 1,2,4-oxadiazolyl]carbonyl)-2-(S)-methylpropyl]-L-prolinamide CE-2173 1-(3-Morpholinoethyl)-5-(R)-benzyl-2,4-imidazolidinedione-N-[1-(2-[5-(3-methylbenzyl)-1,3,4-oxadiazolyl]carbonyl)-2-(R,S)-methylpropyl]acetamide CE-2174 4-(R)-Isopropyl-2,5-imidazolidinedione-N-[1-(2-[5-(3-methylbenzyl)-1,3,4-oxadiazolyl]carbonyl)-2-(S)-methylpropyl]acetamide CE-2176 1-Benzyl-1,2,4-triazolidine-3,5-dione-N-[1-(2-[5-(3-methylbenzyl)-1,3,4-oxadiazolyl]carbonyl)-2-(S)-methylpropyl]acetamide CE-2177 (Benzyloxycarbonyl)-L-valyl-N-[1-(2-[5-(3,4-methylenedioxybenzyl)-1,3,4-oxadiazolyl]carbonyl)-2-(S)-methylpropyl]-L-prolinamide CE-2178 (Benzyloxycarbonyl)-L-valyl-N-[1-(3-[5-(3,4-methylenedioxybenzyl)-1,2,4-oxadiazolyl]carbonyl)-2-(S)-methylpropyl]-L-prolinamide CE-2179 5-(R,S)-Phenyl-1-methyl-2,4-imidazolidinedione-N-[1-(2-[5-(3-methylbenzyl)-1,3,4-oxadiazolyl]carbonyl)-2-(S)-methylpropyl]acetamide CE-2180 1-(N-Morpholinoethyl)-5-(R)-benzyl-2,4-imidazolidinedione-N-[1-(3-[5-(3-trifluoromethylbenzyl)-1,2,4-oxadiazolyl]carbonyl)-2-(R,S)-methylpropyl]acetamide CE-2181 1-(N-Morpholinoethyl)-5-(S)-benzyl-2,4-imidazolidinedione-N-[1-(3-[5-(3-trifluoromethylbenzyl)-1,2,4-oxadiazolyl]carbonyl)-2-(R,S)-methylpropyl]acetamide CE-2182 5-(R,S)-Phenyl-1-methyl-2,4-imidazolidinedione-N-[1-(3-[5-(3 trifluoromethylbenzyl)-1,2,4-oxadiazolyl]carbonyl)-2-(S)-methylpropyl]acetamide CE-2183 Benzyloxycarbonyl-L-(1,2,3,4-tetrahydroisoquinoline)-3-N-[1-(2-[5-(3-methylbenzyl)-1,3,4-oxadiazolyl]carbonyl)-2-(R,S)-methylpropyl]amide CE-2184 1-(N-Morpholinoethyl)-5-(S)-benzyl-2,4-imidazolidinedione-N-[1-(2-[5-(3-methylbenzyl)-1,3,4-oxadiazolyl]carbonyl)-2-(R,S)-methylpropyl]acetamide CE-2185 4-Pyridylmethyleneoxycarbonyl-L-valyl-N-[1-(3-[5-(3-trifluoromethylbenzyl)-1,2,4-oxadiazolyl]carbonyl)-2-(S)-methylpropyl]-L-prolinamide CE-2186 4-Pyridylmethyleneoxycarbonyl-L-valyl-N-[1-(2-[5-(3-methylbenzyl)-1,3,4-oxadiazolyl]carbonyl)-2-(S)-methylpropyl]-L-prolinamide CE-2187 4-[1-(3,4-Ethylenedioxybenzyl)-3-(S)-benzyl-piperazine-2,5-dione-N-[1-(3-[5-(3-trifluoromethylbenzyl)-1,2,4-oxadiazolyl]carbonyl)-2-(S)-methylpropyl]acetamide CE-2188 1-Benzyl-4-(S)-benzyl-2,5-imidazolidinedione-N-[1-(3-[5-( 3-trifluoromethylbenzyl)-1,2,4-oxadiazolyl]carbonyl)-2-(S)-methylpropyl]acetamide CE-2189 1-Benzyl-2,4-imidazolidinedione-N-[1-(3-[5-(3-trifluoromethylbenzyl)-1,2,4-oxadiazolyl]carbonyl)-2-(S)-methylpropyl]acetamide CE-2190 [1-Benzyloxycarbonyl-5-(R)-benzylpiperazin-3-one]-N-[1-(2-[5-(3-methylbenzyl)-1,3,4-oxadiazolyl]carbonyl)-2-(S)-methylpropyl]acetamide CE-2191 1-Benzyl-4-(S)-benzyl-2,5-imidazolidinedione-N-[1-(2-[5-(3-methylbenzyl)-1,3,4-oxadiazolyl]carbonyl)-2-(R,S)-methylpropyl]acetamide CE-2192 1-(N-Morpholinoethyl)-5-(R,S)-phenyl-2,4-imidazolidinedione-N-[1-(2-[5-(3-methylbenzyl)-1,3,4-oxadiazolyl]carbonyl)-2-(R,S)-methylpropyl]acetamide CE-2193 1-(N-Morpholinoethyl)-5-(R,S)-phenyl-2,4-imidazolidinedione-N-[1-(3-[5-(3-trifluoromethylbenzyl)-1,2,4-oxadiazolyl]carbonyl)-2-(R,S)-methylpropyl]acetamide CE-2194 [4-(R,S)-(4-Dimethylaminophenyl)]-2,5-imidazolidinedione-N-[1-(2-[5-(3-methylbenzyl)-1,3,4-oxadiazolyl]carbonyl)-2-(S)-methylpropyl]acetamide CE-2195 (Pyrrole-2-carbonyl)-N-(1-(R,S)-indanyl)glycyl-N-[1-(2-[5-(3-methylbenzyl)-1,3,4-oxadiazolyl]carbonyl)-2-(S)-methylpropyl]amide CE-2196 (6-(R)-Benzylpiperazin-2-one)-N-[1-(2-[5-(3-methylbenzyl)-1,3,4-oxadiazolyl]carbonyl)-2-(R,S)-methylpropyl]acetamide CE-2197 4-[1-(3,4-Methylenedioxybenzyl)-3-(R)-benzylpiperazine-2,5-dione]-N-[1-(2-[5-(3-methylbenzyl)-1,3,4-oxadiazolyl]carbonyl)-2-(S)-methylpropyl]acetamide CE-2198 4-(R,S)-Phenyl-2,5-imidazolidinedione-N-[1-(3-[5-(3-trifluoromethylbenzyl)-1,2,4-oxadiazolyl]carbonyl)-2-(S)-methylpropyl]acetamide CE-2200 [4-(R,S)-(4-Dimethylaminophenyl)]-2,5-imidazolidinedione-N-[1-(3-[5-(3-trifluoromethylbenzyl)-1,2,4-oxadiazolyl]carbonyl)-2-(S)-methylpropyl]acetamide CE-2202 Isopropyloxycarbonyl-L-valyl-N-[1-(2-[5-(3-methylbenzyl)-1,3,4-oxadiazolyl]carbonyl)-2-(S)-methylpropyl]-L-prolinamide CE-2203 [4-(R)-(3-pyridylmethylene)]-2,5-imidazolidinedione-N-[1-(3-[5-(3-trifluoromethylbenzyl)-1,2,4-oxadiazolyl]carbonyl)-2-(S)-methylpropyl]acetamide CE-2204 1-Benzyloxycarbonyl-(2-(R)-phenylpiperazin-5-one)-N-[1-(2-[5-(3-methylbenzyl)-1,3,4-oxadiazolyl]carbonyl)-2-(S)-methylpropyl]acetamide CE-2205 [4-(R)-(3-pyridylmethyl)]-2,5-imidazolidinedione-N-[1-(2-[5-(3-methylbenzyl)-1,3,4-oxadiazolyl]carbonyl)-2-(S)-methylpropyl]acetamide CE-2206 [4-(R,S)-(4-pyridyl)-4-(R,S)-N-succinimidyl]-2,5-imidazolidinedione-N-[1-(2-[5-(3-methylbenzyl)-1,3,4-oxadiazolyl]carbonyl)-2-(S)-methylpropyl]acetamide CE-2207 Isopropyloxycarbonyl-L-valyl-N-[1-(3-[5-(3-trifluoromethylbenzyl)-1,2,4-oxadiazolyl]carbonyl)-2-(S)-methylpropyl]-L-prolinamide CE-2208 (2-(R)-Phenylpiperazin-5-one)-N-[1-(2-[5-(3-methylbenzyl)-1,3,4-oxadiazolyl]carbonyl)-2-(R,S)-methylpropyl]acetamide CE-2209 [4-(R,S)-(4-pyridyl)-4-(R,S)-N-succinimidyl]-2,5-imidazolidinedione-N-[1-(3-[5-(3-trifluoromethylbenzyl)-1,2,4-oxadiazolyl]carbonyl)-2-(S)-methylpropyl]acetamide CE-2210 (N-Benzylcarbonyl)-N-(benzyl)glycyl-N-[1-(2-[5-(3-methylbenzyl)-1,3,4-oxadiazolyl]carbonyl)-2-(S)-methylpropyl]amide CE-2211 (R,S)-3-Amino-2-oxo-5-phenyl-1,4-(6-2'-chlorobenzodiazepine)-N-[1-(2-[5-phenyl-1,3,4-oxadiazolyl]carbonyl)-2-(R,S)-propyl]acetamide CE-2212 3-[1-(4-Piperidine)]-benzimidazolidin-2-one-N-[1-(2-[5-(3-methylbenzyl)-1,3,4-oxadiazolyl]carbonyl)-2-(S)-methylpropyl]acetamide CE-2213 Methyloxycarbonyl-L-valyl-N-[1-(2-[5-(3-methylbenzyl)-1,3,4-oxadiazolyl]carbonyl)-2-(S)-methylpropyl] L-prolinamide CE-2214 Methyloxycarbonyl-L-valyl-N-[1-(3-[5-(3 trifluoromethylbenzyl)-1,2,4-oxadiazolyl]carbonyl)-2-(S)-methylpropyl]-L-prolinamide CE-2215 1,4-Quinazolin-2-one-N-[1-(2-[5-(3-methylbenzyl)-1,3,4-oxadiazolyl]carbonyl)-2-(S)-methylpropyl]acetamide CE-2216 [4-(R,S)-(2-Pyridyl)-4-(R,S)-methyl]-2,5-imidazolidinedione-N-[1-(2-[5-(3-methylbenzyl)-1,3,4-oxadiazolyl]carbonyl)-2-(S)-methylpropyl]acetamide CE-2217 2-Oxo-5-(2-pyridyl)-1,4-benzodiazepine-N-[1-(2-[5-(3-methylbenzyl)-1,3,4-oxadiazolyl]carbonyl)-2-(S)-methylpropyl]acetamide CE-2218 (R,S)-3-Amino-2-oxo-5-(2-pyridyl)-1,4-benzodiazepine-N-[1-(2-[5-(3 methylpropyl)-1,3,4-oxadiazolyl]carbonyl)-2-(R,S)-methylpropyl]acetamide CE-2219 1,4-Quinazolin-2-one-N-[1-(3-[5-(3-trifluoromethylbenzyl)-1,2,4-oxadiazolyl]carbonyl)-2-(S)-methylpropyl]acetamide CE-2220 (2S,5S)-5-Amino-1,2,4,5,6,7-hexahydroazepino-[3.2.1]-indole- 4-one-carbonyl-N-[1-(3-[5-(3-methylbenzyl)-1,2,4-oxadiazolyl]carbonyl)-2-(R,S)-methylpropyl]amide CE-2221 (R,S)-3-Amino-2-oxo-5-phenyl-1,4-benzodiazepine-N-[1-(3-[5-(3-methylbenzyl)-1,2,4-oxadiazolyl]carbonyl)-2-(R,S)-methylpropyl]acetamide CE-2223 (R,S)-3-Amino-2-oxo-5-phenyl-1,4-(2'-chlorobenzodiazepine)-N-[1-(2-[5-(3-methylbenzyl)-1,3,4-oxadiazolyl]carbonyl)-2-(R,S)-methylpropyl]acetamide CE-2224 (R,S)-3-Amino-2-oxo-5-(4-chlorophenyl)-1,4-benzodiazepine-N-[1-(2-[5-(3-methybenzyl)-1,3,4-oxadiazolyl]carbonyl)-2-(R,S)-methylpropyl]acetamide CE-2225 (R,S)-3-Amino-2-oxo-5-methyl-1,4-(2',3'-methylenedioxy) benzodiazepine)-N-[1-(2-[5-(3-methybenzyl)-1,3,4-oxadiazolyl]carbonyl)-2-(R,S)-methylpropyl]acetamide CE-2226 (R,S)-3-Amino-2-oxo-5-methyl-1,4-benzodiazepine-N-[1-(2-[5-(3-methylbenzyl)-1,3,4-oxadiazolyl]carbonyl)-2-(R,S)-methylpropyl]acetamide CE-2227 4-(S)-(2-Isobutyl)-2,5-imidazolidinedione-N-[1-(2-[5-(3-methylbenzyl)-1,3,4-oxadiazolyl]carbonyl)-2-(S)-methylpropyl]acetamide CE-2228 3-(R,S)-Amino-quinolin-2-one-N-[1-(2-[5-(3-methylbenzyl)-1,3,4-oxadiazolyl]carbonyl)-2-(R,S)-methylpropyl]acetamide CE-2229 (R,S)-3-Amino-2-oxo-5-(2-chlorophenyl)-1,4-(2'-chlorobenzodiazepine)-N-[1-(2-[5-(3-methylbenzyl)-1,3,4-oxadiazolyl]carbonyl)-2-(R,S)-methylpropyl]acetamide CE-2230 (R,S)-3-Benzyloxycarbonylamino-2-oxo-5-(2-chlorophenyl)-1,4-(2'-chlorobenzodiazepine)-N-[1-(2-[5-(3-methylbenzyl)-1,3,4-oxadiazolyl]carbonyl)-2-(R,S)-methylpropyl]acetamide CE-2231 4-Spirocyclopentane-2,5-imidazolidinedione-N-[1-(2-[5-(3-methylbenzyl)-1,3,4-oxadiazolyl]carbonyl)-2-(S)-methylpropyl]acetamide CE-2232 Benzyloxycarbonyl-L-valyl-N-(phenyl)glycyl-N-[1-(2-[5-(3-methylbenzyl)-1,3,4-oxadiazolyl]carbonyl)-2-(S)-methylpropyl]amide CE-2233 2-Oxo-5-(4-piperidinyl)-1,4-benzodiazepine-N-[1-(2-[5-(3-methylbenzyl)-1,3,4-oxadiazolyl]carbonyl)-2-(S)-methylpropyl]acetamide CE-2234 2-(2-Pyridyl)-benzimidazole-N-[1-(2-[5-(3-methylbenzyl)-1,3,4-oxadiazolyl]carbonyl)-2-(S)-methylpropyl]acetamide CE-2235 (R,S)-3-Amino-2-oxo-5-methyl-1,4-(2',3'-dimethoxybenzodiazepine)-N-[1-(2-[5-(3-methylbenzyl)-1,3,4-oxadiazolyl]carbonyl)-2-(R,S)-methylpropyl]acetamide CE-2236 (R,S)-3-Amino-2-oxo-5-methyl-1,4-(1-thiophenodiazepine)-N-[1-(2-[5-(3methylbenzyl)-1,3,4-oxadiazolyl]carbonyl)-2-(S)-methylpropyl]acetamide CE-2237 2-Oxo-5-(4-trifluoromethylphenyl)-1,4 benzodiazepine-N-[1-(2-[5-(3-methylbenzyl)-1,3,4-oxadiazolyl]carbonyl)-2-(S)-methylpropyl]acetamide CE-2238 2,5-Imidazolidinedione-N-[1-(2-[5-(3-methylbenzyl)-1,3,4-oxadiazolyl]carbonyl)-2-(S)-methylpropyl]acetamide CE-2239 4,4-Dimethyl-2,5-imidazolidinedione-N-[1-(2-[5-(3-methylbenzyl)-1,3,4-oxadiazolyl]carbonyl)-2-(S)-methylpropyl]acetamide CE-2240 4-(S)-(2-Isopropyl)-2,5-imidazolidinedione-N-[1-(2-[5-(3-methylbenzyl)-1,3,4-oxadiazolyl]carbonyl)-2-(S)-methylpropyl]acetamide CE-2241 4-Spirocyclohexane-2,5-imidazolidinedione-N-[1-(2-[5-(3-methylbenzyl)-1,3,4-oxadiazolyl]carbonyl)-2-(S)-methylpropyl]acetamide CE-2242 2-Oxo-5-phenyl-1,4-(4'-methylbenzodiazepine)-N-[1-(2-[5-(3-methylbenzyl)-1,3,4-oxadiazolyl]carbonyl)-2-(S)-methylpropyl]acetamide CE-2243 4-(R)-(3-Indolyl)-2,5-imidazolidinedione-N-[1-(2-[5-(3-methylbenzyl)-1,3,4-oxadiazolyl]carbonyl)-2-(S)-methylpropyl]acetamide CE-2244 2-Oxo-5-methyl-1,4-(1-thiophenodiazepine)-N-[1-(2-[5-(3-methylbenzyl)-1,3,4-oxadiazolyl]carbonyl)-2-(S)-methylpropyl]acetamide CE-2245 2-Oxo-5-methyl-1,4-(2-phenyl-1-thiophenodiazepine)-N-[1-(2-[5-(3-methylbenzyl)-1,3,4-oxadiazolyl]carbonyl)-2-(S)-methylpropyl]acetamide CE-2246 4-(R)-(2-Isobutyl)-2,5-imidazolidinedione-N-[1-(2-[5-(3-methylbenzyl)-1,3,4-oxadiazolyl]carbonyl)-2-(S)-methylpropyl]acetamide CE-2247 4-(R)-(2-N,N-Dimethylcarboxamido)-2,5-imidazolidinedione-N-[1-(2-[5-(3-methylbenzyl)-1,3,4-oxadiazolyl]carbonyl)-2-(S)-methylpropyl]acetamide CE-2248 2-Oxo-5-(3,4-methylendioxyphenyl)-1,4-benzodiazepine-N-[1-(2-[5-(3-methylbenzyl)-1,3,4-oxadiazolyl]carbonyl)-2-(S)-methylpropyl]acetamide CE-2249 4-(R)-(3-Carbomethoxy)propyl-2,5-imidazolidinedione-N-[1-(2-[5-(3-methylbenzyl)-1,3,4-oxadiazolyl]carbonyl)-2-(S)-methylpropyl]acetamide CE-2250 2-Oxo-5-(2-methoxyphenyl)-1,4-benzodiazepine-N-[1-(2-[5-( 3-methylbenzyl)-1,3,4-oxadiazolyl]carbonyl)-2-(S)-methylpropyl]acetamide CE-2251 2-[5-Amino-6-oxo-2-(4-fluorophenyl)-1,6-dihydro-1-pyridinyl]-N-[1-(2-[5-(3-methylbenzyl)-1,3,4-oxadiazolyl]carbonyl)-2-(S)-methylpropyl]acetamide CE-2252 4,4-Diphenyl-2,5-imidazolidinedione-N-[1-(2-[5-(3-methylbenzyl)-1,3,4-oxadiazolyl]carbonyl)-2-(S)-methylpropyl]acetamide CE-2253 4-Spiro-(2-indanyl)-2,5-imidazolidinedione-N-[1-(2-[5-(3-methylbenzyl)-1,3,4-oxadiazolyl]carbonyl)-2-(S)-methylpropyl]acetamide CE-2254 2-[(4-Fluorophenyl)-1,6-dihydro-1-pyrimidinyl]-N-[1-(2-[5-(3-methylbenzyl)-1,3,4-oxadiazolyl]carbonyl)-2-(S)-methylpropyl]acetamide CE-2255 4-(R)-(4-Hydroxybenzyl)-2,5-imidazolidinedione-N-[1-(2-[5-(3-methylbenzyl)-1,3,4-oxadiazolyl]carbonyl)-2-(S)-methylpropyl]acetamide CE-2256 4-(R)-(4-Hydroxybenzyl)-2,5-imidazolidinedione-N-[1-(2-[5-(3,4-methylenedioxybenzyl)-1,3,4-oxadiazolyl]carbonyl)-2-(S)-methylpropyl]acetamide CE-2257 4-(R)-(2-Imidazolyl)-2,5-imidazolidinedione-N-[1-(2-[5-(3-methylbenzyl)-1,3,4-oxadiazolyl]carbonyl)-2-(S)-methylpropyl]acetarnide CE-2258 2-Oxo-5-phenyl-1,4-(2'-dimethylaminobenzodiazepine)-N-[1-(2-[5-(3-methylbenzyl)-1,3,4-oxadiazolyl]carbonyl)-2-(S)-methylpropyl]acetamide CE-2259 4,4-Diphenyl-2,5-imidazolidinedione-N-[1-(2-[5-(3,4-methylenedioxybenzyl)-1,3,4-oxadiazolyl]carbonyl)-2-(S)-methylpropyl]acetamide CE-2260 2-[5-Amino-6-oxo-2-phenyl-1,6-dihydro-1-pyrimidinyl]-N-[1-(2-[5-(3-methylbenzyl)-1,3,4-oxadiazolyl]carbonyl)-2-(S)-methylpropyl]acetamide CE-2261 2-[5-Amino-6-oxo-2-(4-fluorophenyl)-1,6-dihydro-1-pyridinyl]-N-[1-(2-[5-(3,4-methylenedioxybenzyl)-1,3,4-oxadiazolyl]carbonyl)-2-(S)-methylpropyl]acetamide CE-2262 2-[5-Arnino-6-oxo-2-thiophenyl-1,6-dihydro-1-pyrimidinyl]-N-[1-(2-[5 (3-methylbenzyl)-1,3,4-oxadiazolyl]carbonyl)-2-(S)-methylpropyl]acetamide CE-2263 2-[5-Amino-6-oxo-2-(3-pyridyl)-1,6-dihydro-1-pyrimidinyl]-N-[1-(2-[5 (3-methylbenzyl)-1,3,4-oxadiazolyl]carbonyl)-2-(S)-methylpropyl]acetamide ONO-PO-690 2-[5-(Benzyloxycarbonyl)amino-6-oxo-2-(4-fluorophenyl)-1,6-dihydro-1-pyrimidinyl]-N-[1-(2-[5-(α,α-dimethylbenzyl)-1,3,4-oxadiazolyl]carbonyl)-2-(S)-methylpropyl]acetamide ONO-PO-691 2-[5-Amino-6-oxo-2-(4-fluorophenyl)-1,6-dihydro-1-pyrimidinyl]-N-[1-(2-[5-(α,α-dimethylbenzyl)-1,3,4-oxadiazolyl]carbonyl)-2-(S)-methylpropyl]acetamide ONO-PO-692 2-[5-Amino-6-oxo-2-(4-fluorophenyl)-1,6-dihydro-1-pyrimidinyl]-N-[1-(2-[5-(α,α-dimethyl-3-methylbenzyl)-1,3,4-oxadiazolyl]carbonyl)-2-(S)-methylpropyl]acetamide ONO-PO-693 2-[5-Amino-6-oxo-2-(4-fluorophenyl)-1,6-dihydro-1-pyrimidinyl]-N-[1-(2-[5-(3-methylbenzyl)-1,3,4-oxadiazolyl]carbonyl)-2-(R)-methylpropyl]acetamide ONO-PO-694 2-[5-Amino-6-oxo-2-(4-fluorophenyl)-1,6-dihydro-1-pyrimidinyl]-N-[1-(2-[5-phenyl-1,3,4-oxadiazolyl]carbonyl)-2-(S)-methylpropyl]acetamide ONO-PO-695 2-[5-Amino-6-oxo-2-(4-fluorophenyl)-1,6-dihydro-1-pyrimidinyl]-N-[1-(2-[5-(3-pyridyl)-1,3,4-oxadiazolyl]carbonyl)-2-(S)-methylpropyl]acetamide ONO-PO-696 2-[5-Amino-6-oxo-2-(4-fluorophenyl)-1,6-dihydro-1-pyrimidinyl]-N-[1-(2-[5-tert-butyl-1,3,4-oxadiazolyl]carbonyl)-2-(S)-methylpropyl]acetamide ONO-PO-697 2-[5-(Benzyloxycarbonyl)amino-6-oxo-2-(4-fluorophenyl)-1,6-dihydro-1-pyrimidinyl]-N-[1-(2-[5-phenyl-1,3,4-oxadiazolyl]carbonyl)-2-(S)-methylpropyl]acetamide ONO-PO-698 2-[5-(Benzyloxycarbonyl)amino-6-oxo-2-(4-fluorophenyl)-1,6-dihydro-1-pyrimidinyl]-N-[1-(2-[5-tert-butyl-1,3,4-oxadiazolyl]carbonyl)-2-(S)-methylpropyl]acetamide ONO-PO-699 2-[5-Amino-6-oxo-2-(4-fluorophenyl)-1,6-dihydro-1-pyrimidinyl]-N-[1-(2-[5-(4-methoxyphenyl)-1,3,4-oxadiazolyl]carbonyl)-2-(S)-methylpropyl]acetamide ONO-PO-700 2-[5-Amino-6-oxo-2-(4-fluorophenyl)-1,6-dihydro-1-pyrimidinyl]-N-[1-(2-[5-(α,α-dimethyl-3,4-methylenedioxybenzyl)-1,3,4-oxadiazolyl]carbonyl)-2-(S)-methylpropyl]acetamide ONO-PO-701 2-[5-Amino-6-oxo-2-(4-fluorophenyl)-1,6-dihydro-1 -pyrimidinyl]-N-[1-(2-[5-(α,α-dimethyl-3,4-dihydroxybenzyl)-1,3,4-oxadiazolyl]carbonyl)-2-(S)-methylpropyl]acetamide ONO-PO-702 2-[5-(Methylsulfonyl)amino-6-oxo-2-(4-fluorophenyl)-1,6-dihydro-1-pyrimidinyl]-N-[1-(2-[5-(3-methylbenzyl)-1,3,4-oxadiazolyl]carbonyl)-2-(S)-2-methylpropyl]acetamide ONO-PO-703 2-[5-Amino-6-oxo-2-(4-fluorophenyl)-1,6-dihydro-1-pyrimidinyl]-N-[1-(2-[5-benzyl-1,3,4-oxadiazolyl]carbonyl)-2-(S)-methylpropyl]acetamide ONO-PO-704 2-[5-Amino-6-oxo-2-(4-fluorophenyl)-1,6-dihydro-1-pyrimidinyl]-N-[1-(2-[5-methyl-1,3,4-oxadiazolyl]carbonyl)-2-(S)-methylpropyl]acetamide ONO-PO-705 2-[5-Amino-6-oxo-2-(4-fluorophenyl)-1,6-dihydro-2-[5-isopropyl-1,3,4-oxadiazolyl]carbonyl)-2-(S)-methylpropyl]acetamide ONO-PO-706 2-[5-Amino-6-oxo-2-(4-fluorophenyl)-1,6-dihydro-1-pyrimidinyl]-N-[1-(2-[5-butyl-1,3,4-oxadiazolyl]carbonyl)-2-(S)-methylpropyl]acetamide ONO-PO-707 2-[5-Amino-6-oxo-2-phenyl-1,6-dihydro-1-pyrimidinyl]-N-[1-(2-[5-tert-butyl-1,3,4-oxadiazolyl]carbonyl)-2-(S)-methylpropyl]acetamide ONO-PO-708 4-(S)-(2-Isobutyl)-2,5-imidazolidinedione-N-[1-(2-[5-tert-butyl-1,3,4-oxadiazolyl]carbonyl)-2-(S)-methylpropyl]acetamide ONO-PO-709 4-(S)-(2-Isobutyl)-2,5-imidazolidinedione-N-[1-(2-[5-(α,α-dimethylbenzyl)-1,3,4-oxadiazolyl]carbonyl)-2-(S)-methylpropyl]acetamide ONO-PO-710 Methylsulfonyl-L-valyl-N-[1-(2-[5-(α,α-dimethylbenzyl)-1,3,4-oxadiazolyl]carbonyl)-2-(S)-methylpropyl]-L-prolinamide ONO-PO-711 2-[5-Amino-6-oxo-2-phenyl-1,6-dihydro-1-pyrimidinyl]-N-[1-(2-[5-(α,α-dimethylbenzyl)-1,3,4-oxadiazolyl]carbonyl)-2-(S)-methylpropyl]acetamide ONO-PO-712 2-[5-Arnino-6-oxo-2-(3-pyridyl)-1,6-dihydro-1-pyrimidinyl]-N-[1-(2-[5-tert-butyl-1,3,4-oxadiazolyl]carbonyl)-2-(S)-methylpropyl]acetarnide ONO-PO-713 Methylsulfonyl-L-valyl-N-[1-(2-[5-(iert-butyl-1,3,4-oxadiazolyl]carbonyl)-2-(S)-methylpropyl]-L-prolinamide ONO-PO-714 2-[5-Amino-6-oxo-2-(4-fluorophenyl)-1,6-dihydro-1-pyrimidinyl]-N-[1-(2-[5-(1-methyl-cyclopropyl)-1,3,4-oxadiazolyl]carbonyl)-2-(S)-methylpropyl]acetamide ONO-PO-715 2-[5-Amino-6-oxo-2-(3-pyridyl)-1,6-dihydro-1-pyrimidinyl]-N-[1-(2-[5-(α,α-dimethylbenzyl)-1,3,4-oxadiazolyl]carbonyl)-2-(S)-methylpropyl]acetamide ONO-PO-716 2-[6-oxo-2-(4-fluorophenyl)-1,6-dihydro-1-pyrimidinyl]-N-[1-(2-[5-(tert-butyl)-1,3,4-oxadiazolyl]carbonyl)-2-(S)-methylpropyl]acetamide ONO-PO-717 2-Oxo-5-(4-chlorophenyl)-1,4-benzodiazepine-N-[1-(2-[5-tert-butyl-1,3,4-oxadiazolyl]carbonyl)-2-(S)-methylpropyl]acetamide ONO-PO-718 2-[5-Amino-6-oxo-2-(4-fluorophenyl)-1,6-dihydro-1-pyrimidinyl]-N-[1-(2-[5-(tert-butyl)-1,3,4-oxadiazolyl]carbonyl)-2-(R)-methylpropyl]acetamide ONO-PO-719 4-(R)-Isopropyl-2,5-imidazolidinedione-N-[1-(2-[5-tert-butyl-1,3,4-oxadiazolyl]carbonyl)-2-(S)-methylpropyl]acetamide ONO-PO-720 4-(R)-Isopropyl-2,5-imidazolidinedione-N-[1-(2-[5-(α,α-dimethylbenzyl)-1,3,4-oxadiazolyl]carbonyl)-2-(S)-methylpropyl]acetamide ONO-PO-721 2-[5-Amino-6-oxo-2-(4-fluorophenyl)-1,6-dihydro-1-pyrimidinyl]-N-[1-(2-[5-(α,α-dimethylbenzyl)-1,3,4-oxadiazolyl]carbonyl)-2-(R)-methylpropyl]acetarnide ONO-PO-722 2-[6-Oxo-2-(4-fluorophenyl)-1,6-dihydro-1-pyrimidinyl]-N-[1-(2-[5-(α,α-dimethylbenzyl)-1,3,4-oxadiazolyl]carbonyl)-2-(S)-methylpropyl]acetamide ONO-PO-723 4-(R)-(3-Indolyl)-2,5-imidazolidinedione-N-[1-(2-[5-tert-butyl-1,3,4-oxadiazolyl]carbonyl)-2-(S)-methylpropyl]acetamide ONO-PO-724 4-(R)-(3-Indolyl)-2,5-imidazolidinedione-N-[1-(2-[5-(α,α-dimethylbenzyl)-1,3,4-oxadiazolyl]carbonyl)-2-(S)-methylpropyl]acetamide ONO-PO-725 2-[6-Oxo-2-phenyl-1,6-dihydro-1-pyridinyl]-N-[1-(2-[5-tert-butyl-1,3,4-oxadiazolyl]carbonyl)-2-(S)-methylpropyl]acetamide ONO-PO-726 2-[6-Oxo-2-phenyl-1,6-dihydro-1-pyridinyl]-N-[1-(2-[5-(α,α-dimethylbenzyl)-1,3,4-oxadiazolyl]carbonyl)-2-(S)-methylpropyl]acetamide ONO-PO-727 2-[6-Oxo-2-(4-fluorophenyl)-1,6-dihydro-1-pyrimidinyl]-N-[1-(2-[5-tert-butyl-1,3,4-oxadiazolyl]carbonyl)-2-(R)-methylpropyl]acetamide ONO-PO-728 2-[5-Amino-6-oxo-2-phenyl-1,6-dihydro-1-pyrimidinyl]-N-[1-(2-[5-(1-methylcyclopropyl)-1,3,4-oxadiazolyl]carbonyl)-2-(S)-methylpropyl]acetamide ONO-PO-729 2-[5-Amino-6-oxo-2-phenyl-1,6-dihydro-1-pyrimidinyl]-N-[1-(2-[5-tert-butyl-1,3,4-oxadiazolyl]carbonyl)-2-(R)-methylpropyl]acetamide ONO-PO-730 2-[6-Oxo-2-phenyl-1,6-dihydro-1-pyrimidinyl]-N-[1-(2-[5-tert-butyl-1,3,4-oxadiazolyl]carbonyl)-2-(S)-methylpropyl]acetamide ONO-PO-731 2-[6-Oxo-2-phenyl-1,6-dihydro-1-pyrimidinyl]-N-[1-(2-[5-α,α-dimethylbenzyl-1,3,4-oxadiazolyl]carbonyl)-2-(S)-methylpropyl]acetamide ONO-PO-732 2-[6-Oxo-2-phenyl-1,6-dihydro-1-pyrimidinyl]-N-[1-( 2-[5-tert-butyl-1,3,4-oxadiazolyl]carbonyl)-2-(R)-methylpropyl]acetamide ONO-PO-733 2-[5-Amino-6-oxo-2-(4-fluorophenyl)-1,6-dihydro-1-pyrimidinyl]-N-[1-(2-[5-tert-butyl-1,3,4-oxadiazolyl]carbonyl)-2-(R,S)-methylpropyl]acetamide ONO-PO-734 2-[6-Oxo-2-(4-fluorophenyl)-1,6-dihydro-1-pyrimidinyl]-N-[1-(2-[5-(1-methylcyclopropyl)-1,3,4-oxadiazolyl]carbonyl)-2-(S)-methylpropyl]acetamide ONO-PO-735 2-[6-Oxo-2-phenyl-1,6-dihydro-1-pyrimidinyl]-N-[1-(2-[5-(1-methylcyclopropyl)-1,3,4-oxadiazolyl]carbonyl)-2-(S)-methylpropyl]acetamide ONO-PO-736 2-[5-Amino-6-oxo-2-phenyl-1,6-dihydro-1-pyrimidinyl]-N-[1-(2-[5-tert-butyl-1,3,4-oxadiazolyl]carbonyl)-2-(R,S)-methylpropyl]acetamide ONO-PO-737 2-[6-Oxo-2-phenyl)-1,6-dihydro-1-pyrimidinyl]-N-[1-(2-[5-tert-butyl-1,3,4-oxadiazolyl]carbonyl)-2-(R,S)-methylpropyl]acetamide The compounds of the present invention are not limited to use for inhibition of human elastase. Elastase is a member of the class of enzymes known as serine proteases. This class also includes, for example, the enzymes chymotrypsin, cathepsin G, trypsin and thrombin. These proteases have in common a catalytic triad consisting of Serine-195, Histidine-57 and Aspartic acid-102 (chymotrypsin numbering system). The precise hydrogen bond network that exists between these amino acid residues allows the Serine-195 hydroxyl to form a tetrahedral intermediate with the carbonyl of an amide substrate. The decomposition of this intermediate results in the release of a free amine and the acylated enzyme. In a subsequent step, this newly formed ester is hydrolyzed to give the native enzyme and the carboxylic acid. It is this carboxyl component that helps characterize the specificity for the enzyme. In the example in which the carboxyl component is a peptide, the alpha-substituent of the amino acid is predominately responsible for the specificity toward the enzyme. Utilizing the well accepted subset nomenclature by Schechter and Berger (*Biochem. Biophy. Res. Commun.*, 27:157 (1967) and *Biochem. Biophys. Res. Commun.*, 32:898 (1968)), the amino acid residues in the substrate that undergo the cleavage are defined as $P_l \ldots P_n$ toward the N-terminus and $P_l' \ldots P_n'$ toward the C-terminus. Therefore, the scissile bond is between the $P_l$ and the $P_l'$ residue of the peptide subunits. A similar nomenclature is utilized for the amino acid residues of the enzyme that make up the binding pockets accommodating the subunits of the substrate. The difference is that the binding pocket for the enzyme is designated by $S_l \ldots S_n$ instead of $P_l \ldots P_n$ as for the substrate.

The characteristics for the $P_l$ residue defining serine proteinase specificity is well established. The proteinases may be segregated into three subclasses: elastases, chymases and tryptases based on these differences in the $P_l$ residues. The elastases prefer small aliphatic moieties such as valine whereas the chymases and tryptases prefer large aromatic hydrophobic and positively charged residues respectively.

One additional proteinase that does not fall into one of these categories is propyl endopeptidase. The $P_l$ residue defining the specificity is a proline. This enzyme has been implicated in the progression of memory loss in Alzheimer's patients. Inhibitors consisting of α-keto heterocycles have recently been shown to inhibit propyl endopeptidase; Tsutsumi et al., *J. Med. Chem.*, 37: 3492–3502 (1994). By way of extension, α-keto heterocycles as defined herein allow for an increased binding in P' region of the enzyme.

TABLE 1

$P_1$ Characteristics for Proteinase Specificity

| Proteinase Class | Representative Enzyme | $P_1$ Characteristic |
| --- | --- | --- |
| Elastases | Human Neutrophil Elastase | small aliphatic residues |
| Chymases | alpha-Chymotrypsin, Cathepsin G | aromatic or large hydrophobic residues |
| Tryptases | Thrombin, Trypsin, Urokinase, Plasma Kallikrein, Plasminogen Activator, Plasmin | positively charged residues |
| Other | Prolyl Endopeptidase | proline |

Since the $P_l$ residue predominately defines the specificity of the substrate, the present invention relates to $P_l$-$P_n'$ modifications, specifically, certain alpha-substituted keto-heterocycles composed of 1,3,4 oxadiazoles, 1,2,4-oxadiazoles, 1,3,4-thiadiazoles, 1,2,4-thiadiazoles, 1-substituted, and 4-substituted 1,2,4-triazoles. By altering the alpha-substituent and the substituent on the heterocycle, the specificity of these compounds can be directed toward the desired proteinase (e.g., small aliphatic groups for elastase).

The efficacy of the compounds for the treatment of various diseases can be determined by scientific methods which are known in the art. The following are noted as examples for HNE mediated conditions:

for acute respiratory distress syndrome, the method according to human neutrophil elastase (HNE) model (*AARD*, 141:227–677 (1990)); the endotoxin induced acute lung injury model in minipigs (*AARD*, 142:782–788 (1990)); or the method according to human polymorphonuclear elastase-induced lung hemorrage model in hamsters (European Patent Publication No. 0769498) may be used;

in ischemia/reperfusion, the method according to the canine model of reperfusion injury (*J. Clin. Invest.*, 81: 624–629 (1988)) may be used.

Figure 2:
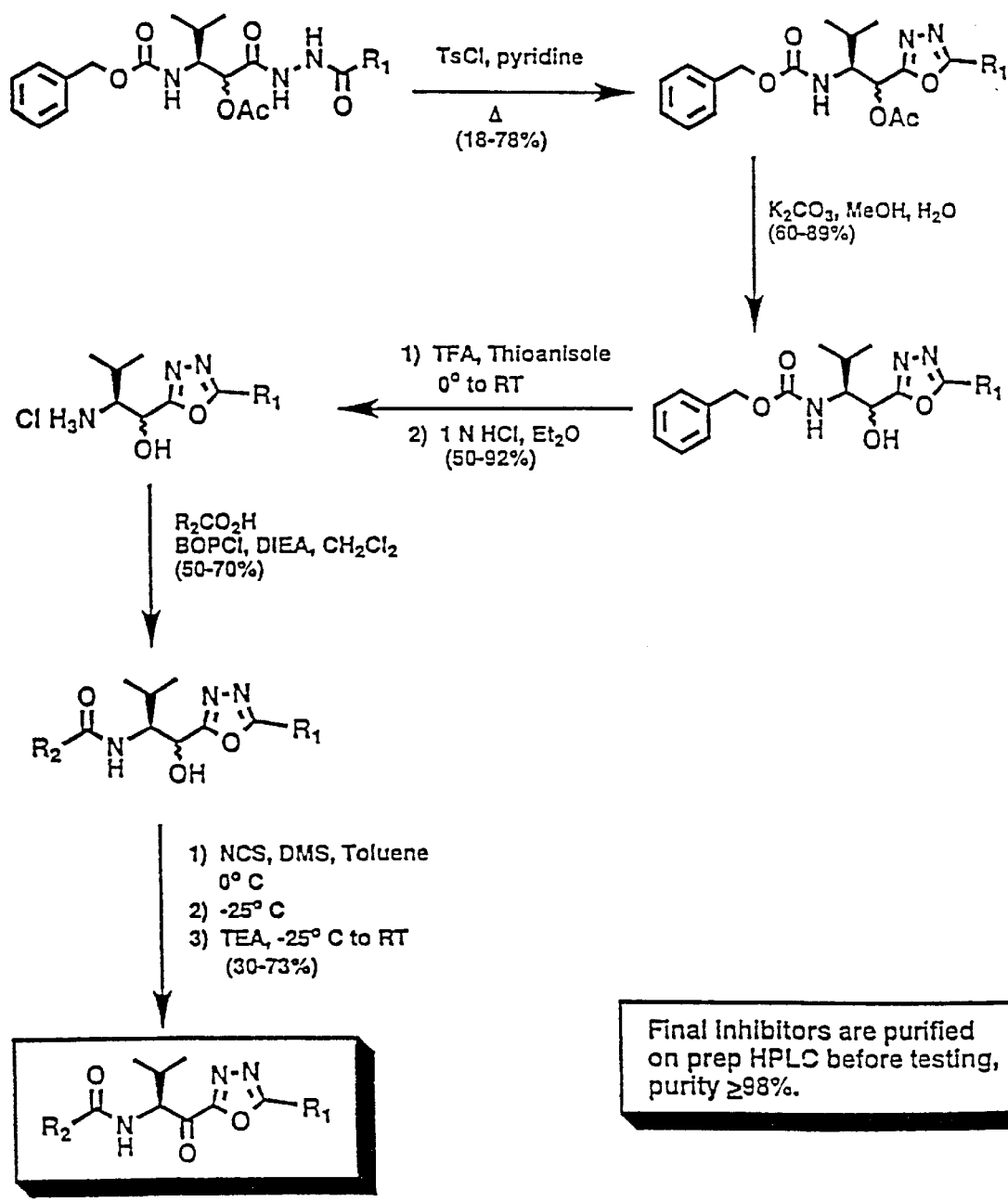
FIG. 2 is a schematic representation of the synthesis of compounds of Group I.
Figure 3:
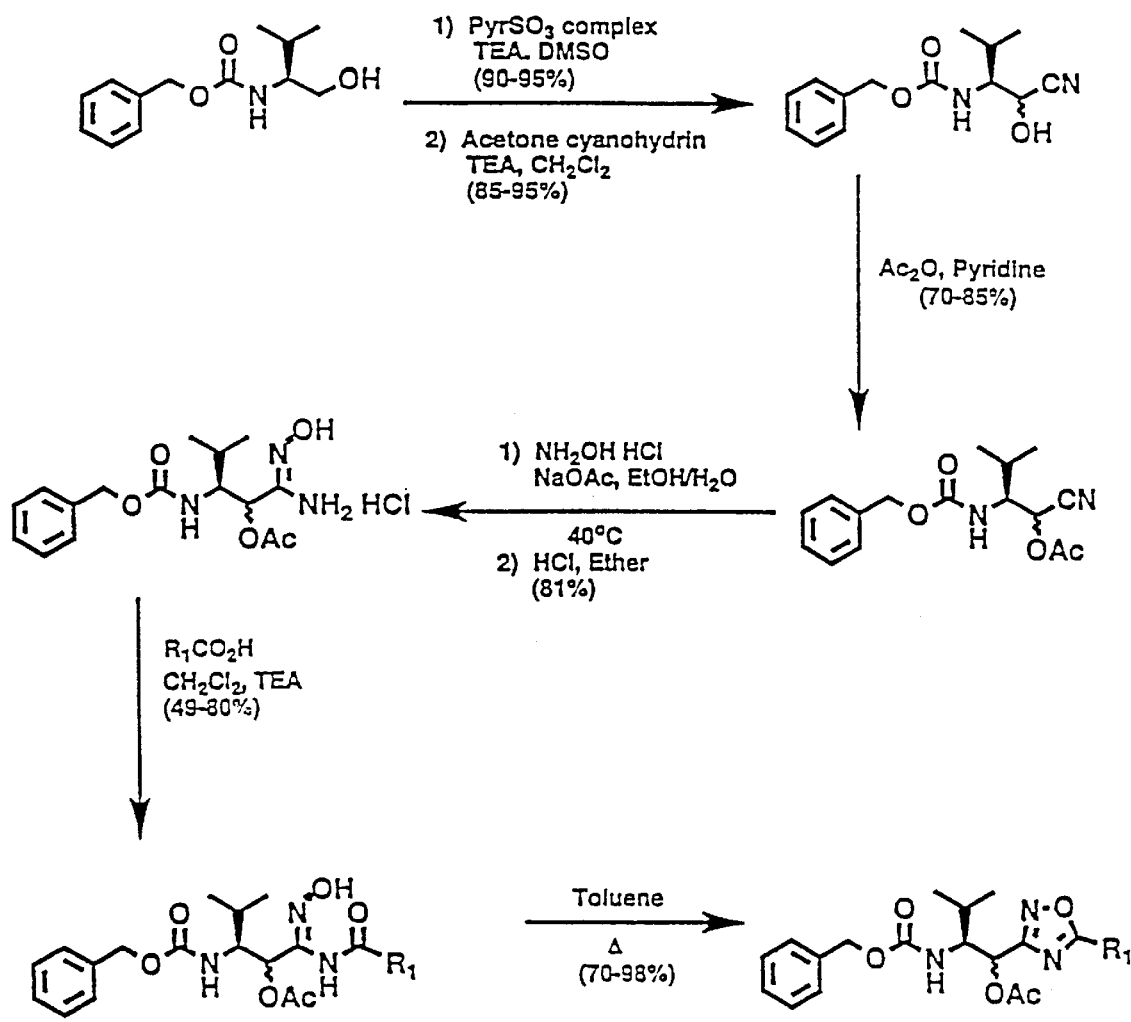
FIG. 3 is a schematic representation of the synthesis of compounds of Group I.
Figure 4:
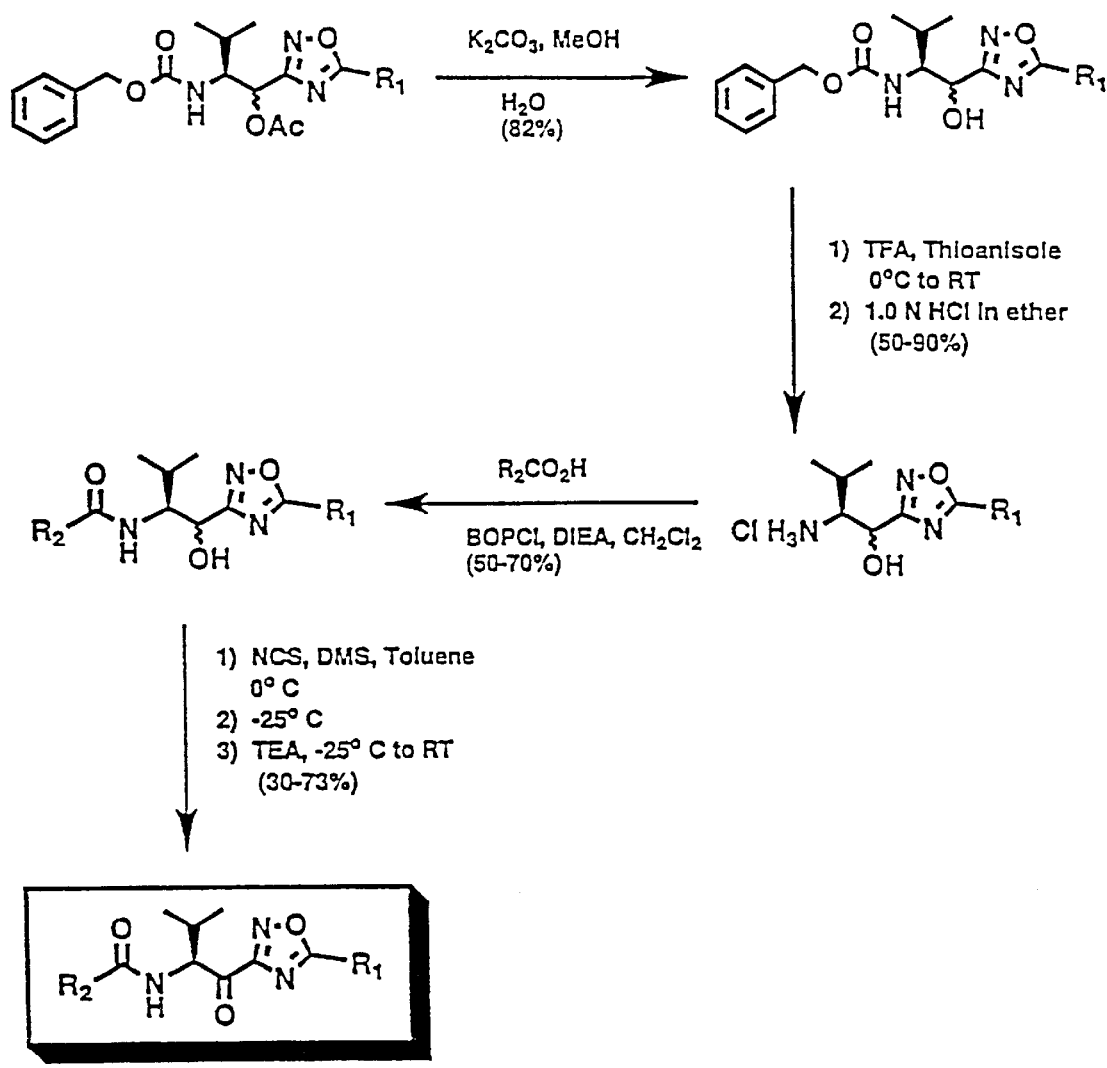
FIG. 4 is a schematic representation of the synthesis of compounds of Group I.
Figure 5:
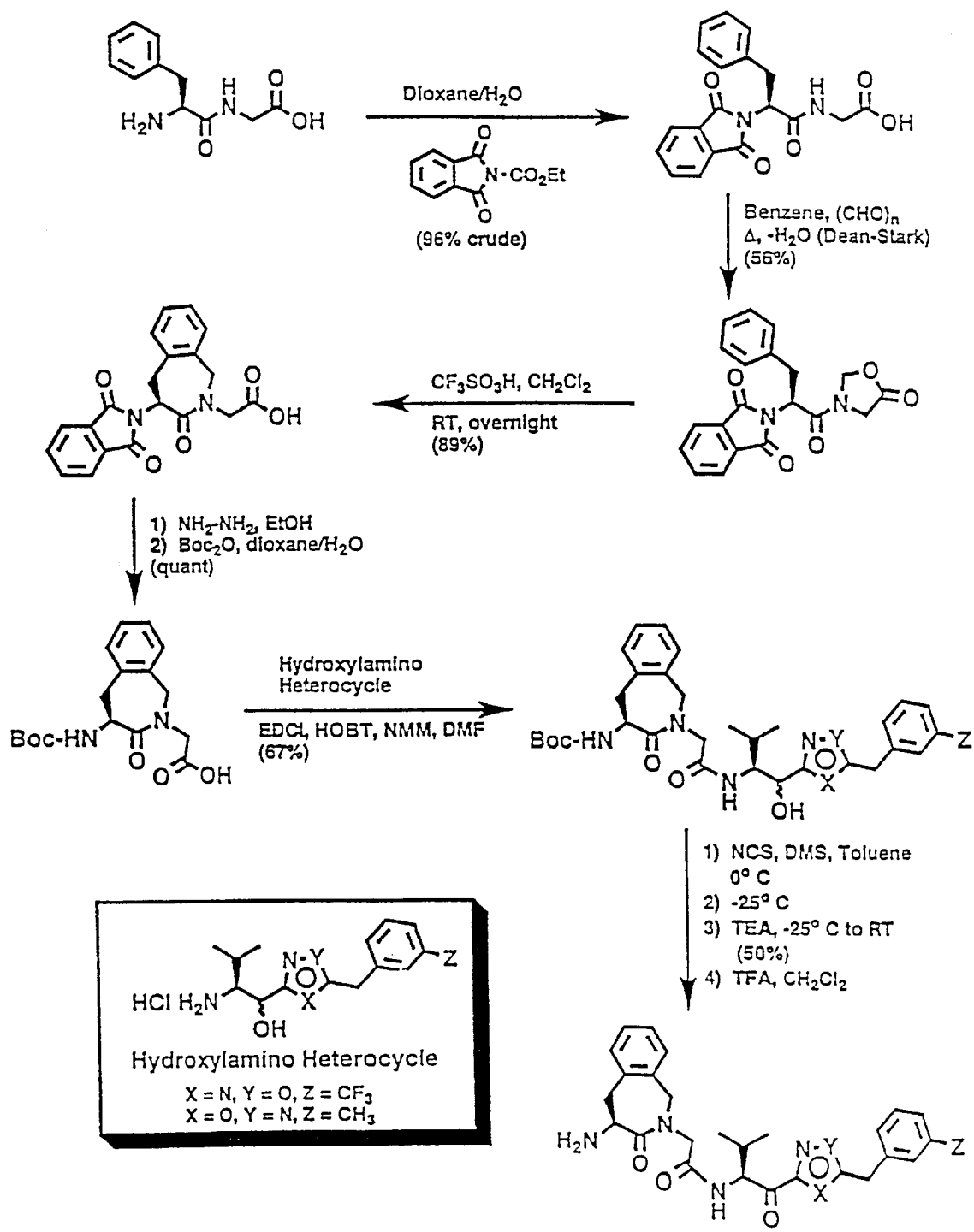
FIG. 5 is a schematic representation of the synthesis of compounds of Group II.
Figure 6:
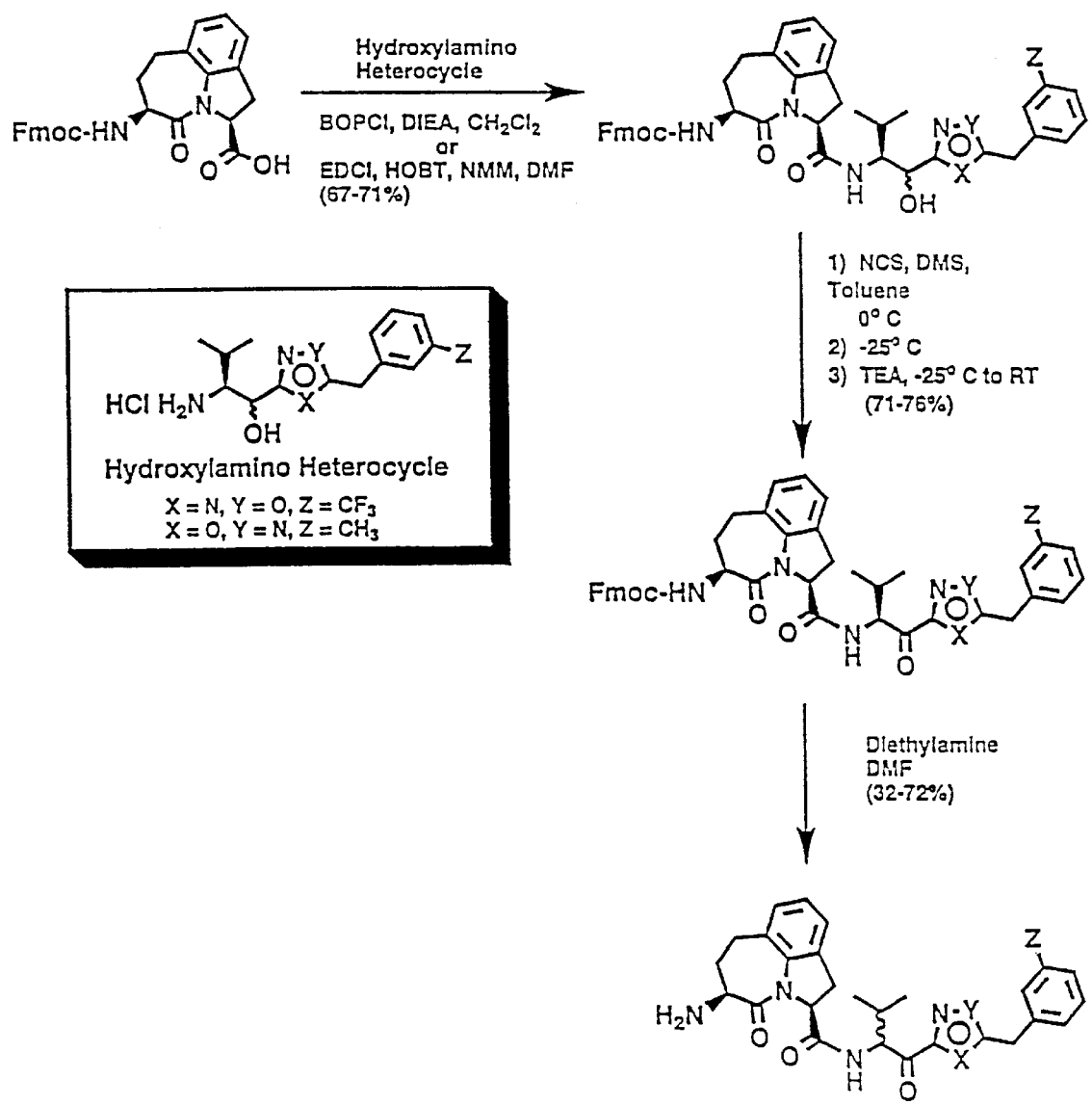
FIG. 6 is a schematic representation of the synthesis of compounds of Group II.
Figure 7:
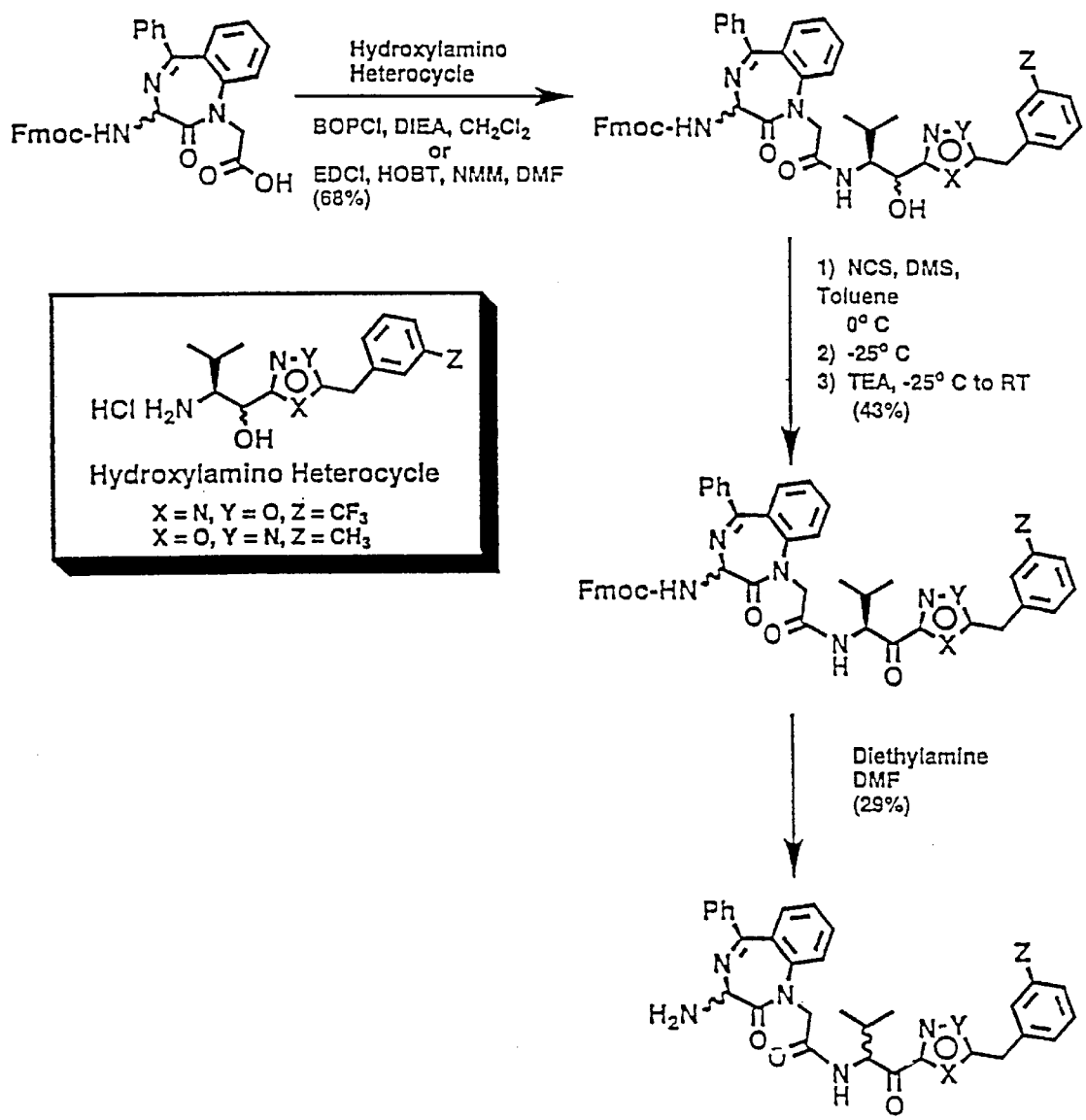
FIG. 7 is a schematic representation of the synthesis of compounds of Group II.
Figure 8:
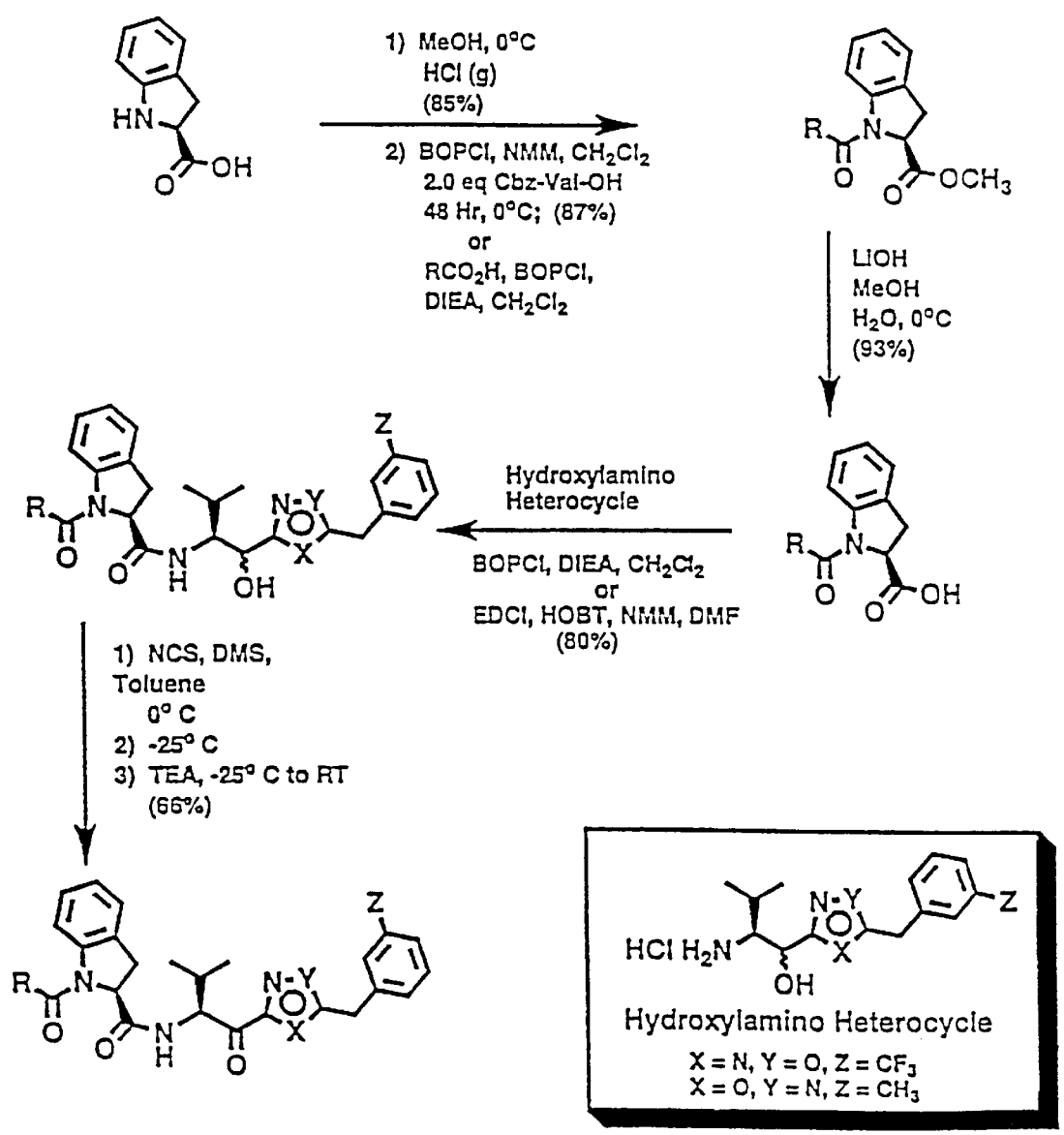
FIG. 8 is a schematic representation of the synthesis of compounds of Group III.
Figure 9:
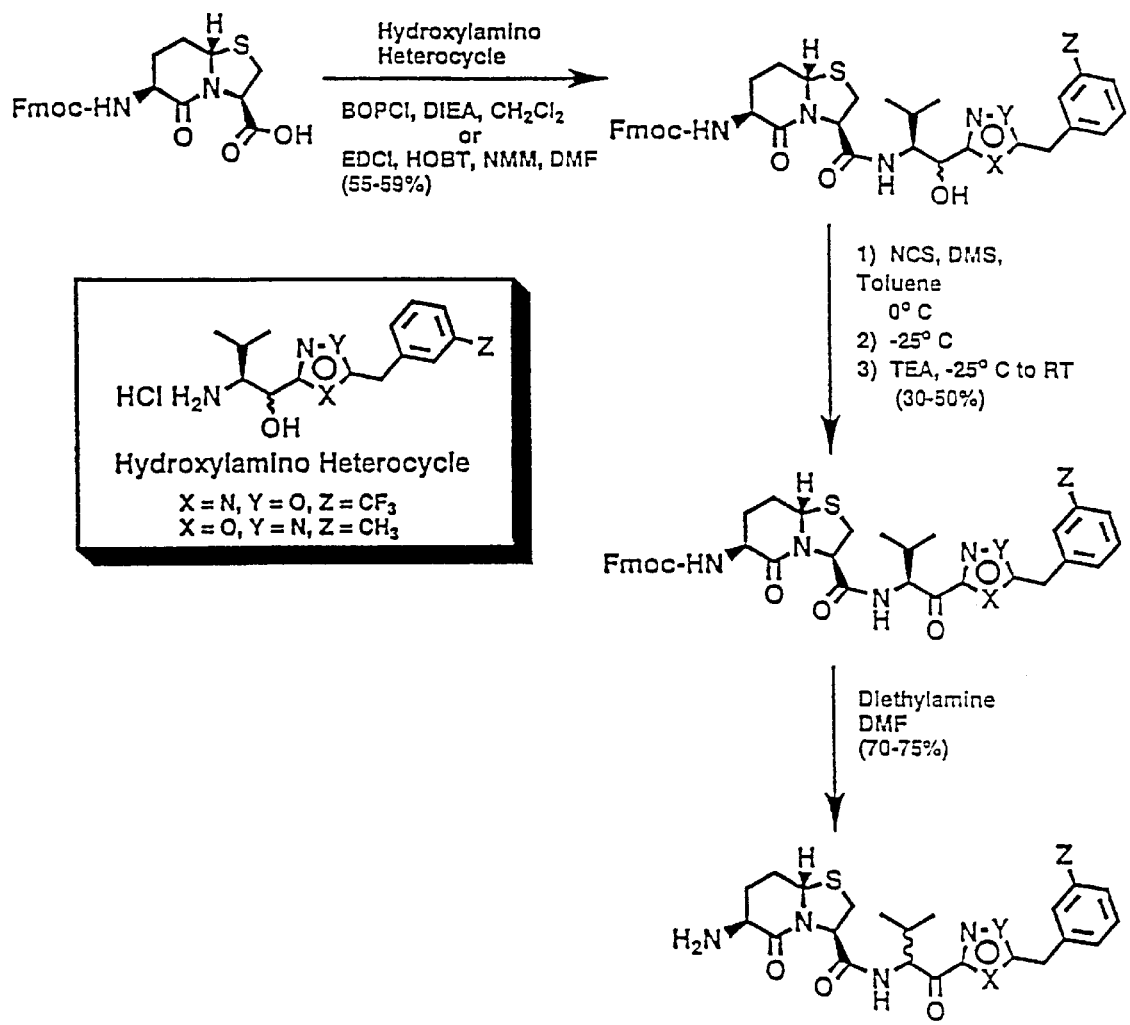
FIG. 9 is a schematic representation of the synthesis of compounds of Group III.
Figure 10:
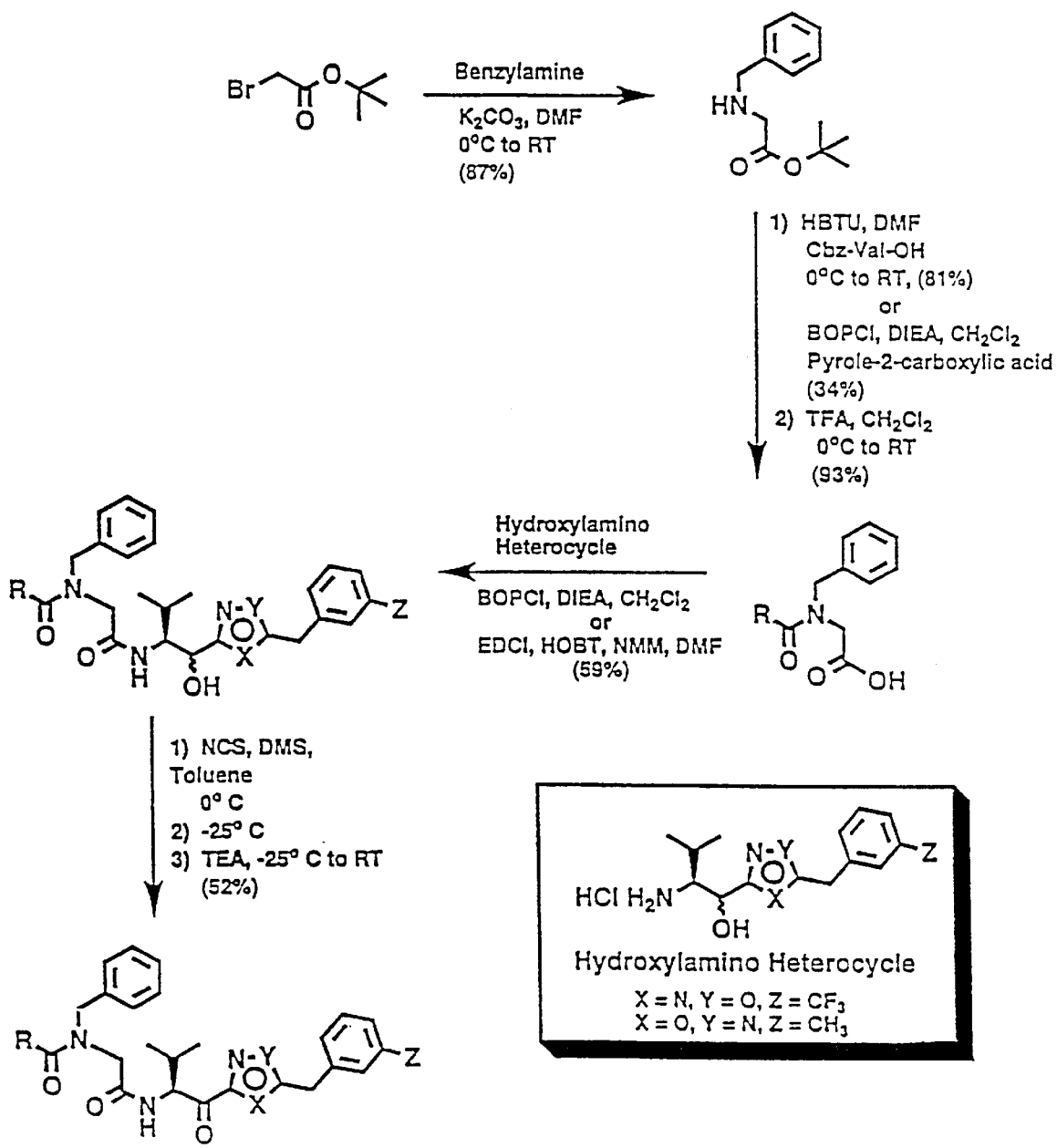
FIG. 10 is a schematic representation of the synthesis of compounds of Group IV.
Figure 11:
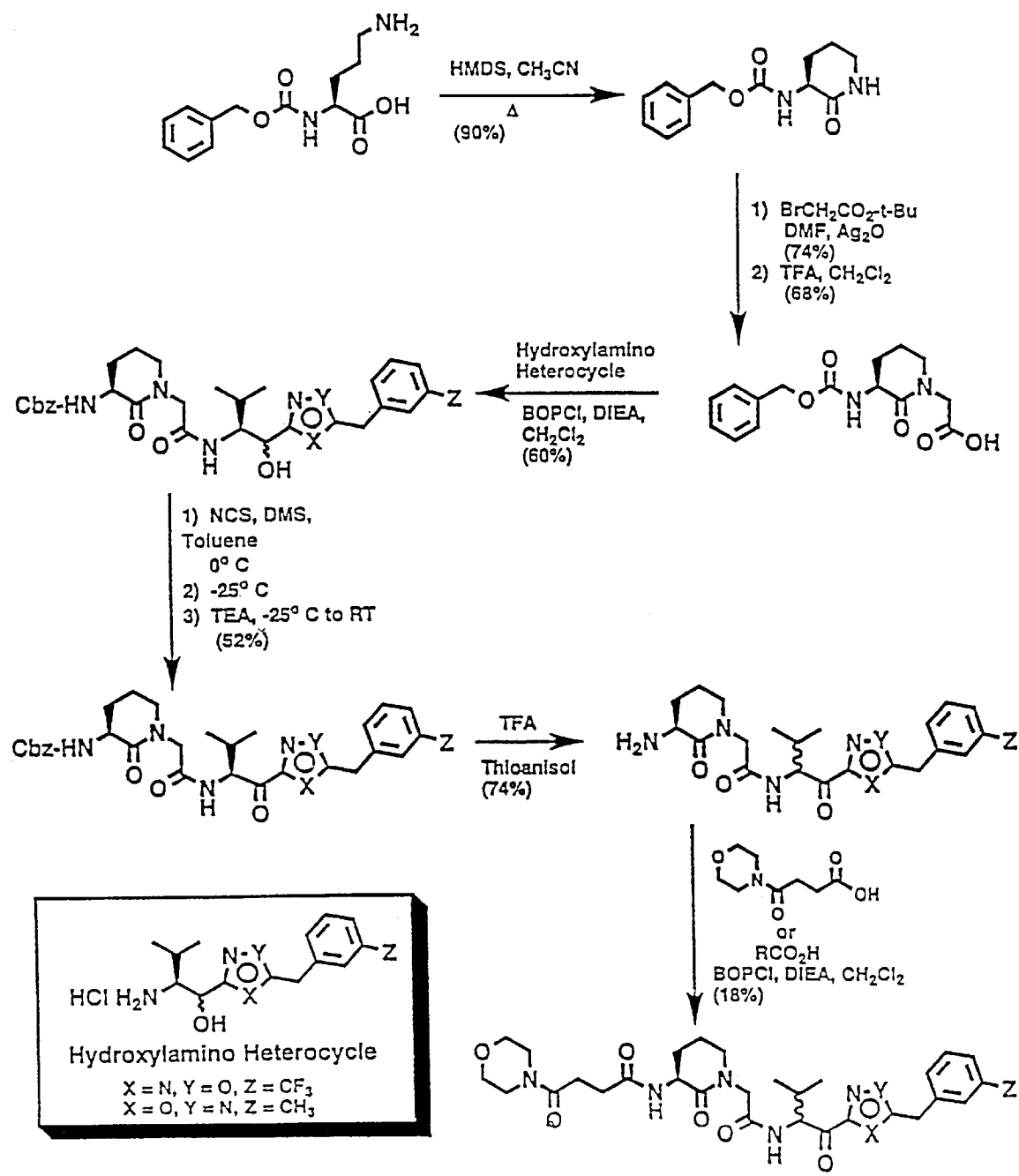
FIG. 11 is a schematic representation of the synthesis of compounds of Group V.
Figure 12:
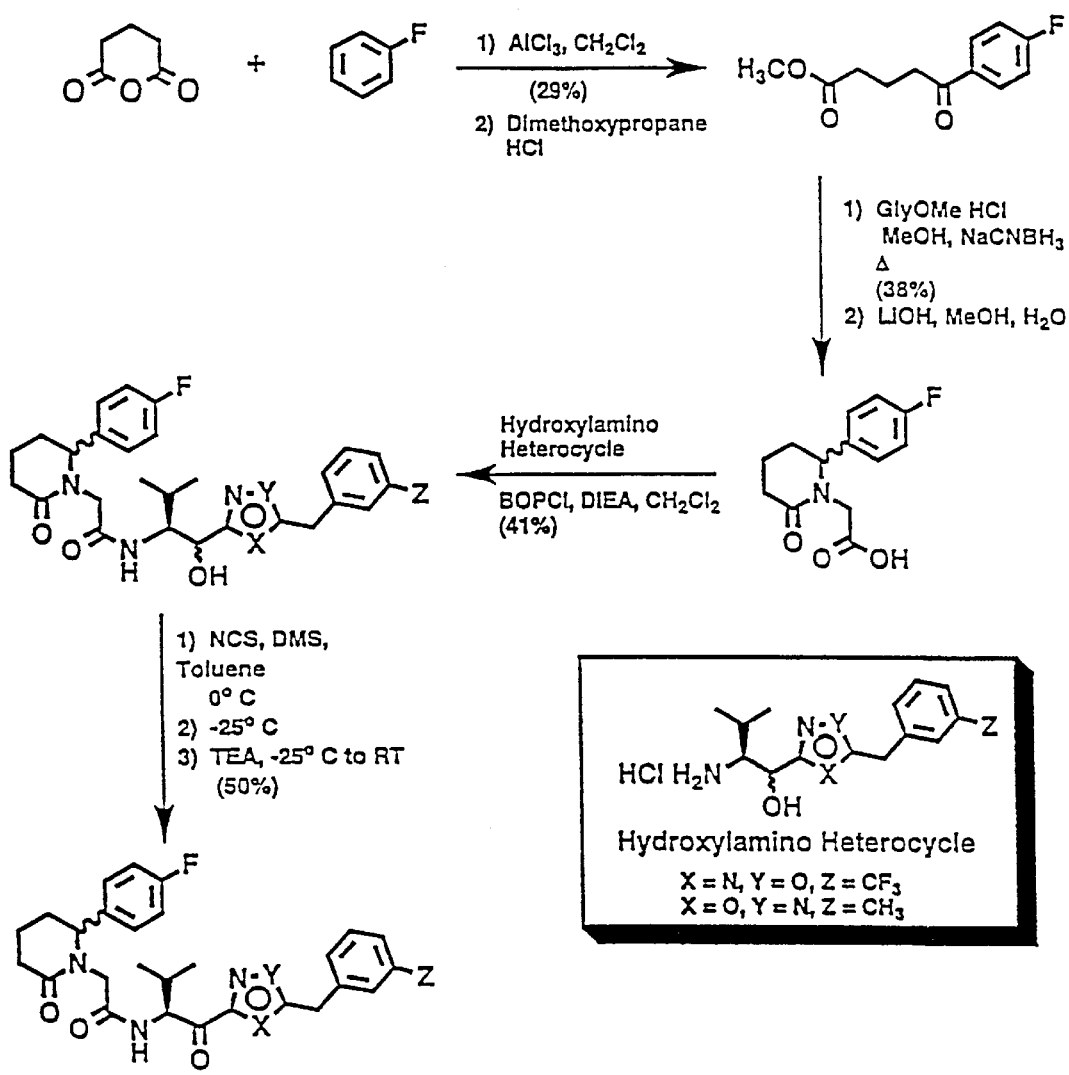
FIG. 12 is a schematic representation of the synthesis of compounds of Group V.
Figure 13:
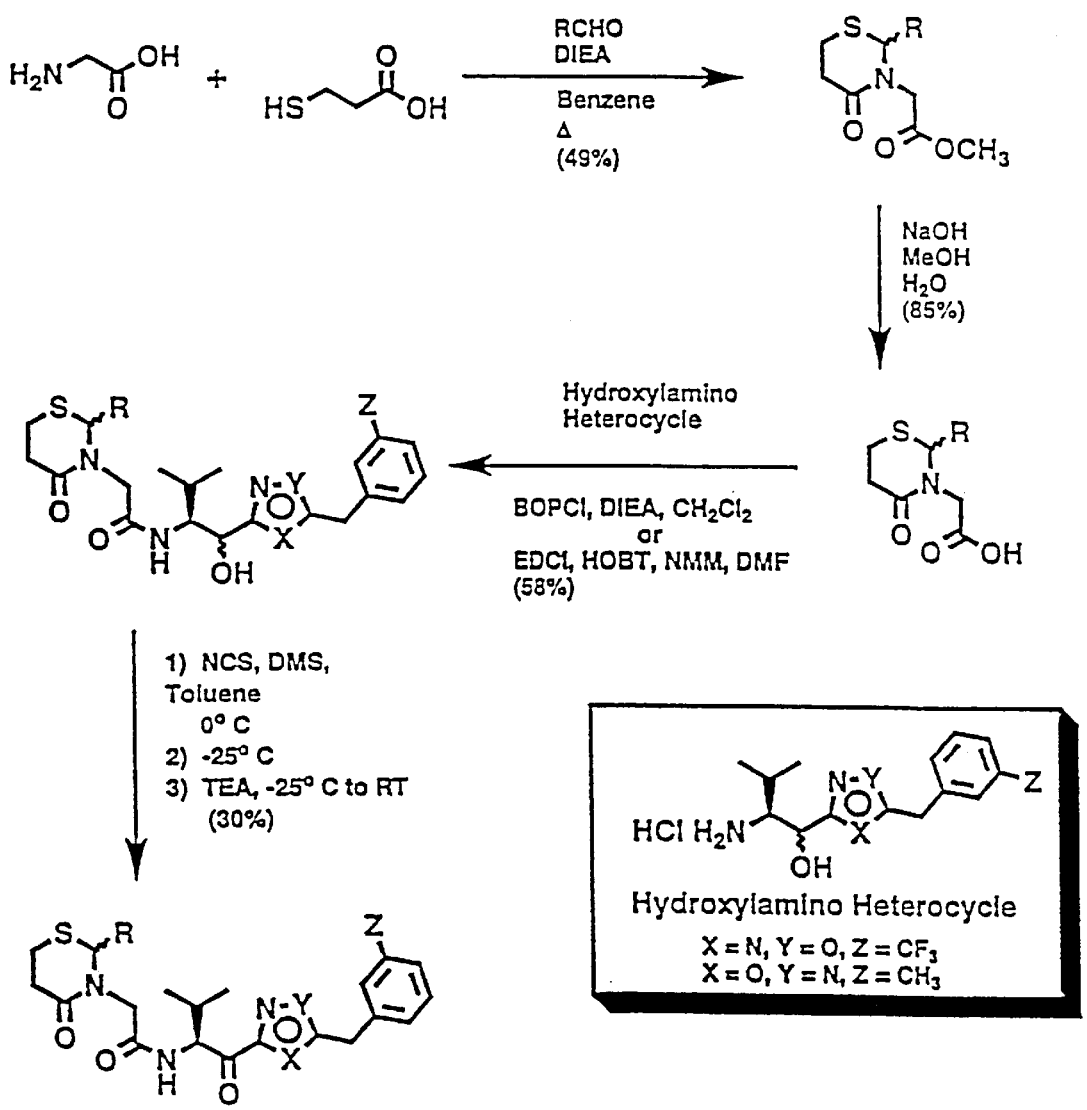
FIG. 13 is a schematic representation of the synthesis of compounds of Group V.
Figure 14:
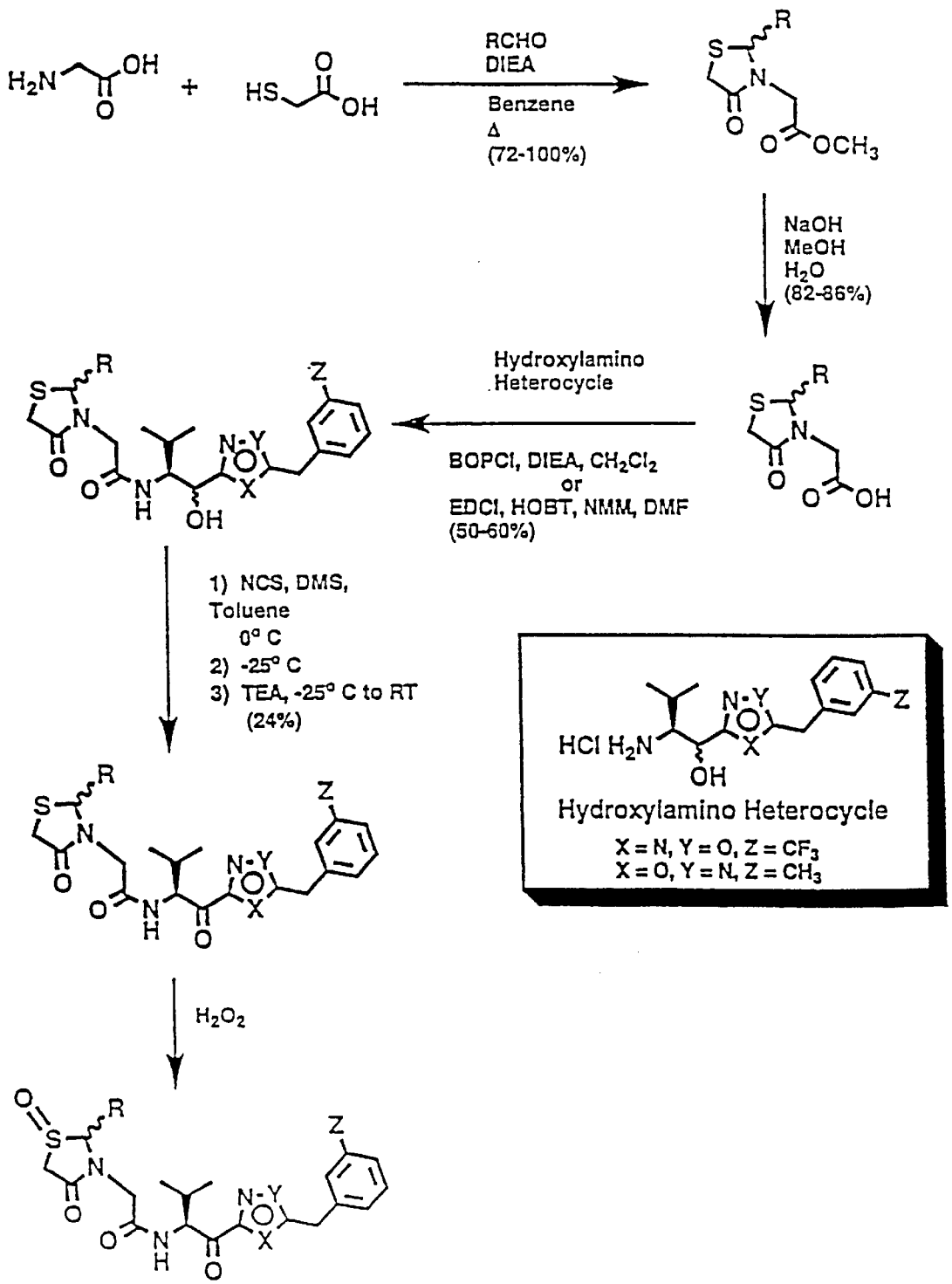
FIG. 14 is a schematic representation of the synthesis of compounds of Group V.
Figure 15:
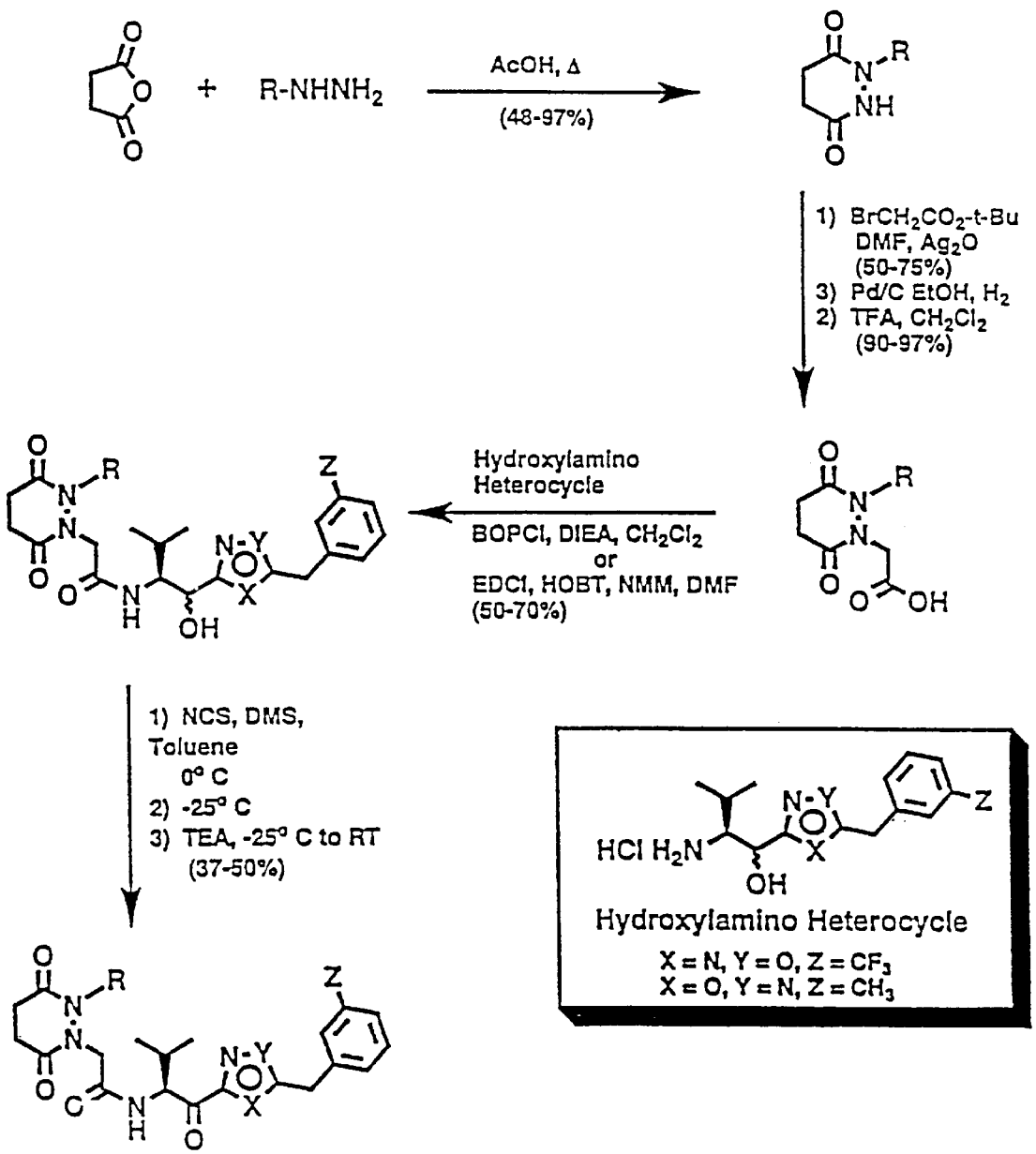
FIG. 15 is a schematic representation of the synthesis of compounds of Group V.
Figure 16:
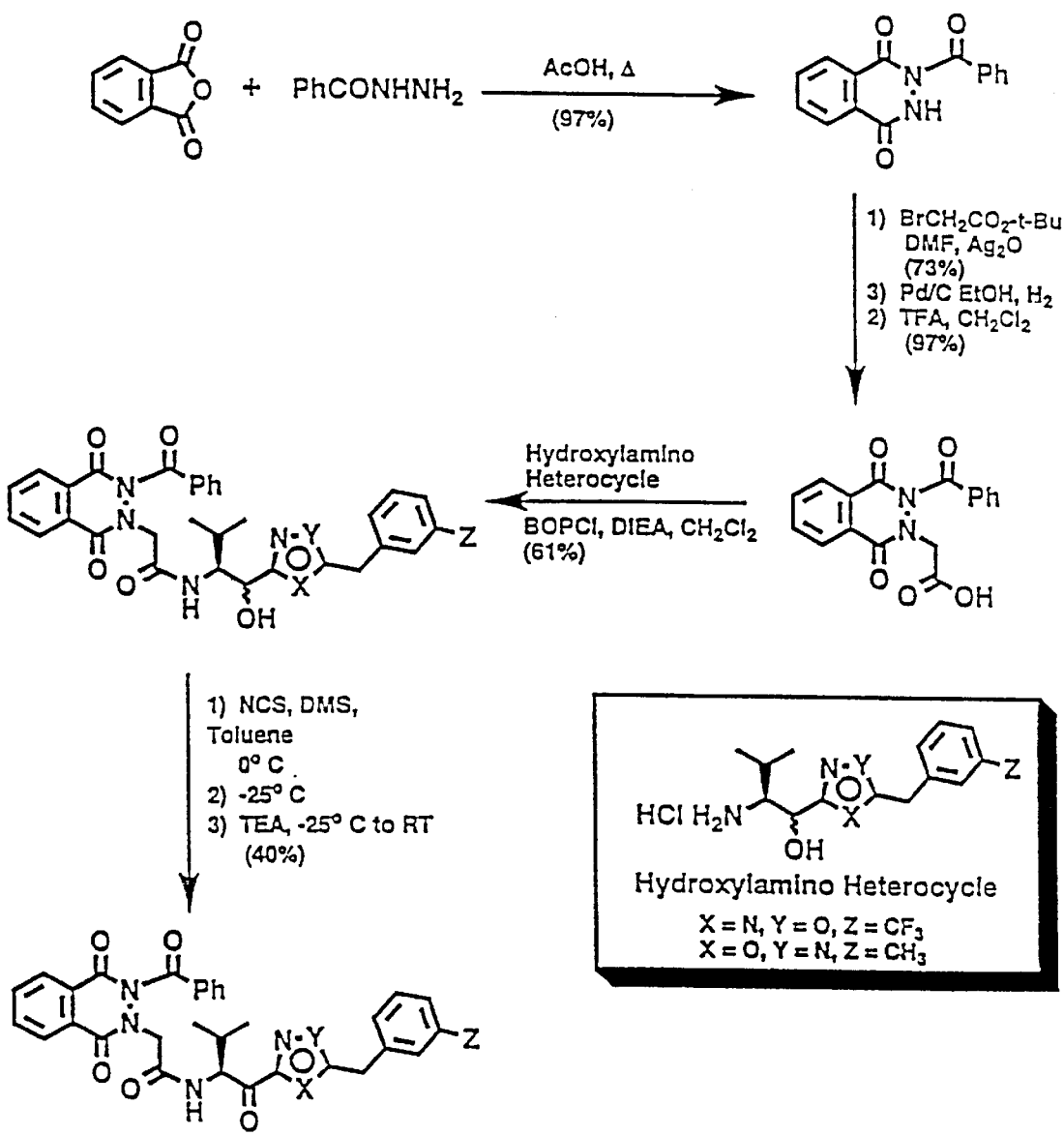
FIG. 16 is a schematic representation of the synthesis of compounds of Group V.
Figure 17:
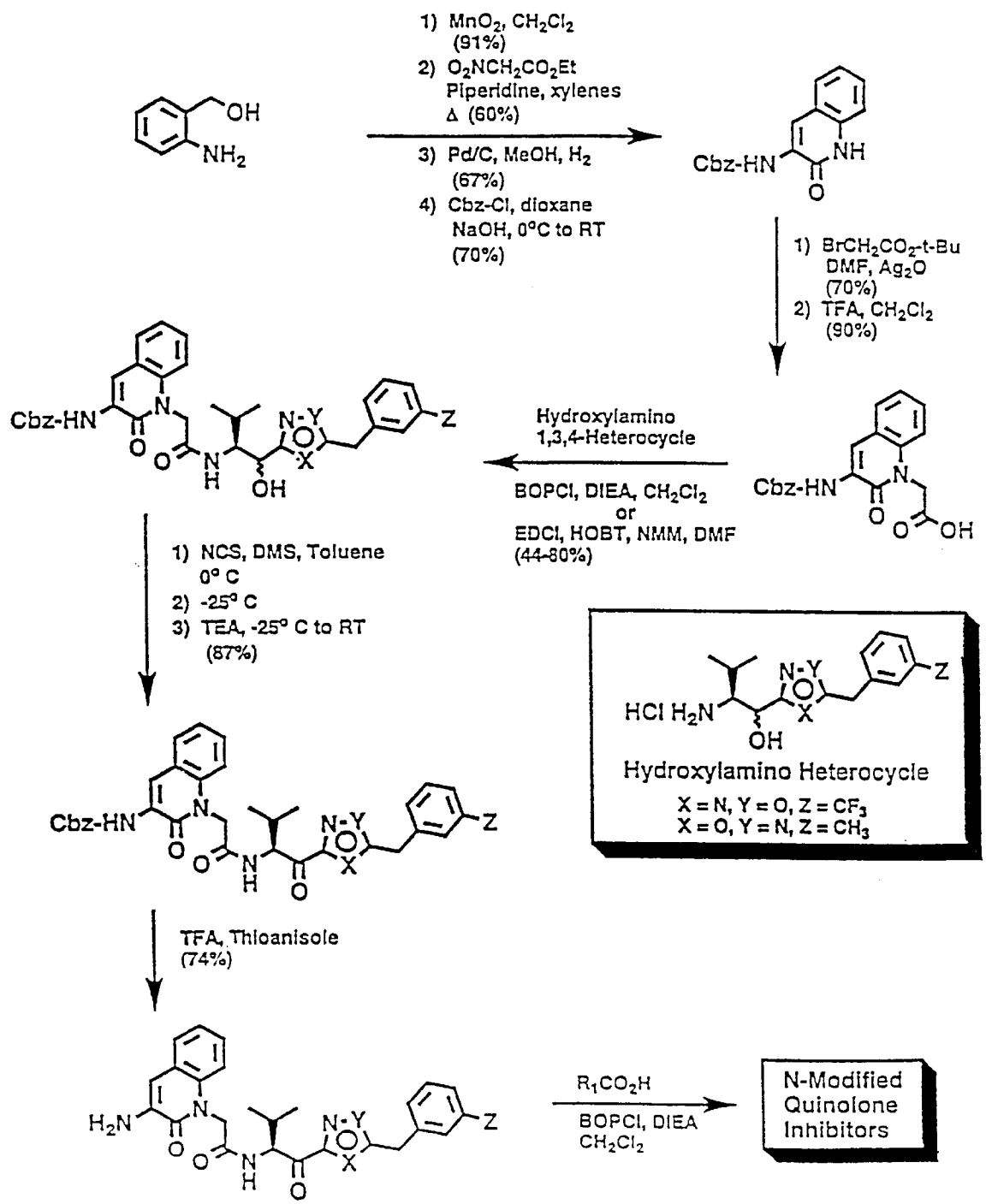
FIG. 17 is a schematic representation of the synthesis of compounds of Group V.
Figure 18:
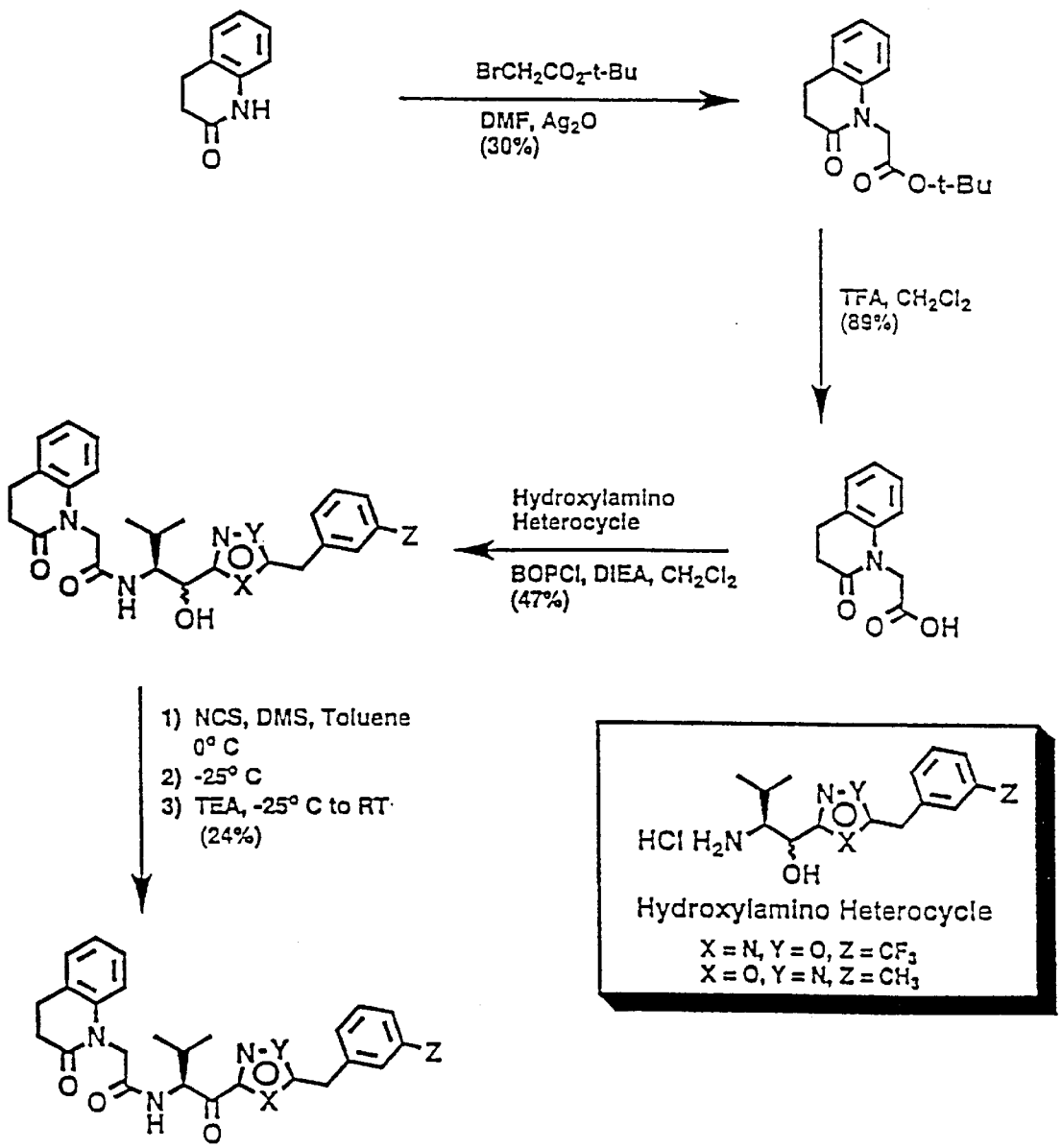
FIG. 18 is a schematic representation of the synthesis of compounds of Group V.
Figure 19:
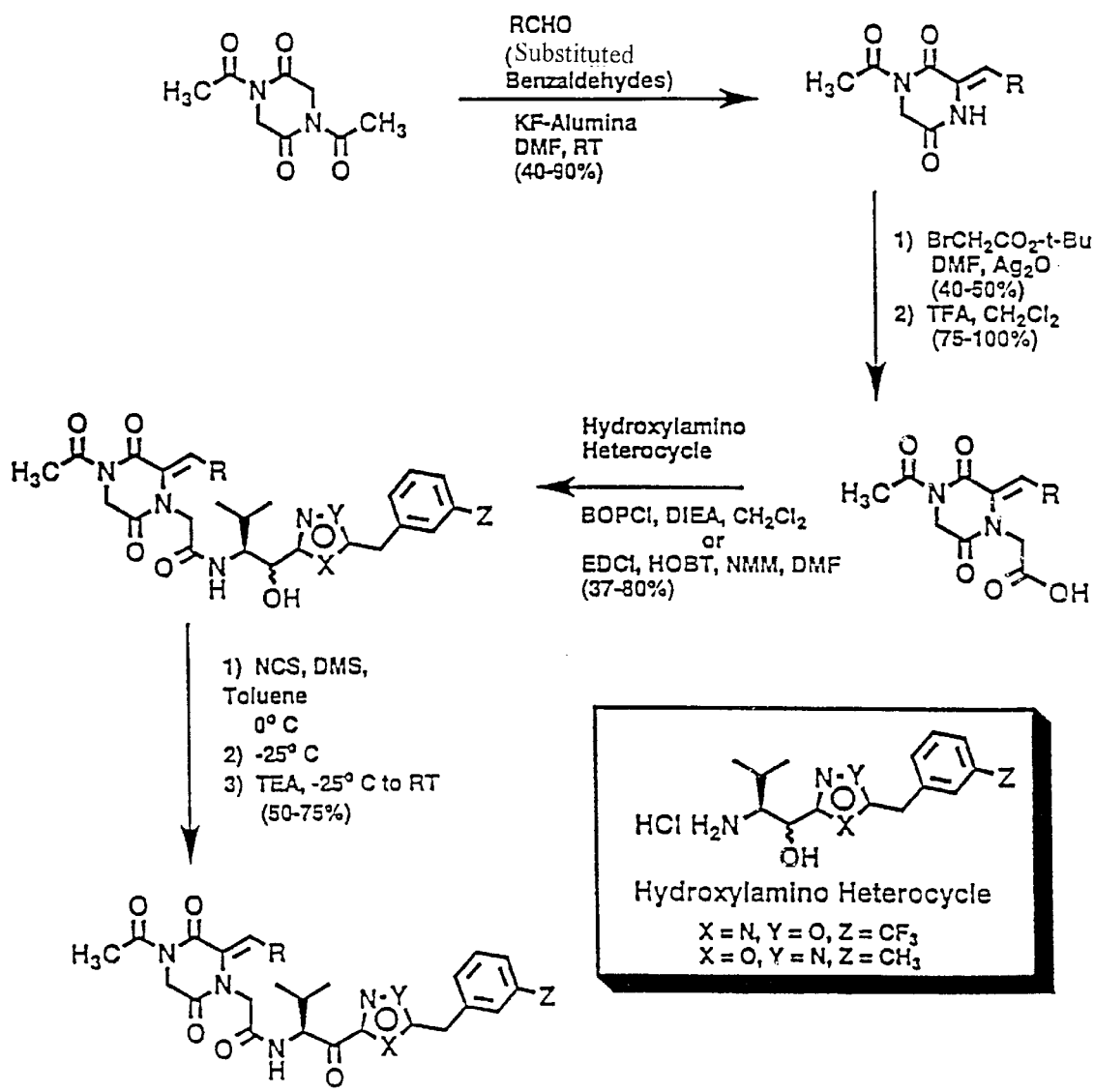
FIG. 19 is a schematic representation of the synthesis of compounds of Group V.
Figure 20:
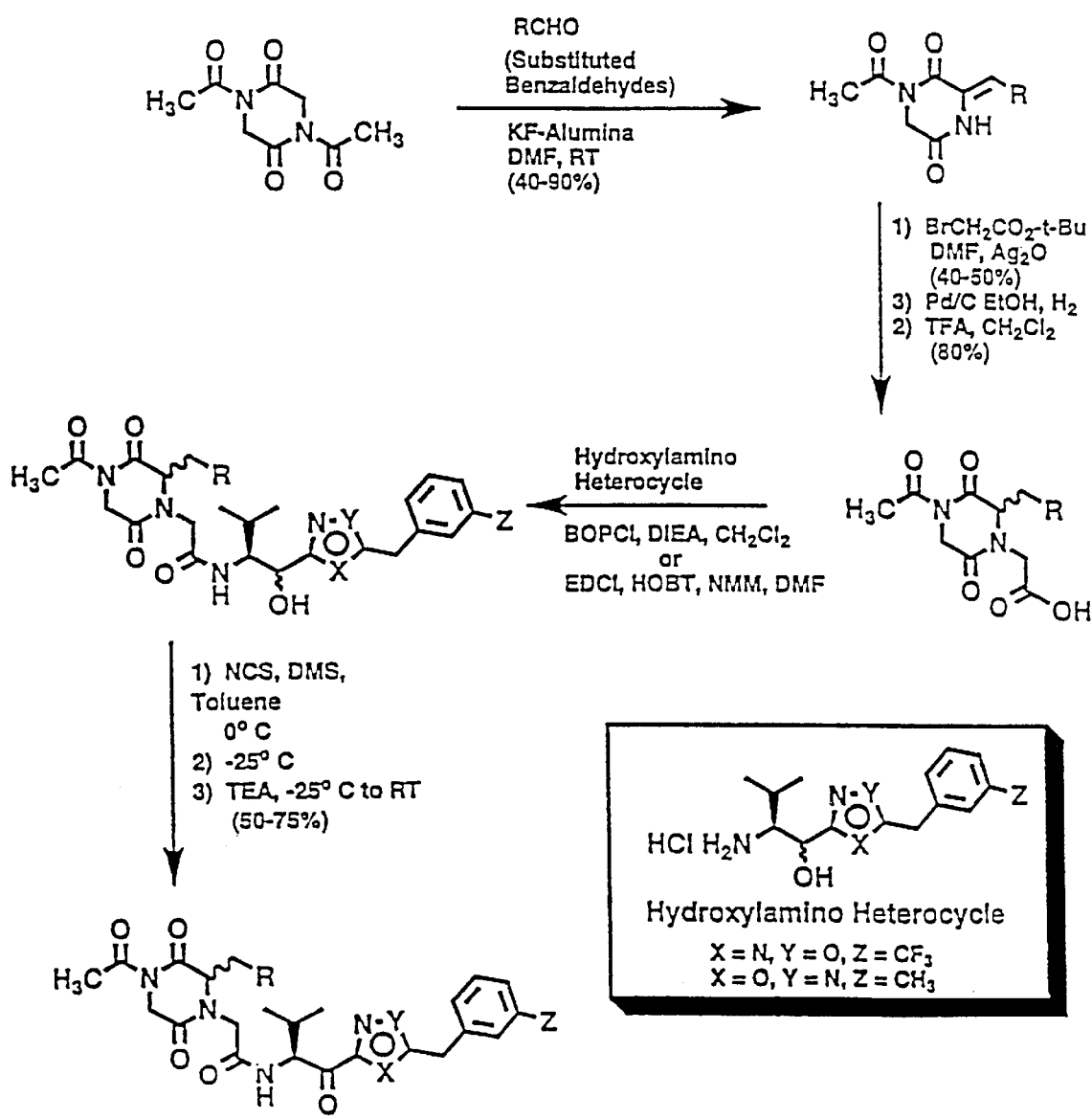
FIG. 20 is a schematic representation of the synthesis of compounds of Group V.
Figure 21:
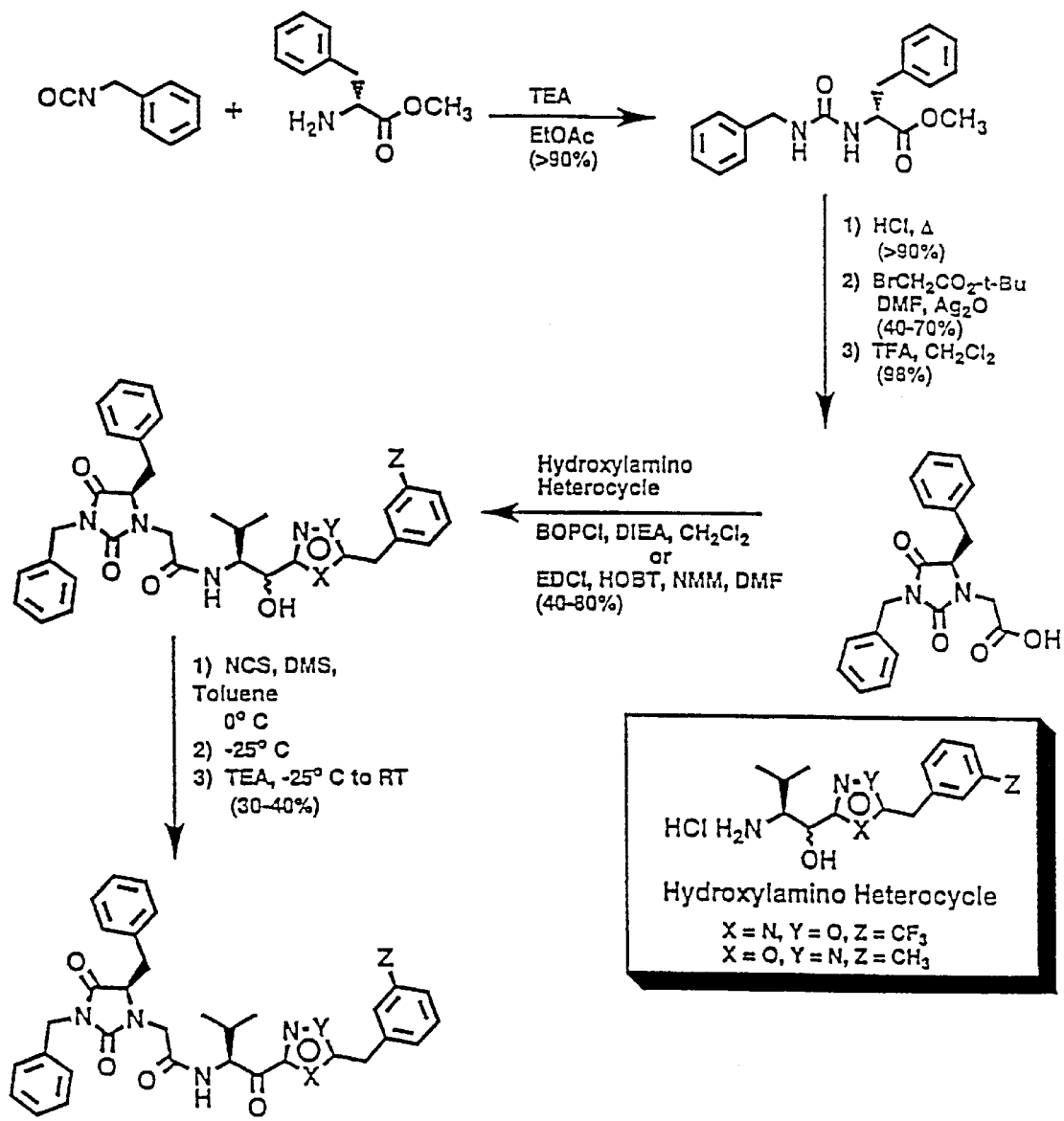
FIG. 21 is a schematic representation of the synthesis of compounds of Group V.
Figure 22:
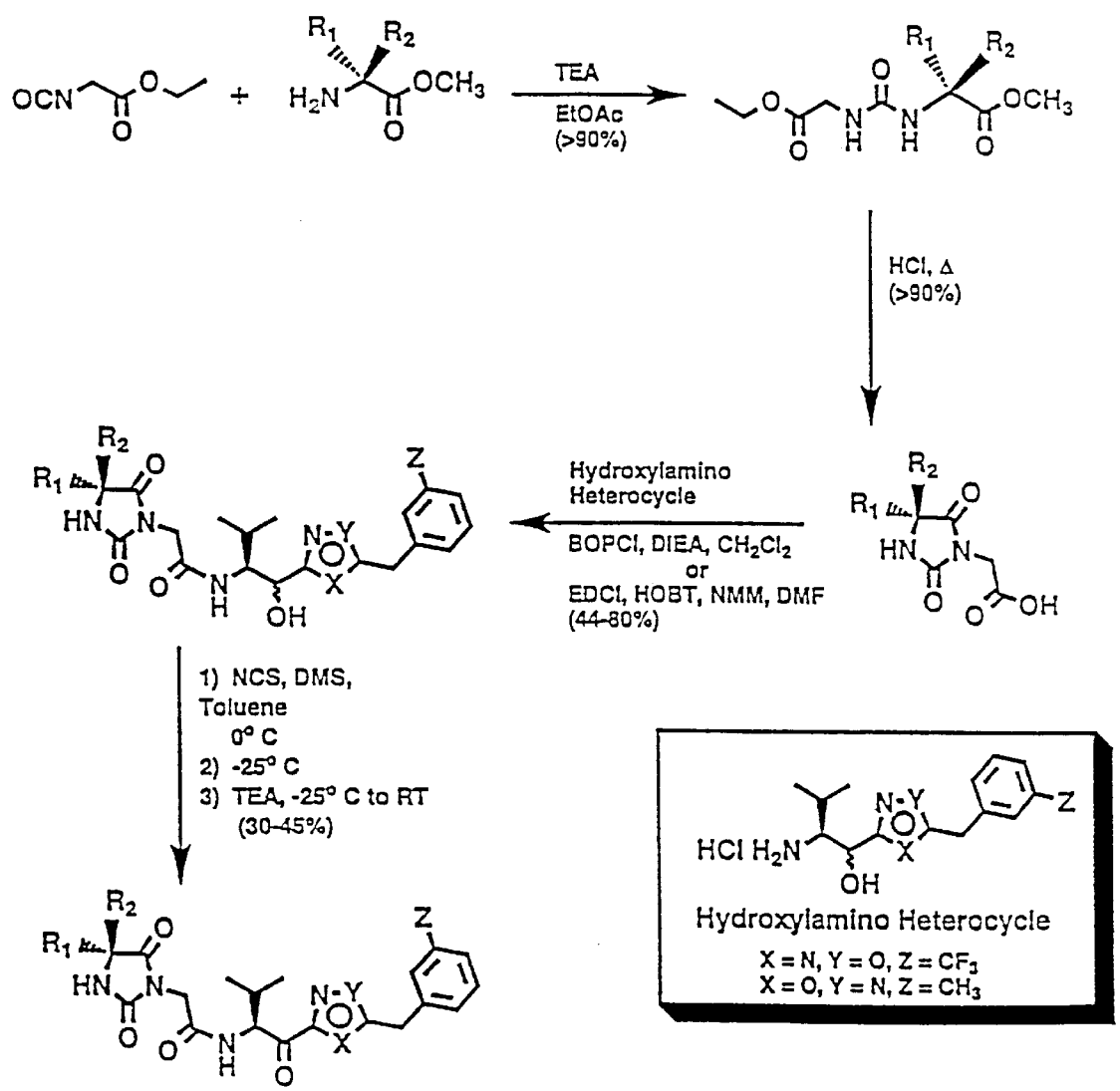
FIG. 22 is a schematic representation of the synthesis of compounds of Group V.
Figure 23:
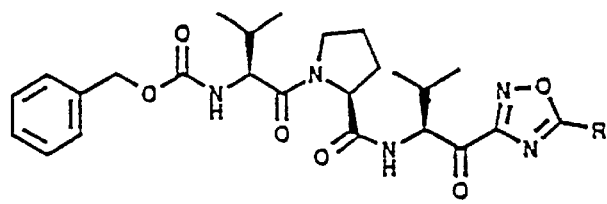
FIG. 23 shows the activity of certain compounds of Group I.
Figure 24:
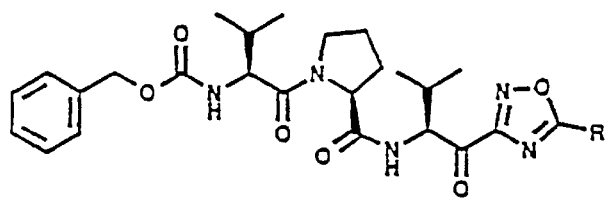
FIG. 24 shows the activity of certain compounds of Group I.
Figure 25:
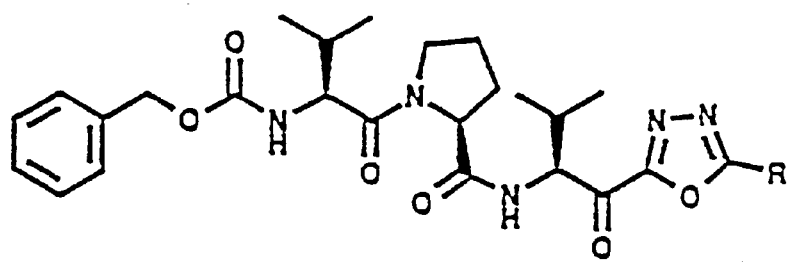
FIG. 25 shows the activity of certain compounds of Group I.
Figure 26:
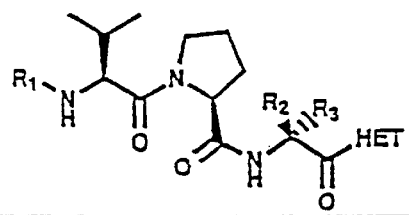
FIG. 26 shows the activity of certain compounds of Group I.
Figure 27:
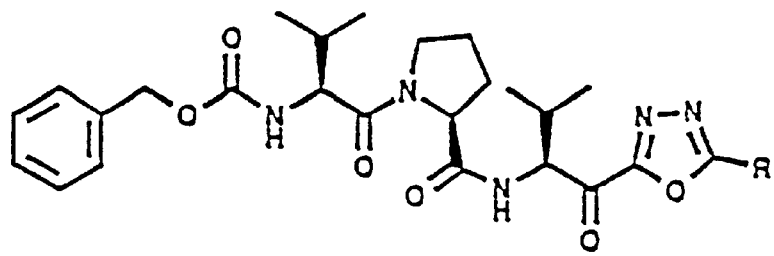
FIG. 27 shows the activity of certain compounds of Group I.
Figure 28:
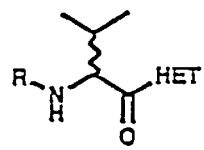
FIG. 28 shows the activity of certain compounds of Group II and III.
Figure 28:
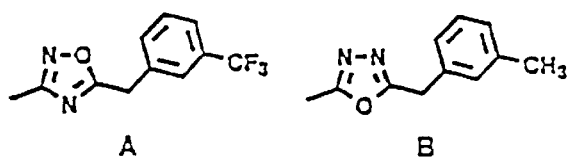
Figure 29:
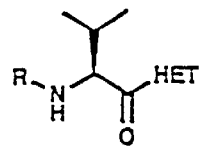
FIG. 29 shows the activity of certain compounds of Groups II, III and IV.
Figure 29:
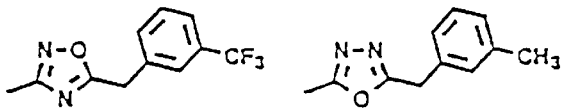
Figure 30:
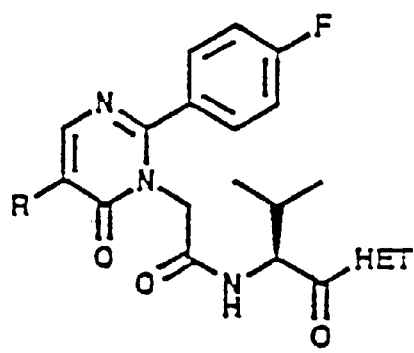
FIG. 30 shows the activity of certain compounds of Group V.
Figure 30:
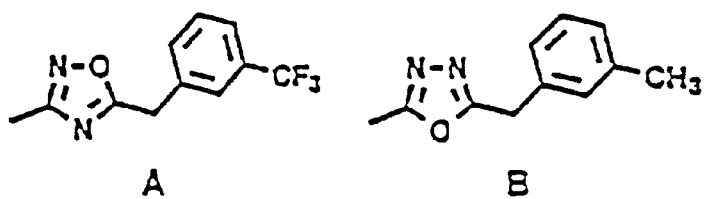
Figure 31:
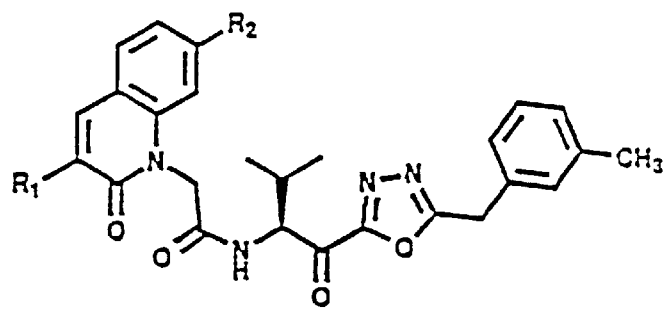
FIG. 31 shows the activity of certain compounds of Group V.
Figure 31:
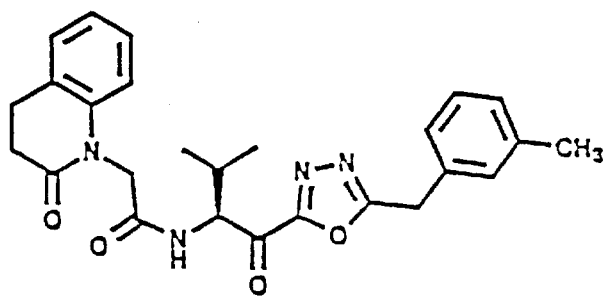
Figure 32:
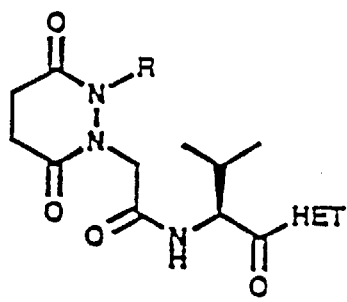
FIG. 32 shows the activity of certain compounds of Group V.
Figure 32:
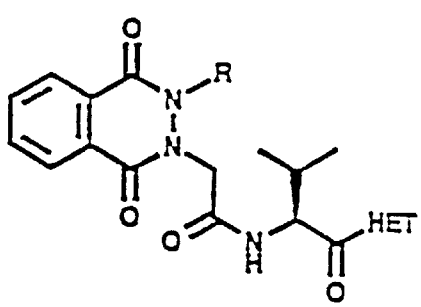
Figure 32:
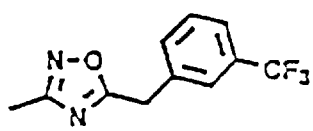
Figure 32:
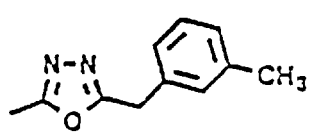
Figure 33:
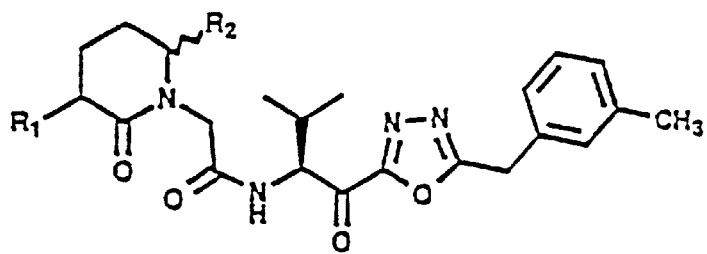
FIG. 33 shows the activity of certain compounds of Group V.
Figure 33:
Figure 33:
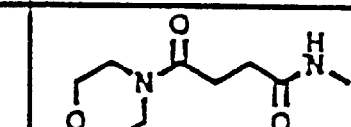
Figure 34:
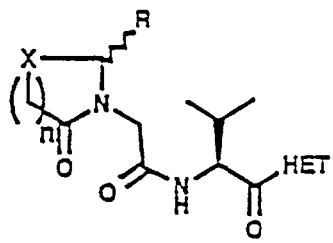
FIG. 34 shows the activity of certain compounds of Group V.
Figure 35:
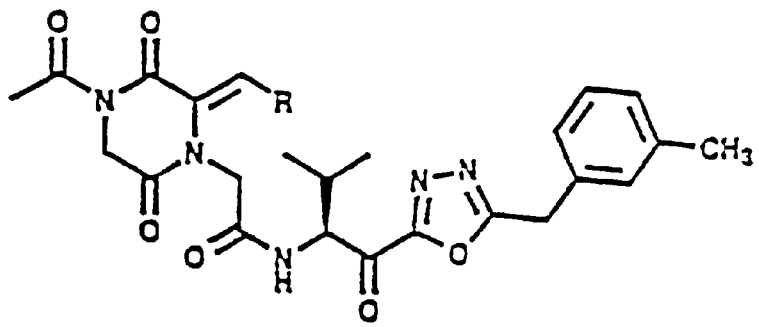
FIG. 35 shows the activity of certain compounds of Group V.
Figure 36:
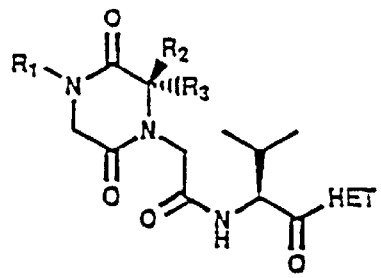
FIG. 36 shows the activity of certain compounds of Group V.
Figure 36:
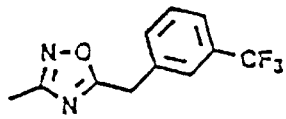
Figure 36:
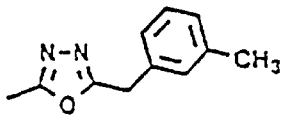
Figure 36:
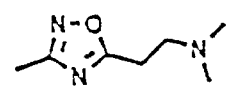
Figure 37:
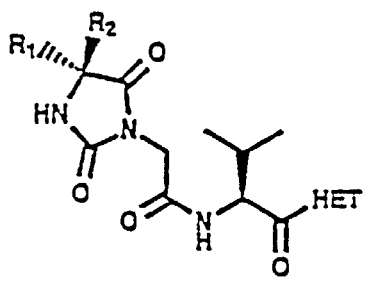
FIG. 37 shows the activity of certain compounds of Group V.
Figure 37:
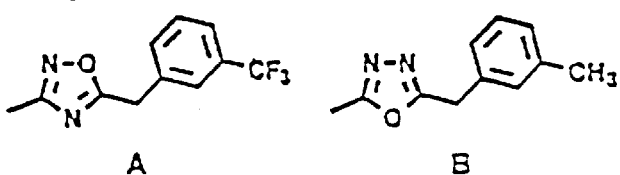
Figure 38:
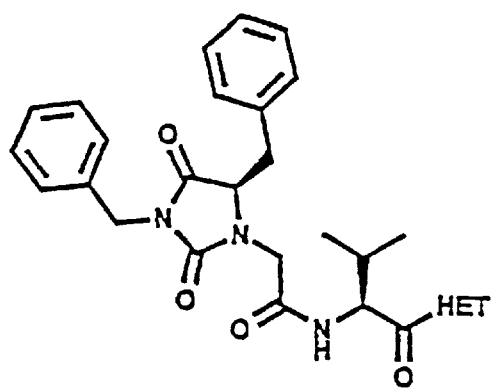
FIG. 38 shows the activity of certain compounds of Group V.

The compounds of the present invention, salts thereof, and their intermediates can be prepared or manufactured as described herein or by various processes known to be present in the chemical art (see also, WO 96/16080). For example, compounds of Group I may be synthesized according to the schemes set forth in FIGS. 1-2 (1,3,4 oxadiazoles) and FIGS. 3-4 (1,2,4 oxadiazoles). FIGS. 5–7 describe the synthesis of compounds of Group II. FIGS. 8-9 describe the synthesis of compounds of Group III; FIG. 10 describes synthesis of Group IV compounds. The several classes of Group V compounds are described in FIGS. 11–22.

Figure 39:
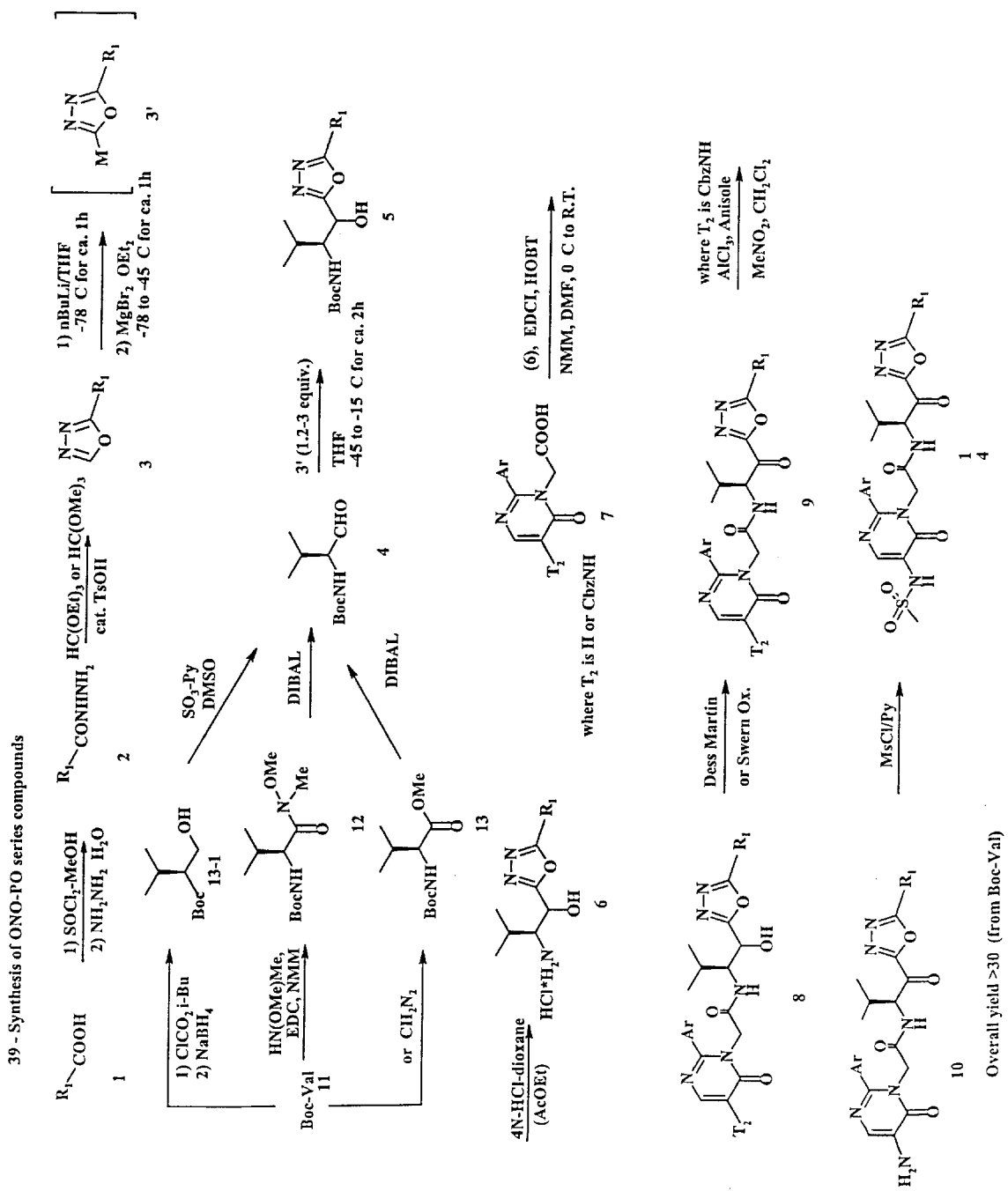
FIG. 39 is a schematic representation of the synthesis of certain compounds of the invention.

Alternatively, the compounds of the present invention may be prepared as described in FIG. 39. The 2-substituted 1,3,4-oxadiazole (3) may be prepared via formation of the acid chloride from an acid (1) utilizing, for example, thionyl chloride or oxalyl chloride, followed by treatment with hydrazine in a suitable solvent to yield the hydrazide (2). Reaction of (2) with triethyl orthoformate or trimethyl orthoformate and TsOH gives the requisite 2-substituted 1,3,4-oxadiazole (3).

Formation of the compound (3') utilizing standard conditions (ie. butyllithium at low temperature in a polar aprotic solvent, and further, if desired, reacting with MgBr-OEt$_2$) followed by addition of the aldehyde (4) yields the alcohol (5).

Deprotection of the protected amine of (5) using hydrochloric acid in dioxane gives the amino hydrochloride (6) which is then coupled to the acid (7) by methods available to one skilled in the art to give intermediate (8). Oxidation using Dess-Martin's Periodinane or other methods as described in Oxidation in Organic Chemistry by Milos Hudlicky, ACS Monograph 186 (1990) yields the ketone (9).

The final step requires removal of the protecting group from the amine. This may be carried out by a number of methods. For example, one may utilize aluminum chloride, anisole and nitromethane in a suitable solvent such as dichloromethane to give the final compound (10). Compound (10) can then be treated with an electrophile (e.g., methanesulfonyl chloride) with added base to give (14).

The aldehyde (4) may be prepared via either of three methods described. The Weinreb amide (12) is prepared from the amino acid (11) which is subsequently reduced to the aldehyde using diisobutylaluminum hydride (DIBAL). Alternatively, one may generate the ester of the amino acid (13) followed by reduction with DIBAL to afford the aldehyde (4). Further, one may generate the alcohol (13–1) followed by oxidation with SO$_3$-Py in DMSO.

The activity of the compounds is presented in FIGS. 23–38 as $K_i$ values (nM). $K_i$ values were determined, unless otherwise indicated, essentially as described in WO 96/16080, incorporated herein by reference.

Although the compounds described herein and/or their its salts may be administered as the pure chemicals, it is preferable to present the active ingredient as a pharmaceutical composition. The invention thus further provides the use of a pharmaceutical composition comprising one or more compounds and/or a pharmaceutically acceptable salt thereof, together with one or more pharmaceutically acceptable carriers thereof and, optionally, other therapeutic and/or prophylactic ingredients. The carrier(s) must be 'acceptable' in the sense of being compatible with the other ingredients of the composition and not deleterious to the recipient thereof.

Pharmaceutical compositions include those suitable for oral or parenteral (including intramuscular, subcutaneous and intravenous) administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration may be presented as discrete unit dosage forms such as hard or soft gelatin capsules, cachets or tablets each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art., e.g., with enteric coatings.

Oral liquid preparations may be in the form of, for example, aqueous or oily suspension, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservative.

The compounds may also be formulated for parenteral administration (e.g., by injection, for example, bolus injection or continuous infusion) and may be presented in unit dose form in ampules, pre-filled syringes, small bolus infusion containers or in multi-does containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in Fisher et al. (U.S. Pat. No. 4,788,603) or Bawas et al. (U.S. Pat. Nos. 4,931,279, 4,668,504 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention may also contain other adjuvants such as flavorings, coloring, antimicrobial agents, or preservatives.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg/day, e.g., from about 1 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 0.5 to 1000 mg, conveniently 5 to 750 mg, most conveniently, 10 to 500 mg of active ingredient per unit dosage form.

Ideally, the active ingredient should be administered to achieve peak plasma concentrations of the active compound of from about 0.5 to about 75 $\mu$M, more preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 0.5–500 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The following examples are given to illustrate the invention and are not intended to be inclusive in any manner:

EXAMPLES

The following abbreviations are used below: TFA—trifluoroacetic acid; HOBT—hydroxybenzotriazole; DIEA—diisopropylethylamine; NMM—4-methylmorpholine; DMF—N,N-dimethylformamide; TEA—triethylamine; EDCI—1-(3-dimethylaminopropyl-3-ethylcarbodiimide; BOPCI—bis(2-oxo-3-oxazolidinyl) phosphinic chloride; FMOC—9-fluorenyl methoxycarbonyl; BTD—bicyclic turned dipeptide (see, e.g., Tetrathedron, 49:3577–3592 (1993)); THF—tetrahydrofuran Example 1

(CE-2072) (Benzyloxycarbonyl)-L-valyl-N-[1-(2-[5-(3-methylbenzyl)-1,3,4-oxadiazolyl]carbonyl)-2-(S)-methylpropyl]-L-prolinamide To a mixture containing 0.79 g (5.94 mmol) of N-chlorosuccinimide in 40 mL of anhydrous toluene at 0° C. under a nitrogen atmosphere was added 0.65 mL (8.85 mmol) of dimethyl sulfide. The reaction was cooled to –25° C. using a carbon tetrachloride/dry ice bath, followed by the dropwise addition of a solution containing (benzyloxycarbonyl)-L-valyl-N-[1-(2-[5-(3-methylbenzyl)-1,3,4 oxadiazolyl]hydroxymethyl)-2-(S)-methylpropyl]-L-prolinamide (0.90 g, 1.49 mmol) in 17 mL of anhydrous toluene. The reaction was allowed to stir for 2 hours at –25° C. followed by the addition of 1.0 mL (7.17 mmol) of triethylamine. The cold bath was removed and the mixture allowed to warm to room temperature and maintained for 20 minutes. The reaction mixture was diluted with ethyl acetate and washed with water. The organic phase was dried over magnesium sulfate, filtered and the solvent removed under reduced pressure. The residue was purified by column chromatography on silica gel with 70% ethyl acetate/hexane to give 0.90 g of material which was further purified via preparative HPLC to afford 665 mg (73.9%) of the title compound as a white solid. FAB MS [M+H] m/z; Calcd: 604, Found 604.

The intermediate (benzyloxycarbonyl)-L-valyl-N-[1-(2-[5-(3-methylbenzyl)-1,3,4-oxadiazolyl]hydroxymethyl)-2-(S)-methylpropyl]-L-prolinamide was prepared as follows:
a. 3-(S)-Amino-2-(R,S)-hydroxy-4-methyl pentanoic acid.

To a solution containing 3-(S)-[(benzyloxycarbonyl) amino]-2-acetoxy-4-methylpentanenitrile (see example 1 of WO 96/16080) (15.2 g, 50.0 mmol) in 183 mL of dioxane was added 183 mL of concentrated hydrochloric acid and 7.45 mL of anisole. The reaction mixture was heated to reflux overnight. The hydrolysis reaction was allowed to cool to room temperature and then concentrated in vacuo. The resulting aqueous solution was extracted with ether (2x). The aqueous phase was placed on a Dowex 50X8-100 column (H+form, preeluted with deionized water to pH=7). The column was eluted with 2.0 N ammonium hydroxide and the pure fractions concentrated to afford 5.53 g (75%) of 3-(S)-amino-2-(R,S)-hydroxy-4-methylpentanoic acid as a pale yellow solid. FAB MS [M+H] m/z; Calcd: 148, Found: 148.

b. 3-(S)-[(Benzyloxycarbonyl)amino]-2-(R,S)-hydroxy-4-methylpentanoic acid.

To a solution under an atmosphere of nitrogen containing 1.0 g (6.8 mmol) of 3-(S)-amino-2-(R,S)-hydroxy-4-methylpentanoic acid in 9.5 mL of 1 N NaOH and 10 mL of dioxane was added 1.43 g (8.4 mmol) of benzyl chloroformate. The pH was maintained above pH 8 with 1 N NaOH as needed. The reaction mixture was allowed to stir at room temperature overnight. The reaction was diluted with water and washed with ether. The aqueous layer was acidified with 1 N HCl to pH=2 and extracted with ether (2x). The combined organic layers were dried over magnesium sulfate, filtered and evaporated in vacuo to afford 1.75 g (92%) of 3-(S)-[(benzyloxycarbonyl)amino]-2-(R,S)-hydroxy-4-methylpentanoic acid as a light yellow viscous oil. FAB MS [M+H] m/z; Calcd: 282, Found: 282.

c. 3-(S)-[(Benzyloxylcarbonyl)amino]-2-(R,S)-acetoxy-4-methyl pentanoic acid.

To a solution of 3-(S)-[(benzyloxycarbonyl)amino]-2-(R,S)-hydroxy-4-methylpentanoic acid (1.70 g, 6.04 mmol) and pyridine (4.9 mL) was added acetic anhydride (5.7 mL, 6.17 g, 60.4 mmol) dropwise at room temperature. The reaction was allowed to stir overnight and was diluted with ethyl acetate and washed with water (2×). The organic layer was dried over magnesium sulfate, filtered and evaporated in vacuo to give a thick oil. The residue was purified by column chromatography on silica gel with 15% methanol/dichloromethane to afford 1.56 g (80%) of 3-(S)-[(benzyloxycarbonyl)amino]-2-(R,S)-acetoxy-4-methyl pentanoic acid as a light yellow viscous oil. FAB MS [M+H] m/z; Calcd: 324, Found: 324.

d. 1-[(3-Methylphenylacetyl)-2-(2-(R,S)-acetoxy)-3-(S)-[(benzyloxycarbonyl)amino]-4-methylpentanoyl]hydrazine.

To a solution containing 3-(S)-[(benzyloxycarbonyl)amino]-2-(R,S)-acetoxy-4-methylpentanoic acid (2.3 g, 7.11 mmol) in 40 mL of DMF under a nitrogen atmosphere at 0° C. was added 1.31 g (9.69 mmol) of HOBT and 1.36 g (7.09 mmol) of EDCI. After stirring for 30 minutes, 1.20 g (7.31 mmol) of 3-methylphenyl acetic hydrazide (prepared analogously to the monoacid hydrazides cited by Rabins et. al. (*J. Org. Chem*, 30:2486 (1965)) and 1.0 mL (9.10 mmol) of NMM were added. The reaction was allowed to warm to room temperature and stir overnight. The reaction was diluted with ethyl acetate and washed with 5% potassium hydrogen sulfate, saturated sodium bicarbonate, brine and water. The organic phase was dried over magnesium sulfate, filtered and evaporated under reduced pressure. The residue was purified by column chromatography on silica gel with 10% methanol/dichloromethane to afford 2.31 g (89.0%) of the title compound as a white solid. FAB MS [M+H] m/z; Calcd: 470, Found: 470.

e. 1-[2-((5-(3-methylphenyl))-1,3,4-oxadiazolyl)]-1-acetoxy-2-(S)-[(benzyloxycarbonyl)amino]amino]-3-methylbutane.

A solution containing 2.31 g (4.92 mmol) of 1-[(3-methylphenylacetyl)-2-(2-(R,S)-acetoxy)-3-(S)-[(benzyloxycarbonyl)amino]-4-methyl pentanoyl]hydrazine in 25 mL of pyridine and 1.88 g (9.86 mmol) of toluene sulfonyl chloride was heated at reflux under a nitrogen atmosphere for 72 hours. The solvent was removed under reduced pressure and the residue dissolved in ethyl acetate and washed with water. The organic phase was dried over magnesium sulfate, filtered and evaporated under reduced pressure. The residue was purified by column chromatography on silica gel with 5% ethyl acetate/hexane to afford 1.41 g (63.5%) of the title compound. FAB MS [M+H] m/z; Calcd: 452, Found: 452.

f. 1-[2-(5-[3-Methylbenzyl]-1,3,4-oxadiazolyl)]-2-(S)-[(benzyloxycarbonyl)amino]-3-methylbutan-1-ol.

A solution containing 1.80 g (3.99 mmol) of 1-[2-(5-[3-methylbenzyl]-1,3,4-oxadiazolyl)]-1-acetoxy-2-(S)-[(benzyloxycarbonyl)amino]-3-methylbutane and 0.72 g (5.21 mmol) of potassium carbonate in 30 mL of methanol and 8 mL of water was allowed to stir at room temperature for 30 minutes. The solvent was removed under reduced pressure and the residue dissolved in ethyl acetate and washed with water. The organic phase was dried over magnesium sulfate, filtered and evaporated under reduced pressure. The residue was purified by column chromatography on silica gel with 50% ethyl acetate/hexane to afford 1.46 g (89.3%) of the title compound. FAB MS [M+H] m/z; Calcd: 410, Found: 410.

g. 1-[2-(5-[3-Methylbenzyl])-1,3,4-oxadiazolyl]-2-(S)-Amino-3-methylbutan-1-ol hydrochloride.

To a solution containing 1.31 g (3.20 mmol) of 1-[2-(5-[3-methylbenzyl])-1,3,4-oxadiazolyl]-2-(S)-[(benzyloxycarbonyl)amino]-3-methylbutan-1-ol in 25 mL of trifluoroacetic acid under a nitrogen atmosphere at 0° C. was added 0.43 mL (3.94 mmol) of thioanisole. The reaction was allowed to warm to room temperature overnight. The solvent was removed under reduced pressure and the residue dissolved in ether and cooled to −78° C. under a nitrogen atmosphere. To this solution was added 3 mL (3 mmol) of 1 N hydrochloric acid in ether. The resulting white solid was allowed to settle and the ether decanted. Additional ether was added and decanted (3×). The solid was dried under vacuum to afford 0.92 g (92.2%) of the title compound. FAB MS [M+H] m/z; Calcd: 276, Found: 276.

h. (Benzyloxycarbonyl)-L-valyl-N-[1-(2-[5-(3-methylbenzyl)-1,3,4-oxadiazolyl/hydroxylmethyl)-2-(S)-methylpropyl]-L-prolinamide.

To a solution containing 1.30 g (3.38 mmol) of Cbz-Val-Pro-OH in 25 mL of anhydrous dichloromethane under a nitrogen atmosphere at 0° C. was added 0.90 g (3.54 mmol) of BOPCl and 0.60 g (3.44 mmol) of DIEA. After stirring for 30 minutes, 0.90 g (2.89 mmol) of 1-[2-(5-[3-methylbenzyl])-1,3,4-oxadiazolyl]-2-(S)-amino-3-methyl butan-1-ol hydrochloride in 15 mL of dichloromethane and 0.6 mL (3.94 mmol) of DIEA was added. The reaction was allowed to stir at 0° C. overnight. The reaction was diluted with dichloromethane and washed with a saturated sodium bicarbonate solution. The organic phase was dried over magnesium sulfate, filtered and evaporated. The residue was purified by column chromatography on silica gel with 5% methanol/dichloromethane to afford 1.0 g (57.3%) of the title compound as a tan solid. FAB MS [M+H] m/z; Calcd: 606, Found: 606.

Example 2

(CE-2074)(Benzyloxycarbonyl)-L-valyl-N-[1-(2-[5-(methyl)-1,3,4-oxadiazoly]carbony)]-2-(S)-methylpropyl]-L-prolinamide. Prepared similar to Example 1. FAB MS [M+H] m/z; Calcd: 514, Found: 514.

Example 3

(CE-2075)(Benzyloxycarbonyl)-L-valyl-N-[1-(2-[5-(3-trifluoromethylbenzyl)-1,3,4-oxadiazolyl]carbonyl)-2-(S)-methylpropyl]-L-prolinamide. Prepared similar to Example 1. FAB MS [M+H] m/z; Calcd: 658, Found: 658.

Example 4

(CE-2100)(Benzyloxycarbonyl)-L-valyl-N-[1-(2-[5-(4-Dimethylamino benzyl)-1,3,4-oxadiazolyl]carbonyl)-2-(S)-methylpropyl]-L-prolinamide. Prepared similar to Example 1. FAB MS [M+H] m/z; Calcd: 633, Found: 633.

Example 5

(CE-2124)(Benzyloxycarbonyl)-L-valyl-N-[1-(2-[5-(1-napthylenyl)-1,3,4-xadiazolyl]carbonyl)-2-(S)-methylpropyl]-L-prolinamide. Prepared similar to Example 1. FAB MS [M+H] m/z; Calcd: 640, Found: 640.

Example 6

(CE-2177)(Benzyloxycarbonyl)-L-valyl-N-[1-(2-[5-(3,4-methylenedioxybenzyl)-1,3,4-oxadiazolyl] carbonyl)-2-(S)-methylpropyl]-L-prolinamide. Prepared similar to Example 1. FAB MS [M+H] m/z; Calcd: 634, Found: 634.

Example 7

(CE-2178)(Benzyloxycarbonyl)-L-valyl-N-[1-(3-[5-(3,4-methylenedioxybenzyl)-1,2,4-oxadiazolyl] carbonyl)-2-(S)-methylpropyl]-L-prolinamide. Prepared similar to Example 1 of WO 96/16080. FAB MS [M+H] m/z; Calcd: 634, Found: 634.

Example 8

(CE-2052)(Benzyloxycarbonyl)-L-valyl-N-[1-(3-[5-(3,5-dimethylbenzyl)-1,2,4-oxadiazolyl]carbonyl)-2-(S)-methylpropyl]-L-prolinamide. Prepared similar to Example 1 of WO 96/16080. FAB MS [M+H] m/z; Calcd: 618, Found: 618.

Example 9

(CE-2053)(Benzyloxycarbonyl)-L-valyl-N-[1-(3-[5-(3,5-dimethoxybenzyl)-1,2,4-oxadiazolyl] carbonyl)-2-(S)-methylpropyl]-L-prolinamide. Prepared similar to Example 1 of WO 96/16080. FAB MS [M+H] m/z; Calcd: 650, Found: 650.

Example 10

(CE-2054)(Benzyloxycarbonyl)-L-valyl-N-[1-(3-[5-(3,5-ditrifluoromethylbenzyl)-1,2,4-oxadiazolyl] carbonyl)-2-(S)-methylpropyl]-L-prolinamide. Prepared similar to Example 1 of WO 96/16080. FAB MS [M+H] m/z; Calcd: 726, Found: 726.

Example 11

(CE-2055)(Benzyloxycarbonyl)-L-valyl-N-[1-(3-[5-(3-methylbenzyl)-1,2,4-oxadiazolyl] carbonyl)-2-(S)-methylpropyl]-L-prolinamide. Prepared similar to Example 1 of WO 96/16080. FAB MS [M+H] m/z; Calcd: 604, Found: 604.

Example 12

(CE-2057)(Benzyloxycarbonyl)-L-valyl-N-[1-(3-[5-biphenylmethine)-1,2,4-oxadiazolyl] carbonyl)-2-(S)-methylpropyl]-L-prolinamide. Prepared similar to Example 1 of WO 96/16080. FAB MS [M+H] m/z; Calcd: 666, Found: 666.

Example 13

(CE-2058)(Benzyloxycarbonyl)-L-valyl-N-[1-(3-[5-(4-phenylbenzyl)-1,2,4-oxadiazolyl] carbonyl)-2-(S)-methylpropyl]-L-prolinamide. Prepared similar to Example 1 of WO 96/16080. FAB MS [M+H] m/z; Calcd: 666, Found: 666.

Example 14

(CE-2062)(Benzyloxycarbonyl)-L-valyl-N-[1-(3-[5-(3-phenylbenzyl)-1,2, 4-oxadiazolyl] carbonyl)-2-(S)-methylpropyl]-L-prolinamide. Prepared similar to Example 1 of WO 96/16080. FAB MS [M+H] m/z; Calcd: 666, Found: 666.

Example 15

(CE-2066)(Benzyloxycarbonyl)-L-valyl-N-[1-(3-[5-(3-phenoxybenzyl)-1,2,4-oxadiazolyl] carbonyl)-2-(S)-methylpropyl]-L-prolinamide. Prepared similar to Example 1 of WO 96/16080. FAB MS [M+H] m/z; Calcd: 682, Found: 682.

Example 16

(CE-2069)(Benzyloxycarbonyl)-L-valyl-N-[1-(3-[5-cyclohexylmethylene)-1,2,4-oxadiazolyl] carbonyl)-2-(S)-methylpropyl]-L-prolinamide. Prepared similar to Example 1 of WO 96/16080. FAB MS [M+H] m/z; Calcd: 596, Found: 596.

Example 17

(CE-2073)(Benzyloxycarbonyl)-L-valyl-N-[1-(3-[5-(α,α-dimethyl-3-trifluoromethylbenzyl)-1,2,4-oxadiazolyl]carbonyl)-2-(S)-methylpropyl]-L-prolinamide. Prepared similar to Example 1 of WO 96/16080. FAB MS [M+H] m/z; Calcd: 686, Found: 686.

Example 18

(CE-2077)(Benzyloxycarbonyl)-L-valyl-N-[1-(3-[5-(1-napthylmethylene)-1,2,4-oxadiazolyl] carbonyl)-2-(S)-methylpropyl]-L-prolinamide. Prepared similar to Example 1 of WO 96/16080. FAB MS [M+H] m/z; Calcd: 640, Found: 640.

Example 19

(CE-2078)(Benzyloxycarbonyl)-L-valyl-N-[1-(3-[5-(3-pyridylmethyl)-1,2,4-oxadiazolyl] carbonyl)-2-(S)-methylpropyl]-L-prolinamide. Prepared similar to Example 1 of WO 96/16080. FAB MS [M+H] m/z; Calcd: 591, Found: 591.

Example 20

(CE-2096)(Benzyloxycarbonyl)-L-valyl-N-[1-(3-[5-(3,5-diphenylbenzyl)-1,2,4-oxadiazolyl ] carbonyl)-2-(S)-methylpropyl]-L-prolinamide. Prepared similar to Example 1 of WO 96/16080. FAB MS [M+H] m/z; Calcd: 742, Found: 742.

Example 21

(CE-2115)(Benzyloxycarbonyl)-L-valyl-N-[1-(3-[5-(4-dimethylaminobenzyl)-1,2,4-oxadiazolyl] carbonyl)-2-(S)-methylpropyl]-L-prolinamide. Prepared similar to Example 1 of WO 96/16080. FAB MS [M+H] m/z; Calcd: 633, Found: 633.

Example 22

(CE-2089) 2-[5-[(Benzyloxycarbonyl)amino]-6-oxo-2-(4-fluorophenyl)-1,6-dihydro-1-pyrimidinyl]-N-[1-(3-[5-(3-trifluoromethylbenzyl)-1,2,4-oxadiazolyl] carbonyl)-(S)-2-methylpropyl]acetamide.

To a mixture containing 1.15 g (8.60 mmol) of N-chlorosuccinimide in 43 mL of anhydrous toluene at 0° C. under a nitrogen atmosphere was added 0.95 mL (12.9 mmol) of dimethyl sulfide. The reaction was cooled to −25° C. using a carbon tetrachloride/dry ice bath, followed by the dropwise addition of a solution containing 2-[5-[(benzyloxycarbonyl)amino]-6-oxo-2-(4-fluorophenyl)-1,6-dihydro-1-pyrimidinyl]-N-[1-(3-[5-(3-trifluoromethylbenzyl)-1,2,4-oxadiazolyl]hydroxymethyl)-(S)-2-methylpropyl]acetamide (1.52 g, 2.15 mmol) in 15 mL of anhydrous toluene. The reaction was allowed to stir for 2 hours at −25° C. followed by the addition of 1.2 mL (8.60 mmol) of triethylamine. The cold bath was removed and the mixture allowed to warm to room temperature over 20 minutes. The reaction mixture was diluted with ethyl acetate and washed with water. The organic phase was dried over magnesium sulfate, filtered and evaporated under reduced pressure. The residue was purified by column chromatography on silica gel using a gradient elution of 2 to 10% methanol/dichloromethane to afford 1.19 g of material which was further purified via preparative HPLC to afford 629 mg (41%) of the title compound as a white solid. FAB MS [M+H] m/z; Calcd: 707, Found: 707.

The intermediate 2-[5-[(benzyloxycarbonyl)amino]-6-oxo-2-(4-fluorophenyl)-1,6-dihydro-1-pyrimidinyl]-N-[1-(3-[5-(3-trifluoromethylbenzyl)-1,2,4-oxadiazolyl] hydroxymethyl)-(S)-2-methylpropyl]acetamide was prepared as follows: to a solution containing 1.35 g (3.7 mmol) of 1-[3-[5-(3-methylbenzyl)-1,2,4-oxadiazolyl]-2-(S)-amino-3-methylbutan-1-ol hydrochloride and [5-[(benzyloxycarbonyl)amino]-6-oxo-2-(4-fluorophenyl)-1,6-dihydro-1-pyrimidinyl]acetic acid (*J. Med. Chem.* 38:98–108 (1995)) in 10 mL of anhydrous DMF was added 1.0 mL (7.44 mmol) of TEA and 0.76 g (4.94 mmol) of HOBT. The mixture was cooled to 0° C. and 0.95 g (4.94 mmol) of EDC was added and the reaction mixture was allowed to stir overnight. An additional 1.0 mL (7.44 mmol) of TEA was added and the reaction again allowed to stir overnight. The reaction was diluted with dichloromethane and washed with a saturated ammonium chloride solution (2×) and water. The organic phase was dried over magnesium sulfate, filtered and evaporated under reduced pressure. The residue was purified by column chromatography on silica gel with 2% methanol/dichloromethane to afford 1.52 g (87%) of the title compound. FAB MS [M+H] m/z; Calcd: 709, Found: 709.

Example 23

(CE-2090) 2-[5-Amino-6-oxo-2-(4-fluorophenyl)-1, 6-dihydro-1-pyrimidinyl]-N-]1-(3-[5-(3-trifluoromethylbenzyl)-1,2,4-oxadiazolyl]carbonyl)-2-(S)-methylpropyl]acetamide.

To a mixture containing 0.41 g (0.56 mmol) of 2-[5-[(benzyloxycarbonyl) amino]-6-oxo-2-(4-fluorophenyl)-1, 6-dihydro-1-pyrimidinyl]-N-[1-(3-[5-(3-1,2,4-oxadiazolyl] carbonyl)-(S)-2-methylpropyl]acetamide in 4 mL of trifluoroacetic acid at room temperature under a nitrogen atmosphere was added 87 mg (0.70 mmol) of thioanisole. The reaction mixture was allowed to stir for 3 days and concentrated in vacuo. The residue was purified via preparative HPLC to afford 269 mg (47%) of the title compound as a white solid. FAB MS [M+H] m/z; Calcd: 573, Found: 573.

Example 24

(CE-2095) 2-[5-[(Benzyloxycarbonyl)amino]-6-oxo-2-(4-fluorophenyl)-1,6-dihydro-1-pyrimidinyl]-N-[1-(2-[5-(3-methylbenzyl)-1,3,4-oxadiazolyl]carbonyl)-(S)-2-methylpropyl]acetamide.

To a mixture containing 0.83 g (6.23 mmol) of N-chlorosuccinimide in 32 mL of anhydrous toluene at 0° C. under a nitrogen atmosphere was added 0.7 mL (9.35 mmol) of dimethyl sulfide. The reaction was cooled to −25° C. using a carbon tetrachloride/dry ice bath, followed by the dropwise addition of a solution containing 2-[5-[(benzyloxycarbonyl)amino]-6-oxo-2-(4-fluorophenyl)-1,6-dihydro-1-pyrimidinyl]-N-[1-(2-[5-(3-methylbenzyl)-1,3,4-oxadiazolyl]hydroxymethyl)-(S)-2-methylpropyl]acetamide (1.02 g, 1.56 mmol) in 12 mL of anhydrous toluene. The reaction was allowed to stir for 2 hours at −25° C. followed by the addition of 0.9 mL (6.23 mmol) of triethylamine. The cold bath was removed and the mixture allowed to warm to room temperature over 20 minutes. The reaction mixture was diluted with ethyl acetate and washed with water. The organic phase was dried over magnesium sulfate, filtered and evaporated. The residue was purified by column chromatography on silica gel using 1% methanol/dichloromethane to afford 1.37 g of material which was further purified via preparative HPLC to give 368 mg (36%) of the title compound as a white solid. FAB MS [M+H] m/z; Calcd: 653, Found: 653.

The intermediate 2-[5-[(benzyloxycarbonyl)amino]-6-oxo-2-(4-fluorophenyl)-1,6-dihydro-1-pyrimidinyl]-N-[1-(2-[5-(3-methylbenzyl)-1,3,4-oxadiazolyl]hydroxymethyl)-(S)-2-methylpropyl]acetamide was prepared as follows: to a solution containing 1.35 g (3.7 mmol) of 1-[2-[5-(3-methylbenzyl)-1,3,4-oxadiazolyl]-2-(S)-amino-3-methyl butane hydrochloride and [5-[(benzyloxycarbonyl)amino]-6-oxo-2-(4-fluorophenyl)-1,6-dihydro-1-pyrimidinyl]acetic acid (*J. Med. Chem.*, 38:98–108 (1995)) in 10 mL of anhydrous DMF was added 0.73 mL (6.6 mmol) of NMM and 0.46 g (3.0 mmol) of HOBT. The mixture was cooled to 0° C. and 0.50 g (2.6 mmol) of EDCI was added and the reaction mixture was allowed to stir for 2 days. The reaction was diluted with dichloromethane and washed with a saturated ammonium chloride solution (2×) and water. The organic phase was dried over magnesium sulfate, filtered and evaporated under reduced pressure. The residue was purified by column chromatography on silica gel using a gradient elution of 2 to 5% methanol/dichloromethane to afford 1.02 g (77%) of the title compound. FAB MS [M+H] m/z; Calcd: 655, Found: 655.

Example 25

(CE-2101) 2-[5-Amino-6-oxo-2-(4-fluorophenyl)-1, 6-dihydro-1-pyrimidinyl]-N-[1-(2-[5-(3-methylbenzyl)-1, 3,4-oxadiazolyl]carbonyl)-2-(S)-methylpropyl]acetamide.

To a mixture containing 0.219 g (0.335 mmol) of 2-[5-[(benzyloxycarbonyl) amino]-6-oxo-2-(4-fluorophenyl)-1, 6-dihydro-1-pyrimidinyl]-N-[1-(2-[5-(3-methylbenzyl)-1,3, 4-oxadiazolyl]carbonyl)-(S)-2-methylpropylyl]acetamide in 3 mL of trifluoroacetic acid at room temperature under a nitrogen atmosphere was added 0.05 mL (0.402 mmol) of thioanisole. The reaction mixture was allowed to stir for 3 days and concentrated in vacuo. The residue was purified via preoperative HPLC to afford 187 mg (88%) of the title compound as a white solid. FAB MS [M+H} m/z; Calcd: 519, Found: 519.

Example 26

(CE-2164)(Pyrrole-2-carbonyl)-N-(benzyl)glycyl-N-[1-(2-[5-(3-methylbenzyl)-1,3,4-oxadiazolyl] carbonyl-2-(S)-methylpropyl]amide.

To a mixture containing 1.97 g (14.7 mmol) of N-chlorosuccinimide on 60 mL of anhydrous toluene at 0° C. under a nitrogen atmosphere was added 1.54 mL (21.0 mmol) of dimethyl sulfide. The mixture was allowed to stir for 1 hr. The reaction was cooled to −25° C. using a carbon tetrachloride/dry ice bath, followed by the dropwise addition of a solution contain (0.90 g, 1.49 mmol) of (pyrrole-2-carbonyl)-N-(benzyl)glycyl-N-[1-(2-[5-(3-methylbenzyl)-1,3,4-oxadiazolyl]hydroxymethyl)]-2-(S)-methylpropyl] amide in 30 mL of anhydrous toluene. The reaction was allowed to stir for 1 hour at −25° C. followed by the addition of 2.16 mL (15.5 mmol) of triethylamine. The cold bath was removed and the mixture allowed to warm to room temperature over 20 minutes. The reaction mixture was diluted with ethyl acetate and washed with water. The organic phase was dried over magnesium sulfate, filtered and evaporated under reduced pressure. The residue was purified by column chromatography on silica gel with ethyl acetate/hexane (4:1). The material was further purified via preparative HPLC to afford 1.20 g (63.4%) of the title compound as a white solid. FAB MS [M+H] m/z; Calcd: 514, Found: 514.

The intermediate (pyrrole-2-carbonyl)-N-(benzyl)glycyl-N-[1-(2-[5-(3-methylbenzyl)-1,3,4-oxadiazolyl] hydroxymethyl)]-2-(S)-methylpropyl]amide was prepared by the following method:

a. (Pyrrole-2-carbonyl)-N-(benzyl)glycine-t-butyl ester.

To a suspension containing 3.00 g (27.0 mmol) of pyrrole-2-carboxylic acid in 75 mL of anhydrous dichloromethane under a nitrogen atmosphere at 0° C. was added 6.96 g (27.0 mmol) of BOPCl and 14.1 mL (81.0 mmol) of DIEA. After stirring for 30 minutes, 5.97 g (27.0 mmol) of N-(benzyl) gylcine-t-butyl ester was added and the reaction allowed to warm to room temperature overnight. The reaction was diluted with ethyl acetate and washed with a 5% potassium hydrogensulfate, saturated sodium bicarbonate solution and brine. The organic phase was dried over magnesium sulfate, filtered and evaporated under reduced pressure. The residue was purified by column chromatography on silica gel using a gradient of 100% hexane to 60% hexane/ethyl acetate to afford 2.92 g (34.4%) of the title compound as a white solid. FAB MS [M+H] m/z Calcd: 315, Found: 315.

b. (Pyrrole-2-carbonyl)-N-(benzyl)glycine.

To a solution containing 2.85 g (9.01 mmol) of (Pyrrole-2-carbonyl)-N-(benzyl)glycine-t-butyl ester in 50 mL of anhydrous dichloromethane cooled to 0° C. was added 25 mL of TFA dropwise. After 90 minutes an additional 25 mL of TFA was added and allowed to stir for 30 minutes. The mixture was evaporated in vacuo to afford 2.19 g of (Pyrole-2-carbonyl)-N-(benzyl)glycine as a tan solid. FAB MS [M+H] m/z; Calcd. 259, Found 259.

c. (Pyrrole-2-carbonyl)-N-(benzyl)glycyl-N-[1-(2-[5-(3-methylbenzyl)-1,3,4-oxadiazolyl]hydroxymethyl)]-(S)-2-methylpropyl]amide.

To a solution containing 1.90 g (7.35 mmol) of (Pyrrole-2-carbonyl)-N-(benzyl)glycine in 75 mL of anhydrous DMF was added 2.4 mL (22.1 mmol) of NMM and 1.29 g (9.56 mmol) of HOBT. The mixture was cooled to 0° C. and 1.69 g (8.82 mmol) of EDCI was added and the reaction mixture was allowed to stir. After 30 minutes 2.17 g (6.99 mmol) of 1-[2-(5-[3-methylbenzyl])-1,3,4-oxadiazolyl]-2-(S)-amino-3-methyl butan-1-ol hydrochloride in 25 mL of anhydrous DMF was added and the mixture was allowed to warm to room temperature overnight. The reaction was diluted with ethyl acetate and washed with 5% potassium hydrogen sulfate and water. The organic phase was dried over magnesium sulfate, filtered and evaporated under reduced pressure. The residue was purified by column chromatography on silica gel using a gradient elution of 20 to 80% ethyl acetate/hexane to afford 2.02 g (56%) of the title compound. FAB MS [M+H] m/z Calcd: 516, Found: 516.

Example 27

(CE-2097)(Pyrrole-2-carbonyl)-N-(benzyl)glycyl-N-[1-(3-[5-(3-trifluoromethylbenzyl)]-1,2,4-oxadiazolyl]carbonyl)-(S)-methylpropyl]amide was prepared in a similar manner to Example 25. FAB MS [M+H] m/z; Calcd: 568, Found: 568.

Example 28

(CE-2130)(2S,5S)-5-Amino-1,2,4,5,6,7-hexahydroazepino-[3,2,1]-indole-4-one-carbonyl-N-[1-(2-[5-(3-methylbenzyl)-1,3,4-oxadiazolyl] carbonyl)-(R,S)-2-methylpropyl]amide.

To a solution containing 0.93 g (1.28 mmol) of (2S,5S)-Fmoc-5-amino-1,2,4, 5,6,7-hexahydroazepino [3,2,1] indole-4-one-carbonyl-N-[1-(2-[5-(3-methylbenzyl)-1,3,4-oxadiazolyl]carbonyl)-(S)-2-methylpropyl]amide in 4.5 mL of anhydrous DMF under an atmosphere of nitrogen was added 0.45 mL of diethylamine. After stirring at room temperature for 15 min the mixture was concentrated under high vacuum. The residue was purified via preparative HPLC to afford 0.57 g (72%) of the title compound as a white solid. FAB MS [M+H] m/z; Calcd: 502, Found 502.

The intermediate (2S,5S)-Fmoc-5-amino-1,2,4,5,6,7-hexahydroazepino-[3,2,1]-indole-4-one-carbonyl-N-[1-(2-[5-(3-methylbenzyl)-1,3,4-oxadiazolyl]carbonyl)-(S)-2-methylpropyl]amide was prepared as follows:

a. (2S, 5S)-Fmoc-5-amino-1,2,4,5,6,7-hexahydroazepino-[3,2,1]-indole-4-one-carbonyl-N-[1-(2-[5-(3-methylbenzyl)-1,3,4-oxadiazolyl]hydroxymethyl)-(S)-2-methylpropyl]amide.

To a solution containing 1.25 g (2.67 mmol) of (2S,5S)-Fmoc-5-amino-1,2,4,5,6,7-hexahydroazepino [3,2,1] indole-4-one-carboxylic acid in 200 mL of anhydrous dichloromethane and 1 mL of anhydrous DMF under a nitrogen atmosphere at 0° C. was added 0.71 g (2.80 mmol) of BOPCl and 0.6 mL (3.45 mmol) of DIEA. After stirring for 1 hr 1.14 g (3.66 mmol) of 1-[2-(5-[3-methylbenzyl])-1,3,4-oxadiazolyl]-2-(S)-amino-3-methylbutan-1-ol hydrochloride in 10 mL of anhydrous dichloromethane was added and the reaction mixture allowed to stir at 4° C. overnight. The reaction was diluted with dichloromethane and washed with water. The organic phase was dried over magnesium sulfate, filtered and evaporated under reduced pressure. The residue was purified by column chromatograph on silica gel using 3% methanol/dichloromethane to afford 1.30 g (67%) of the title compound as tan solid.

b. (2S, 5S)-Fmoc-5-amino-1,2,4,5,6,7-hexahydroazepino-[3,2,1]-indole-4-one-carbonyl-N-[1-(2-[5-(3-methylbenzyl)-1,3,4-oxadiazolyl]carbonyl)]-(S)-2-methylpropyl]amide.

To a mixture containing 0.95 g (7.16 mmol) of N-chlorosuccinimide in 150 mL of anhydrous toluene at 0° C. under a nitrogen atmosphere was added 0.79 mL (10.7 mmol) of dimethyl sulfide. The mixture was allowed to stir for 30 minutes. The reaction was cooled to −25° C. using a carbon tetrachloride/dry ice bath, followed by the dropwise addition of a solution containing 1.30 g (1.79 mmol) of (2S, 5S)-Fmoc-5-amino-1,2,4,5,6,7-hexahydroazepino-[3,2,1]-indole-4-one-carbonyl-N-[1-(2-[5-(3-methylbenzyl)-1,3,4-oxadiazolyl]hydroxymethyl)]-(S)-2-methylpropyl]amide in 10 mL of anhydrous toluene. The reaction was allowed to stir for 2 hours at −25° C. followed by the addition of 1.17 mL (8.4 mmol) of triethylamine. The cold bath was removed and the mixture was allowed to warm to room temperature over 30 minutes. The reaction mixture was diluted with ethyl acetate and washed with water. The organic phase was dried over magnesium sulfate. The residue was filtered, concentrated under reduced pressure and purified by column chromatography on silica gel with 10% ethyl acetate/hexane to give 0.93 g (72%) as a tan foam.

Example 29

(CE-2126) BTD-[1-(2-[5-(3-methylbenzyl)-1,3,4-oxadiazolyl]carbonyl)-2-(S)-methylpropyl]amide.

To a solution containing 0.41 g (0.59 mmol) of FMOC-BTD-[1-(2-[5-(3-methylbenzyl)-1,3,4-oxadiazole]carbonyl)-2-(S)-methylpropyl]amide in 4.5 mL of anhydrous DMF under an atmosphere of nitrogen was added 0.5 mL of diethylamine. After stirring at room temperature for 30 min the mixture concentrated under high vaccum. The residue was purified via preparative HPLC to afford 0.23 g (66%) of the title compound as a white solid. FAB MS [M+H] m/z; Calcd: 472, Found 472.

The intermediate Fmoc-BTD-[1-(2-[5-(3-methylbenzyl)-1,3,4-oxadiazolyl]carbonyl)-2-(S)-methylpropyl]amide was prepared as follows:
a. (2S, 5S)-Fmoc-BTD-[1-(2-[5-(3-methylbenzyl)-1,3,4-oxadiazolyl]hydroxymethyl)-2-(S)-methylpropyl]amide.

To a solution containing 1.25 g (2.85 mmol) of FMOC-BTD in 80 mL of anhydrous dichloromethane and 2.5 mL of anhydrous DMF under a nitrogen atmosphere at 0° C. was added 0.76 g (2.99 mmol) of BOPC1 and 0.6 mL (3.45 mmol) of DIEA. After stirring for 30 minutes and 1.14 g (3.66 mmol) of 1-[2-(5-[3-methylbenzyl])-1,3,4-oxadiazolyl]-2-(S)-amino-3-methylbutan-1-ol hydrochloride and 0.6 mL of DIEA in 10 mL of anhydrous dichloromethane was added and the reaction mixture allowed to stir at 0° C. overnight. The reaction was diluted with dichloromethane and washed with water. The organic phase was dried over magnesium sulfate, filtered and evaporated under reduced presure. The residue was purified by column chromatography on silica gel using 3% methanol/dichloromethane to afford 1.13 g (55%) of the title compound as a tan foam.
b. Fmoc-BTD-[1-(2-[5-(3-methylbenzyl)-1, 3, 4-oxadiazolyl]carbonyl)]-2-(S)-methylpropyl]amide.

To a mixture containing 0.81 g (6.09 mmol) of N-chlorosuccinimide in 110 mL of 1:1 anhydrous dichloromethane/toluene at 0° C. under a nitrogen atmosphere was added 0.67 mL (9.1 mmol) of dimethyl sulfide. The mixture was allowed to stir for 30 minutes. The reaction was cooled to −25° C. using a carbon tetrachloride/dry ice bath, followed by the dropwise addition of a solution containing 1.06 g (1.52 mmol) of Fmoc-BTD-[1-(2-[5-(3-methylbenzyl)-1,3,4-oxadiazolyl]hydroxymethyl)-2-(S)-methylpropyl]amide in 10 mL of anhydrous toluene. The reaction was allowed to stir for 2 hours at −25° C. followed by the addition of 1.0 mL (7.6 mmol) of triethylamine. The cold bath was removed and the mixture was allowed to warm to room temperature over 40 minutes. The reaction mixture was diluted with ethyl acetate and washed with water. The organic phase was dried over magnesium sulfate. The resulting mixture was filtered, concentrated under reduced pressure and purified by column chromatography on silica gel with 70% ethyl acetate/hexane to give 0.53 g of the product as a yellow oil. The material was further purified by preparative HPLC to afford 0.41 g (38.8%) of the title compound as a white solid.

Example 30

(CE-2134)(R,S)-3-Amino-2-oxo-5-phenyl-1,4,-benzodiazepine-N-[1-(2-[5-(3-methylbenzyl)-1,3,4-oxadiazolyl]carbonyl)-2-(S)-methylpropyl] acetamide.

To a solution containing 0.93 g (1.19 mmol) of(R,S)-FMOC-3-amino-2-oxo-5-phenyl-1,4,-benzodiazepine-N-[1-(2-[5-(3-methylbenzyl)-1, 3,4-oxadiazolyl]carbonyl)-2-(S)-methylpropyl]acetamide in 6.0 mL of anhydrous DMF under an atmosphere of nitrogen was added 0.45 mL of diethylamine. After stirring at room temperature for 2.5 hr the mixture was concentrated under high vaccum. The residue was purified via preparative HPLC to afford 0.030 g (4.5%) of the title compound as a white solid. FAB MS [M+H] m/z; Calcd: 565, Found 565.

The intermediate (R,S)-FMOC-3-amino-2-oxo-5-phenyl-1,4,-benzodiazepine-N-[1-(2-[5-(3-methylbenzyl)-1,3,4-oxadiazolyl]carbonyl)-2-(S)-methylpropyl]acetamide was prepared as follows:
a. (R,S)-FMOC-3-amino-2-oxo-5-phenyl-1,4,-benzodiazepine-N-[]-(2-[5-(3-methylbenzyl)-1,3,4-oxadiazolyl]hydroxymethyl)-2-(S)-methylpropyl] acetamide.

To a solution containing 0.75 g (1.41 mmol) of (R,S)-FMOC-3-amino-N-1-carboxymethyl-2-oxo-5-phenyl-1,4,-benzodiazepine in 30 mL of anhydrous dichloromethane under a nitrogen atmosphere at 0° C. was added 0.36 g (1.41 mmol) of BOPC1 and 0.25 mL (1.41 mmol) of DIEA. After stirring for 1 hr 0.48 g (1.55 mmol) of 1-[2-[5-(3-methylbenzyl)-1,3,4-oxadiazolyl]-2-(S)-amino-3-methyl butan-1-ol hydrochloride and 0.49 mL (2.82 mmol) of DIEA in 10 mL of anhydous dichloromethane was added and the reaction mixture allowed to stir at 4° C. overnight. The reaction was diluted with ethyl acetate and washed with water. The organic phase was dried over magnesium sulfate, filtered and evaporated under reduced pressure. The residue was purified by column chromatography on silica gel using a gradient of 2 to 6% methanol/dichloromethane to afford 1.00 g (89%) of the title compound as a yellow solid.
b. (R,S)-FMOC-3-amino-2-oxo-5-phenyl-1,4,-benzodiazepine-N-[1-(2-[5-(3-methylbenzyl)-1,3,4-oxadiazolyl]carbonyl)-2-(S)-methylpropyl]acetamide.

To a mixture containing 0.71 g (7.6 mmol) of N-chlorosuccinimide in 40 mL of anhydrous toluene at 0° C. under a nitrogen atmosphere was added 0.84 mL (11.4 mmol) of dimethyl sulfide. The reaction was cooled to −25° C. using a carbon tetrachloride/dry ice bath followed by the dropwise addition of a solution containing 1.50 g (1.90 mmol) of (R,S)-FMOC-3-amino-2-oxo-5-phenyl-1,4,- benzodiazepine-N-[1-(2-[5-(3-methylbenzyl)-1,3,4-oxadiazolyl]hydroxymethyl)-2-(S)-methylpropyl]acetamide in 10 mL of anhydrous toluene. The reaction was allowed to stir for 2 hours at −25° C. followed by the addition of 1.0 mL (7.6 mmol) of triethylamine. The cold bath was removed and the mixture was allowed to warm to room temperature over 1 hour. The reaction mixture was diluted with ethyl acetate and washed with water. The organic phase was dried over magnesium sulfate. The residue was filtered, concentrated under reduced pressure to afford 0.94 g (62%) of material which was used without further purification. FAB MS [M+H] m/z; Calcd: 787, Found: 787.

Example 31

(CE-2145)(Benzyloxycarbonyl)-L-valyl-2-L-(2,3-dihydro-1H-indole)-N-[1-(2-[5-(3-methylbenzyl)-1, 3, 4-oxadiazolyl]carbonyl)-2-(S)-methylpropyl]amide.

To a mixture containing 0.48 g (3.67 mmol) of N-chlorosuccinimide in 30 mL of anhydrous toluene at 0° C. under a nitrogen atmosphere was added 0.40 mL (5.41 mmol) of dimethyl sulfide. After stirring for 1 hr the reaction mixture was cooled to −25° C. using a carbon tetrachloride/dry ice bath followed by the dropwise addition of a solution containing 0.95 g (1.90 mmol) of (benzyloxycarbonyl)-L-valyl-2-L-(2,3-dihydro-1H-indole)-N-[1-(2-[5-(3-methylbenzyl)-1,3,4-oxadiazolyl]hydroxymethyl)-2-(S)-methylpropyl]amide in 20 mL of anhydrous toluene. The reaction was allowed to stir for 2 hours at −25° C. followed by the addition of 0.50 mL (3.6 mmol) of triethylamine. The cold bath was removed and the mixture was allowed to warm to room temperature. The reaction mixture was diluted with dichloromethane and washed with 1 N HCl (2×), saturated sodium bicarbonate (2×) and water. The organic phase was dried over magnesium sulfate. The mixture was filtered and concentrated under reduced pressure to afford 0.61 g. The residue was purified by column chromatography on silica gel with 50% ethyl acetate/hexane to afford 0.27 g of material which was further purified via preparative HPLC to afford 196 mg (33.4%) of the title compound as a white solid. FAB MS [M+H] m/z Calcd: 652, Found 652.

The intermediate (benzyloxycarbonyl)-L-valyl-2-L-(2,3-dihydro-1H-indole)-N-[1-(2-[5-(3-methylbenzyl)-1,3,4-oxadiazolyl]hydroxymethyl)-2-(S)-methylpropyl]amide was prepared by the following procedures:

a. 2-L-Methyl (2,3-dihydroindole)carboxylate.

To a suspension containing 5.00 g (30.6 mmol) of 2-L-(2,3-dihydroindole)carboxylic acid in 100 mL of anhydrous MeOH cooled to 0° C. was added a slow stream of HCl gas over 20 minutes. The resulting homogeneous solution was allowed to stir overnight warming to room temperature. The mixture was evaporated and the residue was crystallized from methanol/ether to afford, after drying, 5.58 g (85%) of 2-L-methyl (2,3-dihydroindole)carboxylate.

b. 2-Methyl [(S)-1-(N-[benzyloxycarbonyl]-L-valyl)-2,3-dihydro-1H-indole]carboxylate.

To a solution containing 3.00 g (14.0 mmol) of methyl (2,3-dihydroindole)-L-2-carboxylate in 60 mL of anhydrous dichloromethane, under a nitrogen atmosphere at 0° C., 7.15 g (28.8 mmol) of BOPCl and 7.72 mL (70.2 mmol) of DIEA was added a solution of 7.06 g (28.08 mmol) of Cbz-Val-OH in 40 mL of anhydrous dichloromethane and 3 mL of DMF. After stirring for 3 days at 5° C. the mixture was diluted with ethyl acetate and washed with 1 N HCl (2×) and brine. The mixture was filtered and evaporated under reduced pressure. The residue was purified by column chromatography on silica gel using a gradient of 9:1 to 1:1 hexane/ethyl acetate to afford 4.85 g (87%) of the title compound as a white foam.

c. 2-[(S)-1-(N-[Benzyloxycarbonyl]-L-valyl)-2,3-dihydro-1H-indole]carboxylic acid.

To a solution containing 4.85 g (12.17 mmol) of 2-methyl [(S)-1-(N-[benzyloxycarbonyl]-L-valyl)-2,3-dihydro-1H-indole]carboxylate in 45 mL of THF and 15 mL of MeOH at 0° C. was added 15.8 mL of 1 N LiOH dropwise. After 30 minutes 1 N HCl was added to pH 2 and the mixture extracted with ethyl acetate (3×). The combined organic phases were dried over magnesium sulfate, filtered and evaporated under reduced presure to afford 4.51 g (93%) of the title compound as a white solid.

d. (Benzyloxycarbonyl)-L-valyl-2-L-(2,3-dihydro-1H-indole)-N-[1-(2-[5-(3-methylbenzyl)-1,3,4-oxadiazolyl]hydroxymethyl)-2-(S)-methylpropyl]amide.

To a solution containing 1.09 g (3.96 mmol) of 1-[2-(5-[3-methylbenzyl])-1,3,4-oxadiazolyl]-2-(S)-amino-3-methylbutan-1-ol and 1.31 g (3.3 mmol) of 2-[(S)-1-(N-[benzyloxycarbonyl]-L-valyl)-2,3-dihydro-1H-indole] carboxylic acid in 30 mL of anhydrous dichloromethane was added 1.21 mL (6.93 mmol) of DIEA and 0.49 g (3.63 mmol) of HOBT. The mixture was cooled to 0° C. and 0.70 g (3.63 mmol) of EDCI was added and the reaction mixture was allowed to stir overnight. An additional 1.0 mL (7.44 mmol) of TEA was added and the reaction again allowed to stir overnight. The reaction was diluted with dichloromethane and washed with 1 N HCl (2×), saturated sodium bicarbonate (2×) and water. The organic phase was dried over magnesium sulfate, filtered and evaporated under reduced pressure. The residue was purified by column chromatography on silica gel with 80% ethyl acetate/hexane to afford 0.66 g (30%) of the title compound.

Example 32

(CE-2125)(Benzyloxycarbonyl)-L-valyl-2-L-(2,3-dihydro-1H-indole)-N-[1-(3-[5-(3-trifluoromethylbenzyl)-1,2,4-oxadiazolyl]carbonyl)-2-(S)-methylpropyl]amide. Prepared in a similar manner as in Example 30. FAB MS [M+H] m/z; Calcd: 706, Found: 706.

Example 33

(CE-2143) Acetyl-2-L-(2,3-dihydro-1H-indole)-N-[1-(3-[5-(3-trifluoromethylbenzyl)-1,2,4-oxadiazolyl]carbonyl)-2-(S)-methylpropyl]amide. Prepared in a similar manner as in Example 30. FAB MS [M+H] m/z; Calcd: 515, Found: 515.

Example 34

(CE-2165) N-Acetyl-2-(L)-(2,3-dihydro-1H-indole)-N-[1-(2-[5-(3-methylbenzyl)-1,3,4-oxadiazolyl] carbonyl)-2-(S)-methylpropyl]amide. Prepared in a similar manner as in Example 30. FAB MS [M+H] m/z; Calcd: 461; Found: 461.

Example 35

(CE-2104)(Morpholino-N-carbonyl)-L-valyl-N-[1-(2-[5-(3-methylbenzyl)-1,3,4-oxadiazolyl]carbonyl)-2-(S)-methylpropyl]-L-prolinamide.

To a mixture containing 0.69 g (5.17 mmol) of N-chlorosuccinimide in 60 mL of anhydrous toluene at 0° C. under a nitrogen atmosphere was added 0.60 mL (8.17 mmol) of dimethyl sulfide. The reaction was cooled to −25°

C. using a carbon tetrachloride/dry ice bath, followed by the addition of a solution containing (morpholino-N-carbonyl)-L-valyl-N-[1-(2-[5-(3-methyl benzyl)-1,3,4-oxadiazolyl] hydroxymethyl)-2-(S-)methyl propyl]-L-prolinamide (0.75 g, 1.28 mmol) in 10 mL of anhydrous toluene. The reaction was allowed to stir for 2 hours at −25° C. followed by the addition of 1.1 mL (0.83 g, 7,89 mmol) of triethylamine. The cold bath was removed and the reaction was allowed to warm to room temperature over 20 minutes. The reaction was diluted with ethyl acetate and washed with water. The organic phase was dried over magnesium sulfate and filtered. The solvents were evaporated in vacuo and the residue purified by column chromatography, 70% ethyl acetate/hexane on silica gel. Final purification was performed by preparative HPLC to afford 405 mg (54.3%) of the title compound as a white solid. FAB MS [M+H] m/z; Calcd: 583, Found: 583.

The intermediate (Morpholino-N-carbonyl)-L-valyl-N-[1-(2-[5-(3-methylbenzyl)-1,3,4-oxadiazolyl] hydroxymethyl)-2-(S)-methylpropyl]-L-prolinamide was prepared as follows:

a. (Morpholino-N-carbonyl)-L-valyl-L-proline-O-t-butyl ester.

To a solution containing L-valyl-L-proline-O-t-butyl-ester (1.80 g, 5.87 mmol) in 80 mL of anhydrous methylene chloride and 1.5 mL (13.64 mmol) of N-methyl morpholine under a nitrogen atmosphere at 0° C. was added morpholine carbonyl chloride dropwise. The mixture was allowed to warm to room temperature overnight. The reaction was diluted with methylene chloride and washed with water. The organic layer was dried over magnesium sulfate, filtered and evaporated. The residue was purified by column chromatography on silica gel with 10% methanol/dichloromethane to afford 1.98 g (88%) of the title compound as a white solid. FAB MS [M+H] m/z; Calcd: 384, Found 384.

b. (Morpholino-N-carbonyl)-L-valyl-L-proline.

To a solution containing (morpholino-N-carbonyl)-L-valyl-L-proline-O-t-butyl ester (2.0 g, 5.22 mmol) in 80 mL of anhydrous methylene chloride under a nitrogen atmosphere at 0° C. was added trifluoroacetic acid (13 mL, 130 mmol). The mixture was allowed to warm to room temperature overnight and the solvents were evaporated in vacuo to give 2.26 g of a viscous oil. The material was used without further purification.

c. (Morpholino-N-carbonyl)-L-valyl-N-[1-(2-[5-(3-methylbenzyl)-1,3,4-oxadiazolyl] hydroxymethyl)-2-(S)-methylpropyl]-L-prolinamide.

To a solution containingn 0.95 g (2.90 mmol) of (morpholino-N-carbonyl)-L-valyl-Proline in 25 mL of anhydrous dichloromethane under a nitrogen atmosphere at 0° C. was added 0.80 g (3.14 mmol) of BOPCI and 1.5 mL (8.61 mmol) of DIEA. After 30 minutes, 0.75 g (2.41 mmol) of 1-[2-(5-[3-methylbenzyl])-1,3,4-oxadiazolyl]-2-(S)-amino-3-methylbutan-1-ol hydrochloride in 10 mL of dichloromethane and 1.1 mL (6.31 mmol) of DIEA were added. The reaction was allowed to stir at 0° C. overnight. The reaction was diluted with dichloromethane and washed with a saturated NaHCO₃ solution. The organic phase was dried over magnesium sulfate and filtered. The mixture was concentrated in vacuo and the residue purified by column chromatography on silica gel using 6% methanol/dichloromethane to afford 0.77 g (54.84%) of the title compound as a white solid. FAB MS [M+H] m/z; Calcd: 585, Found: 585.

Example 36

(CE-2079) 3-(S)-(Benzyloxycarbonyl)amino)-ε-lactam-N-[1-(2-[5-(3-methylbenzyl)-1,3,4-oxadiazolyl] carbonyl)-2-(S)-methylpropyl] acetamide.

To a mixture containing 2.37 g (17.75 mmol) of N-chlorosuccinimide in 100 mL of anhydrous toluene at 0° C. under a nitrogen atmosphere was added 1.94 mL (2.64 mmol) of dimethyl sulfide. The reaction was cooled to −25° C. using a carbon tetrachloride/dry ice bath, followed by the dropwise addition of a solution containing 2.5 g (4.44 mmol) of 3-(S)-[(benzyloxycarbonyl)amino]-ε-lactam-N-[1-(2-[5-(3-methylbenzyl)-1,2,4-oxadiazolyl]hydroxymethyl)-2-(S)-methyl propyl]acetamide in 20 mL of anhydrous toluene. Upon complete addition, the reaction was allowed to stir at −25° C. for 2 hours, followed by the addition of 3.0 mL (21.52 mmol) of triethylamine. The cold bath was removed and the reaction warmed to room temperature and stirred for 30 minutes. The reaction was diluted with ethyl acetate and washed with water. The organic phase was dried over magnesium sulfate. Filtration, removal of solvent and column chromatography of the residue on silica gel with 5% methanol/dichloromethane afforded 1.8 g of a pale yellow solid. Subsequent preparative HPLC gave 950 mg (38.1%) of the title compound as a white solid. FAB MS [M+H] m/z; Calcd: 562, Found: 562.

The intermediate 3-(S)-[(benzyloxycarbonyl)amino]-ε-lactam-N-[1-(2-[5-(3-methylbenzyl)-1,2,4-oxadiazolyl] hydroxymethyl)-2-(S)-methyl propyl]acetamide was prepared as follows:

a. 3-(S)-[(Benzyloxycarbonyl)amino]-ε-lactam.

To a mixture containing 9.9 g (37.18 mmol) of Cbz-omithine in 150 mL of acetonitrile under a nitrogen atmosphere was added 78 mL (369.70 mmol) of hexamethyldisilazane. The reaction was heated at reflux for 48 hours. The reaction mixture was cooled to room temperature and poured into 250 mL of cold methanol. The solvent was removed under reduced pressure. Chloroform was added and the mixture filtered through a plug of celite. The filtrate was concentrated under reduced pressure and the residue dissolved in ethyl acetate. Hexane was added until the solution was slightly turbid and then allowed to stand overnight. The resultant solid was filtered and dried to afford 8.37 g (90.7%) of the title compound.

b. N-[3-(S)-(Benzyloxycarbonyl)amino]-ε-lactam-t-butyl acetate.

To a solution containing 1.0 g (4.03 mmol) of 3-(S)-[(benzyloxylcarbonyl)amino]-ε-lactam in 20 mL of anhydrous DMF under a nitrogen atmosphere was added 1.50 mL (10.16 mmol) of bromo-t-butyl acetate and 1.17 g (5.05 mmol) of silver oxide. The reaction was heated to 45° C. for 5 hours, diluted with acetonitrile and filtered through a pad of celite. The filtrate was concentrated under reduced pressure and the residue dissolved in ethyl acetate and washed with water. The organic phase was dried over magnesium sulfate. Filtration, removal of solvent and column chromatography of the residue on silica get with 60% ethyl acetate/hexane afforded 1.18 g (80.79%) of the title compound. FAB MS [M+H] m/z; Calcd: 363, Found: 363.

c. N-[3-(S)-(Benzyloxycarbonyl)amino)-ε-lactam-carboxymethane.

To a solution containing 0.55 g (1.52 mmol) of N-[3-(S)-(Benzyloxy carbonyl)amino]-ε-lactam-t-butyl acetate in 20 mL (15.58 mmol) of trifluoroacetic acid. The reaction was allowed to warm to room temperature overnight. The solvent was removed under reduced pressure. The residue was dissolved in ether acetate and washed with water. The organic phase was dried over magnesium sulfate. Filtration and removal of solvent afforded 0.50 of the title compound. FAB MS [M+H] m/z; Calcd: 307, Found: 307.

d. 3-(S)-[Benzyloxycarbonyl)amino)-ε-lactam-N-[] -(2-[5-(3-methylbenzyl)-1,3,4-oxadiazolyl]hydroxymethyl)-2-(S)-methylpropyl]acetamide.

To a solution containing 2.72 g (8.88 mmol) of N-[3-(S)-(Benzyloxycarbonyl) amino]-ε-lactam-carboxymethane in 80 mL of dichloromethane under a nitrogen atmosphere at 0° C. was added 2.37 g (9.31 mmol) of BOPCI and 1.60 mL (9.91 mmol) of DIEA. The reacton was allowed to stir at 0° C. for 30 minutes followed by the addition of 2.37 g (7.60 mmol) of 1-[3-[5-(3-methylbenzyl)-1,3,4-oxadiazolyl]-2-(S)-amino-3methyl butan-1-ol hydrochloride in 20 mL of dichloromethane and 1.60 mL (9.19 mmol) of DIEA. The reaction was allowed to stir at 0° C. overnight. The reaction was diluted with dichloromethane and washed with water. The organic phase was dried over magnesium sulfate. Filtration, removal of solvent and column chromatography of the residue on silica get with 10% methanol/dichloromethane afforded 2.58 g (50.23%) of the title compound. FAB MS [M+H] m/z; Calcd: 564, Found: 564.

Example 37

(CE-2080) 3-(S-(Amino)-ε-lactam-N-[1-(2-[5-(3-methylbenzyl)- 1,3,4-oxadiazolyl]carbonyl)-2-(S)-methylpropyl]acetamide trifluoroacetic acid salt.

This compound was prepared via deprotection of 3-(S)-[benzyloxycarbonyl)amino)-ε-lactam-N-[1-(2-[5-(3-methylbenzyl)-1,3,4-oxadiazolyl]carbonyl)-2-(S)-methyl propyl]acetamide under standard conditions to one skilled in the art to afford the title compound. FAB MS [M+H] m/z; Calcd: 428, Found: 428.

Example 38

(CE-2091) 3-(S)-[(4-Morpholino carbonyl-butanoyl) amino]-ε-lactam-N-[1-(2-[5-(3-methylbenzyl)-1,3,4-oxadiazolyl]carbonyl)-2-(R,S)-methylpropyl] acetamide.

To a solution containing 0.089 g (0.475 mmol) of 4-morpholino carbonyl butanoic acid in 10 mL of dichloromethane under a nitrogen atmosphere at 0° C. was added 0.127 g (0.498 mmol) of BOPCI and 0.09 mL (0.492 mmol) of DIEA. The reaction was allowed to stir for 30 minutes followed by the additin of 0.22 g (0.406 mmol) of 3-(S)-amino-ε-lactam-N-[1-(2-[5-(3-methyl benzyl)-1,3,4-oxadiazolyl]carbonyl)-2-(R,S)-methyl propyl]acetamide trifluoroacetic acid salt. The reaction was allowed to stir at 0° C. overnight. The reaction was diluted with dichloromethane and washed with water. The organic phase was dried over magnesium sulfate. Filtration, removal of solvent and purification via preparative HPLC afforded 0.044 g (18%) of the title compound. FAB MS [M+H] m/z; Calcd: 597, Found: 597.

Example 39

(CE-2087) 6-[4-Fluorophenyl]-ε-lactam-N-[1-(2-[5-(3-methylbenzyl)-1,3,4-oxadiazolyl]carbonyl)-2-(S)-methylpropyl]acetamide.

To a mixture containing 0.70 g (5.24 mmol) and N-chlorosuccinimide in 30 mL of anhydrous toluene at 0° C. under a nitrogen atmosphere was added 0.60 mL (8.17 mmol) of dimethyl sulfide. The reaction was cooled to −25° C. using a carbon tetrachloride/dry ice bath, followed by the dropwise addition of a solution containing 0.67 g (1.32 mmol) of 6-[4-fluorophenyl]-ε-lactam-N-[1-(2-[5-(3-methyl benzyl)-1,3,4-oxadiazolyl]hydroxymethyl)-2-(S)-methylpropyl]acetamide in 15 mL of anhydrous toluene. Upon complete addition, the reaction was allowed to stir at −25° C. for 2 hours followed by the addition of 0.90 mL (6.46 mmol) of triethylamine. The cold bath was removed and the reaction allowed to warm to room temperature and maintained for 20 min. The reaction was diluted with ethyl acetate and washed with water. The organic phase was dried over magnesium sulfate. Filtration, removal of solvent under reduced pressure and column chromotography of the residue on silica gel with 10% methanol/dichloromethane afforded 0.61 g of a pale yellow solid. Subsequent preparative HPLC gave 338 mg (50.5%) of the title compound. FAB MS [M+H] m/z; Calcd: 507, Found: 507.

The intermediate 6-[4-fluorophenyl]-ε-lactam-N-[1-(2-[5-(3-methylbenzyl)-1,3,4-oxadiazolyl]hydroxymethyl)-2-(S)-methylpropyl]acetamide was prepared as follows:

a. 6-[4-Fluorophenyl]–6-carboxymethylene-2-piperidinone.

To a solution containing 2.15 g (8.11 mmol) of 6-[4-fluorophenyl]-1-carbomethoxymethylene-2-piperidinone, prepared in a similar fashion to that reported by Compernolle (*Tetrahedron*, 49:3193 (1993)) in 70 mL of methanol and 20 mL of water under a nitrogen atmosphere was added 0.55 g (13.11 mmol) of lithium hydroxide. The reaction was allowed to stir at room temperature for 2 hours. The solvent was removed under reduced pressure. The residue was diluted with water and washed with ethyl acetate. The aqueous phase was acidified with 1 N hydrochloric acid and extracted with ethyl acetate. The organic phase was dried over magnesium sulfate. Filtration and removal of solvent afforded 2.0 g (98.2%) of the title compound. FAB MS [M+H] m/z; Calcd: 252, Found: 252.

b. 6-[4-Fluorophenyl]-ε-lactam-N-[1-(2-[5-(3-methylbenzyl)-1,3,4-oxadiazolyl]hydroxymethyl)-2-(S)-methylpropyl]acetamide.

To a solution containing 1.04 g (4.14 mmol) of 6-[4-fluorophenyl]-6-carboxymethylene-2-piperidinone in 25 mL of anhydrous dichloromethane under a nitrogen atmosphere at 0° C. was added 1.10 g (4.32 mmol) of BOPCI and 0.80 mL (4.59 mmol) of DIEA. After stirring for 30 minutes, a solution containing 1.1 g (3.53 mmol) of 1-[2-(5-[3-methylbenzyl])-1,3,4-oxadiazolyl]2-(S)-amino-3-methylbutan-1-ol hydrochloride in 10 mL of dichloromethane and 1.10 mL (6.31 mmol) of DIEA. The reaction was allowed to stir at 0° C. overnight. The reaction was diluted with dichloromethane and washed with a saturated sodium bicarbonate solution. The organic phase was dried over magnesium sulfate. Filtration, removal of solvent under reduced pressure and column chromotography of the residue on silica gel with 10% methanol/dichloromethane afforded 736 mg (41.0%) of the title compound. FAB MS [M+H] m/z; Calcd: 509, Found: 509.

Example 40

(CE-2121) 2-[2-(R,S)-Phenyl-4-oxothiazolidin-3-yl]-N-[1-(2-[5-(3-methylbenzyl)-1,3,4-oxadiazolyl] carbonyl)-2-(S)-methylpropyl] acetamide.

To a mixture containing 2.05 g (15.38 mmol) of N-chlorosuccinimide in 250 mL of anhydrous toluene at 0° C. under a nitrogen atmosphere was added 1.70 mL (23.06 mmol) of dimethyl sulfide. The reaction was cooled to −25° C. using a carbon tetrachloride/dry ice bath, followed by the addition of 1.90 g (3.84 mmol) of 2-[2-(R,S)-phenyl-4-oxothiazolidin-3-yl]-N-[1-(2-[5-(3-methylbenzyl)-1,3,4-oxadiazolyl]hydroxymethyl)-2-(S)-methylpropyl]acetamide in 20 mL of anhydrous toluene dropwise. The reaction was allowed to stir at −25° C. for 2 hours, followed by the addition of 2.52 mL (18.07 mmol) of triethylamine. The cold bath was removed and the reaction allowed to warm to room temperature over 40 minutes. The reaction was diluted with ethyl acetate and washed with water. The organic phase was dried over magnesium sulfate. Filtration, removal of solvent and column chromatography of the residue on silica gel with 60% ethyl acetate/hexane afforded 1.10 g of a yellow oil. This was further purified via preparative HPLC to give 0.45 g (24%) of the title compound as an off-white solid. FAB MS [M+H] m/z; Calcd: 493, Found 493.

The intermediate 2-[2-(R,S)-phenyl-4-oxothiazolidin-3-yl]-N-[1-(2-[5-(3-methylbenzyl)-1,3,4-oxadiazolyl]hydroxymethyl)-2-(S)-methypropyl]acetamide was prepared as follows: to a solution containing 1.78 g (7.51 mmol) of 2-(2-phenyl-4-oxothiazolidin-3-yl) acetic acid, prepared according to Holmes (*J. Org. Chem*, 60:7328 (1995)), in 80 mL of dichloromethane under a nitrogen atmosphere at 0° C. was added 2.04 g (8.02 mmol) of BOPCI and 1.35 mL (7.76 mmol) of DIEA. After stirring for 30 minutes, 2.0 g (6.41 mmol) of 1-[3-[5-(3-methylbenzyl)]-1,3,4-oxadiazolyl]-2-(S)-amino-3-methyl-butan-1-ol hydrochloride in 50 mL of dichloromethane and 1.35 mL (7.76 mmol) of DIEA was added. The reaction was allowed to stir at 0° C. overnight. The reaction mixture was diluted with dichloromethane and washed with water. The organic phase was dried over magnesium sulfate, filtered and concentrated under reduced pressure. Column chromatography of the residue on silica gel with 4% methanol/dichloromethane afforded 2.30 g of a yellow foam. Subsequent preparative HPLC gave 1.9 g of the title compound. FAB MS [M+H] m/z; Calcd: 495, Found: 495.

Example 41

(CE-2122) 2-[2-(R,S)-Benzyl-4-oxothiazolidin-3-yl]-N-[1-(2-[5-(3-methylbenzyl)-1,3,4-oxadiazolyl] carbonyl)-2-(S)-methylpropyl] acetamide was prepared in a similar manner as in Example 39. FAB MS [M+H] m/z; Calcd: 507, Found: 507.

Example 42

(CE-2136) 2-[(2-(R,S)-Benzyl-4-oxothiazolidin-3-yl oxide]-N-[1-(2-[5-(3-methyl benzyl)-1,3,4-oxadiazolyl] carbonyl)-2-(R,S,)-methylpropyl] acetamide.

To a solution containing 1.31 g (2.59 mmol) of 2-[2-(R,S)-benzyl-4-oxothiazolidin-3-yl)-N-[1-(2-[5-(3-methylbenzyl)-1,3,4-oxadiazolyl] carbonyl)-2-(S)-methyl propyl]-acetamide in 15 mL of methanol under a nitrogen atmosphere was added 0.51 mL (5.17 mmol) of 30% hydrogen peroxide. The reaction was allowed to stir at room temperature overnight and then partitioned between brine and dichloromethane. The organic phase was dried over magnesium sulfate. Filtration, removal of solvent under reduced pressure and column chromatography of the residue on silica gel with 85% ethyl acetate/hexane afforded 0.73 g of a tan oil. Subsequent preparative HPLC gave 0.54 g (48%) of the title compound. FAB MS [M+H] m/z; Calcd: 523, Found 523.

Example 43

(CE-2137) 2-[2-(R,S)-Benzyl-4-oxothiazolidin-3-yl oxide]-N-[1-(3-[5-(3-trifluoromethylbenzyl)-1,2,4-oxadiazolyl] carbonyl)-2-(R,S,)-methylpropyl] acetamide. Prepared in a similar manner as in Example 41. FAB MS [M+H] m/z; Calcd: 577, Found 577.

Example 44

(CE-2118) 2-[2-(R,S)-Phenyl-4-oxometathiazan-3yl]-N-[1-(2-[5-(3-methylbenzyl)-1,3,4-oxadiazolyl] carbonyl)-2-(S)-methylpropyl] acetamide. Prepared in a similar manner as in Example 39. FAB MS [M+H] m/z; Calcd: 507, Found: 507.

Example 45

(CE-2140)(1-Benzoyl-3,8-quinazolinedione)-N-[1-(2-[5-(3-methylbenzyl)-1,3,4-oxadiazolyl] carbonyl)-2-(S)-methylpropyl] acetamide.

To a mixture containing 1.70 g (2.74 mmol) of N-chlorosuccinimide in 75 mL of anhydrous toluene at 0° C. under a nitrogen atmosphere was added 1.70 mL (23.15 mmol) of dimethyl sulfide. The reaction was cooled to −25° C. using a carbon tetrachloride/dry ice bath, followed by the addition of 1.90 g (3.27 mmol) of (1-Benzoyl-3,8-quinazolinedione)-N-[1-(2-[5-(3-methylbenzyl)-1,3,4-oxadiazolyl]hydroxymethyl)-2-(S)-methyl propyl] acetamide in 10 mL of toluene dropwise. The reaction was allowed to stir at −25° C. for 2 hours, followed by the addition of 3.20 mL (22.96 mmol) of triethylamine. The cold bath was removed and the reaction allowed to warm to room temperature and maintained for 15 minutes. The reaction was diluted with ethyl acetate and washed with water. The organic phase was dried over magnesium sulfate, filtered, and the solvent removed under reduced pressure. The residue was chromatographed on silica gel with 5% methanol/dichloromethane to afford 1.37 g of a brown oil. This was further purified via preparative HPLC to give 450 mg (40.1%) of the title compound. FAB MS [M+H]m/z; Calcd: 580, Found: 580.

The intermediate (1-benzoyl-3,8-quinazolinedione)-N-[1-(2-[5-(3-methylbenzyl)-1,2,4-oxadiazolyl]hydroxymethyl)-2-(S)-methylpropyl]acetamide was prepared as follows:

a. 1-Benzoyl-3,8-quinazolinedione-2-t-butyl acetate.

To a solution containing 5.0 g (18.78 mmol) of 1-Benzoyl-3,8-quinazolinidione prepared in a similar manner to that reported by Melnyk et al. (*Tetrahedron Lett.*, 37:4145 (1996)), in 100 mL of DMF under a nitrogen atmosphere was added 4.30 mL (29.12 mmol) of bromo t-butylacetate and 5.4 g (23.30 mmol) of silver oxide. The reaction was heated to 50° C. overnight, diluted with ethyl acetate and washed with water. The organic phase was dried over magnesium sulfate. Filtration, removal of solvent under reduced pressure and column chromatography of the residue on silica gel with 40% ethyl acetate/hexane gave 5.25 g (73.49%) of product. FAB MS [M+Hl] m/z; Calcd: 381, Found: 381.

b. 1-Benzoyl-2-carboxymethylene-3,8-quinazolinedione.

To a solution containing 5.20 g (13.67 mmol) of 1-benzoyl-3,8-quinazolinedione-2-t-butyl acetate in 300 mL of dichloromethane under a nitrogen atmosphere at 0° C. was added 21.0 mL (211.44 mmol) of trifluroacetic acid. The reaction was allowed to warm to room temperature overnight. The solvent was removed under reduced pressure and the residue dissolved in ethyl acetate and washed with water. The organic phase was dried over magnesium sulfate. Filtration and removal of solvent afforded 4.32 g (97.45%) of the title compound. FAB MS [M+H]m/z; Calcd: 325, Found: 325.

c. (1-Benzoyl-3,8-quinazolinedione)-N-[1-(2-[5-(3-methylbenzyl)-1,3,4-oxadiazolyl] hydroxymethyl)-2-(S)-methylpropyl]acetamide.

To a solution containing 1.80 g (5.55 mmol) of 1-benzoyl-2-carboxymethylene-3,8-quinazolinedione in 100 mL of anhydrous dichloromethane and 5 mL of DMF under a nitrogen atmosphere at 0° C. was added 1.90 g (7.46 mmol) of BOPCI and 1.40 mL (8.05 mmol) of DIEA. After stirring for 30 minutes, a solution containing 1.70 g (5.45 mmol) of 1-[2-(5-[3-methylbenzyl])-1,3,4-oxadiazolyl]-2-(S)-amino-3-methylbutan-1-ol hydrochloride in 20 mL of dichloromethane and 3.80 mL (21.84 mmol) of DIEA was added. The reaction was allowed to stir at 0° C. overnight, diluted with dichloromethane and washed with water. The organic phase was dried over magnesium sulfate. Filtration, removal of solvent under reduced pressure and column chromatography of the residue on silica gel with 10% methanol/dichloromethane afforded 1.93 g (60.9%) of the title compound. FAB MS[M+H]m/z; Calcd: 582, Found: 582.

Example 46

(CE-2138)(1-Benzoyl-3,6-piperazinedione)-N-[1-(2-[5-(3-methylbenzyl)-1,3,4-oxadiazolyl] carbonyl)-2-(S)-methylpropyl]acetamide. Prepared in a similar manner as in Example 44. FAB MS [M+H]m/z; Calcd: 532, Found: 532.

Example 47

(CE-2147)(1-Phenyl-3,6-piperazinedione)-N-[1-(2-[5-(3-methylbenzyl)-1,3,4-oxadiazolyl] carbonyl)-2-(S)-methylpropyl]acetamide. Prepared in a similar manner as in Example 44. FAB MS [M+H]m/z; Calcd: 504, Found: 504.

Example 48

(CE-2148)(1-Phenyl-3,6-piperazinedione)-N-[1-(3-[5-( 3-trifluoromethylbenzyl)-1,2,4-oxadiazolyl] carbonyl)-2-(S)-methylpropyl]acetamide. Prepared in a similar manner as in Example 44. FAB MS [M+H] m/z; Calcd:558, Found: 558.

Example 49

(CE-2108) 3-[(Benzyloxycarbonyl)amino]-quinoline-2-one-N-[1-(2-[5-(3-methybenzyl)-1,3,4-oxadiazolyl] carbonyl)-2-(S)-methylpropyl] acetamide.

To a mixture containing 0.16 g (1.18 mmol) of N-chlorosuccinimide in 20 mL of anhydrous toluene at 0° C. under a nitrogen atmosphere was added 0.13 mL (1.77 mmol) of dimethyl sulfide. The reaction was cooled to −25° C. using a carbon tetrachloride/dry ice bath followed by the addition of a solution containing 0.18 g (0.30 mmol) of 3-[(benzyloxycarbonyl)amino]-quinoline-2-one-N-[1-(2-[5-(3-methylbenzyl)-1,3,4-Oxadiazolyl]hydroxymethyl)-2-(S)-methylpropyl]acetamide in 20 mL of methylene chloride dropwise. The reaction was allowed to stir at −25° C. for 2 hours, followed by the addition of 0.19 mL (1.38 mmol) of triethylamine. The cold bath was removed and the reaction was allowed to warm to room temperature and maintained for 30 minutes. The reaction was diluted with ethyl acetate and washed with water. The organic phase was dried over magnesium sulfate. Filtration, removal of solvent under reduced pressure and column chromatography of the residue on silica gel with 3% methanol/dichloromethane afforded 0.23 g of an oil. Further purification via preparative HPLC gave 100 mg of the title compound.

FAB MS [M+H} m/z; Calcd: 608, Found: 608

The intermediate 3-[(benzyloxycarbonyl)amino]-quinoline-2-one-N-[1-(2-[5-(3-methylbenzyl)-1,3,4-oxadiazolyl]hydroxymethly)-2-(S)-methylpropyl]acetamide was prepared as follows:

a. 3-[(Benzyloxycarbonyl)amino]-quinoline-2-one.

To a solution containing 0.5 g (3.10 mmol) of 3-amino-quinoline-2-(1H)-one described by Anderson, et. al. (*J. Heterocyclic Chem.*, 30:1533 (1993)) in 40 mL of dioxane under a nitrogen atmosphere was added 0.14 g (3.4 mmol) of sodium hydroxide in 14 mL of water. The reaction mixture was cooled to 0° C., followed by the addition of 0.50 mL (3.4 mmol) of benzylchloroformate. The pH of the reaction was maintained above 8.0 with additional 1 N sodium hydroxide. The reaction was allowed to warm to room temperature and stirred for 2 hours. The reaction was diluted with methylene chloride and washed with water. The organic phase was dried over magnesium sulfate. Filtration, removal of solvent under reduced pressure and column chromatography of the residue on silica gel with 2% methanol/dichloromethane afforded 0.32 g (35%) of product as a white solid. FAB MS [M+H] m/z; Calcd: 295, Found: 295 b. 3-[(Benzyloxycarbonyl)amino]-quinoline-2-one-N-t-butyl-acetate.

To a solution containing 0.30 g (1.02 mmol) of 3-[(benzyloxycarbonyl)amino]-quinoline-2-one in 20 mL of DMF under a nitrogen atmosphere was added 0.15 mL (1.02 mmol) of t-butyl bromoacetate and 0.24 g (1.02 mmol) of silver oxide. The reaction was heated to 70° C. and maintained overnight. The reaction mixture was diluted with acetonitrile and filtered through a pad of celite. The filtrate was concentrated under reduced pressure and the residue partitioned between ethyl acetate and water. The organic phase was dried over magnesium sulfate. Filtration, removal of solvent under reduced pressure and column chromatography of the residue on silica gel with dichloromethane afforded 0.20 g (48%) or product as a white solid. FAB MS [M+H] m/z; Calcd: 409, Found: 409.

c. 3-[(Benzyloxycarbonyl)amino]-1-carboxymethylene-quinoline-2-one.

To a solution containing 1.30 g (3.18 mmol) of 3-[(benzyloxycarbonyl)amino]-quinoline-2-one-N-t-butyl-acetate in 35 mL of dichloromethane under a nitrogen atmosphere at 0° C. was added 2.45 mL (31.84 mmol) of trifluoroacetic acid. The reaction was allowed to warm to room temperature overnight. The solvent was removed under reduced pressure to afford 1.09 g (97%) of the title compound. FAB MS [M+H] m/z; Calcd: 353, Found: 353 d. 3-[(Benzyloxycarbonyl)amino]-quinoline-2-one-N-[1-(2-[5-(3-methylbenzyl)-1,3,4-oxadiazolyl] hydroxymethyl)-2-(S)-methylpropyl]acetamide.

To a solution containing 1.09 g (3.09 mmol) of 3-[(benzyloxycarbonyl)amino]-1-carboxymethylene-quinoline-2-one in 50 mL of anhydrous dichloromethane and 3 mL of DMF under a nitrogen atmosphere at 0° C. was added 0.84 (3.31 mmol) of BOPCI and 1.10 mL (6.31 mmol) of DIEA. After stirring for 30 minutes, 0.82 g (2.65 mmol) of 1-[2-(5-[3-methylbenzyl])-1,3,4-oxadiazolyl]-2(S)-amino-3-methylbutan-1-ol hydrochloride in 8 mL of dichloromethane and 0.56 mL (3.20 mmol) of DIEA was added. The reaction was allowed to stir at 0° C. overnight, diluted with dichloromethane and washed with water. The organic phase was dried over magnesium sulfate. Filtration, removal of solvent under reduced pressure and column chromatography of the residue on silica gel with 5% methanol/dichloromethane afforded 0.37 g (30.3%) of product. FAB MS [M+H] m/z; Calcd: 610, Found: 610

Example 50

(CE-2107) 3-[(Benzyloxycarbonyl)amino]-7-piperidinyl-quinoline-2-one-N-[1-(2-[5-(3-methybenzyl)-1,3,4-oxadiazolyl]carbonyl)-2-(S)-methylpropyl]acetamide. Prepared in a similar manner as shown in Example 48. FAB MS [M+H] m/z; Calcd: 691, Found: 691

Example 51

(CE-2117) 3-Carbomethoxy-4-fluoro-quinoline-2-one-N[1-(2-[5-(3-methybenzyl)-1,3,4-oxadiazolyl] carbonyl)-2-(S)-methylpropyl]acetamide. Prepared in a similar manner as shown in Example 48. FAB MS [M+H] m/z; Calcd: 535, Found: 535

Example 52

(CE-2113) 3-(Amino-quinoline-2-one)-N[1-(2-[5-(3-methylbenzyl)-1,3,4-oxadiazolyl]carbonyl)-2-(S)-methylpropyl]acetamide.

To a solution containing 2.30 g (3.79 mmol) of 3-[(benzyloxycarbonyl)amino]-quinoline-2-one-N-[1-(2-[5-

(3-methyl benzyl)-1,3,4-oxadiazolyl]-carbonyl)-2-(S)-methyl propyl]acetamide in 60 mL of trifluoroacetic acid under a nitrogen atmosphere at 0C was added 0.53 mL (4.54 mmol) of thioanisole. The reaction was allowed to warm to room temperature overnight. The solvent was removed under reduced pressure. Subsequent preparative HPLC afforded 0.61 g (27%) of the title compound. FAB MS [M+H] m/z; Calcd: 474, Found: 474

Example 53

(CE-2116) 3-[(4-Morpholino)aceto] amino-quinoline-2-one-N[1-(2-[5-(3methylbenzyl)-1,3,4-oxadiazolyl] carbonyl)-2-(S)-methylpropyl] acetamide.

To a solution containing 0.32 g (1.22 mmol) of 4-morpholino acetic acid in 18 mL of dichloromethane under a nitrogen atmosphere at 0° C. was added 0.33 g (1.30 mmol) of BOPCI and 0.22 mL (1.26 mmol) of DIEA. After stirring for 1.5 hours, a solution containing 0.61 g (1.04 mmol) of 3-(amino-quinoline-2-one)-N-[1-(2-[5-(3-methylbenzyl)-1,3,4-oxadiazolyl]carbonyl)-2-(S)-methypropyl]acetamide in 20 mL of dichloromethane was added followed by 0.22 mL (1.26 mmol) of DIEA. The reaction was allowed to stir at 0° C. overnight, diluted with dichloromethane and washed with water. The organic phase was dried over magnesium sulfate. Filtration, removal of solvent under reduced pressure and preparative HPLC afforded 0.20 g (27%) of the title compound. FAB MS [M+H] m/z; Calcd: 602, Found: 602

Example 54

(CE-2088) 3,4-Dihydro-quinoline-2-one-N[1-(2-[5-(3-methylbenzyl)-1,3,4-oxadiazolyl]carbonyl)-2-N-methylpropyl]acetamide from commercially available 3,4-Dihydro-2(1H)-quinoline-2-one.
Prepared in a similar manner as shown in Example 52. FAB MS [M+H] m/z; Calcd: 461, Found: 461

Example 55

(CE-2099) 1-Acetyl-3-benzylidene piperazine-2,5-dione-N-[ 1-(2-[5-(3-methylbenzyl)-1,3,4-oxadiazolyl]carbonyl)-2-(S)-methylpropyl] acetamide.

To a solution containing 0.55 g (4.15 mmol) of N-chlorosuccinimide in 35 mL of anhydrous toluene at 0° C. under a nitrogen atmosphere was added 0.46 mL (6.22 mmol) of dimethyl sulfide. The reaction was cooled to −25° C. using a carbon tetrachloride/dry ice bath, followed by the addition of a solution containing 0.58 g (1.04 mmol) of 1-acetyl-3-benzylidene piperazine-2,5-dione-N-[1-(2-[5-(3-methylbenzyl)-1,3,4-oxadiazolyl]hydroxymethyl)-2-(S)-methylpropyl]acetamide in 8 mL of toluene. The reaction was allowed to stir at −25° C. for 2 h, followed by the addition of 0.68 mL (4.87 mmol) of triethylamine. The cold bath was removed and the reaction allowed to warm to room temperature and maintained for 40 minutes. The reaction was partitioned between ethyl acetate and water. The organic phase was dried over magnesium sulfate. Filtration, removal of solvent under reduced pressure and column chromatography of the residue on silica gel 60% ethyl acetate/hexane gave 0.54 g of a brown oil which was further purified via preparative HPLC to give 146 mg (25%) of the title compound. FAB MS [M+H] m/z; Calcd: 558, Found: 558

The intermediate 1-acetyl-3-benzylidene piperazine-2,5-dione-N[1-(2-[5-(3-methylbenzyl)-1,3,4-oxadiazolyl] hydroxymethyl)-2-(S)-methylpropyl]acetamide was prepared as follows:

a. 1-Acetyl-3-benzylidene piperazine-2,5-dione-N-t-butyl acetate.

To a solution containing 6.36 g (26.00 mmol) of 1-Acetyl-3-benzylidene piperazine-2,5-dione described by D. Villemn, et al. (*Synthetic Communications*, 20:3325 (1990)), in 100 mL of DMF under a nitrogen atmosphere was added 9.62 mL (65.10 mmol) of t-butyl bromoacetate and 7.55 g (32.60 mmol) of silver oxide. The reaction was heated to 45° C. overnight. The reaction was filtered through a plug of celite and the filtrate concentrated under reduced pressure. The residue was diluted with ethyl acetate and washed with water. The organic phase was dried over magnesium sulfate. Filtration, removal of solvent under reduced pressure and column chromatography of the residue on silica gel with 1% methanol/dichloromethane gave 5.37 g of a tan solid. Further purification via preparative HPLC gave 2.5 g (27%) of the title compound. FAB MS[M+H]m/z; Calcd: 359, Found: 359.

b. 1-Acetyl-3-benzylidene-4-carboxymethylene-piperazine-2,5-dione.

To a solution containing 2.50 g (6.98 mmol) of 1-acetyl-3-benzylidene piperazine-2,5-dione-N-t-butyl acetate in 100 mL of dichloromethane under a nitrogen atmosphere at 0° C. was added 5.40 mL (69.80 mmol) of trifluoroacetic acid. The reaction was allowed to warm to room temperature overnight. The solvent was removed under reduced pressure and the residue diluted with ethyl acetate and washed with a saturated sodium bicarbonate solution. The aqueous phase was acidified with 1 N hydrochloric acid and extracted with ethyl acetate. The organic phase was dried over magnesium sulfate. Filtration and removal of solvent under reduced pressure gave 1.96 g (96%) of product as a tan solid. FAB MS [M+H] m/z; Calcd: 303, Found: 303.

c. 1-Acetyl-3-benzylidene piperazine-2,5-dione-N-[1-(2[5-(3-methylbenzyl)-1,3,4-oxadiazolyl]hydroxymethyl)-2-(S)-methylpropyl]acetamide.

To a solution containing 0.65 g (2.14 mmol) of 1-acetyl-3-benzylidene-4-carboxymethylene-piperazine-2,5-dione in 40 mL of anhydrous dichloromethane and 3 mL of DMF under a nitrogen atmosphere at 0° C. was added 0.57 g (2.24 mmol of BOPCI and 0.39 mL (2.21 mmol) of DIEA. After stirring for 30 minutes, a solution containing 0.57 g (1.83 mmol) of 1-[2-(5-[3-methylbenzyl])-1,3,4-oxadiazolyl]-2-(S)-amino-3-methylbutan-1-ol hydrochloride in 10 mL of dichloromethane and 0.39 mL (2.21 mmol) of DIEA. The reaction was allowed to stir at 0° C. overnight, diluted with dichloromethane and washed with water. The organic phase was dried over magnesium sulfate. Filtration, removal of solvent under reduced pressure and column chromatography of the residue on silica gel with 5% methanol/dichloromethane gave 0.13 g (58%) of product. FAB MS[M+H] m/z; Calcd: 560, Found: 560.

Example 56

(CE-2105) 1-Acetyl-3-(4-fluorobenzylidene) piperazine-2,5-dione-N-[1-(2-[5-(3-methylbenzyl)-1,3,4-oxadiazolyl]carbonyl)-2-(S)-methylpropyl] acetamide. Prepared in a similar manner as shown in Example 54. FAB MS[M+H] m/z; Calcd: 576, Found: 576.

Example 57

(CE-2111) 1-Acetyl-3-(4-dimethylamino benzylidene) piperazine-2,5-dione-N-[1-(2-[5-(3-methylbenzyl)-1,3,4-oxadiazolyl]carbonyl)-2-(S)-methylpropyl]acetamide. Prepared in a similar manner as shown in Example 54. FAB MS[M+H] m/z; Calcd: 601, Found: 601.

Example 58

(CE-2112) 1-Acetyl-3-(4-carbomethoxy benzylidene) piperazine-2,5-dione-N-[1-(2-[5-(3-methylbenzyl)-1,3,4-oxadiazolyl]carbonyl)-2-(S)-methylpropyl]acetamide. Prepared in a similar manner as shown in Example 54. FAB MS[M+H] m/z; Calcd: 616, Found: 616.

Example 59

(CE-2114) 1-Acetyl-3-[(4-pyridyl)methylene] piperazine-2,5-dione-N-[1-(2-[5-(3-methylbenzyl)-1,3,4-oxadiazolyl]carbonyl)-2-(S)-methylpropyl] acetamide. Prepared in a similar manner as shown in Example 54. FAB MS[M+H] m/z; Calcd: 559, Found: 559.

Example 60

(CE-2144) 4-[1-Benzyl-3-(R)-benzyl-piperazine-2, 5,-dione]-N-[1-(2-[5-(3-methylbenzyl)-1,3,4-oxadiazolyl]carbonyl)-2-(S)-methylpropyl] acetamide.

To a mixture containing 2.20 g (16.48 mmol) of N-chlorosuccinimide in 100 mL of anhydrous toluene under a nitrogen atmosphere at 0° C. was added 2.1 mL (28.59 mmol) of dimethyl sulfide. The reaction was cooled to −25° C. using a carbon tetrachloride/dry ice bath, followed by the addition of a solution containing 2.5 g (4.10 mmol) of 4-[1-benzyl-3-(R)-benzyl piperazine-2,5,-dione]-N-[1-(2-[5-(3-methylbenzyl)-1,3,4-oxadiazolyl]hydroxymethyl)-2-(S)-methylpropyl]acetamide in 15 mL of toluene. The reaction was allowed to stir at −25° C. for 2 hours, followed by the addition of 4.0 mL (28.70 mmol) of triethylamine. The cold bath was removed and the reaction allowed to warm to room temperature and maintained for 30 minutes. The reaction was diluted with ethyl acetate and washed with water. The organic phase was dried over magnesium sulfate. Filtration, removal of solvent under reduced pressure, and column chromatography of the residue on silica gel with 5% methanol/dichloromethane afforded 2.27 g of a light brown solid which was further purified via preparative HPLC to give 350 mg (14.4%) of the title compound. FAB MS [M+H]m/z; Calcd: 608, Found: 608.

The intermediate 4-[1-benzyl-3-(R)-benzyl piperazine-2,5,-dione]-N-[1-(2-[5-(3-methylbenzyl)-1,3,4-oxadiazolyl] hydroxymethyl)-2-(S)-methylpropyl]acetamide was prepared as follows:

a. 1-Benzyl-3-(R)-benzylpiperazine-2,5-dione-4-t-butyl acetate.

To a solution containing 7.0 g (23.78 mmol) of 1-benzyl-3-(R)-benzyl piperazine-2,5-dione described by Steele, et al. (*J. Biorg, Med. Chem. Lett.*, 5:47 (1995)) in 125 mL of DMF under a nitrogen atmosphere was added 5.30 mL (35.89 mmol) of t-butyl bromoacetate and 6.80 g (29.34 mmol) of silver oxide. The reaction was heated to 50° C. overnight, diluted with ethyl acetate and washed with water. The organic phase was dried over magnesium sulfate. Filtration, removal of solvent under reduced pressure and column chromatography of the residue on silica gel with 50% ethyl acetate/hexane afforded 7.74 g (79.7%) of the title compound as a white solid. FAB MS[M+H]m/z; Calcd:409, Found::409.

b. 1-Benzyl-3-(R)-benzyl-4-carboxymethylene-piperazine-2,5-dione.

To a solution containing 7.70 g (18.85 mmol) of 1-Benzyl-3-(R)-benzyl piperazine-2,5-dione-4-t-butyl acetate in 300 mL of dichoromethane under a nitrogen atmosphere at 0° C. was added 19.0 mL(191.30 mmol) of trifluroacetic acid. The reaction was allowed to warm to room temperature overnight. The solvent was removed under reduced pressure and the residue dissolved in ethyl acetate and washed with water. The organic phase was dried over magnesium sulfate. Filtration and removal of solvent under reduced pressure afforded 6.69 g of product. FAB MS[M+H]m/z; Calcd:353,Found:353.

c. 4-[1-Benzyl-3(R)-benzyl piperazine-2,5,-dione]-N-[1-(2-[5-(3-methylbenyl)-1,3,4-oxadiazolyl]hydroxymethyl)-2-(S)-methylpropyl]acetamide.

To a solution containing 2.0 g (5.68 mmol) of 1-Benzyl-3-(R)-benzyl-4-carboxymethylene-piperazine-2,5-dione in 100 mL of dichloromethane and 2 mL of DMF under a nitrogen atmosphere at 0° C. was added 2.0 g (7.86 mmol) of BOPCl and 1.50 mL (8.62 mmol) of DIEA. After stirring for 30 minutes, a solution containing 1.80 g (5.7 mmol) of 1-[2-(5-[3-methylbenzyl])-1,3,4-oxadiazolyl]-2-(S)-amino-3-methylbutan-1-ol hydrochloride in 10 mL of dichloromethane and 4.0 mL (22.99 mmol) of DIEA. The reaction was allowed to stir at 0° C. overnight, diluted with dichloromethane and washed with water. The organic phase was dried over magnesium sulfate. Filtration, removal of solvent under reduced pressure and column chromatography of the residue on silica gel with 7% methanol/dichloromethane afforded 2.69 g (77.7%) of product. FAB MS[M+H]m/z; Calcd:610, Found: 610.

Example 61

(CE-2128) 4-[1-Benzyl-3-(S)-benzylpiperazine-2,5,-dione]-N-[1-(2-[5-(3-methylbenzyl)-1,3,4-oxadiazolyl]carbonyl)-2-(S)-methylpropyl] acetamide. Prepared in a similar manner as shown in Example 59. FAB MS[M+H]m/z; Calcd:608, Found: 608.

Example 62

(CE-2146) 4-[1-Benzyl-3-(R)-benzylpiperazine-2,5,-dione]-N-[1-(3-[5-(3-trifluoromethylbenzyl)-1,2,4-oxadiazolyl]carbonyl)-2-(S)-methylpropyl] acetamide. Prepared in a similar manner as shown in Example 59. FAB MS[M+H]m/z; Calcd:662, Found: 662.

Example 63

(CE-2129) 4-[1-Benzyl-3-(S)-benzylpiperazine-2,5,-dione]-N-[1-(3-[5-(3-trifluoromethylbenzyl)-1,2,4-oxadiazolyl]carbonyl)-2-(S)-methylpropyl] acetamide. Prepared in a similar manner as shown in Example 59. FAB MS[M+H]m/z; Calcd:662, Found: 662.

Example 64

(CE-2133) 4-[1-Benzyl-3-(S)-benzylpiperazine-2,5,-dione]-N-[1-(3-[5-(2-dimethylaminoethyl)-1,2,4-oxadiazolyl]carbonyl)-2-(S)-methylpropyl] acetamide. Prepared in a similar manner as shown in Example 59. FAB MS[M+H]m/z; Calcd:575, Found: 575.

Example 65

(CE-2084) 4-[1-Methyl-3-(R,S)-phenylpiperazine-2,5,-dione]-N-[1-(3-[5-(3-trifluoromethylbenzyl)-1,2,4-oxadiazolyl]carbonyl)-2-(S)-methylpropyl] acetamide. Prepared in a similar manner as shown in Example 59. FAB MS[M+H]m/z; Calcd:572, Found: 572.

Example 66

(CE-2106) 4-[1-Methyl-3-(R,S)-phenylpiperazine-2,5,-dione]-N-[1-(2-[5-(3-methylbenzyl)-1,3,4-oxadiazolyl]carbonyl)-2-(S)-methylpropyl] acetamide. Prepared in a similar manner as shown in Example 59. FAB MS[M+H]m/z; Calcd:518, Found: 518.

Example 67

(CE-2162) 4-[1-(2-N-Morpholino ethyl)-3-(R)-benzyl piperazine-2,5,-dione]-N-[ 1-(2-[5-(3-methylbenzyl)-1,3,4-oxadiazolyl]carbonyl)-2-(S)-methylpropyl]acetamide. Prepared in a similar manner as shown in Example 59. FAB MS[M+H] m/z; Calcd:631, Found: 631.

Example 68

(CE-2149) 5-(R,S)-Phenyl-2,4-imidazolidinedione-N-[1-(2-[5-(3-methylbenzyl)-1,3,4-oxadiazolyl] carbonyl)-2-(S)-methylpropyl]acetamide.

To a mixture containing 0.28 g (2.10 mmol) of N-chlorosuccinimide in 50 mL of anhydrous toluene under a nitrogen atmosphere at 0° C. was added 0.23 mL (3.13 mmol) of dimethyl sulfide. The reaction was cooled to –25° C. using a carbon tetrachloride/dry ice bath, followed by the addition of a solution containing 0.26 g (0.52 mmol) of 5-(R,S)-phenyl-2,4-imidazolidinedione-N-[1-(2-[5(3-methylbenzyl)-1,3,4-oxadiazolyl]hydroxymethyl)-2-(S)-methylpropyl]acetamide in 10 mL of toluene. The reaction was allowed to stir at –25° C. for 2 hours, followed by the addition of 0.30 mL (2.15 mmol) of triethylamine. The cold bath was removed and the reaction allowed to warm to room temperature and maintained for 30 minutes. The reaction was diluted with ethyl acetate and washed with water. The organic phase was dried over magnesium sulfate. Filtration, removal of solvent under reduced pressure and column chromatography of the residue of silica gel with 10% methanol/dichloromethane, followed by preparative HPLC gave 120 mg (47.2%) of the title compound. FAB MS[M+H]m/z; Calcd:490, Found: 490.

The intermediate 5-(R,S)-phenyl-2,4-imidazolidinedione-N-[1-(2-[5(3-methylbenzyl)-1,3,4-oxadiazolyl] hydroxymethyl)-2-(S)-methylpropyl]acetamide was prepared as follows:

a. (R)-N-(Ethoxy carbonylmethyl)-N'-(1-methoxy carbonyl-2-phenyl)urea.

To a solution containing 18.45 g (91.49 mmol) of (R)-2-phenylglycine methylester in 250 mL of ethyl acetate and 13.4 mL (96.12 mmol) of triethylamine under a nitrogen atmosphere at 0° C. was added 10 mL (91.49 mmol) of ethyl isocyanatoacetate. After stirring for 1h, the reaction was diluted with ethyl acetate and washed with water. The organic phase was dried over magnesium sulfate. Filtration and removal of solvent under reduced pressure afforded 29.28 g (97.6%) of product as a white solid. FAB MS[M+H]m/z; Calcd: 235, Found: 235.

b. (R)-5-Phenyl-3-carboxymethyl hydantoin.

A mixture containing 29.28 g (99.49 mmol) of (R)-N-(ethoxy carbonylmethyl)-N'-(1-methoxy carbonyl-2-phenyl)urea in 500 mL of concentrated hydrochloric acid was heated to reflux overnight. The reaction mixture was cooled to room temperature and extracted with ethyl acetate. The organic phase was dried over magnesium sulfate. Filtration and removal of solvent under reduced pressure afforded 14.01 g (60%) of the title compound. FAB MS [M+H] m/z; Calcd: 295, Found: 295.

c. 5-(R,S)-phenyl-2,4-imidazolidinedione-N-[1-(2-[5(3-methylbenzyl)- 1,3,4-oxadiazolyl]hydroxymethyl)-2-(S)-methylpropyl]acetamide To a solution containing 2.55 g (10.89 mmol) of (R)-5-phenyl-3-carboxymethyl hydantoin in 100 mL of dichloromethane and 10 mL of DMF under a nitrogen atmosphere at 0° C. was added 2.30 g (12.00 mmol) of EDCI and 1.62 g (11.99 mmol) of HOBT. After stirring 30 minutes, a solution containing 4.43 g (14.21 mmol) of 1-[2-(5-[3-methylbenzyl])-1,3,4-oxadiazolyl]-2-(S)-amino-3-methylbutan-1-ol hydrochloride in 20 mL of dichloromethane and 4.78 mL (43.50 mmol) of NMM. The reaction was allowed to warm to room temperature overnight, diluted with dichloromethane and washed with water. The organic phase was dried over magnesium sulfate. Filtration, removal of solvent under reduced pressure and column chromatography of the residue on silica gel with 50% acetone/dichloromethane afforded 1.90 g (35.5%) of the title compound. FAB MS [M+H] m/z; Calcd: 490, Found: 490.

Example 69

(CE-2154) 5-(S)-Benzyl-2,4-imidazolidinedione-N-[1-(2-[5-(3-methylbenzyl)-1,3,4-oxadiazolyl] carbonyl)-2-(S)-methylpropyl]acetamide. Prepared in a similar manner as shown in Example 67. FAB MS [M+H] m/z; Calcd: 504, Found: 504.

Example 70

(CE-2142) 5-(R)-Benzyl-2,4-imidazolidinedione-N-[1-(2-[5-(3-methylbenzyl)-1,3,4-oxadiazolyl] carbonyl)-2-(S)-methylpropyl]acetamide. Prepared in a similar manner as shown in Example 67. FAB MS [M+H] m/z; Calcd: 504, Found: 504.

Example 71

(CE-2141) 5-(R)-Benzyl-2,4-imidazolidinedione-N-[1-(3-[5-(3-trifluoromethylbenzyl)-1,2,4-oxadiazolyl]carbonyl)-2-(S)-methylpropyl] acetamide. Prepared in a similar manner as shown in Example 67. FAB MS [M+H] m/z; Calcd: 558, Found: 558.

Example 72

(CE-2155) 5-(S)-Benzyl-2,4-imidazolidinedione-N-[1-(3-[5-(3-trifluoromethylbenzyl)-1,2,4-oxadiazolyl]carbonyl)-2-(S)-methylpropyl] acetamide. Prepared in a similar manner as shown in Example 67. FAB MS [M+H] m/z; Calcd: 558, Found: 558.

Example 73

(CE-2151) 1-Benzyl-4-(R)-benzyl-2,5-imidazolidinedione-N-[1-(2-[5-(3-methylbenzyl)-1,3,4-oxadiazolyl]carbonyl)-2-(S)-methylpropyl] acetamide. Prepared in a similar manner as shown in Example 67. FAB MS [M+H] m/z; Calcd: 594, Found: 594.

Example 74

(CE-2150) 1-Benzyl-4-(R)-benzyl-2,5-imidazolidinedione-N-[1-(3-[5-(3-trifluoromethylbenzyl)-1,2,4-oxadiazolyl]carbonyl)-2-(S)-methylpropyl]acetamide. Prepared in a similar manner as shown in Example 67. FAB MS [M+H] m/z; Calcd: 648, Found: 648.

Example 75

(ONO-PO-698) 2-[5-(Benzyloxycarbonyl)amino-6-oxo-2-(4-fluorophenyl)-1,6-dihydro-1-pyrimidinyl]-N-[1-(2-[5-tert-butyl-1,3,4-oxadiazolyl]carbonyl)-2-(S)-methylpropyl]acetamide.

To a mixture containing 410 mg (0.744 mmol, 77% purity) of Dess-Martin Reagent (1,1,1-triacetoxy-1,1-dihydro-1,2,benziodoxol-3-(1H)-one) in 4 mL of dichloromethane was added dropwise a solution containing 410 mg (0.676 mmol) of 2-[5-benzyloxycarbonyl)amino-6-oxo-2-(4-fluorophenyl)-1,6-dihydro-1-pyrimidinyl]-N-[1-(2-[5-tert-butyl-1,3,4-oxadiazolyl]hydroxymethyl)-2-(S)-methylpropyl]acetamide in 5 mL of dichloromethane. The reaction mixture was allowed to stir for 1 hour. The reaction was quenched by addition of water, extracted with ethyl acetate (×2). The extract was washed with water and a saturated sodium chloride solution. The organic phase was dried over anhydrous sodium sulfate, filtered and evaporated under reduced pressure. The residue was purified by column chromatography on silica gel using a elution of 33% ethyl acetate/hexane to afford 372 mg of the tittle compound. APCI, Pos, 40V [M+H] m/z; Calcd: 605, Found: 605.

The intermediate 2-[5-(Benzyloxycarbonyl)amino-6-oxo-2-(4-fluorophenyl)-1,6-dihydro-1-pyrimidinyl]-N-[1-(2-[5-tert-butyl-1,3,4-oxadiazolyl]hydroxymethyl)-2-(S)-methylpropyl]acetamide was prepared as follows: to a solution containing 265 mg (1.01 mmol) of [1-[5-tert-butyl-1,3,4-oxadiazol-2-yl]-2-(S)-amino-1-hydroxy-3-methylbutane hydrochloride and 336 mg (0.843 mmol) of 5-[(Benzyloxycarbonyl)amino]-6-oxo-2-(4-fluorophenyl)-1,6-dihydro-1-pyrimidinyl]acetic acid (*J. Med. Chem.*, 38:98 –108 (1995)) in 2 mL of anhydrous DMF was added 155 mg (1.01 mmol) of HOBT and 231 mg (1.01 mrnol) of EDCl. The mixture was cooled to 0° C. and 0.11 mL (1.0 mmol) of NMM was added dropwise and the reaction mixture was allowed to stir for 3 hours. The reaction was quenched by addition of water and extracted with ethyl acetate (×3). The extract was washed with aqueous 10% citric acid solution, a saturated sodium hydrogencarbonate solution and a saturated sodium chloride solution. The organic phase was dried over anhydrous sodium sulfate, filtered and evaporated under reduced pressure. The residue was purified by column chromatography on silica gel using a gradient elution of 0 to 1% methanol/chloroform to afford 418 mg of the tittle compound. APCI, Pos, 40V [M+H] m/z; Calcd: 607, Found: 607.

Example 76

(ONO-PO-690) 2-[5-(Benzyloxycarbonyl)amino-6-oxo-2-(4-fluorophenyl)-1,6-dihydro-1-pyrimidinyl]-N-[1-(2-[5-(α,α-dimethylbenzyl)-1,3,4-oxadiazolyl]carbonyl)-2-(S)-methylpropyl]acetamide was prepared in a similar manner to Example 75. APCI, Pos, 40V [M+H] m/z; Calcd: 667, Found: 667.

Example 77

(ONO-PO-697) 2-[5-(Benzyloxycarbonyl)amino-6-oxo-2-(4-fluorophenyl)-1,6-dihydro-1-pyrimidinyl]-N-[1-(2-[5-phenyl-1,3,4-oxadiazolyl]carbonyl)-2-(S)-methylpropyl]acetamide was prepared in a similar manner to Example 75. El, Pos, [M+H] m/z; Calcd: 624, Found: 624.

Example 78

(ONO-PO-716) 2-[6-oxo-2-(4-fluorophenyl)-1,6-dihydro-1-pyrimidinyl]-N-[1-(2-[5-tert-butyl-1,3,4-oxadiazolyl]carbonyl)-2-(S)-methylpropyl]acetamide was prepared in a similar manner to Example 75. APCI, Neg, 40V [M–H] m/z; Calcd: 454, Found: 454.

Example 79

(ONO-PO-722) 2-[6-oxo-2-(4-fluorophenyl)-1,6-dihydro-1-pyrimidinyl]-N-[1-(2-[5-(α,α-dimethylbenzyl)-1,3,4-oxadiazolyl]carbonyl)-2-(S)-methylpropyl]acetamide was prepared in a similar manner to Example 75. APCI, Neg, 40V [M-H] m/z; Calcd: 516, Found: 516.

Example 80

(ONO-PO-727) 2-[6-oxo-2-(4-fluorophenyl)-1,6-dihydro- 1-pyrimidinyl]-N-[1-(2-[5-tert-butyl-1,3,4-oxadiazolyl]carbonyl)-2-(R)-methylpropyl] acetamide was prepared in a similar manner to Example 75. APCI, Pos, 40V [M+H] m/z; Calcd: 456, Found: 456.

Example 81

(ONO-PO-730) 2-[6-oxo-2-phenyl-1,6-dihydro-1-pyrimidinyl]-N-[1-(2-[5-tert-butyl-1,3,4-oxadiazolyl]carbonyl)-2-(S)-methylpropyl]acetamide was prepared in a similar manner to Example 75. APCI, Neg, 40V [M-H] m/z; Calcd: 436, Found: 436.

Example 82

(ONO-PO-731) 2-[6-oxo-2-phenyl-1,6-dihydro-1-pyrimidinyl]-N-[1-(2-[5-(α,α-dimethylbenzyl)-1,3,4-oxadiazolyl]carbonyl)-2-(S)-methylpropyl]acetamide was prepared in a similar manner to Example 75. APCI, Neg, 40V [M-H] m/z; Calcd: 498, Found: 498.

Example 83

(ONO-PO-732) 2-[6-oxo-2-phenyl-1,6-dihydro-1-pyrimidinyl]-N-[1-(2-[5-tert-butyl-1,3,4-oxadiazolyl]carbonyl)-2-(R)-methylpropyl]acetamide was prepared in a similar manner to Example 75. APCI, Pos, 40V [M+H] m/z; Calcd: 438, Found: 438.

Example 84

(ONO-PO-734) 2-[6-oxo-2-(4-fluorophenyl)-1,6-dihydro-1-pyrimidinyl]-N-[1-(2-[5-(1-methylcyclopropyl)-1,3,4-oxadiazolyl]carbonyl)-2-(S)-methylpropyl]acetamide was prepared in a similar manner to Example 75. APCI, Pos, 40V [M+H] m/z; Calcd: 454, Found:454.

Example 85

(ONO-PO-735) 2-[6-Oxo-2-phenyl-1,6-dihydro-1-pyrimidinyl]-N-[1-(2-[5-(1-methylcyclopropyl)-1,3,4-oxadiazolyl]carbonyl)-2-(S)-methylpropyl]acetamide was prepared in a similar manner to Example 75. APCI, Pos, 40V [M+H] m/z; Calcd: 436, Found:436.

Example 86

(ONO-PO-737) 2-[6-oxo-2-phenyl-1,6-dihydro-1-pyrimidinyl]-N-[1-(2-[5-tert-butyl-1,3,4-oxadiazolyl]carbonyl)-2-(R,S)-methylpropyl]acetamide was prepared in a similar manner to Example 75. APCI, Pos, 40V [M+H] m/z; Calcd: 438, Found:438.

Example 87

(ONO-PO-696) 2-[5-Amino-6-oxo-2-(4-fluorophenyl)-1,6-dihydro-1-pyrimidinyl]-N-[1-(2-[5-tert-butyl-1,3,4-oxadiazolyl]carbonyl)-2-(S)-methylpropyl]acetamide.

To a mixture containing 296 mg (0.49 mmol) of 2-[5-(benzyloxycarbonyl)amino-6-oxo-2-(4-fluorophenyl)-1,6-dihydro-1-pyrimidinyl]-N-[1-(2-[5-tert-butyl-1,3,4-oxadiazolyl]carbonyl)-2-(S)-methylpropyl]acetamide and 0.32 niL (2.9 mmol) of anisole in 8 mL of dichloromethane at OEC was added dropwise a solution containing 392 mg (2.9 mmol) of aluminum chloride in 4 mL of nitromethane. The reaction mixture was allowed to stir for 1.5 hours, quenched by addition of ice water, extracted with ethyl acetate (×3). The extract was washed with water and a saturated sodium chloride solution. The organic phase was dried over anhydrous magnesium sulfate, filtered and evaporated under reduced pressure. The residue was purified by column chromatography on silica gel using a elution of 66% ethyl acetate/hexane to afford 175 mg of the tittle compound as a white solid. APCI, Pos, 40V [M+H] m/z; Calcd: 471, Found: 471.

Example 88

(ONO-PO-691) 2-[5-Amino-6-oxo-2-(4-fluorophenyl)-1,6-dihydro-1-pyrimidinyl]-N-[1-(2-[5-(α,α-dimethylbenzyl)-1,3,4-oxadiazolyl]carbonyl)-2-(S)-methylpropyl]acetamide was prepared in a similar manner to Example 91. FAB, Pos, [M+H] m/z; Calcd: 533, Found: 533.

Example 89

(ONO-PO-692) 2-[5-Amino-6-oxo-2-(4-fluorophenyl)-1,6-dihydro-1-pyrimidinyl]-N-[1-(2-[5-(α,α-dimethyl-3-methylbenzyl)-1,3,4-oxadiazolyl]carbonyl)-2-(S)-methylpropyl]acetamide was prepared in a similar manner to Example 91. FAB, Pos, [M+H] m/z; Calcd: 547, Found: 547.

Example 90

(ONO-PO-693) 2-[5-Amino-6-oxo-2-(4-fluorophenyl)-1,6-dihydro-1-pyrimidinyl]-N-[1-(2-[5-(3-methylbenzyl)-1,3,4-oxadiazolyl]carbonyl)-2-(R)-methylpropyl]acetamide was prepared in a similar manner to Example 91. FAB, Pos, [M+H] m/z; Calcd: 519, Found: 519.

Example 91

(ONO-PO-694) 2-[5-Amino-6-oxo-2-(4-fluorophenyl)-1,6-dihydro-1-pyrimidinyl]-N-[1-(2-[5-phenyl-1,3,4-oxadiazolyl]carbonyl)-2-(S)-methylpropyl]acetamide was prepared in a similar manner to Example 91. APCI, Pos, 40V [M+H] m/z; Calcd: 491, Found: 491.

Example 92

(ONO-PO-695) 2-[5-Amino-6-oxo-2-(4-fluorophenyl)-1,6-dihydro-1-pyrimidinyl]-N-[1-(2-[5-(3-pyridyl)-1,3,4-oxadiazolyl]carbonyl)-2-(S)-methylpropyl]acetamide was prepared in a similar manner to Example 91. APCI, Pos, 40V [M+H] m/z; Calcd: 492, Found: 492.

Example 93

(ONO-PO-699) 2-[5-Amino-6-oxo-2-(4-fluorophenyl)-1,6-dihydro-1-pyrimidinyl]-N-[1-(2-[5-(4-methoxyphenyl)-1,3,4-oxadiazolyl]carbonyl)-2-(S)-methylpropyl]acetamide was prepared in a similar manner to Example 91. FAB, Pos [M+H] m/z; Calcd: 521, Found: 521.

Example 94

(ONO-PO-701) 2-[5-Amino-6-oxo-2-(4-fluorophenyl)-1,6-dihydro-1-pyrimidinyl]-N-[1-(2-[5-(α,α-dimethyl)-3,4-dihydroxybenzyl)-1,3,4-oxadiazolyl]carbonyl)-2-(S)-methylpropyl]acetamide was prepared in a similar manner to Example 91. APCI, Pos, 40V [M+H] m/z; Calcd: 565, Found: 565.

Example 95

(ONO-PO-703) 2-[5-Amino-6-oxo-2-(4-fluorophenyl)-1,6-dihydro-1-pyrimidinyl]-N-[1-(2-[5-benzyl-1,3,4-oxadiazolyl]carbonyl)-2-(S)-methylpropyl]acetamide was prepared in a similar manner to Example 91. APCI, Pos, 40V [M+H] m/z; Calcd: 505, Found: 505.

Example 96

(ONO-PO-704) 2-[5-Amino-6-oxo-2-(4-fluorophenyl)-1,6-dihydro-1-pyrimidinyl]-N-[1-(2-[5-methyl-1,3,4-oxadiazolyl]carbonyl)-2-(S)-methylpropyl]acetamide was prepared in a similar manner to Example 91. FAB, Pos [M+H] m/z; Calcd: 429, Found: 429.

Example 97

(ONO-PO-705) 2-[5-Amino-6-oxo-2-(4-fluorophenyl)-1,6-dihydro-1-pyrimidinyl]-N-[1-(2-[5-isopropyl-1,3,4-oxadiazolyl]carbonyl)-2-(S)-methylpropyl]acetamide was prepared in a similar manner to Example 91. APCI, Pos, 40V [M+H] m/z; Calcd: 457, Found: 457.

Example 98

(ONO-PO-706) 2-[5-Amino-6-oxo-2-(4-fluorophenyl)-1,6-dihydro-1-pyrimidinyl]-N-[1-(2-[5-butyl-1,3,4-oxadiazolyl]carbonyl)-2-(S)-methylpropyl]acetamide was prepared in a similar manner to Example 91. FAB, Pos [M+H] m/z; Calcd: 471, Found: 471.

Example 99

(ONO-PO-707) 2-[5-Amino-6-oxo-2-phenyl-1,6-dihydro-1-pyrimidinyl]-N-[1-(2-[5-tert-butyl-1,3,4-oxadiazolyl]carbonyl)-2-(S)-methylpropyl]acetamide was prepared in a similar manner to Example 91. FAB, Pos [M+H] m/z; Calcd: 453, Found: 453.

Example 100

(ONO-PO-711) 2-[5-Amino-6-oxo-2-phenyl-1,6-dihydro-1-pyrimidinyl]-N-[1-(2-[5-α,α-dimethybenzyl-1,3,4-oxadiazolyl]carbonyl)-2-(S)-methylpropyl]acetamide was prepared in a similar manner to Example 91. FAB, Pos [M+H] m/z; Calcd: 515, Found: 515.

Example 101

(ONO-PO-712) 2-[5-Amino-6-oxo-2-(3-pyridyl)-1,6-dihydro-1-pyrimidinyl]-N-[1-(2-[5-tert-butyl-1,3,4-oxadiazolyl]carbonyl)-2-(S)-methylpropyl]acetamide was prepared in a similar manner to Example 91. APCI, Pos, 40V [M+H] m/z; Calcd:454, Found:454.

Example 102

(ONO-PO-714) 2-[5-Amino-6-oxo-2-(4-fluorophenyl)-1,6-dihydro-1-pyrimidinyl]-N-[1-(2-[5-[1-methylcyclopropyl)-1,3,4-oxadiazolyl]carbonyl)-2-(S)-methylpropyl]acetamide was prepared in a similar manner to Example 91. APCI, Pos, 40V [M+H] m/z; Calcd: 469, Found: 469.

Example 103

(ONO-PO-715) 2-[5-Amino-6-oxo-2-(3-pyridyl)-1,6-dihydro-1-pyrimidinyl]-N-[1-(2-[5-(α,α-dimethylbenzyl)-1,3,4-oxadiazolyl]carbonyl)-2-(S)-methylpropyl]acetamide was prepared in a similar manner to Example 91. APCI, Pos, 40V [M+H] m/z; Calcd: 516, Found: 516.

Example 104

(ONO-PO-718) 2-[5-Amino-6-oxo-2-(4-fluorophenyl)-1,6-dihydro-1-pyrimidinyl]-N-[1-(2-[5-tert-butyl-1,3,4-oxadiazolyl]carbonyl)-2-(R)-methylpropyl]acetamide was prepared in a similar manner to Example 91. APCI, Pos, 40V [M+H] m/z; Calcd: 471, Found: 471.

Example 105

(ONO-PO-721) 2-[5-Amino-6-oxo-2-(4-fluorophenyl)-1,6-dihydro-1-pyrimidinyl]-N-[1-(2-[5-(α,α-dimethylbenzyl)-1,3,4-oxadiazolyl]carbonyl)-2-(R)-methylpropyl]acetamide was prepared in a similar manner to Example 91. APCI, Pos, 40V [M+H] m/z; Calcd: 533, Found: 533.

Example 106

(ONO-PO-728) 2-[5-Amino-6-oxo-2-phenyl-1,6-dihydro-1-pyrimidinyl]-N-[1-(2-[5-(1-methylcyclopropyl)-1,3,4-oxadiazolyl]carbonyl)-2-(S)-methylpropyl]acetamide was prepared in a similar manner to Example 91. APCI, Neg, 40V [M−H] m/z; Calcd:449, Found:559.

Example 107

(ONO-PO-729) 2-[5-Amino-6-oxo-2-phenyl-1,6-dihydro-1-pyrimidinyl]-N-[1-(2-[5-tert-butyl-1,3,4-oxadiazolyl]carbonyl)-2-(R)-methylpropyl] acetamide was prepared in a similar manner to Example 91. APCI, Pos, 40V [M+H] m/z; Calcd:453, Found:453.

Example 108

(ONO-PO-733) 2-[5-Amino-6-oxo-2-(4-fluorophenyl)-1,6-dihydro-1-pyrimidinyl]-N-[1-(2-[5-tert-butyl-1,3,4-oxadiazolyl]carbonyl)-2-(R,S)-methylpropyl]acetamide was prepared in a similar manner to Example 91. APCI, Pos, 40V [M+H] m/z; Calcd:471, Found:471.

Example 109

(ONO-PO-736) 2-[5-Amino-6-oxo-2-(4-fluorophenyl)-1,6-dihydro-1-pyrimidinyl]-N-[1-(2-[5-tert-butyl-1,3,4-oxadiazolyl]carbonyl)-2-(R,S)-methylpropyl]acetamide was prepared in a similar manner to Example 91. APCI, Pos, 40V [M+H] m/z; Calcd:453, Found:453.

Example 110

(ONO-PO-700) 2-[5-Amino-6-oxo-2-(4-fluorophenyl)-1,6-dihydro-1-pyrimidinyl]-N-[1-(2-[5-(α,α-dimethyl-3,4-methylenedioxybenzyl)- 1,3,4-oxadiazolyl]carbonyl)-2-(S)-methylpropyl]acetamide To a mixture containing 66 mg (0.093 mmol) of 2-[5-(benzyloxycarbonyl)amino-6-oxo-2-(4-fluorophenyl)-1,6-dihydro-1-pyrimidinyl]-N-[1-(2-[5-(α,α-dimethyl-3,4-methylenedioxybenzyl)-1,3,4-oxadiazolyl]carbonyl)-2-(S)-methylpropyl]acetamide (the compound prepared in a similar manner to Example 75) was added 2.5 mL of 30% hydrobromic acid in acetic acid solution. The reaction mixture was allowed to stir for 1 hour, quenched by addition of ice water, extracted with ethyl acetate (×3). The extract was washed with water (×2) and a saturated sodium chloride solution. The organic phase was dried over anhyudrous sodium sulfate, filterd and evaporated under reduced pressure. The residue was purified by column chromatography on silica gel using a gradient elution of 0 to 1% methanol/chloroform to afford 41 mg of the title compound. El, Pos, [M+] m/z; Calcd:576, Found:576.

Example 111

(ONO-PO-702) 2-[5-(Methylsulfonyl)amino-6-oxo-2-(4-fluorphenyl)-1,6-dihydro-1-pyrimidinyl]-N-[1-(2-[5-(3-methylbenzyl)-1,3,4-oxadiazolyl]carbonyl)-2-(S)-methylpropyl]acetamide To a mixture containing 187 mg (0.36 mmol) of 2-[5-amino-6-oxo-2-(4-fluorophenyl)-1,6-dihydro-1-pyrimidinyl]-N-[1-(2-[5-(3-methylbenzyl)-1,3,4-oxadiazolyl]carbonyl)-2-(S)-methylpropyl]acetamide (the compound prepared in Example 25) in 3.5 mL of pyridine at 0EC under an atmosphere of argon was added 0.028 mL (0.36 mmol) of mesyl chloride. The reaction mixture was allowed to stir for 17 hours at room temperature, 15 hours at 50EC and 1 hour at 70EC. The reaction mixture was quenched by addition of ice water, extracted with dichloromethane. The extract was washed with a saturated sodium chloride solution. The organic phase was dried over anhydrous sodium sulfate, filtered and evaporated under reduced pressure. The residue was purified by column chromatography on silica gel using a gradient elution of 50 to 66% ethyl acetate/hexane to afford 60 mg of the title compound. APCI, Pos, 40V [M+H] m/z; Calcd: 597, Found: 597.

Example 112

In Vitro Inhibition of Elastase

The following protocol was used to determine inhibitory activity of ONO-PO series of compounds. The elastase used in the protocol was derived from human sputum (HSE). A mother solution of the HSE enzyme was prepared from commercially available HSE (875 U/mg protein, SE-563, Elastin Product Co., Inc, Missouri, USA) by diluting with saline to 1,000 U/ml, which was further diluted to 2 U/ml at 0° C. prior to use.

A solution was prepared by mixing 100 μl 0.2 M HEPES-NaOH buffer (pH 8.0), 40 μl 2.5 M NaCl, 20 μl 1% polyethyleneglycol 6000, 8 μl distilled water, 10 μl of a DMSO solution of inhibitor and 2 μl solution of N-methoxysuccinyl-Ala-Ala-Pro-Val-p-nitroaniline (SEQ ID NO:1) (at concentrations of 100, 200 and 400 μM). The solution was incubated for 10 minutes at 37° C. To this was added an enzyme solution of HSE (elastase derived from human sputum). The resulting mixture was subjected to the following rate assay.

Optical density (SPECTRA MAX 250, Molecular Devices) at 405 nm due to p-nitroaniline generated by the enzyme reaction was measured at 37° C. in order to measure the reaction rate during the period that the production rate of p-nitroaniline remains linear. The rate, mO.D./min., was measured for 10 minutes at 30 second intervals immediately after the addition of the enzyme solution. $IC_{50}$ values were determined by log-logit method and converted to $K_i$ values by Dixson plot method. The values are presented in Table 2 below. Table 2.

| Compound | $K_i$ (nM) | Compound | $K_i$ (nM) | Compound | $K_i$ (nM) |
| --- | --- | --- | --- | --- | --- |
| ONO-PO-690 | 78.3 | ONO-PO-710 | 2.39 | ONO-PO-730 | 23.5 |
| ONO-PO-691 | 0.52 | ONO-PO-711 | 2.55 | ONO-PO-731 | 4.02 |
| ONO-PO-692 | 1.37 | ONO-PO-712 | 16.6 | ONO-PO-732 | 62.2 |
| ONO-PO-693 | 2.71 | ONO-PO-713 | 12 | ONO-PO-733 | 11.8 |
| ONO-PO-694 | 24.8 | ONO-PO-714 | 15.3 | ONO-PO-734 | 43.8 |
| ONO-PO-695 | 13.9 | ONO-PO-715 | 3.54 | ONO-PO-735 | 26.4 |
| ONO-PO-696 | 6.38 | ONO-PO-716 | 44.3 | ONO-PO-736 | 6.43 |
| ONO-PO-697 | 27.3 | ONO-PO-717 | 57.8 | ONO-PO-737 | 36.3 |
| ONO-PO-698 | 0.77 | ONO-PO-718 | 26.2 | | |
| ONO-PO-699 | 21.2 | ONO-PO-719 | 836.3 | | |
| ONO-PO-700 | 1.18 | ONO-PO-720 | 25.9 | | |
| ONO-PO-701 | 2.98 | ONO-PO-721 | 13.5 | | |
| ONO-PO-702 | 1.78 | ONO-PO-722 | 3.35 | | |
| ONO-PO-703 | 2.25 | ONO-PO-723 | 163.1 | | |
| ONO-PO-704 | 14.0 | ONO-PO-724 | 14.4 | | |
| ONO-PO-705 | 10.7 | ONO-PO-725 | 4281.4 | | |
| ONO-PO-706 | 6.76 | ONO-PO-726 | 589.5 | | |
| ONO-PO-707 | 3.59 | ONO-PO-727 | 132.8 | | |
| ONO-PO-708 | 729.9 | ONO-PO-728 | 8.75 | | |
| ONO-PO-709 | 25.7 | ONO-PO-729 | 29.1 | | |

CE compounds were tested as described in WO 96/16080. Results are presented in Table 2 below. As shown, the compounds of the invention are potent inhibitors of elastase, with certain compounds showing subnanomolar levels of inhibitory activity.

Example 113

Blood Level Screening

The inhibitors were dissolved or suspended in polyethylene glycol (PEG), PEG-400 or PEG:H$_2$O:EtOH at a concentration of 10 mg/ml. Unfasted male Sprague-Dawley rats were given an oral dose of this solution by gavage. Rats received 10 mg inhibitor/kg 10 body weight in a volume of 1 ml/kg. After 1,3 or 6 hr., the rats were killed with an overdose of urethane (2.5 g/kg; i.p.) and the blood collected in a heparinized tube via cardiac puncture. Red blood cells were separated from the plasma by centrifligation.

Depending on the inhibitor, one of four organics (ethyl acetate, toluene, isopropyl ether or methyl t-butyl ether) was used to extract the compound from the plasma. Inhibitor concentrations were measured by HPLC or LC/MS analysis. The results are presented in Table 3 below. Certain compounds of the invention demonstrate high levels of oral bioavailability as shown by their blood level concentrations over time.

Example 114

Extracellular Matrix (ECM) Assay Procedure

Forty-eight well plates on which extracellular matix had been established were supplied to Cortech by Dr. Simon's group at the State University of New York at Stony Brook. Briefly, the plates were prepared as follows: R22 rat heart smooth muscle cells were seeded into wells at 2.5×10$^4$ cells/cm. The cells were fed every 4 days with Eagle's Minimal Essential Media supplemented with fetal bovine serum, tryptose phosphate broth, cefotaxime and streptomycin. At confluence, daily supplements of 50 ug/ml ascorbic acid were added for 8 to 10 days during the synthesis of the ECM layer. [$^{35}$S]sulfate and [$^3$H]proline were also added to the culture media to incorporate radiolabel into the matrix. Cells were later lysed with 25 mM NH$_4$OH. Plates were washed three times with water and once with phosphate-buffered saline containing 0.02% NaN$_3$. Plates were stored at 4° C. until use.

Matrix degradation assays were performed as follows: 0.40 ml of Hanks balance salt solution (HBSS) containing 1 or 5 uM test inhibitor (final concentration; diluted from DMSO stock solution; <2% DMSO final concentration) was added to the wells. After 30 minutes, 50 ul of a polymorphoneucleocyte (PMN) suspension was added resulting in 5×10$^5$ cells/well. PMN's were stimulated with opsonized zymosan. Zymosan particles were washed and suspended in 0.5 ml human serum for 1 hr at 37° C., vortexing every 15 min. The particles were then washed three times with HBSS and added to wells at a ratio of 10 particles/PMN in a volume of 50 ul. After a 4 hr incubation at 37° C., a 100 ul aliquot of the supernatant was withdrawn for scintillation counting. Following removal of the remaining supernatant, the residual ECM was solubilized with 0.5 ml 2M NaOH. The amount of tritium in this solubilized ECM was accessed by scintillation. ECM degradation data are expressed as (soluble counts released/total ECM counts)−(basal counts released without PMN's/total ECM counts). The results are presented in Table 3 below.

TABLE 3

| CE # | HNE K$_i$ (nM) | ECM Data % Inhibition 1 uM | ECM Data % Inhibition 5 uM | Plasma Levels (μM) 1 hr | Plasma Levels (μM) 3 hr | Plasma Levels (μM) 6 hr |
|---|---|---|---|---|---|---|
| CE2048 | 0.2 | | | | | |
| CE2049 | 0.5 | | | | | |
| CE2050 | 1.84 | | | | | |
| CE2051 | 1.56 | | | | | |
| CE2052 | 0.37 | | | | | |
| CE2053 | 0.41 | | | | | |
| CE2054 | 0.29 | | | | | |
| CE2055 | 0.49 | | | 0.002 | | |
| CE2056 | 0.98 | | | | | |
| CE2057 | 0.375 | | | | | |
| CE2058 | 0.564 | | | | | |
| CE2061 | 71600 | | | | | |
| CE2062 | 0.3 | | | | | |
| CE2064 | 0.44 | | | | | |
| CE2065 | 0.47 | | | | | |
| CE2066 | 0.98 | | | | | |
| CE2067 | 3.6 | | | | | |
| CE2068 | 800 | | | | | |
| CE2069 | 4.4 | | | | | |
| CE2072 | 0.025 | 64.8 | 74.55 | 0.277 | 0.115 | 0.061 |
| CE2073 | 0.235 | | | | | |
| CE2074 | 1 | | | | | |
| CE2075 | 0.039 | | | | | |
| CE2076 | 1.5 | | | | | |
| CE2077 | 0.15 | | | | | |
| CE2078 | 1.05 | | | | | |
| CE2079 | 34 | | | | | |
| CE2080 | 62 | | | | | |
| CE2082 | 53 | | | | | |
| CE2083 | 73 | | | | | |
| CE2084 | 133 | | | | | |
| CE2087 | 20 | | | | | |
| CE2088 | 66 | | | 0.801 | 0.755 | |
| CE2089 | 1.5 | | | | | |
| CE2090 | 2.7 | | | | | |
| CE2091 | 270 | | | | | |
| CE2092 | 6.3 | | | | | |
| CE2093 | 0.26 | | | | | |
| CE2094 | 10 | | | | | |
| CE2095 | 0.21 | 60.43 | 55.63 | | | |
| CE2096 | 0.79 | | | | | |
| CE2097 | 115 | | | | | |
| CE2098 | 85 | | | | | |
| CE2099 | 1.9 | | | 0.042 | | |
| CE2100 | 0.069 | 57.63 | 56.56 | 0.064 | | |
| CE2101 | 0.64 | 44.582 | 51.18 | 1.238 | 1.369 | 1.042 |
| CE2102 | 258 | | | | | |
| CE2103 | 12.4 | | | | | |
| CE2104 | 0.33 | | | | | |
| CE2105 | 0.72 | | | | | |
| CE2106 | 41 | | | | | |
| CE2107 | 17 | | | | | |
| CE2108 | 10.5 | | | | | |
| CE2109 | 126 | | | | | |
| CE2110 | 0.13 | | | | | |
| CE2111 | 20 | | | 0.69 | | |
| CE2112 | 1.2 | | | | | |
| CE2113 | 39 | | | 1.835 | 0.909 | |
| CE2114 | 25 | | | | | |
| CE2115 | 1 | | | | | |
| CE2116 | 76 | | | | | |
| CE2117 | 586 | | | | | |
| CE2118 | 13.2 | | | | | |
| CE2119 | 7.7 | | | | | |
| CE2120 | 51 | | | | | |
| CE2121 | 28 | | | | | |
| CE2122 | 63 | | | | | |
| CE2123 | 15 | | | | | |
| CE2124 | 0.033 | | | | | |
| CE2125 | 0.4 | | | 0.011 | | |
| CE2126 | 5 | | | 0.161 | | |
| CE2127 | 34 | | | | | |
| CE2128 | 64 | | | | | |
| CE2129 | 300 | | | | | |
| CE2130 | 2.1 | 16.32 | 29.02 | 0.162 | | |

TABLE 3-continued

| CE # | HNE K$_i$ (nM) | ECM Data % Inhibition 1 uM | 5 uM | Plasma Levels (μM) 1 hr | 3 hr | 6 hr |
|---|---|---|---|---|---|---|
| CE2131 | 265 | | | | | |
| CE2132 | 23.5 | | | | | |
| CE2133 | 33000 | | | | | |
| CE2134 | 2 | 21.71 | 25.724 | | 5.02 | |
| CE2135 | 17.5 | 0 | 37 | | | |
| CE2136 | 104 | | | | | |
| CE2137 | 558 | | | | | |
| CE2138 | 294 | | | | | |
| CE2139 | 41 | | | | | |
| CE2140 | 204 | | | | | |
| CE2141 | 64 | | | | 0.005 | |
| CE2142 | 8.7 | | | | | |
| CE2143 | 11.5 | | | | | |
| CE2144 | 9.3 | | | | | |
| CE2145 | 0.038 | | | | | |
| CE2146 | 67 | | | | | |
| CE2147 | 1600 | | | | | |
| CE2149 | 0.28 | 51.275 | 55.9 | 0 | 0 | 0 |
| CE2151 | 59 | 14.25 | −8.3 | | | |
| CE2152 | 0.24 | | | | | |
| CE2154 | 10 | 54.6 | 65.4 | | | |
| CE2155 | 57 | | | | | |
| CE2156 | 512 | | | | | |
| CE2157 | 1.4 | 9.96 | 13.42 | | 3.81 | |
| CE2159 | 52 | | | | | |
| CE2160 | 260 | | | | | |
| CE2161 | 0.082 | 25 | 55 | | | |
| CE2162 | 10.6 | | | | 0.025 | |
| CE2163 | 0.75 | 54.7 | 64 | | 0.316 | |
| CE2164 | 17 | | | | 0.034 | |
| CE2165 | 2.6 | | | | 0.067 | |
| CE2166 | 145 | | | | | |
| CE2168 | 0.15 | | | | | |
| CE2170 | 297 | | | | | |
| CE2171 | 0.64 | | | | | |
| CE2172 | 2.2 | | | | 0.021 | |
| CE2173 | 6.5 | 35.9 | 47.1 | | | |
| CE2174 | 15.2 | 1.49 | 18.3 | 1.86 | 0.97 | |
| CE2176 | 52 | | | | | |
| CE2177 | 0.016 | 74.2 | 76.78 | 0.393 | 0.41 | 0 |
| CE2178 | 0.29 | | 34 | | 0.185 | |
| CE2179 | 7.6 | 48.8 | 45.9 | 1.229 | 0.599 | |
| CE2180 | 44 | | | | | |
| CE2181 | 46 | | | | | |
| CE2182 | 54 | | | | | |
| CE2183 | 0.23 | | | | | |
| CE2184 | 8.2 | 30.5 | 32.4 | | 0.57 | |
| CE2185 | 0.27 | | | | | |
| CE2186 | 0.037 | | | | | |
| CE2187 | 42 | | | | | |
| CE2189 | 99 | | | | | |
| CE2190 | 29 | | | | | |
| CE2191 | 85 | 29.35 | 30.5 | | | |
| CE2192 | 7.3 | 40.8 | 49.7 | | | |
| CE2193 | 36 | | | | | |
| CE2194 | 2.4 | 41 | 58.7 | 1.11 | 0.553 | |
| CE2195 | 10.6 | | | | | |
| CE2196 | 96 | | | | | |
| CE2197 | 4.8 | | | | | |
| CE2198 | 3.1 | | | | | |
| CE2200 | 13.7 | | | | | |
| CE2202 | 0.12 | | | | | |
| CE2203 | 79 | | | | 0.004 | |
| CE2204 | 7.4 | | | | 0.48 | |
| CE2205 | 37 | | | | 0.475 | |
| CE2206 | 8.7 | 47.4 | 62.3 | | | |
| CE2207 | 1.2 | | | | 0 | |
| CE2208 | 40 | | | | | |
| CE2209 | 36.4 | | | | 0 | |
| CE2210 | 22.7 | | | | | |
| CE2211 | 348 | | | | | |
| CE2212 | 124 | | | | | |
| CE2213 | 0.14 | | | | 0.19 | |
| CE2214 | 0.92 | | | | 0 | |
| CE2215 | 163 | | | 1.16 | 0.83 | 0.63 |
| CE2216 | 4.1 | 32.1 | 37.15 | 0.77 | 0.47 | 0.25 |
| CE2217 | 5.5 | 28.1 | 41.2 | 1.99 | 0.521 | |
| CE2218 | 1.6 | 30.5 | 33.15 | | | |
| CE2219 | 537 | | | | | |
| CE2220 | 52 | | | | | |
| CE2221 | 34 | | | | | |
| CE2223 | 0.93 | 34.15 | 36.15 | | | |
| CE2224 | 1 | 43.25 | 66.8 | 1.843 | 1.943 | 1.961 |
| CE2225 | 8.2 | 30.85 | 43.45 | | | |
| CE2226 | 10.3 | 27.55 | 52.25 | | | |
| CE2227 | 40 | | | 1.276 | 0.74 | 0.962 |
| CE2228 | 40 | | | 0.714 | 1.393 | 0.409 |
| CE2229 | 9.5 | 31.25 | 48.2 | | | |
| CE2230 | 2.6 | 37.7 | 37.8 | | 0 | |
| CE2231 | 16 | | | 1.226 | 0.787 | 0.531 |
| CE2232 | 0.15 | | | 0.44 | 0.44 | 0.26 |
| CE2233 | 41.6 | 54.7 | 55.4 | 0.07 | 0.065 | 0.036 |
| CE2234 | 796 | 39.7 | 35 | | | |
| CE2235 | 9.5 | 19.75 | 13.25 | | | |
| CE2236 | 7.1 | 31.9 | 31.75 | | | |
| CE2237 | 3 | 34.6 | 42.6 | 1.02 | 1.8 | 0.84 |
| CE2238 | 162 | 10.1 | 18.8 | 2.573 | 1.739 | 1.028 |
| CE2239 | 43 | 11.9 | 11.3 | 1.46 | 1.15 | 0.71 |
| CE2240 | 30 | 16.8 | 13.5 | 1.12 | 0.5 | 0.29 |
| CE2241 | 14 | 18.6 | 31.7 | 0.598 | 0.289 | 0.078 |
| CE2242 | 27 | 29.4 | 40.7 | | | |
| CE2243 | 11 | 48 | 54.9 | 2.801 | 2.104 | 1.598 |
| CE2244 | 78.5 | | | | | |
| CE2245 | 24 | 34.7 | 39.3 | | | |
| CE2246 | 18.5 | −2.3 | 32.6 | 1.182 | 0.837 | 0.496 |
| CE2247 | 62.4 | 13.3 | 21.2 | 1.017 | 0.572 | 0.186 |
| CE2248 | 3.1 | 39.4 | 63.2 | 1.65 | 1.58 | 1.22 |
| CE2249 | 13 | 22.4 | 42.4 | 1.179 | 0.704 | 0.213 |
| CE2250 | 6.9 | 27.4 | 48.6 | | | |
| CE2251 | 0.43 | 54.1 | 74.5 | 1.63 | 1.11 | 0.73 |
| CE2252 | 1.9 | 45.4 | 65.2 | 0.114 | 0.188 | 0.1 |
| CE2253 | 11 | 31.9 | 45.9 | 0.282 | 0.246 | 0.163 |
| CE2254 | 2.4 | 57.2 | 58.4 | 1.751 | 1.575 | 2.316 |
| CE2255 | 18 | 20.7 | 42 | | | |
| CE2256 | 16 | 24 | 47.8 | 0.9 | 0.33 | 0.2 |
| CE2257 | 30 | 48.3 | 61.4 | | | |
| CE2258 | 3.7 | 42.9 | 38.1 | 1.624 | 1.5 | 1.212 |
| CE2259 | 3.3 | 43 | 59.6 | 0.597 | 0.846 | 0.502 |
| CE2260 | 0.39 | 68.3 | 59.7 | 3.532 | 3.053 | 1.894 |
| CE2261 | 0.36 | | | | | |
| CE2262 | 0.42 | | | | | |
| CE2263 | 0.67 | | | | | |

Example 115

Ex vivo Inhibition of Elastase

Sixty (60) minutes after the oral adminstration of an inhibitor with an appropriate vehicle, a blood sample (0.9 ml) is collected through the abdominal aorta by a syringe containing 0.1 ml of a 3.8% sodium citrate solution.

The blood sample is processed as follows: 60 μl of (final 0.1–1 mg/ml) a suspended solution of opsonized zymosan in Hank's buffer is added to the preincubated whole blood (540 μl) for 5 minutes at 37° C., and the resulting mixture is incubated for 30 minutes at the same termperature. The reaction is terminated by immersing the test tube into ice water. The reaction mixture is then centrifuged at 3,000 rpm for 10 minutes at 4° C. Twenty (20) μl each of the resulting supernatant (the Sample) is measured for elastase activity.

The mixture consisting of the following components is incubated for 24 hours at 37° C., and then optical density is measured at 405 nm:

| | |
|---|---|
| 0.2M tris-HCl buffer (pH 8.0) | 100 μl |
| 2.5M NaCl | 40 μl |
| Distilled water | 36 μl |
| 50 mM solution of a substrate (*) | 4 μl |
| The Sample | 20 μl |

(*) N-Methylsuccinyl-Ala-Ala-Pro-Val-p-nitroanlide (SEQ ID NO: 1)

A test sample mixed with 1-methyl-2-pyrrolidone instead of the substrate is regarded as Substrate (−). A test sample mixed with saline instead of the Sample is regarded as Blank. The remaining elastase activity in the Sample is calculated according to the following:

optical density of Substrate (+)−(optical density of Substrate (−)+optical density of Blank) as a total production of p-nitroaniline over 24 hours based on a standard curve for the amount of p-nitroaniline.

An average activity is calculated based on the test sample of 5–6 animals. An agent at 3, 10 or 30 mg/kg is orally given by a forced administration to a 24 hour fasted animal at 60 minutes before the blood sampling. Optical density is measured by SPECTRA MAX 250 (Molecular Devices).

carboxyl, carboalkoxy, alkylcarboxamide, arylcarboxamide or —O—($C_5$–$C_6$)aryl; hydroxyl, amino, alkylamino or dialkylamino; or cycloalkyl, alkylcycloalkyl, alkenylcycloalkyl, cycloalkenyl, alkylcycloalkenyl, alkenylcycloalkenyl, ($C_5$–$C_{12}$)aryl, ($C_5$–$C_{12}$)arylalkyl, ($C_5$–$C_{12}$)arylalkenyl, fused($C_5$–$C_{12}$)aryl-cycloalkyl or alkyl fused($C_5$–$C_{12}$)aryl-cycloalkyl optionally comprising 1–4 heteroatoms selected from N, O and S, and optionally substituted with halo, cyano, nitro, hydroxyl, haloalkyl, amino, aminoalkyl, dialkylamino, alkyl, alkenyl, alkylenedioxy, alkynyl, alkoxy, haloalkoxy, carboxyl, carboalkoxy, alkylcarboxamide, ($C_5$–$C_6$)aryl, —O—($C_5$–$C_6$)aryl, arylcarboxamide, alkylthio or haloalkylthio;

$R_2$ and $R_3$ are independently or together H; alkyl or alkenyl optionally substituted with 1–3 halo, hydroxyl, thio, alkylthio, amino, alkylamino, dialkylamino, alkylguanidinyl, dialkylguanidinyl, guanidinyl, or amidylguanidine; —RCOR', —RCOOR', —RNR'R"R° or —RC(O)NR'R" where R is alkyl or alkenyl, and R', R" and R° are independently H, alkyl, alkenyl, cycloalkyl or ($C_5$–$C_6$)aryl; or cycloalkyl, alkylcycloalkyl, alkenylcycloalkyl, alkyl-oxyaryl,

We claim:

1. A compound of the formula:

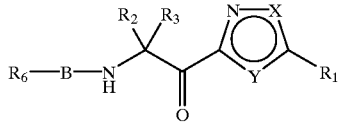

wherin

X and Y are independently O, S or N, wherein N is optionally substituted with alkyl or alkenyl optionally substituted with 1–3 halo atoms; ($C_5$–$C_6$)aryl, arylalkyl or arylalkenyl optionally comprising 1–3 heteroatoms selected from N, O and S, and optionally substituted with halo, cyano, nitro, hydroxyl, haloalkyl, amino, aminoalkyl, dialkylamino, alkyl, alkenyl, alkynyl, alkoxy, haloalkoxy, carboxyl, carboalkoxy, alkylcarboxamide, arylcarboxamide, alkylthio or haloalkylthio, provided that at least one of X or Y is N;

$R_1$ is alkyl, alkenyl or alkynyl optionally substituted with 1 or more halo, hydroxyl, cyano, nitro, haloalkyl, alkylamino, dialkylamino, alkoxy, haloalkoxy, alkyl-thioaryl, alkyl-aminoaryl, ($C_5$–$C_{12}$)aryl, ($C_5$–$C_{12}$)arylalkyl or ($C_5$–$C_{12}$)arylalkenyl optionally comprising 1–4 heteroatoms selected from N, O and S, and optionally substituted with halo, cyano, keto, nitro, hydroxyl, haloalkyl, amino, aminoalkyl, dialkylamino, amidine, alkylamidine, dialkylamidine, alkyl, alkenyl, alkylenedioxy, alkynyl, alkoxy, haloalkoxy, carboxyl, carboalkoxy, alkylcarboxamide, ($C_5$–$C_6$)aryl, —O—($C_5$–$C_6$)aryl, arylcarboxamide, alkylthio or haloalkylthio;

B is —S(O)$_2$—, —C(O)—, —OC(O)— or —CH$_2$—C(O)—; and $R_6$ is aryl, arylalkyl, cycloalkyl, alkylcycloalkyl, or is of formula (I)

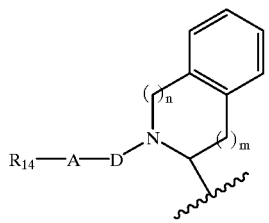
(I)

wherein m and n are independently 0 or 1;
D is a direct bond or an amino acid selected from proline, isoleucine, cyclohexylalanine, cysteine optionally substituted at the sulfur with alkyl, alkenyl or phenyl optionally substituted with halogen, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; phenylalanine, indoline-2-carboxylic acid, tetrahydrosioquinoline-2-carboxylic acid optionally substituted with alkyl, alkenyl, haloalkenyl, alkynyl, halogen, cyano, nitro, haloalkyl, amino, aminoalkyl, dialkylamino, alkoxyl, haloalkoxy, carbonyl, carboalkoxy, alkylcarboxamide, arylcarboxamide, alkyithio or haloalkythio; tryptophan, valine, norvaline, norleucine, octahydroindole-2-carboxylic acid; or lysine optionally substituted at the side chain nitrogen with alkyl, alkenyl, alkynyl, alkoxyalkyl, alkylthioalkyl, alkylaminoalkyl, dialkylaminoalkyl, carboxyalkyl or alkoxycarbonylalkyl; or cycloalkyl, cycloalkylalkyl, fused aryl-cycloalkyl or alkyl fused aryl-cycloalkyl optionally comprising 1 or more heteroatoms selected from N, O and S;

A is a direct bond, —C(O)—, —NH—C(O)—, —S(O)$_2$—, —OC(O)— or —CH$_2$—; and
R$_{14}$ is H, alkyl, alkenyl; or aryl, arylalkyl, cycloalkyl, alkylcycloalkyl, fused aryl-cycloalkyl or alkyl fused aryl-cycloalkyl optionally comprising 1 or more heteroatoms selected from N, O and S, and optionally substituted with alkyl, halo, alkoxy, amino, alkylamino, dialkylamino, carboxy, alkenyl, alkynyl, haloalkoxy, carboalkoxy, alkylcarboxamide, aryl, arylalkyl, arylcarboxamide, alkylthio or haloalkylthio.

2. A compound of claim 1 wherein R$_6$ is of formula (I).
3. A compound of claim 2 wherein D is Val.
4. A compound of claim 3 wherein R$_{14}$—A is Cbz.
5. A compound of claim 4: Benzyloxycarbonyl-L-(1,2,3,4-tetrahydroisoquinoline)-3-N-[1-(2-[5-(3-methylbenzyl)-1,3,4-oxadiazolyl]carbonyl)2-(R,S)-methylpropyl]amide.
6. A compound of claim 1 wherein R$_6$ is aryl, arylalkyl, cycloalkyl, or alkylcycloalkyl.
7. A compound of claim 6 wherein R$_6$ is arylalkyl.
8. A compound of claim 7 wherein R$_6$—B— is benzyloxycarbonyl.
9. A method of inhibiting one or more serine proteases comprising administering to a host in need of such inhibition an effective amount of a compound of claim 1.
10. A method of claim 9 wherein the serine protease in elastase.
11. A method of claim 10 wherein the elastase is human neutrophil elastase.
12. A method of claim 9 wherein said compound is administered orally.
13. A pharmaceutical composition comprising one or more compounds of claim 1 and a pharmaceutically acceptable carrier.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Human
<220> FEATURE:
<221> NAME/KEY: BLOCKED
<222> LOCATION: (1)...(1)
<223> OTHER INFORMATION: MeOSucc
<220> FEATURE:
<221> NAME/KEY: BLOCKED
<222> LOCATION: (4)...(4)
<223> OTHER INFORMATION: p-nitroanilide

<400> SEQUENCE: 1

Ala Ala Pro Val